United States Patent
Ngo

(10) Patent No.: US 10,717,782 B2
(45) Date of Patent: Jul. 21, 2020

(54) SYNTHETIC PROTEIN FOR MODULATING GENE EXPRESSION

(71) Applicant: TRUSTEES OF BOSTON UNIVERSITY, Boston, MA (US)

(72) Inventor: John T. Ngo, Cambridge, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 53 days.

(21) Appl. No.: 16/141,491

(22) Filed: Sep. 25, 2018

(65) Prior Publication Data

US 2019/0010245 A1  Jan. 10, 2019

Related U.S. Application Data

(63) Continuation of application No. 15/994,330, filed on May 31, 2018.

(60) Provisional application No. 62/586,451, filed on Nov. 15, 2017, provisional application No. 62/513,031, filed on May 31, 2017.

(51) Int. Cl.
| | |
|---|---|
| C07K 16/28 | (2006.01) |
| C07K 19/00 | (2006.01) |
| C07K 14/705 | (2006.01) |
| C07K 14/71 | (2006.01) |
| C07K 16/30 | (2006.01) |
| C07K 16/46 | (2006.01) |
| C12N 5/09 | (2010.01) |

(52) U.S. Cl.
CPC ........... *C07K 16/30* (2013.01); *C07K 14/705* (2013.01); *C07K 16/2863* (2013.01); *C07K 16/462* (2013.01); *C07K 19/00* (2013.01); *C12N 5/0693* (2013.01); *C07K 16/28* (2013.01); *C07K 2317/56* (2013.01); *C07K 2317/569* (2013.01); *C07K 2317/622* (2013.01); *C07K 2317/732* (2013.01); *C07K 2317/734* (2013.01); *C07K 2317/76* (2013.01); *C07K 2319/00* (2013.01); *C07K 2319/02* (2013.01); *C07K 2319/03* (2013.01); *C07K 2319/70* (2013.01); *C07K 2319/74* (2013.01)

(58) Field of Classification Search
CPC ........... C07K 2317/56; C07K 2317/76; C07K 2317/622; C07K 16/28; C07K 14/705; C07K 16/2863; C07K 16/18; C07K 14/71; C07K 19/00; C07K 2319/00; C07K 2317/60; C07K 16/2896; A61K 39/3955; A61K 2039/505
See application file for complete search history.

(56) References Cited

U.S. PATENT DOCUMENTS

| | | | | |
|---|---|---|---|---|
| 8,404,239 | B2 * | 3/2013 | Siebel | C07K 16/28 424/143.1 |
| 8,846,871 | B2 * | 9/2014 | Siebel | A61K 39/3955 530/388.1 |
| 9,433,687 | B2 * | 9/2016 | Geles | C07K 16/32 |
| 2005/0214309 | A1 | 9/2005 | Hinrichs et al. | |
| 2009/0226960 | A1 | 9/2009 | Yamazaki et al. | |
| 2010/0080808 | A1 | 4/2010 | Siebel et al. | |
| 2016/0264665 | A1 | 9/2016 | Lim et al. | |
| 2016/0347858 | A1 * | 12/2016 | Sakamoto | C07K 16/303 |

FOREIGN PATENT DOCUMENTS

| | | |
|---|---|---|
| WO | 2008/150525 A1 | 12/2008 |
| WO | 2017004022 A2 | 1/2017 |

OTHER PUBLICATIONS

Falk et al. Generation of anti-Notch antibodies and their application in blocking Notch signalling in neural stem cells. Methods 58: 69-78, 2012.*
Ho et al. Isolated of anti-CD22 Fv with high affinity by Fv display on human cells. Proc Natl Acad Sci USA 103(25): 9637-9642, 2006.*
Aste-Amezaga et al. "Characterization of Notch1 antibodies that inhibit signaling of both normal and mutated Notch1 receptors" PloS one 5(2):e9094 (2010).
Wu et al., "Therapeutic antibody targeting of individual Notch receptors." Nature 464(7291):1052 (2010).
Chung et al., "Tunable and reversible drug control of protein production via a self-excising degron." Nature Chemical Biology 11(9):713-720 (2015).
Gordon et al., "Mechanical Allostery: Evidence for a Force Requirement in the Proteolytic Activation of Notch." Developmental Cell 33(6):729-736 (2015).
Morsut et al., "Engineering customized cell sensing and response behaviors using synthetic notch receptors." Cell 164(4):780-791 (2016).
Roybal et al., "Engineering T cells with customized therapeutic response programs using synthetic notch receptors." Cell 167(2):419-432 (2016).

\* cited by examiner

*Primary Examiner* — Bridget E Bunner
(74) *Attorney, Agent, or Firm* — Nixon Peabody LLP; Ronald I. Eisenstein

(57) ABSTRACT

Described herein are compositions, methods, and systems for modulating Notch receptor activation. Aspects of the invention relate to synthetic proteins comprising at least a Notch NRR (Negative Regulatory Region)-binding scFV fused to a transmembrane domain. Another aspect of the invention relates to drug-dependent synthetic proteins. Constructs and engineered cells comprising the synthetic proteins are additionally described herein.

8 Claims, 70 Drawing Sheets
Specification includes a Sequence Listing.

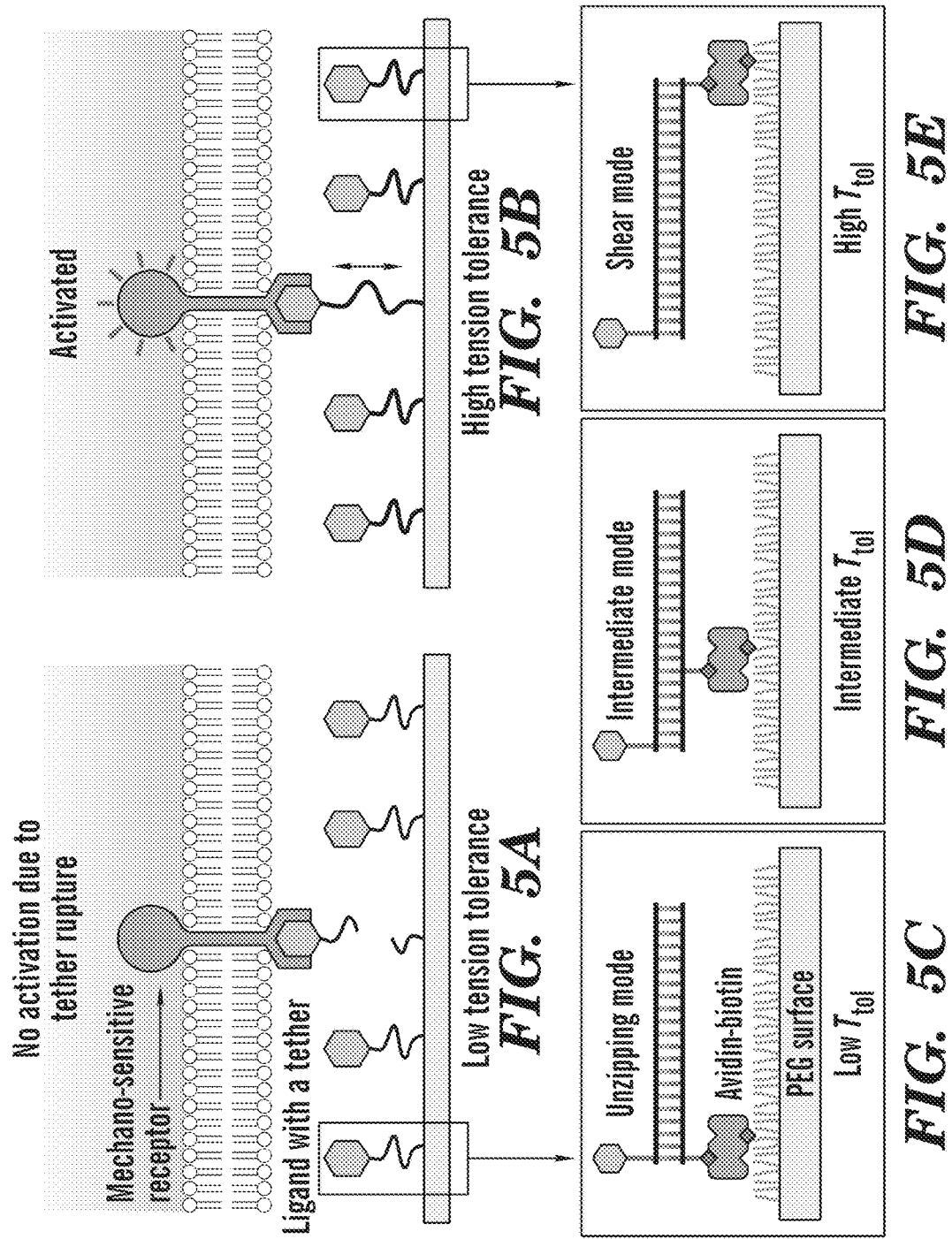

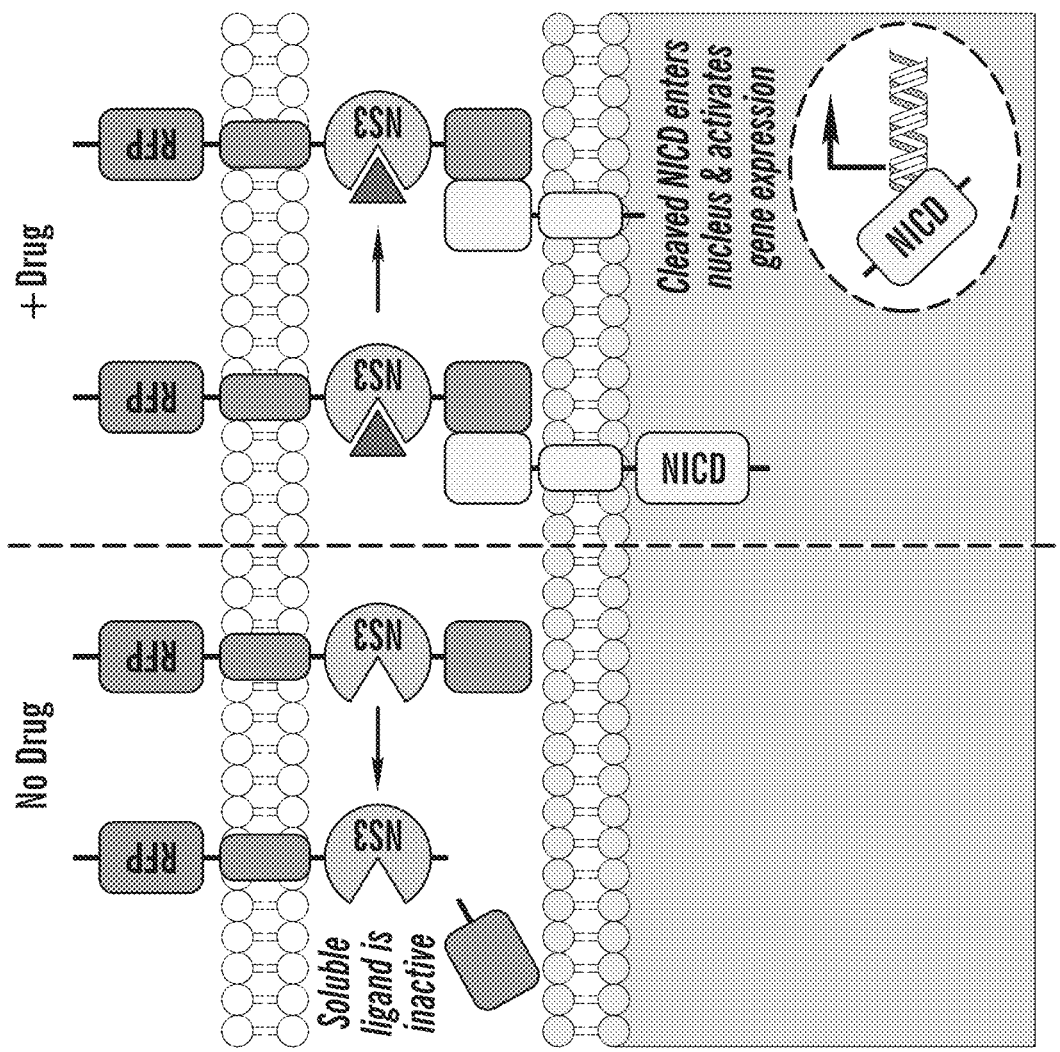

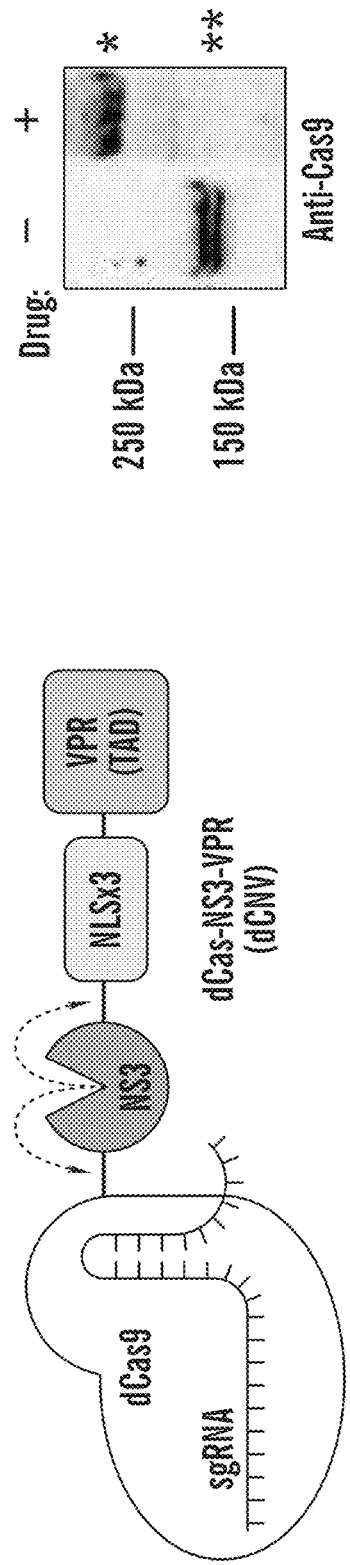
*FIG. 11A*
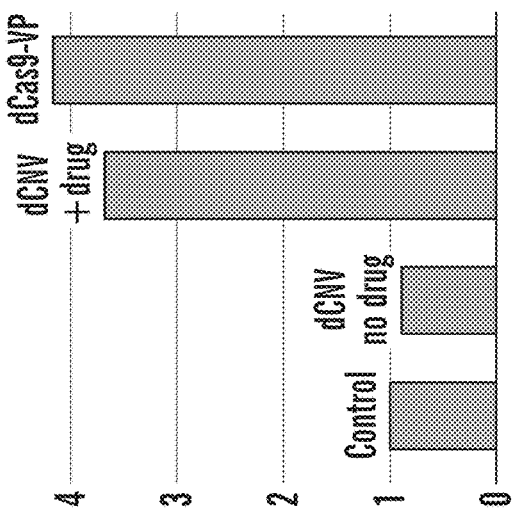
*FIG. 11B*
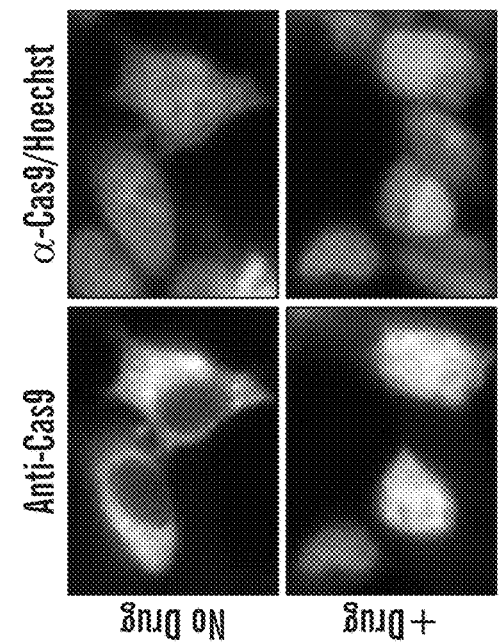
*FIG. 11C*
*FIG. 11D*

```
44.6% identity in 312 residues overlap; Score: 628.0; Gap frequency: 7.4%

NRR1-TM    15  PPPQIEEACELPECQVDAGNKVCNLQCNNHACGWDCGDCSLNPNDPMKNCTQSLQCWKYF
NRR2-TM     5  PPSTPPATCLSQYCADKARDGVCDEACNSHACQWDCGDXCSLTMENPMANCSSPLPCWDYI
                **  * ** * * ** ***  *** ** ****** ***** *   * ** ** ** *

NRR1-TM    75  SDGHCDSQCNSAGCLFDGFPDCQLTEGQCNPLYDQYCKDHFSDGHCDQCNSAECEWDGLD
NRR2-TM    65  NN-QCDELCNTVECLFDNFECQGNSKTCK--YDKYCADHFFRDNICDQGCNSEEGMDGLD
                    ** ** ** ***   *     **    ** ****    * ** *** *  ****

NRR1-TM   135  CAEHVPERLAAGTLVLVLVLLPPDQLRNNSFHFLRELSHVLHTNVVFKRDAQGQMIFPYY
NRR2-TM   122  CAADQPENLAEGTLVIVVLMPPEQLLQDARSFLRALGTLLHTNLRIKRDSQGELMVPYY
                **    * **  *** *   *  **   *   ** *  ***   ***** ** ** **

NRR1-TM   195  GHEEELRKHPIKRSTVGWATSSLLPGTSGGRQRRELDPMDIRGSIVYLEIDNRQCVQSSS
NRR2-TM   182  GEKSAAMKQRM-----TRRSLPGEQ------EQEVAGSKVFLEIDNRQCVQDSD
                *   *  *   *        * ***              *   ********  *

NRR1-TM   255  QCFQSATDVAAFLGALASLGSLNIPYKIEAVKSEPVEPPLPSQLHLMYVAAAAFVLLFFV
NRR2-TM   226  HCFKNTDAAALLASHAIQGTLSYP--LVSVVSESLTPERQLLYLL--AVAVVIILFII
                 **   * **   *  *    *    *           *  *     * *   * *

NRR1-TM   315  GCGVLLSRKRRR    SEQ ID NO: 46
NRR2-TM   282  LLGVIMAKRKRK    SEQ ID NO: 47
                  *    *  *
```

FIG. 13B

```
85.0% identity in 247 residues overlap; Score: 1060.0; Gap frequency: 1.2% scFv-NRR1    1 EVQLVESGGGLVQPGGSLRLSCAASGFTFSSYWINWVRQAPGKGLEWVARINPPNRSNQY
scFv-NRR2    1 EVQLVESGGGLVQPGGSLRLSCAASGYTFSSYGMSWVRQAPGKGLEWVSYIYPYSGATYY
                ****************************   **************    *   * scFv-NRR1   61 ADSVKGRFTISADTSKNTAYLQMNSLRAEDTAVYYCARGSGFRWV---MDYWGQGTLVTV
scFv-NRR2   61 ADSVKGRFTISADTSKNTAYLQMNSLRAEDTAVYYCARHSGYYRISSAMDVWGQGTLVTV
               *********************************   *     ******* scFv-NRR1  118 SSGGSSRSSSSGGGGSGGGGDIQMTQSPSSLSASVGDRVTITCRASQDVSTAVAWYQQKP
scFv-NRR2  121 SAGGSSRSSSSGGGGSGGGGDIQMTQSPSSLSASVGDRVTITCRASQNIKRFLAWYQQKP
                * *****************************************   *  ******** scFv-NRR1  178 GKAPKLLIYSASFLYSGVPSRFSGSGSGTDFTLTISSLQPEDFATYYCQQFYTTPSTFGQ
scFv-NRR2  181 GKAPKLLIYGASTRESGVPSRFSGSGSGTDFTLTISSLQPEDFATYYCQQYYRSPHTFGQ
               *******   *********************************** *   ***** scFv-NRR1  238 GTKVEIK   SEQ ID NO: 48
scFv-NRR2  241 GTKVEIK   SEQ ID NO: 49
               *******
```

FIG. 13C

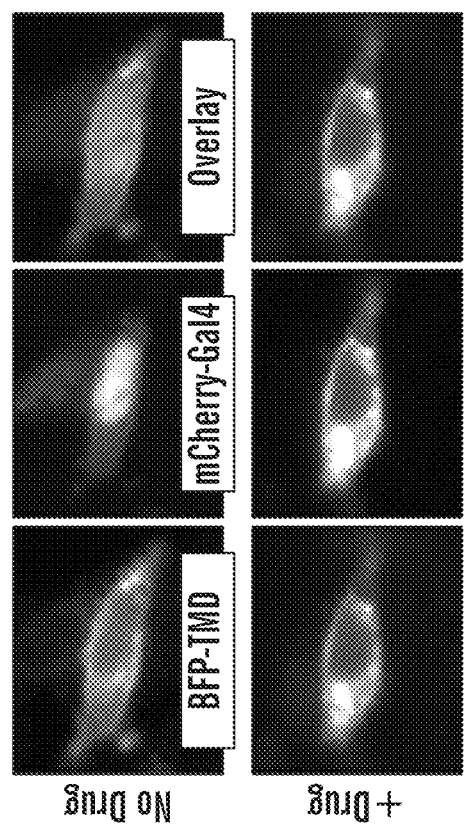
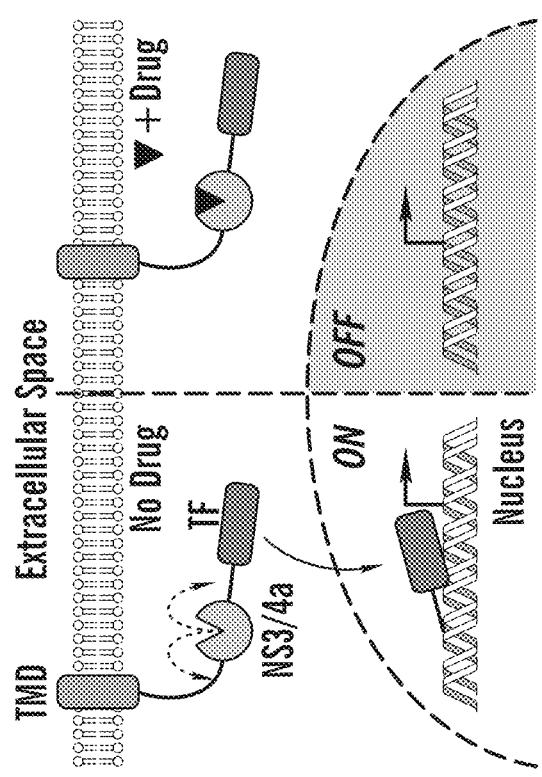
FIG. 15F
FIG. 15E

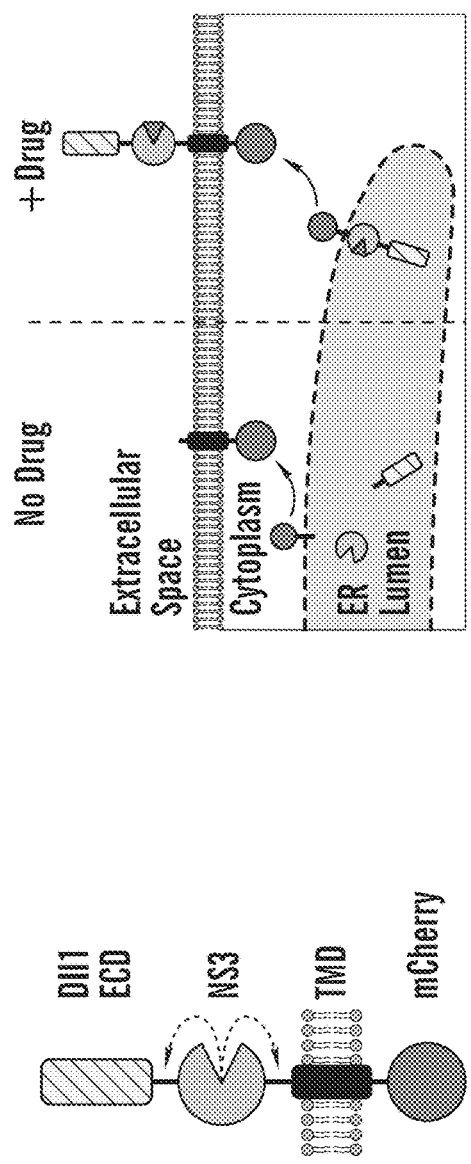
FIG. 17B
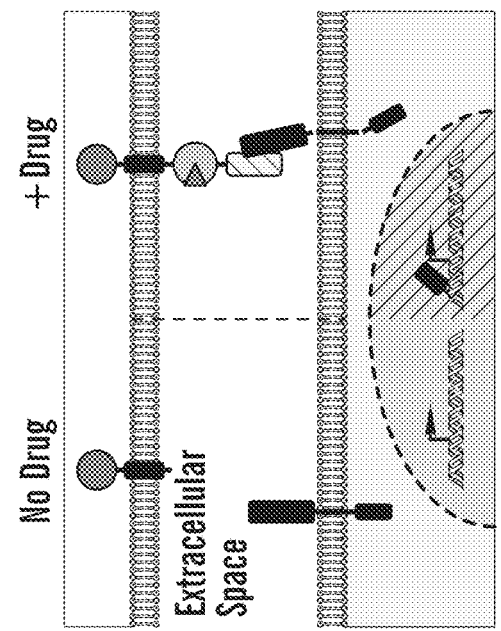
FIG. 17A
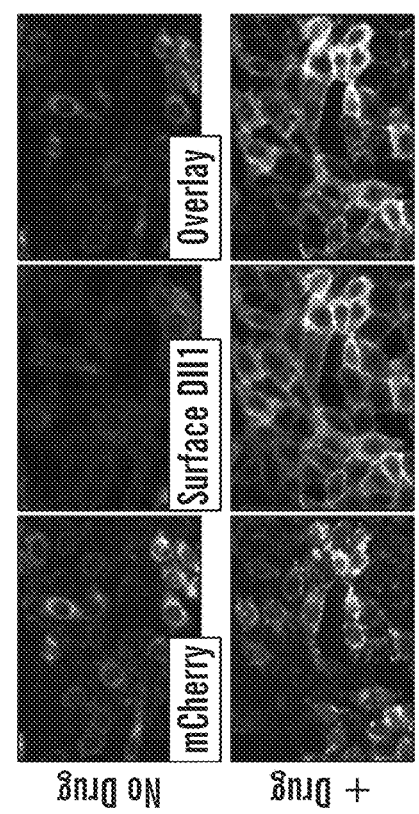
FIG. 17C
FIG. 17D

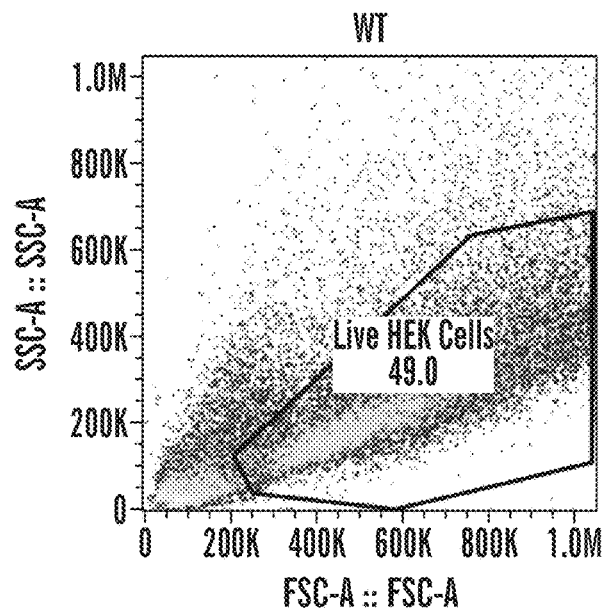
FIG. 26A
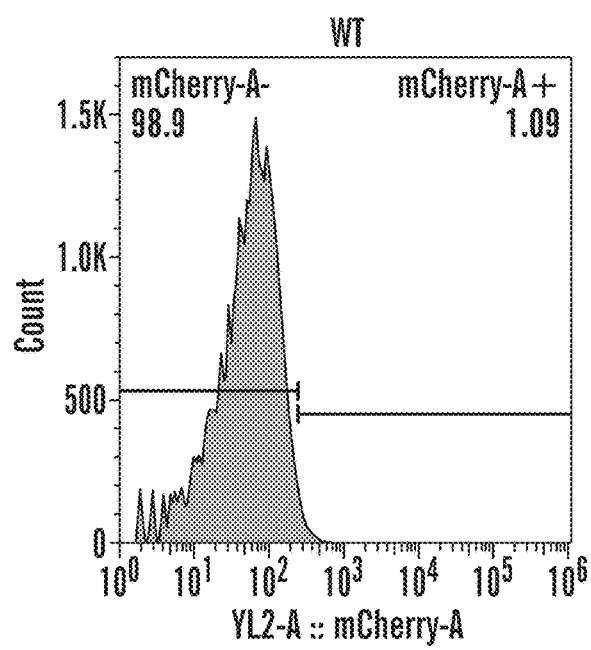    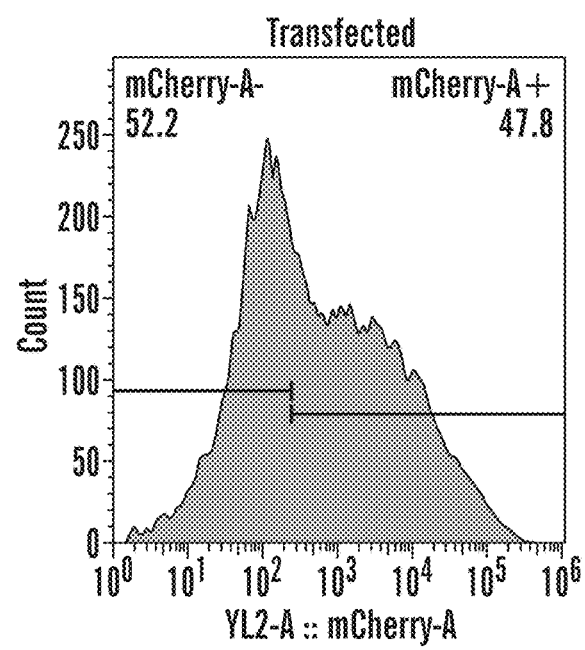
FIG. 26B    FIG. 26C

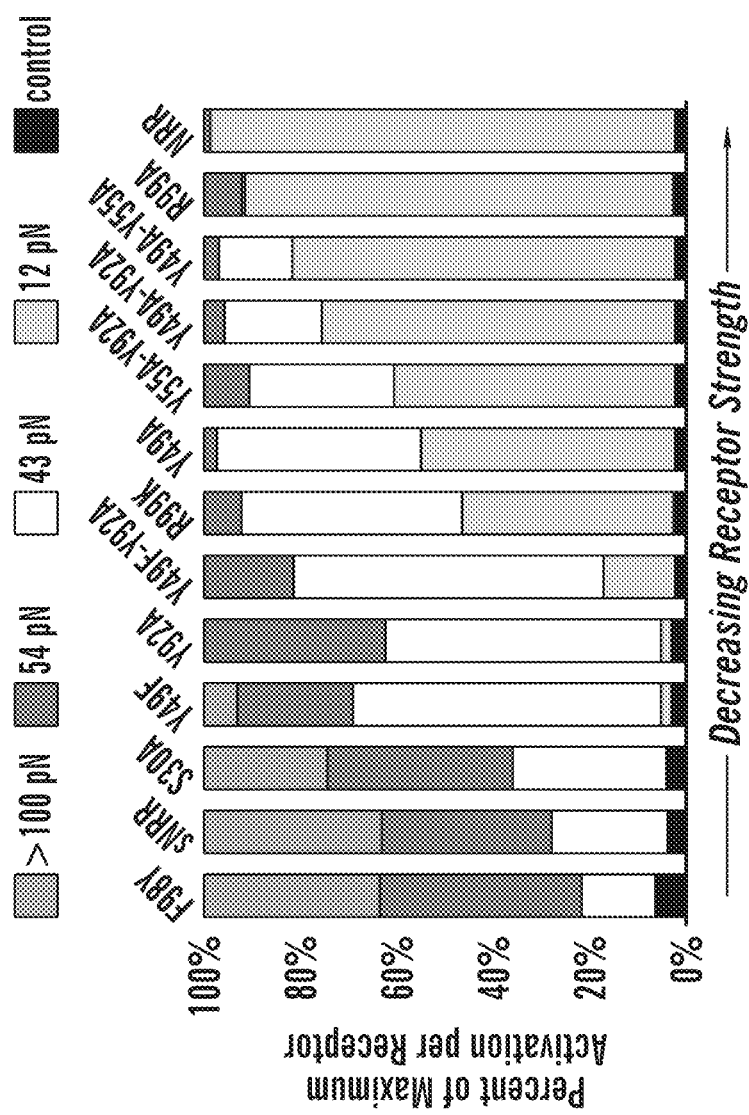
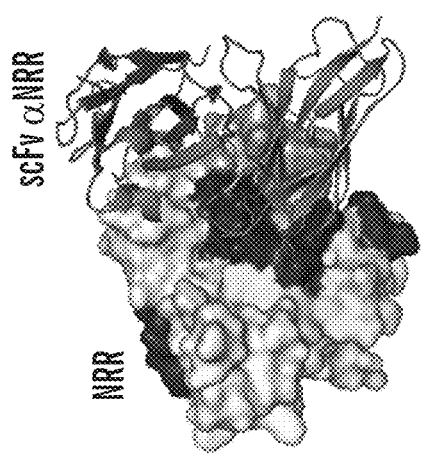
FIG. 34B
FIG. 34A

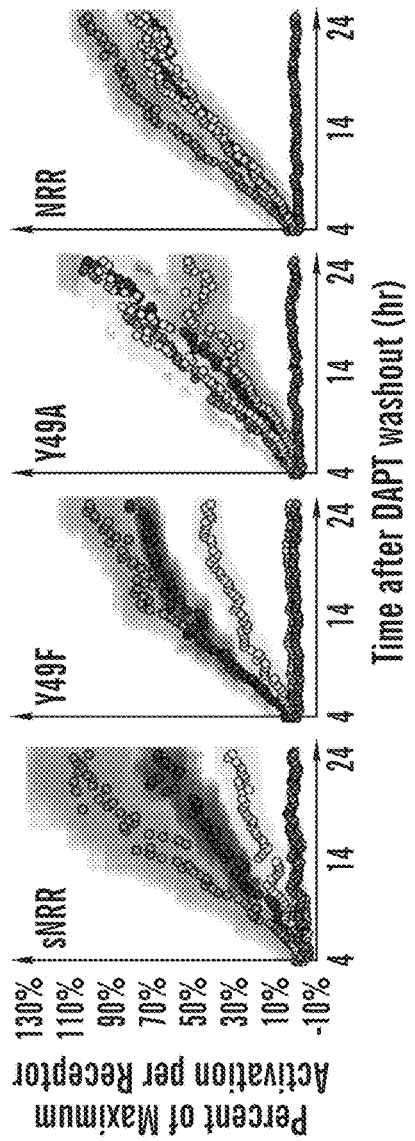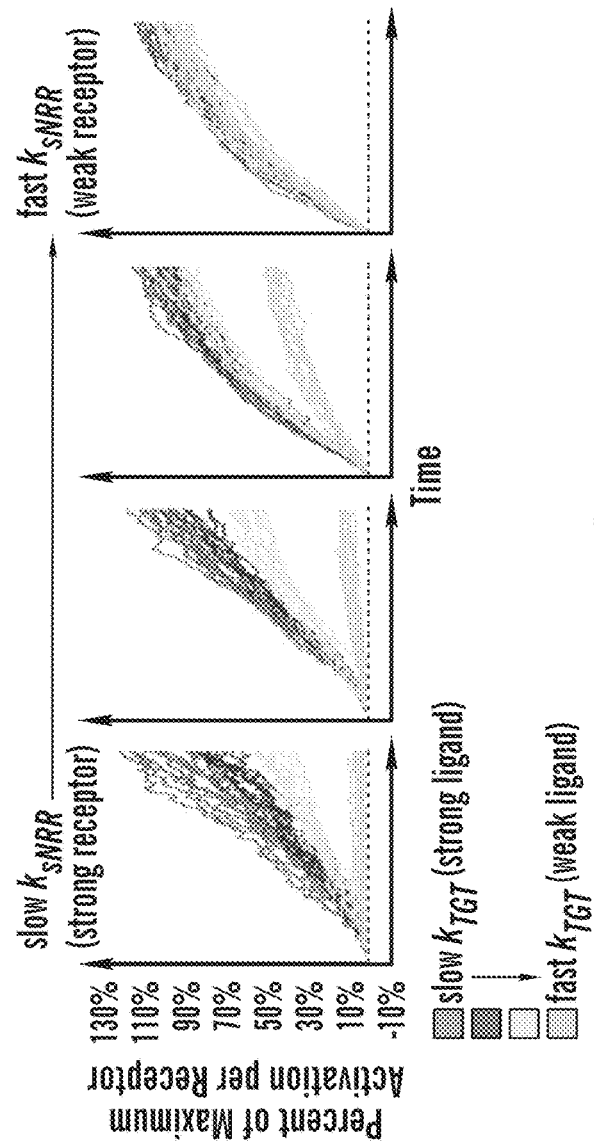
FIG. 34D
FIG. 34E

*ATGGAGACCGACACCCTGCTCCTGTGGGTGTTGTTGCTCTGGGTCCCAGGTTCTACCGGC*
*GACGGAGGAGGCGGC*GAAGTACAGCTGGTGGAGTCCGGCGGTGGCCTCGTGCAACCC
GGAGGGTCCTTGAGGCTGTCCTGTGCAGCCAGCGGTTTCACGTTCAGCAGCTACTGG
ATTCACTGGGTGAGGCAAGCTCCGGGCAAGGGCCTGGAGTGGGTTGCGAGGATAAA
CCCCCCCAACAGGTCCAACCAGTACGCCGATAGCGTGAAGGGTCGGTTCACCATCAG
CGCCGACACTAGCAAGAACACGGCCTACCTGCAGATGAACTCTCTGAGGGCCGAGG
ACACAGCGGTGTACTATTGCGCCAGGGGCTCAGGGTTTCGATGGGTCATGGATTACT
GGGGCCAAGGCACCCTGGTTACCGTTTCTAGCGGCGGATCTAGCAGGAGCTCATCAT
CCGGGGGTGGCGGGAGCGGAGGTGGTGGGGATATTCAGATGACGCAATCTCCGTCC
TCCCTCAGCGCAAGCGTGGGCGACAGGGTGACCATTACTTGTCGCGCCTCTCAGGAT
GTGAGCACTGCTGTGGCCTGGTATCAACAAAAACCCGGCAAAGCCCCCAAACTGCTG
ATCTACTCTGCCAGCTTTCTGTACTCAGGCGTGCCCAGCAGGTTTTCCGGCTCCGGCA
GCGGCACCGACTTCACCCTTACCATTAGCAGCCTGCAGCCCGAGGATTTTGCAACCT
ACTACTGCCAACAGTTCTACACCACTCCCAGCACTTTCGGCCAGGGCACGAAGGTTG
AGATCAAGGGGGGAGGAAGTGAGCAAAAGCTGATTTCCGAGGAGGACCTTGGAGGG
GGCTCCGCCGTGGGGCAAGACACCCAGGAGGTGATCGTGGTGCCTCATAGCCTCCCT
TTCAAAGTGGTGGTGATTTCAGCCATCCTGGCATTGGTTGTGCTGACCATCATAAGCT
TGATTATACTGATCATGCTTTGGCAGAAGAAGCCCAGGCGTACGATGGCCAGCATGA
CTGGTGGACAGCAAATGGGGTCGACG*GAGGACGTGGTGTGCTGCCACTCAATCTAC*G
GCAAGAAGAAGGGTGATATCGACACCTACCGATACATAGGCTCTTCCGGGACA*GGCT*
*GCGTGGTCATAGTGGGCAGGATCGTCTTGTCCGGA*TCCGGCACTAGT<ins>GCGCCCATCAC</ins>
<ins>GGCGTACGCCCAGCAGACGAGAGGCCTCCTAGGGTGTATAATCACCAGCCTGA</ins>
<ins>CTGGCCGGGACAAAAACCAAGTGGAGGGTGAGGTCCAGATCGTGTCAACTGCT</ins>
<ins>ACCCAAACCTTCCTGGCAACGTGCATCAATGGGGTATGCTGGGCAGTCTACCAC</ins>
<ins>GGGGCCGGAACGAGGACCATCGCATCACCCAAGGGTCCTGTCATCCAGATGTA</ins>
<ins>TACCAATGTGGACCAAGACCTTGTGGGCTGGCCCGCTCCTCAAGGTTCCCGCTC</ins>
<ins>ATTGACACCCTGTACCTGCGGCTCCTCGGACCTTTACCTGGTCACGAGGCACGC</ins>
<ins>CGATGTCATTCCCGTGCGCCGGCGAGGTGATAGCAGGGGTAGCCTGCTTTCGC</ins>
<ins>CCCGGCCCATTTCCTACTTGAAAGGCTCCTCGGGGGTCCGCTGTTGTGCCCCG</ins>
<ins>CGGGACACGCCGTGGGCCTATTCAGGGCCGCGGTGTGCACCCGTGGAGTGGCT</ins>
<ins>AAAGCGGTGGACTTTATCCCTGTGGAGAACCTAGAGACAACCATGAGATCCCCG</ins>
<ins>GTGTTCACGGACAACTCCTCT</ins>CCACCAGCAGTCACCCTGACGCACCCAATCACCAA
AATCGATAGGGAGGTT*CTCTACCAGGAGTTCGATGAGATGGAAGAGTGCTCTCAGCAC*
*TATCCCTACGATGTGCCCGATTACGCTGGCGCGTCTGCATGCGGTACC*ATGAAGTTG

FIGURE 37

CTGAGCAGCATAGAGCAAGCATGTGATATCTGCCGGTTGAAGAAGCTGAAGTG
TAGCAAGGAGAAGCCCAAGTGCGCCAAGTGTCTCAAGAATAATTGGGAGTGTA
GGTATAGCCCCAAGACCAAGCGAAGCCCGCTTACGAGAGCACACCTTACCGAG
GTCGAGAGCCGCCTGGAAAGACTCGAACAACTTTTTCTTCTGATTTTCCCCAGG
GAGGACCTGGACATGATCCTGAAGATGGACAGCCTCCAGGACATCAAAGCCCT
TCTTACCGGGCTGTTCGTGCAGGACAACGTCAACAAGGATGCGGTGACCGACA
GATTGGCGAGCGTGGAGACGGACATGCCCTTGACCCTCAGACAACATAGGATC
AGCGCGACAAGCTCATCTGAAGAATCTAGCAATAAGGGACAGCGACAGCTGAC
CGTTAGT<u>GCCAACTTTAATCAAAGTGGAAACATCGCGGACAGCTCACTCAGCTT</u>
<u>TACCTTCACCAATAGCAGTAACGGGCCGAACCTCATAACCACCCAGACCAACAG</u>
<u>CCAGGCCTTGAGCCAGCCGATCGCCTCATCTAACGTGCATGATAACTTTATGAA</u>
<u>CAACGAGATCACCGCGAGTAAGATAGACGACGGGAACAACAGCAAGCCCCTTA</u>
<u>GCCCAGGTTGGACGGACCAGACCGCCTACAACGCTTTCGGCATTACGACCGGC</u>
<u>ATGTTCAACACCACGACCATGGACGATGTGTACAACTACCTGTTCGATGACGAA</u>
<u>GACACACCGCCAAACCCCAAAAAGAA</u> (SEQ ID NO: 56)

FIGURE 37, continued...

*ATGGAGACAGATACCCTCCTCCTTTGGGTGCTCCTTCTCTGGGTGCCCGGGTCCACAGGA*
*GACGGGGGCGGAGGC*ATGGTTTCTAAAGGAGAGGAGCTCATAAAAGAAAACATG
CATATGAAGCTCTATATGGAAGGTACCGTAGACAACCACCATTTCAAATGCACC
TCCGAGGGGAGGGTAAGCCTTATGAAGGCACACAGACAATGCGGATTAAAGT
TGTCGAAGGGGACCACTCCCCTTTGCCTTCGACATACTGGCAACTTCTTTCCT
GTACGGCAGCAAAACATTCATCAATCACACTCAGGGGATACCAGATTTCTTCAA
GCAGAGCTTCCCCGAAGGCTTTACTTGGGAACGAGTAACTACCTACGAGGACG
GGGGGTCCTCACCGCCACCCAGGATACAAGTCTCCAGGACGGGTGCTTGATC
TACAATGTAAAGATAAGAGGGGTAAACTTTACATCAAACGGCCCCGTCATGCAA
AAGAAACCCTTGGTTGGGAGGCATTCACCGAGACACTGTACCCTGCAGACGG
AGGACTCGAAGGCCGCAACGATATGGCTCTTAAGCTCGTAGGCGGTAGCCACC
TTATCGCCAACGCTAAGACCACCTACCGAAGTAAAAGCCAGCCAAAAACCTGA
AAATGCCTGGTGTTTATTACGTAGACTACCGCCTCGAGCGCATCAAGGAGGCAA
ACAACGAAACCTATGTGGAGCAACACGAAGTCGCCGTGGCTCGCTATTGCGAC
CTGCCATCTAAGTTGGGTCACAAACTCAACGGTGGCGGGTCAGAGCAGAAACTTA
TCTCAGAGGAAGATCTGGGTGGAGGATCAGCTGTGGGGCAGGATACCCAAGAGGTC
ATAGTTGTACCACATAGTCTGCCATTCAAGGTCGTTGTTATAAGCGCTATCTTGGCCC
TCGTCGTCCTGACCATCATCAGCTTGATTATTCTCATAATGCTTTGGCAGAAGAAACC
CAGACGGACCATGGCCTCAATGACTGGAGGGCAGCAGATGGGGAGCACT*GAGGATG*
*TTGTATGTTGTCATAGCATTTAT*GGGAAAAAAAAGGCGACATCGACACCTATAGAT
ATATCGGAAGTAGTGGGACC*GGCTGCGTGGTGATCGTAGGGCGGATAGTGCTGTCTGG*
*CTCCGGCACTAGT*GCGCCCATCACGGCGTACGCCCAGCAGACGAGAGGCCTCCT
AGGGTGTATAATCACCAGCCTGACTGGCCGGGACAAAAACCAAGTGGAGGGTG
AGGTCCAGATCGTGTCAACTGCTACCCAAACCTTCCTGGCAACGTGCATCAATG
GGGTATGCTGGGCAGTCTACCACGGGGCCGGAACGAGGACCATCGCATCACCC
AAGGGTCCTGTCATCCAGATGTATACCAATGTGGACCAAGACCTTGTGGGCTGG
CCCGCTCCTCAAGGTTCCCGCTCATTGACACCCTGTACCTGCGGCTCCTCGGAC
CTTTACCTGGTCACGAGGCACGCCGATGTCATTCCCGTGCGCCGGCGAGGTGA
TAGCAGGGGTAGCCTGCTTTCGCCCCGGCCCATTTCCTACTTGAAAGGCTCCTC
GGGGGGTCCGCTGTTGTGCCCCGCGGGACACGCCGTGGGCCTATTCAGGGCCG
CGGTGTGCACCCGTGGAGTGGCTAAAGCGGTGGACTTTATCCCTGTGGAGAAC
CTAGAGACAACCATGAGATCCCCGGTGTTCACGGACAACTCCTCTCCACCAGCA
GTCACCCTGACGCACCCAATCACCAAAATCGATAGGGAGGTT*CTCTACCAGGAGTTC*
*GATGAGATGGAAGAGTGCTCTCAGCAC*TATCCCTACGATGTGCCCGATTACGCTGGCG

FIGURE 38

CGTCTGCATGCGGTACCATGAAGTTGCTGAGCAGCATAGAGCAAGCATGTGATAT
CTGCCGGTTGAAGAAGCTGAAGTGTAGCAAGGAGAAGCCCAAGTGCGCCAAGT
GTCTCAAGAATAATTGGGAGTGTAGGTATAGCCCCAAGACCAAGCGAAGCCCG
CTTACGAGAGCACACCTTACCGAGGTCGAGAGCCGCCTGGAAAGACTCGAACA
ACTTTTTCTTCTGATTTTCCCCAGGGAGGACCTGGACATGATCCTGAAGATGGA
CAGCCTCCAGGACATCAAAGCCCTTCTTACCGGGCTGTTCGTGCAGGACAACGT
CAACAAGGATGCGGTGACCGACAGATTGGCGAGCGTGGAGACGGACATGCCCT
TGACCCTCAGACAACATAGGATCAGCGCGACAAGCTCATCTGAAGAATCTAGCA
ATAAGGGACAGCGACAGCTGACCGTTAGT*ATGGTGAGCAAGGGCGAGGAGGATAAC*
*ATGGCCATCATCAAGGAGTTCATGCGCTTCAAGGTGCACATGGAGGGCTCCGTGAACGGC*
*CACGAGTTCGAGATCGAGGGCGAGGGCGAGGGCCGCCCCTACGAGGGCACCCAGACCG*
*CCAAGCTGAAGGTGACCAAGGGTGGCCCCCTGCCCTTCGCCTGGGACATCCTGTCCCCTC*
*AGTTCATGTACGGCTCCAAGGCCTACGTGAAGCACCCCGCCGACATCCCCGACTACTTGA*
*AGCTGTCCTTCCCCGAGGGCTTCAAGTGGGAGCGCGTGATGAACTTCGAGGACGGCGGC*
*GTGGTGACCGTGACCCAGGACTCCTCCCTGCAGGACGGCGAGTTCATCTACAAGGTGAAG*
*CTGCGCGGCACCAACTTCCCCTCCGACGGCCCCGTAATGCAGAAGAAGACCATGGGCTG*
*GGAGGCCTCCTCCGAGCGGATGTACCCCGAGGACGGCGCCCTGAAGGGCGAGATCAAGC*
*AGAGGCTGAAGCTGAAGGACGGCGGCCACTACGACGCTGAGGTCAAGACCACCTACAAG*
*GCCAAGAAGCCCGTGCAGCTGCCCGGCGCCTACAACGTCAACATCAAGTTGGACATCACC*
*TCCCACAACGAGGACTACACCATCGTGGAACAGTACGAACGCGCCGAGGGCCGCCACTC*
*CACCGGCGGCATGGACGAGCTGTACAAG*GCCAACTTTAATCAAAGTGGAAACATCG
CGGACAGCTCACTCAGCTTTACCTTCACCAATAGCAGTAACGGGCCGAACCTCA
TAACCACCCAGACCAACAGCCAGGCCTTGAGCCAGCCGATCGCCTCATCTAACG
TGCATGATAACTTTATGAACAACGAGATCACCGCGAGTAAGATAGACGACGGGA
ACAACAGCAAGCCCCTTAGCCCAGGTTGGACGGACCAGACCGCCTACAACGCT
TTCGGCATTACGACCGGCATGTTCAACACCACGACCATGGACGATGTGTACAAC
TACCTGTTCGATGACGAAGACACACCGCCAAACCCCAAAAAAGAA (SEQ ID NO: 57)

FIGURE 38, continued...

*ATGGAGACCGACACCCTGCTCCTGTGGGTGTTGTTGCTCTGGGTCCCAGGTTCTACCGGC*
*GACGGAGGAGGCGGC*GAAGTACAGCTGGTGGAGTCCGGCGGTGGCCTCGTGCAA
CCCGGAGGGTCCTTGAGGCTGTCCTGTGCAGCCAGCGGTTTCACGTTCAGCAG
CTACTGGATTCACTGGGTGAGGCAAGCTCCGGGCAAGGGCCTGGAGTGGGTTG
CGAGGATAAACCCCCCAACAGGTCCAACCAGTACGCCGATAGCGTGAAGGGT
CGGTTCACCATCAGCGCCGACACTAGCAAGAACACGGCCTACCTGCAGATGAA
CTCTCTGAGGGCCGAGGACACAGCGGTGTACTATTGCGCCAGGGGCTCAGGGT
TTCGATGGGTCATGGATTACTGGGGCCAAGGCACCCTGGTTACCGTTTCTAGCG
GCGGATCTAGCAGGAGCTCATCATCCGGGGGTGGCGGGAGCGGAGGTGGTGG
GGATATTCAGATGACGCAATCTCCGTCCTCCCTCAGCGCAAGCGTGGGCGACA
GGGTGACCATTACTTGTCGCGCCTCTCAGGATGTGAGCACTGCTGTGGCCTGGT
ATCAACAAAAACCCGGCAAAGCCCCCAAACTGCTGATCTACTCTGCCAGCTTTC
TGTACTCAGGCGTGCCCAGCAGGTTTTCCGGCTCCGGCAGCGGCACCGACTTC
ACCCTTACCATTAGCAGCCTGCAGCCCGAGGATTTTGCAACCTACTACTGCCAA
CAGTTCTACACCACTCCCAGCACTTTCGGCCAGGGCACGAAGGTTGAGATCAAG
GGGGGAGGAAGTGAGCAAAAGCTGATTTCCGAGGAGGACCTTGGAGGGGCTCCGC
CGTGGGGCAAGACACCCAGGAGGTGATCGTGGTGCCTCATAGCCTCCCTTTCAAAGT
GGTGGTGATTTCAGCCATCCTGGCATTGGTTGTGCTGACCATCATAAGCTTGATTATA
CTGATCATGCTTTGGCAGAAGAAGCCCAGGCGTACGATGGCCAGCATGACTGGTGGA
CAGCAAATGGGGTCGACG*GAGGACGTGGTGTGCTGCCACTCAATCTAC*GGCAAGAAG
AAGGGTGATATCGACACCTACCGATACATAGGCTCTTCCGGGACA*GGCTGCGTGGTC*
*ATAGTGGGCAGGATCGTCTTGTCCGGA*TCCGGCACTAGTGCGCCCATCACGGCGTAC
GCCCAGCAGACGAGAGGCCTCCTAGGGTGTATAATCACCAGCCTGACTGGCCG
GGACAAAAACCAAGTGGAGGGTGAGGTCCAGATCGTGTCAACTGCTACCCAAA
CCTTCCTGGCAACGTGCATCAATGGGGTATGCTGGGCAGTCTACCACGGGGCC
GGAACGAGGACCATCGCATCACCCAAGGGTCCTGTCATCCAGATGTATACCAAT
GTGGACCAAGACCTTGTGGGCTGGCCCGCTCCTCAAGGTTCCCGCTCATTGACA
CCCTGTACCTGCGGCTCCTCGGACCTTTACCTGGTCACGAGGCACGCCGATGTC
ATTCCCGTGCGCCGGCGAGGTGATAGCAGGGGTAGCCTGCTTTCGCCCCGGCC
CATTTCCTACTTGAAAGGCTCCTCGGGGGTCCGCTGTTGTCCCCGCGGGACA
CGCCGTGGGCCTATTCAGGGCCGCGGTGTGCACCCGTGGAGTGGCTAAAGCGG
TGGACTTTATCCCTGTGGAGAACCTAGAGACAACCATGAGATCCCCGGTGTTCA
CGGACAACTCCTCTCCACCAGCAGTCACCCTGACGCACCCAATCACCAAAATCGAT
AGGGAGGTT*CTCTACCAGGAGTTCGATGAGATGGAAGAGTGCTCTCAGCAC*TATCCCT

FIGURE 39

ACGATGTGCCCGATTACGCTGGCGCGTCTGCATGCGGTACCATGAAGTTGCTGAGC
AGCATAGAGCAAGCATGTGATATCTGCCGGTTGAAGAAGCTGAAGTGTAGCAA
GGAGAAGCCCAAGTGCGCCAAGTGTCTCAAGAATAATTGGGAGTGTAGGTATA
GCCCCAAGACCAAGCGAAGCCCGCTTACGAGAGCACACCTTACCGAGGTCGAG
AGCCGCCTGGAAAGACTCGAACAACTTTTTCTTCTGATTTTCCCCAGGGAGGAC
CTGGACATGATCCTGAAGATGGACAGCCTCCAGGACATCAAAGCCCTTCTTACC
GGGCTGTTCGTGCAGGACAACGTCAACAAGGATGCGGTGACCGACAGATTGGC
GAGCGTGGAGACGGACATGCCCTTGACCCTCAGACAACATAGGATCAGCGCGA
CAAGCTCATCTGAAGAATCTAGCAATAAGGGACAGCGACAGCTGACCGTTAGTG
ACGCATTGGACGATTTTGATCTGGATATGCTGGGAAGTGACGCCCTCGATGATT
TTGACCTTGACATGCTTGGTTCGGATGCCCTTGATGACTTTGACCTCGACATGC
TCGGCAGTGACGCCCTTGATGATTTCGACCTGGACATGCTG (SEQ ID NO: 59)

FIGURE 39, continued...

ATGGACAAGAAGTACTCCATTGGGCTCGCTATCGGCACAAACAGCGTCGGCTGGGCCG
TCATTACGGACGAGTACAAGGTGCCGAGCAAAAAATTCAAAGTTCTGGGCAATACCGA
TCGCCACAGCATAAAGAAGAACCTCATTGGCGCCCTCCTGTTCGACTCCGGGGAGACG
GCCGAAGCCACGCGGCTCAAAAGAACAGCACGGCGCAGATATACCCGCAGAAAGAAT
CGGATCTGCTACCTGCAGGAGATCTTTAGTAATGAGATGGCTAAGGTGGATGACTCTT
TCTTCCATAGGCTGGAGGAGTCCTTTTTGGTGGAGGAGGATAAAAAGCACGAGCGCCA
CCCAATCTTTGGCAATATCGTGGACGAGGTGGCGTACCATGAAAGTACCCAACCATA
TATCATCTGAGGAAGAAGCTTGTAGACAGTACTGATAAGGCTGACTTGCGGTTGATCT
ATCTCGCGCTGGCGCATATGATCAAATTTCGGGGACACTTCCTCATCGAGGGGACCT
GAACCCAGACAACAGCGATGTCGACAAACTCTTTATCCAACTGGTTCAGACTTACAATC
AGCTTTTCGAAGAGAACCCGATCAACGCATCCGGAGTTGACGCCAAAGCAATCCTGAG
CGCTAGGCTGTCCAAATCCCGGCGGCTCGAAAACCTCATCGCACAGCTCCCTGGGGAG
AAGAAGAACGGCCTGTTTGGTAATCTTATCGCCCTGTCACTCGGGCTGACCCCCAACTT
TAAATCTAACTTCGACCTGGCCGAAGATGCCAAGCTTCAACTGAGCAAAGACACCTAC
GATGATGATCTCGACAATCTGCTGGCCCAGATCGGCGACCAGTACGCAGACCTTTTTT
GGCGGCAAAGAACCTGTCAGACGCCATTCTGCTGAGTGATATTCTGCGAGTGAACACG
GAGATCACCAAAGCTCCGCTGAGCGCTAGTATGATCAAGCGCTATGATGAGCACCACC
AAGACTTGACTTTGCTGAAGGCCCTTGTCAGACAGCAACTGCCTGAGAAGTACAAGGA
AATTTTCTTCGATCAGTCTAAAAATGGCTACGCCGGATACATTGACGGCGGAGCAAGC
CAGGAGGAATTTTACAAATTTATTAAGCCCATCTTGGAAAAAATGGACGGCACCGAGG
AGCTGCTGGTAAAGCTTAACAGAGAAGATCTGTTGCGCAAACAGCGCACTTTCGACAA
TGGAAGCATCCCCCACCAGATTCACCTGGGCGAACTGCACGCTATCCTCAGGCGGCAA
GAGGATTTCTACCCCTTTTTGAAAGATAACAGGGAAAGATTGAGAAAATCCTCACATT
TCGGATACCCTACTATGTAGGCCCCCTCGCCCGGGGAAATTCCAGATTCGCGTGGATG
ACTCGCAAATCAGAAGAGACCATCACTCCCTGGAACTTCGAGGAAGTCGTGGATAAGG
GGGCCTCTGCCCAGTCCTTCATCGAAAGGATGACTAACTTTGATAAAAATCTGCCTAAC
GAAAAGGTGCTTCCTAAACACTCTCTGCTGTACGAGTACTTCACAGTTTATAACGAGCT
CACCAAGGTCAAATACGTCACAGAAGGGATGAGAAAGCCAGCATTCCTGTCTGGAGAG
CAGAAGAAAGCTATCGTGGACCTCCTCTTCAAGACGAACCGGAAAGTTACCGTGAAAC
AGCTCAAAGAAGACTATTTCAAAAAGATTGAATGTTTCGACTCTGTTGAAATCAGCGGA
GTGGAGGATCGCTTCAACGCATCCCTGGGAACGTATCACGATCTCCTGAAAATCATTA
AAGACAAGGACTTCCTGGACAATGAGGAGAACGAGGACATTCTTGAGGACATTGTCCT
CACCCTTACGTTGTTTGAAGATAGGGAGATGATTGAAGAACGCTTGAAAACTTACGCTC
ATCTCTTCGACGACAAAGTCATGAAACAGCTCAAGAGGCGCCGATATACAGGATGGGG

FIGURE 40

GCGGCTGTCAAGAAAACTGATCAATGGGATCCGAGACAAGCAGAGTGGAAAGACAATC
CTGGATTTTCTTAAGTCCGATGGATTTGCCAACCGGAACTTCATGCAGTTGATCCATGA
TGACTCTCTCACCTTTAAGGAGGACATCCAGAAAGCACAAGTTTCTGGCCAGGGGAC
AGTCTTCACGAGCACATCGCTAATCTTGCAGGTAGCCCAGCTATCAAAAGGGAATAC
TGCAGACCGTTAAGGTCGTGGATGAACTCGTCAAAGTAATGGGAAGGCATAAGCCCGA
GAATATCGTTATCGAGATGGCCCGAGAGAACCAAACTACCCAGAAGGGACAGAAGAAC
AGTAGGGAAAGGATGAAGAGGATTGAAGAGGGTATAAAAGAACTGGGGTCCCAAATC
CTTAAGGAACACCCAGTTGAAAACACCCAGCTTCAGAATGAGAAGCTCTACCTGTACTA
CCTGCAGAACGGCAGGGACATGTACGTGGATCAGGAACTGGACATCAATCGGCTCTCC
GACTACGACGTGGCTGCTATCGTGCCCCAGTCTTTTCTCAAAGATGATTCTATTGATAA
TAAAGTGTTGACAAGATCCGATAAAgcTAGAGGGAAGAGTGATAACGTCCCCTCAGAAG
AAGTTGTCAAGAAAATGAAAAATTATTGGCGGCAGCTGCTGAACGCCAAACTGATCAC
ACAACGGAAGTTCGATAATCTGACTAAGGCTGAACGAGGTGGCCTGTCTGAGTTGGAT
AAAGCCGGCTTCATCAAAGGCAGCTTGTTGAGACACGCCAGATCACCAAGCACGTGG
CCCAAATTCTCGATTCACGCATGAACACCAAGTACGATGAAAATGACAAACTGATTCGA
GAGGTGAAAGTTATTACTCTGAAGTCTAAGCTGGTCTCAGATTTCAGAAAGGACTTTCA
GTTTTATAAGGTGAGAGAGATCAACAATTACCACCATGCGCATGATGCCTACCTGAATG
CAGTGGTAGGCACTGCACTTATCAAAAAATATCCCAAGCTTGAATCTGAATTTGTTTAC
GGAGACTATAAAGTGTACGATGTTAGGAAAATGATCGCAAAGTCTGAGCAGGAAATAG
GCAAGGCCACCGCTAAGTACTTCTTTTACAGCAATATTATGAATTTTTTCAAGACCGAG
ATTACACTGGCCAATGGAGAGATTCGGAAGCGACCACTTATCGAAACAAACGGAGAAA
CAGGAGAAATCGTGTGGGACAAGGGTAGGGATTTCGCGACAGTCCGGAAGGTCCTGT
CCATGCCGCAGGTGAACATCGTTAAAAGACCGAAGTACAGACCGGAGGCTTCTCCAA
GGAAAGTATCCTCCCGAAAAGGAACAGCGACAAGCTGATCGCACGCAAAAAGATTGG
GACCCCAAGAAATACGGCGGATTCGATTCTCCTACAGTCGCTTACAGTGTACTGGTTGT
GGCCAAAGTGGAGAAAGGGAAGTCTAAAAAACTCAAAAGCGTCAAGGAACTGCTGGG
CATCACAATCATGGAGCGATCAAGCTTCGAAAAAACCCCATCGACTTTCTCGAGGCG
AAAGGATATAAAGAGGTCAAAAAGACCTCATCATTAAGCTTCCCAAGTACTCTCTCTT
TGAGCTTGAAAACGGCCGGAAACGAATGCTCGCTAGTGCGGGCGAGCTGCAGAAAGG
TAACGAGCTGGCACTGCCCTCTAAATACGTTAATTTCTTGTATCTGGCCAGCCACTATG
AAAAGCTCAAAGGGTCTCCCGAAGATAATGAGCAGAAGCAGCTGTTCGTGGAACAACA
CAAACACTACCTTGATGAGATCATCGAGCAAATAAGCGAATTCTCCAAAAGAGTGATCC
TCGCCGACGCTAACCTCGATAAGGTGCTTTCTGCTTACAATAAGCACAGGGATAAGCC
CATCAGGGAGCAGGCAGAAAACATTATCCACTTGTTTACTCTGACCAACTTGGGCGCG

FIGURE 40, continued...

*CCTGCAGCCTTCAAGTACTTCGACACCACCATAGACAGAAAGCGGTACACCTCTACAA*
*AGGAGGTCCTGGACGCCACACTGATTCATCAGTCAATTACGGGGCTCTATGAAACAAG*
*AATCGACCTCTCTCAGCTCGGTGGAGAC*
AGCAGGGCTGACATGGCCAGCATGACTGGTGGACAGCAAATGGGGTCGACG*GAGGA*
*CGTGGTGTGCTGCCACTCAATCTAC*GGCAAGAAGAAGGGTGATATCGACACCTACCG
ATACATAGGCTCTTCCGGGACA*GGCTGCGTGGTCATAGTGGGCAGGATCGTCTTGTCCG*
*G*ATCCGGCACTAGTG<u>CGCCCATCACGGCGTACGCCCAGCAGACGAGAGGCCTCC</u>
<u>TAGGGTGTATAATCACCAGCCTGACTGGCCGGGACAAAAACCAAGTGGAGGGT</u>
<u>GAGGTCCAGATCGTGTCAACTGCTACCCAAACCTTCCTGGCAACGTGCATCAAT</u>
<u>GGGGTATGCTGGGCAGTCTACCACGGGGCCGGAACGAGGACCATCGCATCACC</u>
<u>CAAGGGTCCTGTCATCCAGATGTATACCAATGTGGACCAAGACCTTGTGGGCTG</u>
<u>GCCCGCTCCTCAAGGTTCCCGCTCATTGACACCCTGTACCTGCGGCTCCTCGGA</u>
<u>CCTTTACCTGGTCACGAGGCACGCCGATGTCATTCCCGTGCGCCGGCGAGGTG</u>
<u>ATAGCAGGGGTAGCCTGCTTTCGCCCCGGCCCATTTCCTACTTGAAAGGCTCCT</u>
<u>CGGGGGGTCCGCTGTTGTGCCCCGCGGGACACGCCGTGGGCCTATTCAGGGCC</u>
<u>GCGGTGTGCACCCGTGGAGTGGCTAAAGCGGTGGACTTTATCCCTGTGGAGAA</u>
<u>CCTAGAGACAACCATGAGATCCCCGGTGTTCACGGACAACTCCTCT</u>CCACCAGC
AGTCACCCTGACGCACCCAATCACCAAAATCGATAGGGAGGTT*CTCTACCAGGAGTT*
*CGATGAGATGGAAGAGTGCTCTCAGCAC*TATCCCTACGATGTGCCCGATTACGCTGGC
GCGTCTGCATGCCCCAAGAAGAAGAGGAAGGTGTCGCCAGGGATCCGTCGACTTG
ACGCGTTGATATCAACAAGTTTGTACAAAAAAGCAGGCTACAAAGAGGCCAGCGGT
TCCGGACGGGCT<u>GACGCATTGGACGATTTTGATCTGGATATGCTGGGAAGTGACGCC</u>
<u>CTCGATGATTTTGACCTTGACATGCTTGGTTCGGATGCCCTTGATGACTTTGACCTCG</u>
<u>ACATGCTCGGCAGTGACGCCCTTGATGATTTCGACCTGGACATGCTG</u>ATTAACTCTA
GAAGTTCCGGATCTCCGAAAAAGAAACGCAAAGTTGGTAGC*CAGTACCTGCCCGAC*
*ACCGACGACCGGCACCGGATCGAGGAAAAGCGGAAGCGGACCTACGAGACATTCAAGAG*
*CATCATGAAGAAGTCCCCCTTCAGCGGCCCCACCGACCCTAGACCTCCACCTAGAAGAAT*
*CGCCGTGCCCAGCAGATCCAGCGCCAGCGTGCCAAAACCTGCCCCCAGCCTTACCCCTT*
*CACCAGCAGCCTGAGCACCATCAACTACGACGAGTTCCCTACCATGGTGTTCCCCAGCGG*
*CCAGATCTCTCAGGCCTCTGCTCTGGCTCCAGCCCCTCCTCAGGTGCTGCCTCAGGCTCC*
*TGCTCCTGCACCAGCTCCAGCCATGGTGTCTGCACTGGCTCAGGCACCAGCACCCGTGCC*
*TGTGCTGGCTCCTGGACCTCCACAGGCTGTGGCTCCACCAGCCCCTAAACCTACACAGGC*
*CGGCGAGGGCACACTGTCTGAAGCTCTGCTGCAGCTGCAGTTCGACGACGAGGATCTGG*
*GAGCCCTGCTGGGAAACAGCACCGATCCTGCCGTGTTCACCGACCTGGCCAGCGTGGAC*

FIGURE 40, continued...

*AACAGCGAGTTCCAGCAGCTGCTGAACCAGGGCATCCCTGTGGCCCCTCACACCACCGAG CCCATGCTGATGGAATACCCCGAGGCCATCACCCGGCTCGTGACAGGCGCTCAGAGGCC TCCTGATCCAGCTCCTGCCCCTCTGGGAGCACCAGGCCTGCCTAATGGACTGCTGTCTGG CGACGAGGACTTCAGCTCTATCGCCGATATGGATTTCTCAGCCTTGCT*GGCTCTGGCAG CGGCAGCCGGGATTCCAGGGAAGGGATGTTTTGCCGAAGCCTGAGGCCGGCT CCGCTATTAGTGACGTGTTTGAGGGCCGCGAGGTGTGCCAGCCAAAACGAATC CGGCCATTTCATCCTCCAGGAAGTCCATGGGCCAACCGCCCACTCCCCGCCAGC CTCGCACCAACACCAACCGGTCCAGTACATGAGCCAGTCGGGTCACTGACCCC GGCACCAGTCCCTCAGCCACTGGATCCAGCGCCCGCAGTGACTCCCGAGGCCA GTCACCTGTTGGAGGATCCCGATGAAGAGACGAGCCAGGCTGTCAAAGCCCTT CGGGAGATGGCCGATACTGTGATTCCCCAGAAGGAAGAGGCTGCAATCTGTGG CCAAATGGACCTTTCCCATCCGCCCCAAGGGGCCATCTGGATGAGCTGACAAC CACACTTGAGTCCATGACCGAGGATCTGAACCTGGACTCACCCCTGACCCCGGA ATTGAACGAGATTCTGGATACCTTCCTGAACGACGAGTGCCTCTTGCATGCCAT GCATATCAGCACAGGACTGTCCATCTTCGACACATCTCTGTTTtga (SEQ ID NO: 60)

FIGURE 40, continued...

atggacaaagactgcgaaatgaagcgcaccaccctggatagccctctgggcaagctggaactgtctgggtgcgaacagggcctgcaccgt
atcatcttcctgggcaaaggaacatctgccgccgacgccgtggaagtgcctgccccagccgccgtgctgggcggaccagagccactgatg
caggccaccgcctggctcaacgcctactttcaccagcctgaggccatcgaggagttccctgtgccagccctgcaccacccagtgttccagc
aggagagctttacccgccaggtgctgtggaaactgctgaaagtggtgaagttcggagaggtcatcagctacagccacctggccgccctggc
cggcaatcccgccgccaccgccgccgtgaaaaccgccctgagcggaaatcccgtgcccattctgatccctgccaccgggtggtgcagg
gcgacctggacgtgggggctacgagggcgggctcgccgtgaaagagtggctgctggcccacgagggccacagactgggcaagcctg
ggctgggtcctgcaggcg*AC*gccacc*ATGGACAAGAAGTACTCCATTGGGCTCGCTATCGGCACAA*
*ACAGCGTCGGCTGGGCCGTCATTACGGACGAGTACAAGGTGCCGAGCAAAAAATTCAA*
*AGTTCTGGGCAATACCGATCGCCACAGCATAAAGAAGAACCTCATTGGCGCCCTCCTG*
*TTCGACTCCGGGGAGACGGCCGAAGCCACGCGGCTCAAAAGAACAGCACGGCGCAGA*
*TATACCCGCAGAAAGAATCGGATCTGCTACCTGCAGGAGATCTTTAGTAATGAGATGG*
*CTAAGGTGGATGACTCTTTCTTCCATAGGCTGGAGGAGTCCTTTTTGGTGGAGGAGGA*
*TAAAAAGCACGAGCGCCACCCAATCTTTGGCAATATCGTGGACGAGGTGGCGTACCAT*
*GAAAAGTACCCAACCATATATCATCTGAGGAAGAAGCTTGTAGACAGTACTGATAAGG*
*CTGACTTGCGGTTGATCTATCTCGCGCTGGCGCATATGATCAAATTTCGGGGACACTTC*
*CTCATCGAGGGGGACCTGAACCCAGACAACAGCGATGTCGACAAACTCTTTATCCAAC*
*TGGTTCAGACTTACAATCAGCTTTTCGAAGAGAACCCGATCAACGCATCCGGAGTTGA*
*CGCCAAAGCAATCCTGAGCGCTAGGCTGTCCAAATCCCGGCGGCTCGAAAACCTCATC*
*GCACAGCTCCCTGGGGAGAAGAAGAACGGCCTGTTTGGTAATCTTATCGCCCTGTCAC*
*TCGGGCTGACCCCCAACTTTAAATCTAACTTCGACCTGGCCGAAGATGCCAAGCTTCAA*
*CTGAGCAAAGACACCTACGATGATGATCTCGACAATCTGCTGGCCCAGATCGGCGACC*
*AGTACGCAGACCTTTTTTTGGCGGCAAAGAACCTGTCAGACGCCATTCTGCTGAGTGA*
*TATTCTGCGAGTGAACACGGAGATCACCAAAGCTCCGCTGAGCGCTAGTATGATCAAG*
*CGCTATGATGAGCACCACCAAGACTTGACTTTGCTGAAGGCCCTTGTCAGACAGCAAC*
*TGCCTGAGAAGTACAAGGAAATTTTCTTCGATCAGTCTAAAAATGGCTACGCCGGATAC*
*ATTGACGGCGGAGCAAGCCAGGAGGAATTTTACAAATTTATTAAGCCCATCTTGGAAA*
*AAATGGACGGCACCGAGGAGCTGCTGGTAAAGCTTAACAGAGAAGATCTGTTGCGCAA*
*ACAGCGCACTTTCGACAATGGAAGCATCCCCCACCAGATTCACCTGGGCGAACTGCAC*
*GCTATCCTCAGGCGGCAAGAGGATTTCTACCCCTTTTTGAAAGATAACAGGGAAAAGA*
*TTGAGAAAATCCTCACATTTCGGATACCCTACTATGTAGGCCCCCTCGCCCGGGGAAAT*
*TCCAGATTCGCGTGGATGACTCGCAAATCAGAAGAGACCATCACTCCCTGGAACTTCG*
*AGGAAGTCGTGGATAAGGGGGCCTCTGCCCAGTCCTTCATCGAAGGATGACTAACTT*
*TGATAAAAATCTGCCTAACGAAAGGTGCTTCCTAAACACTCTCTGCTGTACGAGTACT*
*TCACAGTTTATAACGAGCTCACCAAGGTCAAATACGTCACAGAAGGGATGAGAAAGCC*

FIGURE 41

AGCATTCCTGTCTGGAGAGCAGAAGAAAGCTATCGTGGACCTCCTCTTCAAGACGAAC
CGGAAAGTTACCGTGAAACAGCTCAAAGAAGACTATTTCAAAAGATTGAATGTTTCGA
CTCTGTTGAAATCAGCGGAGTGGAGGATCGCTTCAACGCATCCCTGGGAACGTATCAC
GATCTCCTGAAAATCATTAAAGACAAGGACTTCCTGGACAATGAGGAGAACGAGGACA
TTCTTGAGGACATTGTCCTCACCCTTACGTTGTTTGAAGATAGGGAGATGATTGAAGAA
CGCTTGAAAACTTACGCTCATCTCTTCGACGACAAAGTCATGAAACAGCTCAAGAGGC
GCCGATATACAGGATGGGGCGGCTGTCAAGAAAACTGATCAATGGGATCCGAGACAA
GCAGAGTGGAAAGACAATCCTGGATTTTCTTAAGTCCGATGGATTTGCCAACCGGAAC
TTCATGCAGTTGATCCATGATGACTCTCTCACCTTTAAGGAGGACATCCAGAAAGCACA
AGTTTCTGGCCAGGGGACAGTCTTCACGAGCACATCGCTAATCTTGCAGGTAGCCCA
GCTATCAAAAAGGGAATACTGCAGACCGTTAAGGTCGTGGATGAACTCGTCAAAGTAA
TGGGAAGGCATAAGCCCGAGAATATCGTTATCGAGATGGCCCGAGAGAACCAAACTAC
CCAGAAGGGACAGAAGAACAGTAGGGAAAGGATGAAGAGGATTGAAGAGGGTATAAA
AGAACTGGGGTCCCAAATCCTTAAGGAACACCCAGTTGAAAACACCCAGCTTCAGAAT
GAGAAGCTCTACCTGTACTACCTGCAGAACGGCAGGGACATGTACGTGGATCAGGAAC
TGGACATCAATCGGCTCTCCGACTACGACGTGGCTGCTATCGTGCCCCAGTCTTTTCTC
AAAGATGATTCTATTGATAATAAAGTGTTGACAAGATCCGATAAAgcTAGAGGGAAGAG
TGATAACGTCCCCTCAGAAGAAGTTGTCAAGAAAATGAAAAATTATTGGCGGCAGCTG
CTGAACGCCAAACTGATCACACAACGGAAGTTCGATAATCTGACTAAGGCTGAACGAG
GTGGCCTGTCTGAGTTGGATAAAGCCGGCTTCATCAAAAGGCAGCTTGTTGAGACACG
CCAGATCACCAAGCACGTGGCCCAAATTCTCGATTCACGCATGAACACCAAGTACGAT
GAAAATGACAAACTGATTCGAGAGGTGAAAGTTATTACTCTGAAGTCTAAGCTGGTCTC
AGATTTCAGAAAGGACTTTCAGTTTTATAAGGTGAGAGAGATCAACAATTACCACCATG
CGCATGATGCCTACCTGAATGCAGTGGTAGGCACTGCACTTATCAAAAAATATCCCAA
GCTTGAATCTGAATTTGTTTACGGAGACTATAAAGTGTACGATGTTAGGAAAATGATCG
CAAAGTCTGAGCAGGAAATAGGCAAGGCCACCGCTAAGTACTTCTTTTACAGCAATATT
ATGAATTTTTTCAAGACCGAGATTACACTGGCCAATGGAGAGATTCGGAAGCGACCAC
TTATCGAAACAAACGGAGAAACAGGAGAAATCGTGTGGGACAAGGGTAGGGATTTCGC
GACAGTCCGGAAGGTCCTGTCCATGCCGCAGGTGAACATCGTTAAAAAGACCGAAGTA
CAGACCGGAGGCTTCTCCAAGGAAAGTATCCTCCCGAAAAGGAACAGCGACAAGCTGA
TCGCACGCAAAAAGATTGGGACCCCAAGAAATACGGCGGATTCGATTCTCCTACAGT
CGCTTACAGTGTACTGGTTGTGGCCAAAGTGGAGAAAGGGAAGTCTAAAAAACTCAAA
AGCGTCAAGGAACTGCTGGGCATCACAATCATGGAGCGATCAAGCTTCGAAAAAAACC
CCATCGACTTTCTCGAGGCGAAAGGATATAAAGAGGTCAAAAAAGACCTCATCATTAA

FIGURE 41, continued...

*GCTTCCCAAGTACTCTCTCTTTGAGCTTGAAAACGGCCGGAAACGAATGCTCGCTAGT*
*GCGGGCGAGCTGCAGAAAGGTAACGAGCTGGCACTGCCCTCTAAATACGTTAATTTCT*
*TGTATCTGGCCAGCCACTATGAAAAGCTCAAAGGGTCTCCCGAAGATAATGAGCAGAA*
*GCAGCTGTTCGTGGAACAACACAAACACTACCTTGATGAGATCATCGAGCAAATAAGC*
*GAATTCTCCAAAAGAGTGATCCTCGCCGACGCTAACCTCGATAAGGTGCTTTCTGCTTA*
*CAATAAGCACAGGGATAAGCCCATCAGGGAGCAGGCAGAAAACATTATCCACTTGTTT*
*ACTCTGACCAACTTGGGCGCGCCTGCAGCCTTCAAGTACTTCGACACCACCATAGACA*
*GAAAGCGGTACACCTCTACAAAGGAGGTCCTGGACGCCACACTGATTCATCAGTCAAT*
*TACGGGGCTCTATGAAACAAGAATCGACCTCTCTCAGCTCGGTGGAGAC*AGCAGGGCT
GACATGGCCAGCATGACTGGTGGACAGCAAATGGGGTCGACG*GAGGACGTGGTGTG*
*CTGCCACTCAATCTAC*GGCAAGAAGAAGGGTGATATCGACACCTACCGATACATAGG
CTCTTCCGGGACA*GGCTGCGTGGTCATAGTGGGCAGGATCGTCTTGTCCGGATCCGGCA*
CTAGT<u>GCGCCCATCACGGCGTACGCCCAGCAGACGAGAGGCCTCCTAGGGTGT</u>
<u>ATAATCACCAGCCTGACTGGCCGGGACAAAAACCAAGTGGAGGGTGAGGTCCA</u>
<u>GATCGTGTCAACTGCTACCCAAACCTTCCTGGCAACGTGCATCAATGGGGTATG</u>
<u>CTGGGCAGTCTACCACGGGGCCGGAACGAGGACCATCGCATCACCCAAGGGTC</u>
<u>CTGTCATCCAGATGTATACCAATGTGGACCAAGACCTTGTGGGCTGGCCCGCTC</u>
<u>CTCAAGGTTCCGCTCATTGACACCCTGTACCTGCGGCTCCTCGGACCTTTACC</u>
<u>TGGTCACGAGGCACGCCGATGTCATTCCCGTGCGCCGGCGAGGTGATAGCAGG</u>
<u>GGTAGCCTGCTTTCGCCCCGGCCCATTTCCTACTTGAAAGGCTCCTCGGGGGGT</u>
<u>CCGCTGTTGTGCCCCGCGGGACACGCCGTGGGCCTATTCAGGGCCGCGGTGTG</u>
<u>CACCCGTGGAGTGGCTAAAGCGGTGGACTTTATCCCTGTGGAGAACCTAGAGA</u>
<u>CAACCATGAGATCCCCGGTGTTCACGGACAACTCCTCT</u>CCACCAGCAGTCACCCT
GACGCACCCAATCACCAAAATCGATAGGGAGGTT*CTCTACCAGGAGTTCGATGAGAT*
*GGAAGAGTGCTCTCAGCAC*TATCCCTACGATGTGCCCGATTACGCTGGCGCGTCTGCA
TGCCCCAAGAAGAAGAGGAAGGTGTCGCCAGGGATCCGTCGACTTGACGCGTTGA
TATCAACAAGTTTGTACAAAAAGCAGGCTACAAAGAGGCCAGCGGTTCCGGACGG
GCTGACGCATTGGACGATTTTGATCTGGATATGCTGGGAAGTGACGCCCTCGATGAT
TTTGACCTTGACATGCTTGGTTCGGATGCCCTTGATGACTTTGACCTCGACATGCTCG
GCAGTGACGCCCTTGATGATTTCGACCTGGACATGCTGATTAACTCTAGAAGTTCCG
GATCTCCGAAAAGAAACGCAAAGTTGGTAGC*CAGTACCTGCCCGACACCGACGAC*
*CGGCACCGGATCGAGGAAAAGCGGAAGCGGACCTACGAGACATTCAAGAGCATCATGAAG*
*AAGTCCCCCTTCAGCGGCCCCACCGACCCTAGACCTCCACCTAGAAGAATCGCCGTGCCC*
*AGCAGATCCAGCGCCAGCGTGCCAAAACCTGCCCCCAGCCTTACCCCTTCACCAGCAGC*

FIGURE 41, continued...

*CTGAGCACCATCAACTACGACGAGTTCCCTACCATGGTGTTCCCCAGCGGCCAGATCTCTC*
*AGGCCTCTGCTCTGGCTCCAGCCCCTCCTCAGGTGCTGCCTCAGGCTCCTGCTCCTGCAC*
*CAGCTCCAGCCATGGTGTCTGCACTGGCTCAGGCACCAGCACCCGTGCCTGTGCTGGCTC*
*CTGGACCTCCACAGGCTGTGGCTCCACCAGCCCCTAAACCTACACAGGCCGGCGAGGGC*
*ACACTGTCTGAAGCTCTGCTGCAGCTGCAGTTCGACGACGAGGATCTGGGAGCCCTGCTG*
*GGAAACAGCACCGATCCTGCCGTGTTCACCGACCTGGCCAGCGTGGACAACAGCGAGTTC*
*CAGCAGCTGCTGAACCAGGGCATCCCTGTGGCCCCTCACACCACCGAGCCCATGCTGATG*
*GAATACCCCGAGGCCATCACCCGGCTCGTGACAGGCGCTCAGAGGCCTCCTGATCCAGCT*
*CCTGCCCCTCTGGGAGCACCAGGCCTGCCTAATGGACTGCTGTCTGGCGACGAGGACTTC*
*AGCTCTATCGCCGATATGGATTTCTCAGCCTTGCTG*GGCTCTGGCAGCGGCAGCCGGGA
TTCCAGGGAAGGGATGTTTTTGCCGAAGCCTGAGGCCGGCTCCGCTATTAGTGA
CGTGTTTGAGGGCCGCGAGGTGTGCCAGCCAAAACGAATCCGGCCATTTCATC
CTCCAGGAAGTCCATGGGCCAACCGCCCACTCCCGCCAGCCTCGCACCAACA
CCAACCGGTCCAGTACATGAGCCAGTCGGGTCACTGACCCCGGCACCAGTCCC
TCAGCCACTGGATCCAGCGCCCGCAGTGACTCCCGAGGCCAGTCACCTGTTGG
AGGATCCCGATGAAGAGACGAGCCAGGCTGTCAAAGCCCTTCGGGAGATGGCC
GATACTGTGATTCCCCAGAAGGAAGAGGCTGCAATCTGTGGCCAAATGGACCTT
TCCCATCCGCCCCCAAGGGGCCATCTGGATGAGCTGACAACCACACTTGAGTCC
ATGACCGAGGATCTGAACCTGGACTCACCCCTGACCCCGGAATTGAACGAGATT
CTGGATACCTTCCTGAACGACGAGTGCCTCTTGCATGCCATGCATATCAGCACA
GGACTGTCCATCTTCGACACATCTCTGTTTtga (SEQ ID NO: 61)

FIGURE 41, continued...

MALPVTALLLPLALLLHAARPEQKLISEEDLTG*VSKGEELFTGVVPILVELDGDVNGHKFSVRGE GEGDATNGKLTLKFISTTGKLPVPWPTLVTTLTYGVQSFSRYPDHMKRHDFFKSAMPEGYVQERT ISFKDDGTYKTRAEVKFEGDTLVNRIELKGIDFKEDGNILGHKLEYNFNSHNVYITADKQKNGIK ANFKIRHNVEDGSVQLADHYQQNTPIGDGPVLLPDNHYLSTQSKLSKDPNEKRDHMVLLEFVTAA GITHGMDELYKGS*PVEPPLPSQLHLMYVAAAAFVLLFFVGCGVLLSRKRRRGSSMKLLSSIEQAC DICRLKKLKCSKEKPKCAKCLKNNWECRYSPKTKRSPLTRAHLTEVESRLERLEQLFLLIFPRED LDMILKMDSLQDIKALLTGLFVQDNVNKDAVTDRLASVETDMPLTLRQHRISATSSSEESSNKGQ RQLTVSAAAGGSGGSGGSDALDDFDLDMLGSDALDDFDLDMLGSDALDDFDLDMLGSDALDDFDL DMLGS (SEQ ID NO: 68)

FIGURE 42

SEQUENCE LISTING

<160> NUMBER OF SEQ ID NOS: 70

<210> SEQ ID NO 1
<211> LENGTH: 51
<212> TYPE: PRT
<213> ORGANISM: Unknown
<220> FEATURE:
<223> OTHER INFORMATION: Description of Unknown:
      signal sequence

<400> SEQUENCE: 1

Ala Val Gly Gln Asp Thr Gln Glu Val Ile Val Val Pro His Ser Leu
1               5                   10                  15

Pro Phe Lys Val Val Val Ile Ser Ala Ile Leu Ala Leu Val Val Leu
                20                  25                  30

Thr Ile Ile Ser Leu Ile Ile Leu Ile Met Leu Trp Gln Lys Lys Pro
            35                  40                  45

Arg Arg Thr
    50

<210> SEQ ID NO 2
<211> LENGTH: 1408
<212> TYPE: PRT
<213> ORGANISM: Homo sapiens

<400> SEQUENCE: 2

Arg Gly Pro Arg Cys Ser Gln Pro Gly Glu Thr Cys Leu Asn Gly Gly
1               5                   10                  15

Lys Cys Glu Ala Ala Asn Gly Thr Glu Ala Cys Val Cys Gly Gly Ala
                20                  25                  30

Phe Val Gly Pro Arg Cys Gln Asp Pro Asn Pro Cys Leu Ser Thr Pro
            35                  40                  45

Cys Lys Asn Ala Gly Thr Cys His Val Val Asp Arg Arg Gly Val Ala
        50                  55                  60

Asp Tyr Ala Cys Ser Cys Ala Leu Gly Phe Ser Gly Pro Leu Cys Leu
65                  70                  75                  80

Thr Pro Leu Asp Asn Ala Cys Leu Thr Asn Pro Cys Arg Asn Gly Gly
                85                  90                  95

Thr Cys Asp Leu Leu Thr Leu Thr Glu Tyr Lys Cys Arg Cys Pro Pro
            100                 105                 110

Gly Trp Ser Gly Lys Ser Cys Gln Gln Ala Asp Pro Cys Ala Ser Asn
        115                 120                 125

Pro Cys Ala Asn Gly Gly Gln Cys Leu Pro Phe Glu Ala Ser Tyr Ile
    130                 135                 140

Cys His Cys Pro Pro Ser Phe His Gly Pro Thr Cys Arg Gln Asp Val
145                 150                 155                 160

Asn Glu Cys Gly Gln Lys Pro Gly Leu Cys Arg His Gly Gly Thr Cys
                165                 170                 175

His Asn Glu Val Gly Ser Tyr Arg Cys Val Cys Arg Ala Thr His Thr
            180                 185                 190

Gly Pro Asn Cys Glu Arg Pro Tyr Val Pro Cys Ser Pro Ser Pro Cys
        195                 200                 205

Gln Asn Gly Gly Thr Cys Arg Pro Thr Gly Asp Val Thr His Glu Cys
    210                 215                 220

Ala Cys Leu Pro Gly Phe Thr Gly Gln Asn Cys Glu Glu Asn Ile Asp
225                 230                 235                 240

Asp Cys Pro Gly Asn Asn Cys Lys Asn Gly Gly Ala Cys Val Asp Gly

```
            245                 250                 255
Val Asn Thr Tyr Asn Cys Arg Cys Pro Pro Glu Trp Thr Gly Gln Tyr
            260                 265                 270

Cys Thr Glu Asp Val Asp Glu Cys Gln Leu Met Pro Asn Ala Cys Gln
            275                 280                 285

Asn Gly Gly Thr Cys His Asn Thr His Gly Gly Tyr Asn Cys Val Cys
            290                 295                 300

Val Asn Gly Trp Thr Gly Glu Asp Cys Ser Glu Asn Ile Asp Asp Cys
305                 310                 315                 320

Ala Ser Ala Ala Cys Phe His Gly Ala Thr Cys His Asp Arg Val Ala
                325                 330                 335

Ser Phe Tyr Cys Glu Cys Pro His Gly Arg Thr Gly Leu Leu Cys His
                340                 345                 350

Leu Asn Asp Ala Cys Ile Ser Asn Pro Cys Asn Glu Gly Ser Asn Cys
                355                 360                 365

Asp Thr Asn Pro Val Asn Gly Lys Ala Ile Cys Thr Cys Pro Ser Gly
            370                 375                 380

Tyr Thr Gly Pro Ala Cys Ser Gln Asp Val Asp Glu Cys Ser Leu Gly
385                 390                 395                 400

Ala Asn Pro Cys Glu His Ala Gly Lys Cys Ile Asn Thr Leu Gly Ser
                405                 410                 415

Phe Glu Cys Gln Cys Leu Gln Gly Tyr Thr Gly Pro Arg Cys Glu Ile
                420                 425                 430

Asp Val Asn Glu Cys Val Ser Asn Pro Cys Gln Asn Asp Ala Thr Cys
            435                 440                 445

Leu Asp Gln Ile Gly Glu Phe Gln Cys Ile Cys Met Pro Gly Tyr Glu
            450                 455                 460

Gly Val His Cys Glu Val Asn Thr Asp Glu Cys Ala Ser Ser Pro Cys
465                 470                 475                 480

Leu His Asn Gly Arg Cys Leu Asp Lys Ile Asn Glu Phe Gln Cys Glu
                485                 490                 495

Cys Pro Thr Gly Phe Thr Gly His Leu Cys Gln Tyr Asp Val Asp Glu
            500                 505                 510

Cys Ala Ser Thr Pro Cys Lys Asn Gly Ala Lys Cys Leu Asp Gly Pro
            515                 520                 525

Asn Thr Tyr Thr Cys Val Cys Thr Glu Gly Tyr Thr Gly Thr His Cys
            530                 535                 540

Glu Val Asp Ile Asp Glu Cys Asp Pro Asp Pro Cys His Tyr Gly Ser
545                 550                 555                 560

Cys Lys Asp Gly Val Ala Thr Phe Thr Cys Leu Cys Arg Pro Gly Tyr
                565                 570                 575

Thr Gly His His Cys Glu Thr Asn Ile Asn Glu Cys Ser Ser Gln Pro
                580                 585                 590

Cys Arg His Gly Gly Thr Cys Gln Asp Arg Asp Asn Ala Tyr Leu Cys
                595                 600                 605

Phe Cys Leu Lys Gly Thr Thr Gly Pro Asn Cys Glu Ile Asn Leu Asp
            610                 615                 620

Asp Cys Ala Ser Ser Pro Cys Asp Ser Gly Thr Cys Leu Asp Lys Ile
625                 630                 635                 640

Asp Gly Tyr Glu Cys Ala Cys Glu Pro Gly Tyr Thr Gly Ser Met Cys
                645                 650                 655

Asn Ile Asn Ile Asp Glu Cys Ala Gly Asn Pro Cys His Asn Gly Gly
            660                 665                 670
```

-continued

```
Thr Cys Glu Asp Gly Ile Asn Gly Phe Thr Cys Arg Cys Pro Glu Gly
        675                 680                 685

Tyr His Asp Pro Thr Cys Leu Ser Glu Val Asn Glu Cys Asn Ser Asn
        690                 695                 700

Pro Cys Val His Gly Ala Cys Arg Asp Ser Leu Asn Gly Tyr Lys Cys
705                 710                 715                 720

Asp Cys Asp Pro Gly Trp Ser Gly Thr Asn Cys Asp Ile Asn Asn Asn
                725                 730                 735

Glu Cys Glu Ser Asn Pro Cys Val Asn Gly Thr Cys Lys Asp Met
                740                 745                 750

Thr Ser Gly Tyr Val Cys Thr Cys Arg Glu Gly Phe Ser Gly Pro Asn
        755                 760                 765

Cys Gln Thr Asn Ile Asn Glu Cys Ala Ser Asn Pro Cys Leu Asn Gln
        770                 775                 780

Gly Thr Cys Ile Asp Asp Val Ala Gly Tyr Lys Cys Asn Cys Leu Leu
785                 790                 795                 800

Pro Tyr Thr Gly Ala Thr Cys Glu Val Val Leu Ala Pro Cys Ala Pro
                805                 810                 815

Ser Pro Cys Arg Asn Gly Gly Cys Arg Gln Ser Glu Asp Tyr Glu
                820                 825                 830

Ser Phe Ser Cys Val Cys Pro Thr Gly Trp Gln Ala Gly Gln Thr Cys
        835                 840                 845

Glu Val Asp Ile Asn Glu Cys Val Leu Ser Pro Cys Arg His Gly Ala
850                 855                 860

Ser Cys Gln Asn Thr His Gly Gly Tyr Arg Cys His Cys Gln Ala Gly
865                 870                 875                 880

Tyr Ser Gly Arg Asn Cys Glu Thr Asp Ile Asp Asp Cys Arg Pro Asn
                885                 890                 895

Pro Cys His Asn Gly Gly Ser Cys Thr Asp Gly Ile Asn Thr Ala Phe
                900                 905                 910

Cys Asp Cys Leu Pro Gly Phe Arg Gly Thr Phe Cys Glu Glu Asp Ile
        915                 920                 925

Asn Glu Cys Ala Ser Asp Pro Cys Arg Asn Gly Ala Asn Cys Thr Asp
930                 935                 940

Cys Val Asp Ser Tyr Thr Cys Thr Cys Pro Ala Gly Phe Ser Gly Ile
945                 950                 955                 960

His Cys Glu Asn Asn Thr Pro Asp Cys Thr Glu Ser Ser Cys Phe Asn
                965                 970                 975

Gly Gly Thr Cys Val Asp Gly Ile Asn Ser Phe Thr Cys Leu Cys Pro
                980                 985                 990

Pro Gly Phe Thr Gly Ser Tyr Cys  Gln His Asp Val Asn  Glu Cys Asp
        995                 1000                1005

Ser Gln  Pro Cys Leu His Gly  Thr Cys Gln Asp  Gly Cys Gly
        1010                1015                1020

Ser Tyr  Arg Cys Thr Cys Pro  Gln Gly Tyr Thr Gly  Pro Asn Cys
        1025                1030                1035

Gln Asn  Leu Val His Trp Cys  Asp Ser Ser Pro  Cys Lys Asn Gly
        1040                1045                1050

Gly Lys  Cys Trp Gln Thr His  Thr Gln Tyr Arg Cys  Glu Cys Pro
        1055                1060                1065

Ser Gly  Trp Thr Gly Leu Tyr  Cys Asp Val Pro Ser  Val Ser Cys
        1070                1075                1080
```

```
Glu Val Ala Ala Gln Arg Gln Gly Val Asp Val Ala Arg Leu Cys
    1085                1090                1095

Gln His Gly Gly Leu Cys Val Asp Ala Gly Asn Thr His His Cys
    1100                1105                1110

Arg Cys Gln Ala Gly Tyr Thr Gly Ser Tyr Cys Glu Asp Leu Val
    1115                1120                1125

Asp Glu Cys Ser Pro Ser Pro Cys Gln Asn Gly Ala Thr Cys Thr
    1130                1135                1140

Asp Tyr Leu Gly Gly Tyr Ser Cys Lys Cys Val Ala Gly Tyr His
    1145                1150                1155

Gly Val Asn Cys Ser Glu Glu Ile Asp Glu Cys Leu Ser His Pro
    1160                1165                1170

Cys Gln Asn Gly Gly Thr Cys Leu Asp Leu Pro Asn Thr Tyr Lys
    1175                1180                1185

Cys Ser Cys Pro Arg Gly Thr Gln Gly Val His Cys Glu Ile Asn
    1190                1195                1200

Val Asp Asp Cys Asn Pro Pro Val Asp Pro Val Ser Arg Ser Pro
    1205                1210                1215

Lys Cys Phe Asn Asn Gly Thr Cys Val Asp Gln Val Gly Gly Tyr
    1220                1225                1230

Ser Cys Thr Cys Pro Pro Gly Phe Val Gly Glu Arg Cys Glu Gly
    1235                1240                1245

Asp Val Asn Glu Cys Leu Ser Asn Pro Cys Asp Ala Arg Gly Thr
    1250                1255                1260

Gln Asn Cys Val Gln Arg Val Asn Asp Phe His Cys Glu Cys Arg
    1265                1270                1275

Ala Gly His Thr Gly Arg Arg Cys Glu Ser Val Ile Asn Gly Cys
    1280                1285                1290

Lys Gly Lys Pro Cys Lys Asn Gly Gly Thr Cys Ala Val Ala Ser
    1295                1300                1305

Asn Thr Ala Arg Gly Phe Ile Cys Lys Cys Pro Ala Gly Phe Glu
    1310                1315                1320

Gly Ala Thr Cys Glu Asn Asp Ala Arg Thr Cys Gly Ser Leu Arg
    1325                1330                1335

Cys Leu Asn Gly Gly Thr Cys Ile Ser Gly Pro Arg Ser Pro Thr
    1340                1345                1350

Cys Leu Cys Leu Gly Pro Phe Thr Gly Pro Glu Cys Gln Phe Pro
    1355                1360                1365

Ala Ser Ser Pro Cys Leu Gly Gly Asn Pro Cys Tyr Asn Gln Gly
    1370                1375                1380

Thr Cys Glu Pro Thr Ser Glu Ser Pro Phe Tyr Arg Cys Leu Cys
    1385                1390                1395

Pro Ala Lys Phe Asn Gly Leu Leu Cys His
    1400                1405

<210> SEQ ID NO 3
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Asp Val Gln Leu Val Glu Ser Gly Gly Gly Leu Val Gln Ala
1               5                   10                  15
```

```
Gly Gly Ser Leu Arg Leu Ser Cys Ala Ala Ser Gly Arg Thr Ile Ser
            20                  25                  30

Met Ala Ala Met Ser Trp Phe Arg Gln Ala Pro Gly Lys Glu Arg Glu
        35                  40                  45

Phe Val Ala Gly Ile Ser Arg Ser Ala Gly Ser Ala Val His Ala Asp
    50                  55                  60

Ser Val Lys Gly Arg Phe Thr Ile Ser Arg Asp Asn Thr Lys Asn Thr
65                  70                  75                  80

Leu Tyr Leu Gln Met Asn Ser Leu Lys Ala Glu Asp Thr Ala Val Tyr
                85                  90                  95

Tyr Cys Ala Val Arg Thr Ser Gly Phe Phe Gly Ser Ile Pro Arg Thr
            100                 105                 110

Gly Thr Ala Phe Asp Tyr Trp Gly Gln Gly Thr Gln Val Thr Val Ser
        115                 120                 125
```

<210> SEQ ID NO 4
<211> LENGTH: 251
<212> TYPE: PRT
<213> ORGANISM: Unknown
<220> FEATURE:
<223> OTHER INFORMATION: Description of Unknown:
      scFv alphaFITC

<400> SEQUENCE: 4

```
Gln Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Gly Ser Phe
            20                  25                  30

Ser Met Ser Trp Val Arg Gln Ala Pro Gly Gly Gly Leu Glu Trp Val
        35                  40                  45

Ala Gly Leu Ser Ala Arg Ser Ser Leu Thr His Tyr Ala Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Val Glu Asp Thr Ala Val Tyr Tyr Cys
                85                  90                  95

Ala Arg Arg Ser Tyr Asp Ser Ser Gly Tyr Ala Gly His Phe Tyr Ser
            100                 105                 110

Tyr Met Asp Val Trp Gly Gln Gly Thr Leu Val Thr Val Ser Gly Gly
        115                 120                 125

Gly Gly Ser Gly Gly Gly Ser Gly Gly Gly Ser Ser Val Leu
    130                 135                 140

Thr Gln Pro Ser Ser Val Ser Ala Ala Pro Gly Gln Lys Val Thr Ile
145                 150                 155                 160

Ser Cys Ser Gly Ser Thr Ser Asn Ile Gly Asn Asn Tyr Val Ser Trp
            165                 170                 175

Tyr Gln Gln His Pro Gly Lys Ala Pro Lys Leu Met Ile Tyr Asp Val
        180                 185                 190

Ser Lys Arg Pro Ser Gly Val Pro Asp Arg Phe Ser Gly Ser Lys Ser
    195                 200                 205

Gly Asn Ser Ala Ser Leu Asp Ile Ser Gly Leu Gln Ser Glu Asp Glu
    210                 215                 220

Ala Asp Tyr Tyr Cys Ala Ala Trp Asp Asp Ser Leu Ser Glu Phe Leu
225                 230                 235                 240

Phe Gly Thr Gly Thr Lys Leu Thr Val Leu Gly
```

```
<210> SEQ ID NO 5
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Arg Ile Ile
            20                  25                  30

Phe Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Ala Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Ser His Leu Ala Ala Leu Ala Gly Asn Pro Ala Ala Thr Ala
        115                 120                 125

Ala Val Lys Thr Ala Leu Ser Gly Asn Pro Val Pro Ile Leu Ile Pro
    130                 135                 140

Cys His Arg Val Val Gln Gly Asp Leu Asp Val Gly Gly Tyr Glu Gly
145                 150                 155                 160

Gly Leu Ala Val Lys Glu Trp Leu Leu Ala His Glu Gly His Arg Leu
                165                 170                 175

Gly Lys Pro Gly Leu Gly
            180

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Tyr Lys Asp Asp Asp Asp Lys Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Gln Lys Leu Ile Ser Glu Glu Asp Leu
1               5                   10

<210> SEQ ID NO 8
```

```
<211> LENGTH: 307
<212> TYPE: PRT
<213> ORGANISM: Homo sapiens

<400> SEQUENCE: 8

Ile Leu Asp Tyr Ser Phe Gly Gly Ala Gly Arg Asp Ile Pro Pro
1               5                   10                  15

Pro Leu Ile Glu Glu Ala Cys Glu Leu Pro Glu Cys Gln Glu Asp Ala
            20                  25                  30

Gly Asn Lys Val Cys Ser Leu Gln Cys Asn Asn His Ala Cys Gly Trp
        35                  40                  45

Asp Gly Gly Asp Cys Ser Leu Asn Phe Asn Asp Pro Trp Lys Asn Cys
    50                  55                  60

Thr Gln Ser Leu Gln Cys Trp Lys Tyr Phe Ser Asp Gly His Cys Asp
65              70                  75                  80

Ser Gln Cys Asn Ser Ala Gly Cys Leu Phe Asp Gly Phe Asp Cys Gln
                85                  90                  95

Arg Ala Glu Gly Gln Cys Asn Pro Leu Tyr Asp Gln Tyr Cys Lys Asp
            100                 105                 110

His Phe Ser Asp Gly His Cys Asp Gln Gly Cys Asn Ser Ala Glu Cys
        115                 120                 125

Glu Trp Asp Gly Leu Asp Cys Ala Glu His Val Pro Glu Arg Leu Ala
    130                 135                 140

Ala Gly Thr Leu Val Val Val Val Leu Met Pro Pro Glu Gln Leu Arg
145                 150                 155                 160

Asn Ser Ser Phe His Phe Leu Arg Glu Leu Ser Arg Val Leu His Thr
                165                 170                 175

Asn Val Val Phe Lys Arg Asp Ala His Gly Gln Gln Met Ile Phe Pro
            180                 185                 190

Tyr Tyr Gly Arg Glu Glu Glu Leu Arg Lys His Pro Ile Lys Arg Ala
        195                 200                 205

Ala Glu Gly Trp Ala Ala Pro Asp Ala Leu Leu Gly Gln Val Lys Ala
    210                 215                 220

Ser Leu Leu Pro Gly Gly Ser Glu Gly Gly Arg Arg Arg Arg Glu Leu
225                 230                 235                 240

Asp Pro Met Asp Val Arg Gly Ser Ile Val Tyr Leu Glu Ile Asp Asn
                245                 250                 255

Arg Gln Cys Val Gln Ala Ser Ser Gln Cys Phe Gln Ser Ala Thr Asp
            260                 265                 270

Val Ala Ala Phe Leu Gly Ala Leu Ala Ser Leu Gly Ser Leu Asn Ile
        275                 280                 285

Pro Tyr Lys Ile Glu Ala Val Gln Ser Glu Thr Val Glu Pro Pro Pro
    290                 295                 300

Pro Ala Gln
305

<210> SEQ ID NO 9
<211> LENGTH: 297
<212> TYPE: PRT
<213> ORGANISM: Mus sp.

<400> SEQUENCE: 9

Ile Leu Asp Tyr Ser Phe Thr Gly Gly Ala Gly Arg Asp Ile Pro Pro
1               5                   10                  15

Pro Gln Ile Glu Glu Ala Cys Glu Leu Pro Glu Cys Gln Val Asp Ala
            20                  25                  30
```

Gly Asn Lys Val Cys Asn Leu Gln Cys Asn Asn His Ala Cys Gly Trp
                35                  40                  45

Asp Gly Gly Asp Cys Ser Leu Asn Phe Asn Asp Pro Trp Lys Asn Cys
     50                  55                  60

Thr Gln Ser Leu Gln Cys Trp Lys Tyr Phe Ser Asp Gly His Cys Asp
 65                  70                  75                  80

Ser Gln Cys Asn Ser Ala Gly Cys Leu Phe Asp Gly Phe Asp Cys Gln
                 85                  90                  95

Leu Thr Glu Gly Gln Cys Asn Pro Leu Tyr Asp Gln Tyr Cys Lys Asp
                100                 105                 110

His Phe Ser Asp Gly His Cys Asp Gln Gly Cys Asn Ser Ala Glu Cys
                115                 120                 125

Glu Trp Asp Gly Leu Asp Cys Ala Glu His Val Pro Glu Arg Leu Ala
        130                 135                 140

Ala Gly Thr Leu Val Leu Val Val Leu Pro Pro Asp Gln Leu Arg
145                 150                 155                 160

Asn Asn Ser Phe His Phe Leu Arg Glu Leu Ser His Val Leu His Thr
                165                 170                 175

Asn Val Val Phe Lys Arg Asp Ala Gln Gly Gln Gln Met Ile Phe Pro
            180                 185                 190

Tyr Tyr Gly His Glu Glu Leu Arg Lys His Pro Ile Lys Arg Ser
                195                 200                 205

Thr Val Gly Trp Ala Thr Ser Ser Leu Leu Pro Gly Thr Ser Gly Gly
    210                 215                 220

Arg Gln Arg Arg Glu Leu Asp Pro Met Asp Ile Arg Gly Ser Ile Val
225                 230                 235                 240

Tyr Leu Glu Ile Asp Asn Arg Gln Cys Val Gln Ser Ser Ser Gln Cys
                245                 250                 255

Phe Gln Ser Ala Thr Asp Val Ala Ala Phe Leu Gly Ala Leu Ala Ser
            260                 265                 270

Leu Gly Ser Leu Asn Ile Pro Tyr Lys Ile Glu Ala Val Lys Ser Glu
        275                 280                 285

Pro Val Glu Pro Pro Leu Pro Ser Gln
    290                 295

<210> SEQ ID NO 10
<211> LENGTH: 265
<212> TYPE: PRT
<213> ORGANISM: Mus sp.

<400> SEQUENCE: 10

Leu Tyr Thr Ala Pro Pro Ser Thr Pro Pro Ala Thr Cys Leu Ser Gln
  1               5                  10                  15

Tyr Cys Ala Asp Lys Ala Arg Asp Gly Val Cys Asp Glu Ala Cys Asn
                20                  25                  30

Ser His Ala Cys Gln Trp Asp Gly Gly Asp Cys Ser Leu Thr Met Glu
            35                  40                  45

Asn Pro Trp Ala Asn Cys Ser Ser Pro Leu Pro Cys Trp Asp Tyr Ile
     50                  55                  60

Asn Asn Gln Cys Asp Glu Leu Cys Asn Thr Val Glu Cys Leu Phe Asp
 65                  70                  75                  80

Asn Phe Glu Cys Gln Gly Asn Ser Lys Thr Cys Lys Tyr Asp Lys Tyr
                85                  90                  95

Cys Ala Asp His Phe Lys Asp Asn His Cys Asp Gln Gly Cys Asn Ser

```
            100                 105                 110
Glu Glu Cys Gly Trp Asp Gly Leu Asp Cys Ala Ala Asp Gln Pro Glu
        115                 120                 125

Asn Leu Ala Glu Gly Thr Leu Val Ile Val Val Leu Met Pro Pro Glu
130                 135                 140

Gln Leu Leu Gln Asp Ala Arg Ser Phe Leu Arg Ala Leu Gly Thr Leu
145                 150                 155                 160

Leu His Thr Asn Leu Arg Ile Lys Arg Asp Ser Gln Gly Glu Leu Met
                165                 170                 175

Val Tyr Pro Tyr Tyr Gly Glu Lys Ser Ala Ala Met Lys Lys Gln Arg
            180                 185                 190

Met Thr Arg Arg Ser Leu Pro Gly Glu Gln Glu Gln Glu Val Ala Gly
        195                 200                 205

Ser Lys Val Phe Leu Glu Ile Asp Asn Arg Gln Cys Val Gln Asp Ser
    210                 215                 220

Asp His Cys Phe Lys Asn Thr Asp Ala Ala Ala Leu Leu Ala Ser
225                 230                 235                 240

His Ala Ile Gln Gly Thr Leu Ser Tyr Pro Leu Val Ser Val Val Ser
                245                 250                 255

Glu Ser Leu Thr Pro Glu Arg Thr Gln
                260                 265

<210> SEQ ID NO 11
<211> LENGTH: 793
<212> TYPE: PRT
<213> ORGANISM: Unknown
<220> FEATURE:
<223> OTHER INFORMATION: Description of Unknown:
      NICD sequence

<400> SEQUENCE: 11

Gln His Gly Gln Leu Trp Phe Pro Glu Gly Phe Lys Val Ser Glu Ala
1               5                   10                  15

Ser Lys Lys Lys Arg Arg Glu Pro Leu Gly Glu Asp Ser Val Gly Leu
            20                  25                  30

Lys Pro Leu Lys Asn Ala Ser Asp Gly Ala Leu Met Asp Asp Asn Gln
        35                  40                  45

Asn Glu Trp Gly Asp Glu Asp Leu Glu Thr Lys Lys Phe Arg Phe Glu
    50                  55                  60

Glu Pro Val Val Leu Pro Asp Leu Asp Asp Gln Thr Asp His Arg Gln
65                  70                  75                  80

Trp Thr Gln Gln His Leu Asp Ala Ala Asp Leu Arg Met Ser Ala Met
                85                  90                  95

Ala Pro Thr Pro Pro Gln Gly Glu Val Asp Ala Asp Cys Met Asp Val
            100                 105                 110

Asn Val Arg Gly Pro Asp Gly Phe Thr Pro Leu Met Ile Ala Ser Cys
        115                 120                 125

Ser Gly Gly Gly Leu Glu Thr Gly Asn Ser Glu Glu Glu Glu Asp Ala
    130                 135                 140

Pro Ala Val Ile Ser Asp Phe Ile Tyr Gln Gly Ala Ser Leu His Asn
145                 150                 155                 160

Gln Thr Asp Arg Thr Gly Glu Thr Ala Leu His Leu Ala Ala Arg Tyr
                165                 170                 175

Ser Arg Ser Asp Ala Ala Lys Arg Leu Leu Glu Ala Ser Ala Asp Ala
            180                 185                 190
```

-continued

```
Asn Ile Gln Asp Asn Met Gly Arg Thr Pro Leu His Ala Ala Val Ser
            195                 200                 205

Ala Asp Ala Gln Gly Val Phe Gln Ile Leu Ile Arg Asn Arg Ala Thr
210                 215                 220

Asp Leu Asp Ala Arg Met His Asp Gly Thr Thr Pro Leu Ile Leu Ala
225                 230                 235                 240

Ala Arg Leu Ala Val Glu Gly Met Leu Glu Asp Leu Ile Asn Ser His
            245                 250                 255

Ala Asp Val Asn Ala Val Asp Leu Gly Lys Ser Ala Leu His Trp
            260                 265                 270

Ala Ala Ala Val Asn Asn Val Asp Ala Ala Val Val Leu Leu Lys Asn
            275                 280                 285

Gly Ala Asn Lys Asp Met Gln Asn Asn Arg Glu Glu Thr Pro Leu Phe
290                 295                 300

Leu Ala Ala Arg Glu Gly Ser Tyr Glu Thr Ala Lys Val Leu Leu Asp
305                 310                 315                 320

His Phe Ala Asn Arg Asp Ile Thr Asp His Met Asp Arg Leu Pro Arg
            325                 330                 335

Asp Ile Ala Gln Glu Arg Met His His Asp Ile Val Arg Leu Leu Asp
            340                 345                 350

Glu Tyr Asn Leu Val Arg Ser Pro Gln Leu His Gly Ala Pro Leu Gly
            355                 360                 365

Gly Thr Pro Thr Leu Ser Pro Pro Leu Cys Ser Pro Asn Gly Tyr Leu
    370                 375                 380

Gly Ser Leu Lys Pro Gly Val Gln Gly Lys Lys Val Arg Lys Pro Ser
385                 390                 395                 400

Ser Lys Gly Leu Ala Cys Gly Ser Lys Glu Ala Lys Asp Leu Lys Ala
            405                 410                 415

Arg Arg Lys Lys Ser Gln Asp Gly Lys Gly Cys Leu Leu Asp Ser Ser
            420                 425                 430

Gly Met Leu Ser Pro Val Asp Ser Leu Glu Ser Pro His Gly Tyr Leu
            435                 440                 445

Ser Asp Val Ala Ser Pro Pro Leu Leu Pro Ser Pro Phe Gln Gln Ser
450                 455                 460

Pro Ser Val Pro Leu Asn His Leu Pro Gly Met Pro Asp Thr His Leu
465                 470                 475                 480

Gly Ile Gly His Leu Asn Val Ala Ala Lys Pro Glu Met Ala Ala Leu
            485                 490                 495

Gly Gly Gly Gly Arg Leu Ala Phe Glu Thr Gly Pro Pro Arg Leu Ser
            500                 505                 510

His Leu Pro Val Ala Ser Gly Thr Ser Thr Val Leu Gly Ser Ser Ser
            515                 520                 525

Gly Gly Ala Leu Asn Phe Thr Val Gly Gly Ser Thr Ser Leu Asn Gly
    530                 535                 540

Gln Cys Glu Trp Leu Ser Arg Leu Gln Ser Gly Met Val Pro Asn Gln
545                 550                 555                 560

Tyr Asn Pro Leu Arg Gly Ser Val Ala Pro Gly Pro Leu Ser Thr Gln
            565                 570                 575

Ala Pro Ser Leu Gln His Gly Met Val Gly Pro Leu His Ser Ser Leu
            580                 585                 590

Ala Ala Ser Ala Leu Ser Gln Met Met Ser Tyr Gln Gly Leu Pro Ser
            595                 600                 605

Thr Arg Leu Ala Thr Gln Pro His Leu Val Gln Thr Gln Gln Val Gln
```

```
                610               615                 620
Pro Gln Asn Leu Gln Met Gln Gln Asn Leu Gln Pro Ala Asn Ile
625                 630                 635                 640

Gln Gln Gln Gln Ser Leu Gln Pro Pro Pro Pro Pro Gln Pro His
                645                 650                 655

Leu Gly Val Ser Ser Ala Ala Ser Gly His Leu Gly Arg Ser Phe Leu
                660                 665                 670

Ser Gly Glu Pro Ser Gln Ala Asp Val Gln Pro Leu Gly Pro Ser Ser
                675                 680                 685

Leu Ala Val His Thr Ile Leu Pro Gln Glu Ser Pro Ala Leu Pro Thr
                690                 695                 700

Ser Leu Pro Ser Ser Leu Val Pro Pro Val Thr Ala Ala Gln Phe Leu
705                 710                 715                 720

Thr Pro Pro Ser Gln His Ser Tyr Ser Ser Pro Val Asp Asn Thr Pro
                725                 730                 735

Ser His Gln Leu Gln Val Pro Glu His Pro Phe Leu Thr Pro Ser Pro
                740                 745                 750

Glu Ser Pro Asp Gln Trp Ser Ser Ser Pro His Ser Asn Val Ser
                755                 760                 765

Asp Trp Ser Glu Gly Val Ser Ser Pro Pro Thr Ser Met Gln Ser Gln
770                 775                 780

Ile Ala Arg Ile Pro Glu Ala Phe Lys
785                 790

<210> SEQ ID NO 12
<211> LENGTH: 211
<212> TYPE: PRT
<213> ORGANISM: Unknown
<220> FEATURE:
<223> OTHER INFORMATION: Description of Unknown:
      Gal4DBD-VP64 sequence

<400> SEQUENCE: 12

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro
                35                  40                  45

Leu Thr Arg Ala His Leu Thr Glu Val Glu Ser Arg Leu Glu Arg Leu
                50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
                115                 120                 125

Ala Thr Ser Ser Ser Glu Glu Ser Ser Asn Lys Gly Gln Arg Gln Leu
                130                 135                 140

Thr Val Ser Ala Ala Ala Gly Gly Ser Gly Gly Ser Gly Gly Ser Asp
145                 150                 155                 160

Ala Leu Asp Asp Phe Asp Leu Asp Met Leu Gly Ser Asp Ala Leu Asp
                165                 170                 175
```

```
Asp Phe Asp Leu Asp Met Leu Gly Ser Asp Ala Leu Asp Asp Phe Asp
            180                 185                 190

Leu Asp Met Leu Gly Ser Asp Ala Leu Asp Asp Phe Asp Leu Asp Met
        195                 200                 205

Leu Gly Ser
    210

<210> SEQ ID NO 13
<211> LENGTH: 29
<212> TYPE: PRT
<213> ORGANISM: Homo sapiens

<400> SEQUENCE: 13

Leu His Phe Met Tyr Val Ala Ala Ala Phe Val Leu Leu Phe Phe
1               5                   10                  15

Val Gly Cys Gly Val Leu Leu Ser Arg Lys Arg Arg Arg
            20                  25

<210> SEQ ID NO 14
<211> LENGTH: 29
<212> TYPE: PRT
<213> ORGANISM: Mus sp.

<400> SEQUENCE: 14

Leu His Leu Met Tyr Val Ala Ala Ala Phe Val Leu Leu Phe Phe
1               5                   10                  15

Val Gly Cys Gly Val Leu Leu Ser Arg Lys Arg Arg Arg
            20                  25

<210> SEQ ID NO 15
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ala Arg Ile Asn Pro Pro Asn Arg Ser Asn Gln Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Phe Arg Trp Val Met Asp Tyr Trp Gly Gln Gly
            100                 105                 110

Thr Leu Val Thr Val Ser Ser Gly Gly Ser Arg Ser Ser Ser Ser
        115                 120                 125

Gly Gly Gly Gly Ser Gly Gly Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Asp Val Ser Thr Ala Val Ala Trp Tyr Gln Gln Lys
```

```
                        165                 170                 175

Pro Gly Lys Ala Pro Lys Leu Leu Ile Tyr Ser Ala Ser Phe Leu Tyr
                180                 185                 190

Ser Gly Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
    210                 215                 220

Cys Gln Gln Phe Tyr Thr Thr Pro Ser Thr Phe Gly Gln Gly Thr Lys
225                 230                 235                 240

Val Glu Ile Lys

<210> SEQ ID NO 16
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ala Arg Ile Asn Pro Pro Ala Arg Ser Asn Gln Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Phe Arg Trp Val Met Asp Tyr Trp Gly Gln Gly
            100                 105                 110

Thr Leu Val Thr Val Ser Ser Gly Gly Ser Ser Arg Ser Ser Ser Ser
        115                 120                 125

Gly Gly Gly Gly Ser Gly Gly Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Asp Val Ser Thr Ala Val Ala Trp Tyr Gln Gln Lys
                165                 170                 175

Pro Gly Lys Ala Pro Lys Leu Leu Ile Tyr Ser Ala Ser Phe Leu Tyr
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Phe Tyr Thr Thr Pro Ser Thr Phe Gly Gln Gly Thr Lys
225                 230                 235                 240

Val Glu Ile Lys

<210> SEQ ID NO 17
<211> LENGTH: 244
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ala Arg Ile Asn Pro Pro Asn Arg Ser Asn Gln Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Phe Lys Trp Val Met Asp Tyr Trp Gly Gln Gly
            100                 105                 110

Thr Leu Val Thr Val Ser Ser Gly Gly Ser Ser Arg Ser Ser Ser Ser
        115                 120                 125

Gly Gly Gly Gly Ser Gly Gly Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Asp Val Ser Thr Ala Val Ala Trp Tyr Gln Gln Lys
                165                 170                 175

Pro Gly Lys Ala Pro Lys Leu Leu Ile Tyr Ser Ala Ser Phe Leu Tyr
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Phe Tyr Thr Thr Pro Ser Thr Phe Gly Gln Gly Thr Lys
225                 230                 235                 240

Val Glu Ile Lys

<210> SEQ ID NO 18
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ala Arg Ile Asn Pro Pro Asn Arg Ser Asn Gln Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ala Arg Gly Ser Gly Phe Ala Trp Val Met Asp Tyr Trp Gly Gln Gly
            100                 105                 110

Thr Leu Val Thr Val Ser Ser Gly Gly Ser Ser Arg Ser Ser Ser Ser
            115                 120                 125

Gly Gly Gly Gly Ser Gly Gly Gly Asp Ile Gln Met Thr Gln Ser
            130                 135                 140

Pro Ser Ser Leu Ser Ala Ser Val Gly Asp Arg Val Thr Ile Thr Cys
145                 150                 155                 160

Arg Ala Ser Gln Asp Val Ser Thr Ala Val Ala Trp Tyr Gln Gln Lys
                165                 170                 175

Pro Gly Lys Ala Pro Lys Leu Leu Ile Tyr Ser Ala Ser Phe Leu Tyr
            180                 185                 190

Ser Gly Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
            210                 215                 220

Cys Gln Gln Phe Tyr Thr Thr Pro Ser Thr Phe Gly Gln Gly Thr Lys
225                 230                 235                 240

Val Glu Ile Lys

<210> SEQ ID NO 19
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Gln Pro Gly Gly
1               5                   10                  15

Ser Leu Arg Leu Ser Ser Ala Ala Ser Gly Phe Thr Phe Ser Ser Tyr
            20                  25                  30

Trp Ile His Trp Val Arg Gln Ala Pro Gly Lys Gly Leu Glu Trp Val
            35                  40                  45

Ala Arg Ile Asn Pro Pro Asn Arg Ser Asn Gln Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Ala
                85                  90                  95

Ala Arg Gly Ser Gly Phe Arg Trp Val Met Asp Tyr Trp Gly Gln Gly
            100                 105                 110

Thr Leu Val Thr Val Ser Ser Gly Gly Ser Ser Arg Ser Ser Ser Ser
            115                 120                 125

Gly Gly Gly Gly Ser Gly Gly Gly Asp Ile Gln Met Thr Gln Ser
            130                 135                 140

Pro Ser Ser Leu Ser Ala Ser Val Gly Asp Arg Val Thr Ile Thr Cys
145                 150                 155                 160

Arg Ala Ser Gln Asp Val Ser Thr Ala Val Ala Trp Tyr Gln Gln Lys
                165                 170                 175

Pro Gly Lys Ala Pro Lys Leu Leu Ile Tyr Ser Ala Ser Phe Leu Tyr
            180                 185                 190
```

```
Ser Gly Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
        210                 215                 220

Cys Gln Gln Phe Tyr Thr Thr Pro Ser Thr Phe Gly Gln Gly Thr Lys
225                 230                 235                 240

Val Glu Ile Lys

<210> SEQ ID NO 20
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ala Arg Ile Asn Pro Pro Asn Arg Ser Asn Gln Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Phe Arg Trp Val Met Asp Tyr Trp Gly Gln Gly
            100                 105                 110

Thr Leu Val Thr Val Ser Ser Gly Gly Ser Arg Ser Ser Ser Ser
        115                 120                 125

Gly Gly Gly Gly Ser Gly Gly Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Asp Val Ala Thr Ala Val Ala Trp Tyr Gln Gln Lys
                165                 170                 175

Pro Gly Lys Ala Pro Lys Leu Leu Ile Tyr Ser Ala Ser Phe Leu Tyr
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Phe Tyr Thr Thr Pro Ser Thr Phe Gly Gln Gly Thr Lys
225                 230                 235                 240

Val Glu Ile Lys

<210> SEQ ID NO 21
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ala Arg Ile Asn Pro Pro Asn Arg Ser Asn Gln Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Gly Ser Gly Phe Arg Trp Val Met Asp Tyr Trp Gly Gln Gly
            100                 105                 110

Thr Leu Val Thr Val Ser Ser Gly Gly Ser Arg Ser Ser Ser Ser
        115                 120                 125

Gly Gly Gly Gly Ser Gly Gly Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Asp Val Ser Thr Ala Val Ala Trp Tyr Gln Gln Lys
            165                 170                 175

Pro Gly Lys Ala Pro Lys Leu Leu Ile Ala Ser Ala Ser Phe Leu Tyr
            180                 185                 190

Ser Gly Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
        210                 215                 220

Cys Gln Gln Phe Tyr Thr Thr Pro Ser Thr Phe Gly Gln Gly Thr Lys
225                 230                 235                 240

Val Glu Ile Lys

<210> SEQ ID NO 22
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ala Arg Ile Asn Pro Pro Asn Arg Ser Asn Gln Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Gly Ser Gly Phe Arg Trp Val Met Asp Tyr Trp Gly Gln Gly
            100                 105                 110

```
Thr Leu Val Thr Val Ser Ser Gly Gly Ser Arg Ser Ser Ser Ser
            115                 120                 125
Gly Gly Gly Gly Ser Gly Gly Gly Asp Ile Gln Met Thr Gln Ser
            130                 135                 140
Pro Ser Ser Leu Ser Ala Ser Val Gly Asp Arg Val Thr Ile Thr Cys
145                 150                 155                 160
Arg Ala Ser Gln Asp Val Ser Thr Ala Val Ala Trp Tyr Gln Gln Lys
                    165                 170                 175
Pro Gly Lys Ala Pro Lys Leu Leu Ile Tyr Ser Ala Ser Phe Leu Ala
                    180                 185                 190
Ser Gly Val Pro Ser Arg Phe Ser Gly Ser Gly Ser Gly Thr Asp Phe
                    195                 200                 205
Thr Leu Thr Ile Ser Ser Leu Gln Pro Glu Asp Phe Ala Thr Tyr Tyr
                    210                 215                 220
Cys Gln Gln Phe Tyr Thr Thr Pro Ser Thr Phe Gly Gln Gly Thr Lys
225                 230                 235                 240
Val Glu Ile Lys
```

<210> SEQ ID NO 23
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Trp Ile His Trp Val Arg Gln Ala Pro Gly Lys Gly Leu Glu Trp Val
            35                  40                  45
Ala Arg Ile Asn Pro Pro Asn Arg Ser Asn Gln Tyr Ala Asp Ser Val
50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Gly Ser Gly Phe Arg Trp Val Met Asp Tyr Trp Gly Gln Gly
                100                 105                 110
Thr Leu Val Thr Val Ser Ser Gly Gly Ser Arg Ser Ser Ser Ser
            115                 120                 125
Gly Gly Gly Gly Ser Gly Gly Gly Asp Ile Gln Met Thr Gln Ser
            130                 135                 140
Pro Ser Ser Leu Ser Ala Ser Val Gly Asp Arg Val Thr Ile Thr Cys
145                 150                 155                 160
Arg Ala Ser Gln Asp Val Ser Thr Ala Val Ala Trp Tyr Gln Gln Lys
                    165                 170                 175
Pro Gly Lys Ala Pro Lys Leu Leu Ile Tyr Ser Ala Ser Phe Leu Tyr
                    180                 185                 190
Ser Gly Val Pro Ser Arg Phe Ser Gly Ser Gly Ser Gly Thr Asp Phe
                    195                 200                 205
Thr Leu Thr Ile Ser Ser Leu Gln Pro Glu Asp Phe Ala Thr Tyr Tyr
                    210                 215                 220
```

```
Cys Gln Gln Ala Tyr Thr Thr Pro Ser Thr Phe Gly Gln Gly Thr Lys
225                 230                 235                 240

Val Glu Ile Lys

<210> SEQ ID NO 24
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ala Arg Ile Asn Pro Pro Asn Arg Ser Asn Gln Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Phe Arg Trp Val Met Asp Tyr Trp Gly Gln Gly
            100                 105                 110

Thr Leu Val Thr Val Ser Ser Gly Gly Ser Ser Arg Ser Ser Ser Ser
        115                 120                 125

Gly Gly Gly Gly Ser Gly Gly Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Asp Val Ser Thr Ala Val Ala Trp Tyr Gln Gln Lys
                165                 170                 175

Pro Gly Lys Ala Pro Lys Leu Leu Ile Tyr Ser Ala Ser Phe Leu Tyr
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Phe Ala Thr Thr Pro Ser Thr Phe Gly Gln Gly Thr Lys
225                 230                 235                 240

Val Glu Ile Lys

<210> SEQ ID NO 25
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Gly Ser Phe
```

```
            20                  25                  30
Ser Met Ser Trp Val Arg Gln Ala Pro Gly Gly Leu Glu Trp Val
        35                  40                  45
Ala Gly Leu Ser Ala Arg Ser Ser Leu Thr His Tyr Ala Asp Ser Val
50                  55                  60
Lys Gly Arg Phe Thr Ile Ser Arg Asp Asn Ala Lys Asn Ser Val Tyr
65                  70                  75                  80
Leu Gln Met Asn Ser Leu Arg Val Glu Asp Thr Ala Val Tyr Tyr Cys
                85                  90                  95
Ala Arg Arg Ser Tyr Asp Ser Gly Tyr Ala Gly His Phe Tyr Ser
            100                 105                 110
Tyr Met Asp Val Trp Gly Gln Gly Thr Leu Val Thr Val Ser Gly Gly
            115                 120                 125
Gly Gly Ser Gly Gly Gly Ser Gly Gly Gly Ser Ser Val Leu
        130                 135                 140
Thr Gln Pro Ser Val Ser Ala Ala Pro Gly Gln Lys Val Thr Ile
145                 150                 155                 160
Ser Cys Ser Gly Ser Thr Ser Asn Ile Gly Asn Asn Tyr Val Ser Trp
                165                 170                 175
Tyr Gln Gln His Pro Gly Lys Ala Pro Lys Leu Met Ile Tyr Asp Val
            180                 185                 190
Ser Lys Arg Pro Ser Gly Val Pro Asp Arg Phe Ser Gly Ser Lys Ser
            195                 200                 205
Gly Asn Ser Ala Ser Leu Asp Ile Ser Gly Leu Gln Ser Glu Asp Glu
        210                 215                 220
Ala Asp Tyr Tyr Cys Ala Ala Trp Asp Asp Ser Leu Ser Glu Phe Leu
225                 230                 235                 240
Phe Gly Thr Gly Thr Lys Leu Thr Val Leu Gly
            245                 250

<210> SEQ ID NO 26
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Gln Ser Gly Ala Glu Val Lys Lys Pro Gly Ser
1               5                   10                  15
Ser Val Lys Val Ser Cys Lys Ala Ser Gly Gly Thr Leu Ser Ser Tyr
            20                  25                  30
Thr Val Ser Trp Leu Arg Gln Ala Pro Gly Gln Gly Leu Glu Trp Met
        35                  40                  45
Gly Arg Ile Ile Pro Ile Leu Asp Arg Ala Asn Tyr Ala Gln Lys Phe
50                  55                  60
Gln Gly Arg Val Thr Ile Thr Ala Asp Lys Ser Thr Ser Thr Ala Tyr
65                  70                  75                  80
Met Glu Leu Asn Ser Leu Arg Ser Asp Asp Thr Ala Val Tyr Tyr Cys
                85                  90                  95
Ala Arg Ser Ile Gly Ala Ala Gly Asp Gly Val Trp Phe Asp Pro Trp
            100                 105                 110
Gly Gln Gly Thr Met Val Thr Val Ser Ser Gly Ser Ser Arg Ser
        115                 120                 125
```

```
Ser Ser Ser Gly Gly Gly Ser Gly Gly Gly Gln Ala Val Leu
    130             135             140

Thr Gln Pro Ser Val Ser Gly Ala Pro Gly Gln Arg Val Thr Ile
145             150             155                 160

Ser Cys Thr Gly Ser Ser Ser Asn Ile Gly Ala Gly Tyr Asp Val His
                165                 170                 175

Trp Tyr Gln Gln Leu Pro Gly Thr Ala Pro Lys Leu Leu Ile Phe Asp
            180                 185                 190

Asn Lys Asn Arg Pro Ser Gly Val Pro Asp Arg Phe Ser Gly Ser Asn
            195                 200                 205

Ser Gly Thr Ser Ala Ser Leu Ala Ile Thr Gly Leu Gln Ala Glu Asp
    210                 215                 220

Glu Ala Glu Tyr Tyr Cys Gln Ser Tyr Asp Asn Asn Leu Ser Gly Arg
225                 230                 235                 240

Val Phe Gly Gly Gly Thr Lys Leu Thr Val
                245                 250

<210> SEQ ID NO 27
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Leu Val Gln Pro Gly Gly Ser Leu Arg Leu Ser Cys Ala Ala Ser Gly
1               5                   10                  15

Phe Thr Phe Asp Asp Tyr Ala Met His Trp Val Arg Gln Ala Pro Gly
            20                  25                  30

Lys Gly Leu Glu Trp Val Ser Ser Ile Ser Trp His Ser Arg Thr Ile
        35                  40                  45

Ala Tyr Ala Asp Ser Val Lys Gly Arg Phe Ser Ile Ser Arg Asp Asn
    50                  55                  60

Ala Lys Asn Ser Leu Tyr Leu Gln Met Asn Ser Leu Arg Pro Glu Asp
65                  70                  75                  80

Thr Ala Val Tyr Tyr Cys Ala Lys Ala Ser Tyr Leu Ser Thr Ser Ser
                85                  90                  95

Ser Leu Asp Tyr Trp Gly Arg Gly Thr Leu Val Thr Val Ser Ser Gly
            100                 105                 110

Gly Ser Ser Arg Ser Ser Ser Gly Gly Gly Ser Gly Gly Gly
        115                 120                 125

Gly Gln Ser Val Leu Thr Gln Pro Gly Ser Val Ser Gly Ser Pro Gly
    130                 135                 140

Gln Ser Ile Thr Ile Ser Cys Thr Gly Thr Ser Ser Asp Val Gly Gly
145                 150                 155                 160

Tyr Asn Tyr Val Ser Trp Tyr Gln Gln His Pro Gly Lys Ala Pro Lys
                165                 170                 175

Leu Met Ile Tyr Glu Gly Ser Lys Arg Pro Ser Gly Val Ser Asn Arg
            180                 185                 190

Phe Ser Gly Ser Lys Ser Gly Asn Thr Ala Ser Leu Thr Ile Ser Gly
        195                 200                 205

Leu Gln Ala Glu Asp Glu Ala Asp Tyr Tyr Cys Ser Ser Tyr Thr Thr
    210                 215                 220

Arg Ser Thr Arg Val Phe Gly Gly Gly Thr Lys Leu Thr Val Leu
225                 230                 235
```

```
<210> SEQ ID NO 28
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Gly Met Ser Trp Val Arg Gln Ala Pro Gly Lys Gly Leu Glu Trp Val
        35                  40                  45

Ser Tyr Ile Tyr Pro Tyr Ser Gly Ala Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Ser Gly Tyr Tyr Arg Ile Ser Ser Ala Met Asp Val Trp
            100                 105                 110

Gly Gln Gly Thr Leu Val Thr Val Ser Ala Gly Gly Ser Ser Arg Ser
        115                 120                 125

Ser Ser Ser Gly Gly Gly Gly Ser Gly Gly Gly Gly Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Asn Ile Lys Arg Phe Leu Ala Trp Tyr
                165                 170                 175

Gln Gln Lys Pro Gly Lys Ala Pro Lys Leu Leu Ile Tyr Gly Ala Ser
            180                 185                 190

Thr Arg Glu Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Tyr Tyr Arg Ser Pro His Thr Phe Gly Gln
225                 230                 235                 240

Gly Thr Lys Val Glu Ile Lys Arg Gly Gly
                245                 250

<210> SEQ ID NO 29
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ala Gln Val Gln Leu Val Gln Ser Gly Ala Glu Val Lys Lys Pro Gly
1               5                   10                  15

Ala Ser Val Lys Val Ser Cys Lys Ala Ser Gly Tyr Thr Phe Thr Ser
            20                  25                  30

Tyr Ala Met His Trp Val Arg Gln Ala Pro Gly Gln Arg Leu Glu Trp
        35                  40                  45
```

```
Met Gly Trp Met Asn Ala Gly Asn Gly Asn Thr Lys Tyr Ser Gln Lys
 50                  55                  60

Phe Gln Gly Arg Val Thr Ile Thr Arg Asp Thr Ser Ala Ser Thr Ala
 65                  70                  75                  80

Tyr Met Glu Leu Ser Ser Leu Arg Ser Glu Asp Thr Ala Val Tyr Tyr
                 85                  90                  95

Cys Ala Arg Asp Arg Val Pro Thr Ile Pro Ala Tyr Arg Ile Asp Tyr
                100                 105                 110

Trp Gly Gln Gly Thr Leu Val Thr Val Ser Ser Leu Glu Gly Gly Gly
                115                 120                 125

Gly Ser Gly Gly Gly Ser Gly Gly Ala Ser Asp Ile Gln Met
                130                 135                 140

Thr Gln Ser Pro Ser Ser Val Ser Ala Ser Val Gly Asp Arg Val Thr
145                 150                 155                 160

Ile Thr Cys Arg Ala Ser Gln Gly Ile Ser Ser Trp Leu Ala Trp Tyr
                165                 170                 175

Gln Gln Lys Pro Gly Lys Ala Pro Arg Leu Leu Ile Tyr Ala Ala Ser
                180                 185                 190

Ser Leu Gln Ser Gly Val Pro Ser Arg Phe Ser Gly Ser Gly Ser Gly
                195                 200                 205

Thr Asp Phe Thr Leu Thr Ile Ser Ser Leu Gln Pro Glu Asp Phe Ala
                210                 215                 220

Thr Tyr Tyr Cys Gln Gln Ala Asn Ser Phe Pro Leu Thr Phe Gly Gly
225                 230                 235                 240

Gly Thr Lys Leu Glu Ile Lys Arg
                245

<210> SEQ ID NO 30
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Gln Val Gln Leu Val Gln Ser Gly Ala Glu Val Lys Lys Pro Gly
 1               5                  10                  15

Ala Ser Val Lys Val Ser Cys Lys Ala Ser Gly Tyr Thr Phe Thr Ser
                 20                  25                  30

Tyr Ala Met His Trp Val Arg Gln Ala Pro Gly Gln Arg Leu Glu Trp
                 35                  40                  45

Met Gly Trp Ile Asn Ala Gly Asn Gly Asn Thr Lys Tyr Ser Gln Lys
 50                  55                  60

Phe Gln Gly Arg Val Thr Ile Thr Arg Asp Thr Ser Ala Ser Thr Ala
 65                  70                  75                  80

Tyr Met Glu Leu Ser Ser Leu Arg Ser Glu Asp Thr Ala Val Tyr Tyr
                 85                  90                  95

Cys Ala Arg Gly Pro Arg Ser Tyr Gly Ala Gly Gly Met Asp Val Trp
                100                 105                 110

Gly Gln Gly Thr Leu Val Thr Val Ser Ser Leu Glu Gly Gly Gly Gly
                115                 120                 125

Ser Gly Gly Gly Ser Gly Gly Gly Ala Ser Asp Ile Gln Met Thr
                130                 135                 140

Gln Ser Pro Ser Ser Val Ser Ala Ser Val Gly Asp Arg Val Thr Ile
```

```
                      145                 150                 155                 160
Thr Cys Arg Ala Ser Gln Gly Ile Ser Ser Trp Leu Ala Trp Tyr Gln
                    165                 170                 175

Gln Lys Pro Gly Lys Ala Pro Lys Phe Leu Ile Tyr Ala Ala Ser Ser
                180                 185                 190

Leu Gln Ser Gly Val Pro Ser Arg Phe Ser Gly Ser Gly Ser Gly Thr
            195                 200                 205

Asp Phe Thr Leu Thr Ile Ser Ser Leu Gln Pro Glu Asp Phe Ala Thr
        210                 215                 220

Tyr Tyr Cys Gln Gln Ala Asn Ser Phe Pro Leu Thr Phe Gly Gly Gly
225                 230                 235                 240

Thr Lys Val Glu Ile Lys Arg
                245

<210> SEQ ID NO 31
<211> LENGTH: 51
<212> TYPE: PRT
<213> ORGANISM: Unknown
<220> FEATURE:
<223> OTHER INFORMATION: Description of Unknown:
      Platelet Derived Growth Factor Receptor (PDGFR) TM domain

<400> SEQUENCE: 31

Ala Val Gly Gln Asp Thr Gln Glu Val Ile Val Val Pro His Ser Leu
1               5                   10                  15

Pro Phe Lys Val Val Val Ile Ser Ala Ile Leu Ala Leu Val Val Leu
                20                  25                  30

Thr Ile Ile Ser Leu Ile Ile Leu Ile Met Leu Trp Gln Lys Lys Pro
            35                  40                  45

Arg Arg Thr
    50

<210> SEQ ID NO 32
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Asp Val Val Cys Cys His Ser Ile Tyr Gly Lys Lys Lys Gly Asp
1               5                   10                  15

Ile Asp Thr Tyr Arg Tyr Ile Gly Ser Ser Gly Thr Gly Cys Val Val
                20                  25                  30

Ile Val Gly Arg Ile Val Leu Ser Gly Ser Gly Thr Ser Ala Pro Ile
            35                  40                  45

Thr Ala Tyr Ala Gln Gln Thr Arg Gly Leu Leu Gly Cys Ile Ile Thr
        50                  55                  60

Ser Leu Thr Gly Arg Asp Lys Asn Gln Val Glu Gly Glu Val Gln Ile
65                  70                  75                  80

Val Ser Thr Ala Thr Gln Thr Phe Leu Ala Thr Cys Ile Asn Gly Val
                85                  90                  95

Cys Trp Ala Val Tyr His Gly Ala Gly Thr Arg Thr Ile Ala Ser Pro
                100                 105                 110

Lys Gly Pro Val Ile Gln Met Tyr Thr Asn Val Asp Gln Asp Leu Val
            115                 120                 125

Gly Trp Pro Ala Pro Gln Gly Ser Arg Ser Leu Thr Pro Cys Thr Cys
```

```
                130                 135                 140
Gly Ser Ser Asp Leu Tyr Leu Val Thr Arg His Ala Asp Val Ile Pro
145                 150                 155                 160

Val Arg Arg Arg Gly Asp Ser Arg Gly Ser Leu Leu Ser Pro Arg Pro
                165                 170                 175

Ile Ser Tyr Leu Lys Gly Ser Ser Gly Gly Pro Leu Leu Cys Pro Ala
                180                 185                 190

Gly His Ala Val Gly Leu Phe Arg Ala Ala Val Cys Thr Arg Gly Val
                195                 200                 205

Ala Lys Ala Val Asp Phe Ile Pro Val Glu Asn Leu Glu Thr Thr Met
                210                 215                 220

Arg Ser Pro Val Phe Thr Asp Asn Ser Ser Pro Pro Ala Val Thr Leu
225                 230                 235                 240

Thr His Pro Ile Thr Lys Ile Asp Arg Glu Val Leu Tyr Gln Glu Phe
                245                 250                 255

Asp Glu Met Glu Glu Cys Ser Gln His
                260                 265

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Thr Tyr Arg Tyr Ile
1               5

<210> SEQ ID NO 34
<211> LENGTH: 537
<212> TYPE: PRT
<213> ORGANISM: Rattus sp.

<400> SEQUENCE: 34

Met Gly Arg Arg Ser Ala Leu Ala Leu Ala Val Val Ser Ala Leu Leu
1               5                   10                  15

Cys Gln Val Trp Ser Ser Gly Val Phe Glu Leu Lys Leu Gln Glu Phe
                20                  25                  30

Val Asn Lys Lys Gly Leu Leu Gly Asn Arg Asn Cys Cys Arg Gly Gly
                35                  40                  45

Ser Gly Pro Pro Cys Ala Cys Arg Thr Phe Phe Arg Val Cys Leu Lys
                50                  55                  60

His Tyr Gln Ala Ser Val Ser Pro Glu Pro Pro Cys Thr Tyr Gly Ser
65                  70                  75                  80

Ala Val Thr Ala Val Leu Gly Val Asp Ser Phe Ser Leu Pro Asp Gly
                85                  90                  95

Ala Gly Ile Asp Pro Ala Phe Ser Asn Pro Ile Arg Phe Pro Phe Gly
                100                 105                 110

Phe Thr Trp Pro Gly Thr Phe Ser Leu Ile Ile Glu Ala Leu His Thr
                115                 120                 125

Asp Ser Pro Asp Asp Leu Ala Thr Glu Asn Pro Glu Arg Leu Ile Ser
                130                 135                 140

Arg Leu Thr Thr Gln Arg His Leu Thr Val Gly Glu Glu Trp Ser Gln
145                 150                 155                 160

Asp Leu His Ser Ser Gly Arg Thr Asp Leu Arg Tyr Ser Tyr Arg Phe
```

```
                 165                 170                 175
Val Cys Asp Glu His Tyr Tyr Gly Glu Gly Cys Ser Val Phe Cys Arg
            180                 185                 190
Pro Arg Asp Asp Ala Phe Gly His Phe Thr Cys Gly Glu Arg Gly Glu
        195                 200                 205
Lys Met Cys Asp Pro Gly Trp Lys Gly Gln Tyr Cys Thr Asp Pro Ile
    210                 215                 220
Cys Leu Pro Gly Cys Asp Asp Gln His Gly Tyr Cys Asp Lys Pro Gly
225                 230                 235                 240
Glu Cys Lys Cys Arg Val Gly Trp Gln Gly Arg Tyr Cys Asp Glu Cys
                245                 250                 255
Ile Arg Tyr Pro Gly Cys Leu His Gly Thr Cys Gln Gln Pro Trp Gln
            260                 265                 270
Cys Asn Cys Gln Glu Gly Trp Gly Gly Leu Phe Cys Asn Gln Asp Leu
        275                 280                 285
Asn Tyr Cys Thr His His Lys Pro Cys Arg Asn Gly Ala Thr Cys Thr
    290                 295                 300
Asn Thr Gly Gln Gly Ser Tyr Thr Cys Ser Cys Arg Pro Gly Tyr Thr
305                 310                 315                 320
Gly Ala Asn Cys Glu Leu Glu Val Asp Glu Cys Ala Pro Ser Pro Cys
                325                 330                 335
Arg Asn Gly Gly Ser Cys Thr Asp Leu Glu Asp Ser Tyr Ser Cys Thr
            340                 345                 350
Cys Pro Pro Gly Phe Tyr Gly Lys Val Cys Glu Leu Ser Ala Met Thr
        355                 360                 365
Cys Ala Asp Gly Pro Cys Phe Asn Gly Gly Arg Cys Ser Asp Asn Pro
    370                 375                 380
Asp Gly Gly Tyr Thr Cys His Cys Pro Ala Gly Phe Ser Gly Phe Asn
385                 390                 395                 400
Cys Glu Lys Lys Ile Asp Leu Cys Ser Ser Ser Pro Cys Ser Asn Gly
                405                 410                 415
Ala Lys Cys Val Asp Leu Gly Asn Ser Tyr Leu Cys Arg Cys Gln Thr
            420                 425                 430
Gly Phe Ser Gly Arg Tyr Cys Glu Asp Asn Val Asp Asp Cys Ala Ser
        435                 440                 445
Ser Pro Cys Ala Asn Gly Gly Thr Cys Arg Asp Ser Val Asn Asp Phe
    450                 455                 460
Ser Cys Thr Cys Pro Pro Gly Tyr Thr Gly Arg Asn Cys Ser Ala Pro
465                 470                 475                 480
Val Ser Arg Cys Glu His Ala Pro Cys His Asn Gly Ala Thr Cys His
                485                 490                 495
Gln Arg Gly Gln Arg Tyr Met Cys Glu Cys Ala Gln Gly Tyr Gly Gly
            500                 505                 510
Ala Asn Cys Gln Phe Leu Leu Pro Glu Pro Pro Asp Leu Ile Val
        515                 520                 525
Ala Ala Gln Gly Gly Ser Phe Pro Trp
530                 535

<210> SEQ ID NO 35
<211> LENGTH: 177
<212> TYPE: PRT
<213> ORGANISM: Rattus sp.

<400> SEQUENCE: 35
```

Val Ala Val Cys Ala Gly Val Val Leu Val Leu Leu Leu Leu Gly
1               5                   10                  15

Cys Ala Ala Val Val Cys Val Arg Leu Lys Leu Gln Lys His Gln
            20                  25                  30

Pro Pro Pro Asp Pro Cys Gly Gly Glu Thr Glu Thr Met Asn Asn Leu
        35                  40                  45

Ala Asn Cys Gln Arg Glu Lys Asp Val Ser Val Ser Ile Ile Gly Ala
50                  55                  60

Thr Gln Ile Lys Asn Thr Asn Lys Lys Ala Asp Phe His Gly Asp His
65                  70                  75                  80

Gly Ala Asp Lys Ser Ser Phe Lys Ala Arg Tyr Pro Thr Val Asp Tyr
                85                  90                  95

Asn Leu Ile Arg Asp Leu Lys Gly Asp Glu Ala Thr Val Arg Asp Ala
            100                 105                 110

His Ser Lys Arg Asp Thr Lys Cys Gln Ser Gln Gly Ser Val Gly Glu
            115                 120                 125

Glu Lys Ser Thr Ser Thr Leu Arg Gly Gly Glu Val Pro Asp Arg Lys
    130                 135                 140

Arg Pro Glu Ser Val Tyr Ser Thr Ser Lys Asp Thr Lys Tyr Gln Ser
145                 150                 155                 160

Val Tyr Val Leu Ser Ala Glu Lys Asp Glu Cys Val Ile Ala Thr Glu
                165                 170                 175

Val

<210> SEQ ID NO 36
<211> LENGTH: 529
<212> TYPE: PRT
<213> ORGANISM: Homo sapiens

<400> SEQUENCE: 36

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
            115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
                195                 200                 205

Leu Pro Gly Trp Thr Gly Glu Tyr Cys Gln Gln Pro Ile Cys Leu Ser
210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
                260                 265                 270

Asp Glu Gly Trp Gly Gly Leu Phe Cys Asp Gln Asp Leu Asn Tyr Cys
                275                 280                 285

Thr His His Ser Pro Cys Lys Asn Gly Ala Thr Cys Ser Asn Ser Gly
            290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
                340                 345                 350

Gly Tyr Tyr Gly Leu His Cys Glu His Ser Thr Leu Ser Cys Ala Asp
            355                 360                 365

Ser Pro Cys Phe Asn Gly Gly Ser Cys Arg Glu Arg Asn Gln Gly Ala
            370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
                420                 425                 430

Thr Gly Thr Tyr Cys Glu Leu His Val Ser Asp Cys Ala Arg Asn Pro
            435                 440                 445

Cys Ala His Gly Gly Thr Cys His Asp Leu Glu Asn Gly Leu Met Cys
450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
            515                 520                 525

Trp

<210> SEQ ID NO 37
<211> LENGTH: 156
<212> TYPE: PRT
<213> ORGANISM: Homo sapiens

<400> SEQUENCE: 37

Val Ala Val Ser Leu Gly Val Gly Leu Ala Val Leu Val Leu Leu
1               5                   10                  15

Gly Met Val Ala Val Ala Val Arg Gln Leu Arg Leu Arg Arg Pro Asp
                20                  25                  30

```
Asp Gly Ser Arg Glu Ala Met Asn Asn Leu Ser Asp Phe Gln Lys Asp
             35                  40                  45

Asn Leu Ile Pro Ala Ala Gln Leu Lys Asn Thr Asn Gln Lys Lys Glu
 50                  55                  60

Leu Glu Val Asp Cys Gly Leu Asp Lys Ser Asn Cys Gly Lys Gln Gln
 65                  70                  75                  80

Asn His Thr Leu Asp Tyr Asn Leu Ala Pro Gly Pro Leu Gly Arg Gly
                 85                  90                  95

Thr Met Pro Gly Lys Phe Pro His Ser Asp Lys Ser Leu Gly Glu Lys
                100                 105                 110

Ala Pro Leu Arg Leu His Ser Glu Lys Pro Glu Cys Arg Ile Ser Ala
                115                 120                 125

Ile Cys Ser Pro Arg Asp Ser Met Tyr Gln Ser Val Cys Leu Ile Ser
            130                 135                 140

Glu Arg Asn Glu Cys Val Ile Ala Thr Glu Val
145                 150                 155

<210> SEQ ID NO 38
<211> LENGTH: 532
<212> TYPE: PRT
<213> ORGANISM: Mus sp.

<400> SEQUENCE: 38

Met Thr Pro Ala Ser Arg Ser Ala Cys Arg Trp Ala Leu Leu Leu Leu
 1               5                  10                  15

Ala Val Leu Trp Pro Gln Gln Arg Ala Ala Gly Ser Gly Ile Phe Gln
                 20                  25                  30

Leu Arg Leu Gln Glu Phe Val Asn Gln Arg Gly Met Leu Ala Asn Gly
             35                  40                  45

Gln Ser Cys Glu Pro Gly Cys Arg Thr Phe Phe Arg Ile Cys Leu Lys
 50                  55                  60

His Phe Gln Ala Thr Phe Ser Glu Gly Pro Cys Thr Phe Gly Asn Val
 65                  70                  75                  80

Ser Thr Pro Val Leu Gly Thr Asn Ser Phe Val Val Arg Asp Lys Asn
                 85                  90                  95

Ser Gly Ser Gly Arg Asn Pro Leu Gln Leu Pro Phe Asn Phe Thr Trp
                100                 105                 110

Pro Gly Thr Phe Ser Leu Asn Ile Gln Ala Trp His Thr Pro Gly Asp
            115                 120                 125

Asp Leu Arg Pro Glu Thr Ser Pro Gly Asn Ser Leu Ile Ser Gln Ile
            130                 135                 140

Ile Ile Gln Gly Ser Leu Ala Val Gly Lys Ile Trp Arg Thr Asp Glu
145                 150                 155                 160

Gln Asn Asp Thr Leu Thr Arg Leu Ser Tyr Ser Tyr Arg Val Ile Cys
                165                 170                 175

Ser Asp Asn Tyr Tyr Gly Glu Ser Cys Ser Arg Leu Cys Lys Lys Arg
                180                 185                 190

Asp Asp His Phe Gly His Tyr Glu Cys Gln Pro Asp Gly Ser Leu Ser
            195                 200                 205

Cys Leu Pro Gly Trp Thr Gly Lys Tyr Cys Asp Gln Pro Ile Cys Leu
            210                 215                 220

Ser Gly Cys His Glu Gln Asn Gly Tyr Cys Ser Lys Pro Asp Glu Cys
225                 230                 235                 240

Ile Cys Arg Pro Gly Trp Gln Gly Arg Leu Cys Asn Glu Cys Ile Pro
                245                 250                 255
```

His Asn Gly Cys Arg His Gly Thr Cys Ser Ile Pro Trp Gln Cys Ala
                260                 265                 270

Cys Asp Glu Gly Trp Gly Leu Phe Cys Asp Gln Asp Leu Asn Tyr
            275                 280                 285

Cys Thr His His Ser Pro Cys Lys Asn Gly Ser Thr Cys Ser Asn Ser
        290                 295                 300

Gly Pro Lys Gly Tyr Thr Cys Thr Cys Leu Pro Gly Tyr Thr Gly Glu
305                 310                 315                 320

His Cys Glu Leu Gly Leu Ser Lys Cys Ala Ser Asn Pro Cys Arg Asn
                325                 330                 335

Gly Gly Ser Cys Lys Asp Gln Glu Asn Ser Tyr His Cys Leu Cys Pro
            340                 345                 350

Pro Gly Tyr Tyr Gly Gln His Cys Glu His Ser Thr Leu Thr Cys Ala
            355                 360                 365

Asp Ser Pro Cys Phe Asn Gly Gly Ser Cys Arg Glu Arg Asn Gln Gly
        370                 375                 380

Ser Ser Tyr Ala Cys Glu Cys Pro Pro Asn Phe Thr Gly Ser Asn Cys
385                 390                 395                 400

Glu Lys Lys Val Asp Arg Cys Thr Ser Asn Pro Cys Ala Asn Gly Gly
                405                 410                 415

Gln Cys Gln Asn Arg Gly Pro Ser Arg Thr Cys Arg Cys Arg Pro Gly
            420                 425                 430

Phe Thr Gly Thr His Cys Glu Leu His Ile Ser Asp Cys Ala Arg Ser
            435                 440                 445

Pro Cys Ala His Gly Gly Thr Cys His Asp Leu Glu Asn Gly Pro Val
        450                 455                 460

Cys Thr Cys Pro Ala Gly Phe Ser Gly Arg Arg Cys Glu Val Arg Ile
465                 470                 475                 480

Thr His Asp Ala Cys Ala Ser Gly Pro Cys Phe Asn Gly Ala Thr Cys
                485                 490                 495

Tyr Thr Gly Leu Ser Pro Asn Asn Phe Val Cys Asn Cys Pro Tyr Gly
            500                 505                 510

Phe Val Gly Ser Arg Cys Glu Phe Pro Val Gly Leu Pro Pro Ser Phe
            515                 520                 525

Pro Trp Val Ala
    530

<210> SEQ ID NO 39
<211> LENGTH: 154
<212> TYPE: PRT
<213> ORGANISM: Mus sp.

<400> SEQUENCE: 39

Val Ser Leu Gly Val Gly Leu Val Val Leu Val Leu Leu Val Met
1               5                   10                  15

Val Val Val Ala Val Arg Gln Leu Arg Leu Arg Arg Pro Asp Asp Glu
                20                  25                  30

Ser Arg Glu Ala Met Asn Asn Leu Ser Asp Phe Gln Lys Asp Asn Leu
            35                  40                  45

Ile Pro Ala Ala Gln Leu Lys Asn Thr Asn Gln Lys Lys Glu Leu Glu
        50                  55                  60

Val Asp Cys Gly Leu Asp Lys Ser Asn Cys Gly Lys Leu Gln Asn His
65                  70                  75                  80

Thr Leu Asp Tyr Asn Leu Ala Pro Gly Leu Leu Gly Arg Gly Gly Met

```
                    85                  90                  95
Pro Gly Lys Tyr Pro His Ser Asp Lys Ser Leu Gly Glu Lys Val Pro
                100                 105                 110
Leu Arg Leu His Ser Glu Lys Pro Glu Cys Arg Ile Ser Ala Ile Cys
            115                 120                 125
Ser Pro Arg Asp Ser Met Tyr Gln Ser Val Cys Leu Ile Ser Glu Glu
130                 135                 140
Arg Asn Glu Cys Val Ile Ala Thr Glu Val
145                 150
```

<210> SEQ ID NO 40
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Met Val Ser Lys Gly Glu Glu Asp Asn Met Ala Ile Ile Lys Glu Phe
1               5                   10                  15
Met Arg Phe Lys Val His Met Glu Gly Ser Val Asn Gly His Glu Phe
                20                  25                  30
Glu Ile Glu Gly Glu Gly Glu Gly Arg Pro Tyr Glu Gly Thr Gln Thr
            35                  40                  45
Ala Lys Leu Lys Val Thr Lys Gly Gly Pro Leu Pro Phe Ala Trp Asp
        50                  55                  60
Ile Leu Ser Pro Gln Phe Met Tyr Gly Ser Lys Ala Tyr Val Lys His
65                  70                  75                  80
Pro Ala Asp Ile Pro Asp Tyr Leu Lys Leu Ser Phe Pro Glu Gly Phe
                85                  90                  95
Lys Trp Glu Arg Val Met Asn Phe Glu Asp Gly Gly Val Val Thr Val
                100                 105                 110
Thr Gln Asp Ser Ser Leu Gln Asp Gly Glu Phe Ile Tyr Lys Val Lys
            115                 120                 125
Leu Arg Gly Thr Asn Phe Pro Ser Asp Gly Pro Val Met Gln Lys Lys
        130                 135                 140
Thr Met Gly Trp Glu Ala Ser Ser Glu Arg Met Tyr Pro Glu Asp Gly
145                 150                 155                 160
Ala Leu Lys Gly Glu Ile Lys Gln Arg Leu Lys Leu Lys Asp Gly Gly
                165                 170                 175
His Tyr Asp Ala Glu Val Lys Thr Thr Tyr Lys Ala Lys Lys Pro Val
                180                 185                 190
Gln Leu Pro Gly Ala Tyr Asn Val Asn Ile Lys Leu Asp Ile Thr Ser
            195                 200                 205
His Asn Glu Asp Tyr Thr Ile Val Glu Gln Tyr Glu Arg Ala Glu Gly
        210                 215                 220
Arg His Ser Thr Gly Gly Met Asp Glu Leu Tyr Lys
225                 230                 235
```

<210> SEQ ID NO 41
<211> LENGTH: 25
<212> TYPE: PRT
<213> ORGANISM: Unknown
<220> FEATURE:
<223> OTHER INFORMATION: Description of Unknown:
      amino acid sequence encoding SS for cis-inhibitors

```
<400> SEQUENCE: 41

Met Glu Thr Asp Thr Leu Leu Leu Trp Val Leu Leu Leu Trp Val Pro
1               5                   10                  15

Gly Ser Thr Gly Asp Gly Gly Gly Gly
            20                  25

<210> SEQ ID NO 42
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Gly Gly Gly Ser Thr Gly Asp Gly Gly Gly Glu Val Gln Leu
1               5                   10                  15

Val Glu Ser Gly Gly Gly Leu Val Gln Pro Gly Gly Ser Leu Arg Leu
                20                  25                  30

Ser Cys Ala Ala Ser Gly Phe Thr Phe Ser Ser Tyr Trp Ile His Trp
            35                  40                  45

Val Arg Gln Ala Pro Gly Lys Gly Leu Glu Trp Val Ala Arg Ile Asn
    50                  55                  60

Pro Pro Asn Arg Ser Asn Gln Tyr Ala Asp Ser Val Lys Gly Arg Phe
65                  70                  75                  80

Thr Ile Ser Ala Asp Thr Ser Lys Asn Thr Ala Tyr Leu Gln Met Asn
                85                  90                  95

Ser Leu Arg Ala Glu Asp Thr Ala Val Tyr Tyr Cys Ala Arg Gly Ser
            100                 105                 110

Gly Phe Arg Trp Val Met Asp Tyr Trp Gly Gln Gly Thr Leu Val Thr
        115                 120                 125

Val Ser Ser Gly Gly Ser Ser Arg Ser Ser Ser Gly Gly Gly Gly
    130                 135                 140

Ser Gly Gly Gly Gly Asp Ile Gln Met Thr Gln Ser Pro Ser Ser Leu
145                 150                 155                 160

Ser Ala Ser Val Gly Asp Arg Val Thr Ile Thr Cys Arg Ala Ser Gln
                165                 170                 175

Asp Val Ser Thr Ala Val Ala Trp Tyr Gln Gln Lys Pro Gly Lys Ala
            180                 185                 190

Pro Lys Leu Leu Ile Tyr Ser Ala Ser Phe Leu Tyr Ser Gly Val Pro
        195                 200                 205

Ser Arg Phe Ser Gly Ser Gly Ser Gly Thr Asp Phe Thr Leu Thr Ile
    210                 215                 220

Ser Ser Leu Gln Pro Glu Asp Phe Ala Thr Tyr Tyr Cys Gln Gln Phe
225                 230                 235                 240

Tyr Thr Thr Pro Ser Thr Phe Gly Gln Gly Thr Lys Val Glu Ile Lys
                245                 250                 255

Gly Gly Gly Ser Glu Gln Lys Leu Ile Ser Glu Glu Asp Leu Gly Gly
            260                 265                 270

Gly Ser

<210> SEQ ID NO 43
<211> LENGTH: 1225
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 43

```
Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Gln
            20                  25                  30

Val Gln Leu Val Glu Ser Gly Gly Asn Leu Val Gln Pro Gly Gly Ser
        35                  40                  45

Leu Arg Leu Ser Cys Ala Ala Ser Gly Phe Thr Phe Gly Ser Phe Ser
    50                  55                  60

Met Ser Trp Val Arg Gln Ala Pro Gly Gly Leu Glu Trp Val Ala
65                  70                  75                  80

Gly Leu Ser Ala Arg Ser Ser Leu Thr His Tyr Ala Asp Ser Val Lys
                85                  90                  95

Gly Arg Phe Thr Ile Ser Arg Asp Asn Ala Lys Asn Ser Val Tyr Leu
            100                 105                 110

Gln Met Asn Ser Leu Arg Val Glu Asp Thr Ala Val Tyr Tyr Cys Ala
        115                 120                 125

Arg Arg Ser Tyr Asp Ser Gly Tyr Ala Gly His Phe Tyr Ser Tyr
130                 135                 140

Met Asp Val Trp Gly Gln Gly Thr Leu Val Thr Val Ser Gly Gly Gly
145                 150                 155                 160

Gly Ser Gly Gly Gly Gly Ser Gly Gly Gly Gly Ser Ser Val Leu Thr
                165                 170                 175

Gln Pro Ser Ser Val Ser Ala Ala Pro Gly Gln Lys Val Thr Ile Ser
            180                 185                 190

Cys Ser Gly Ser Thr Ser Asn Ile Gly Asn Asn Tyr Val Ser Trp Tyr
        195                 200                 205

Gln Gln His Pro Gly Lys Ala Pro Lys Leu Met Ile Tyr Asp Val Ser
    210                 215                 220

Lys Arg Pro Ser Gly Val Pro Asp Arg Phe Ser Gly Ser Lys Ser Gly
225                 230                 235                 240

Asn Ser Ala Ser Leu Asp Ile Ser Gly Leu Gln Ser Glu Asp Glu Ala
                245                 250                 255

Asp Tyr Tyr Cys Ala Ala Trp Asp Asp Ser Leu Ser Glu Phe Leu Phe
            260                 265                 270

Gly Thr Gly Thr Lys Leu Thr Val Leu Gly Gly Gly Ser Met Ala
        275                 280                 285

Asp Val Gln Leu Val Glu Ser Gly Gly Gly Leu Val Gln Ala Gly Gly
    290                 295                 300

Ser Leu Arg Leu Ser Cys Ala Ala Ser Gly Arg Thr Ile Ser Met Ala
305                 310                 315                 320

Ala Met Ser Trp Phe Arg Gln Ala Pro Gly Lys Glu Arg Glu Phe Val
                325                 330                 335

Ala Gly Ile Ser Arg Ser Ala Gly Ser Ala Val His Ala Asp Ser Val
            340                 345                 350

Lys Gly Arg Phe Thr Ile Ser Arg Asp Asn Thr Lys Asn Thr Leu Tyr
        355                 360                 365

Leu Gln Met Asn Ser Leu Lys Ala Glu Asp Thr Ala Val Tyr Tyr Cys
    370                 375                 380

Ala Val Arg Thr Ser Gly Phe Phe Gly Ser Ile Pro Arg Thr Gly Thr
385                 390                 395                 400
```

Ala Phe Asp Tyr Trp Gly Gln Gly Thr Gln Val Thr Val Ser Gly Gly
                    405                 410                 415

Gly Gly Ser Thr Gly Asp Gly Gly Gly Glu Val Gln Leu Val Glu
            420                 425                 430

Ser Gly Gly Gly Leu Val Gln Pro Gly Gly Ser Leu Arg Leu Ser Cys
            435                 440                 445

Ala Ala Ser Gly Phe Thr Phe Ser Ser Tyr Trp Ile His Trp Val Arg
450                 455                 460

Gln Ala Pro Gly Lys Gly Leu Glu Trp Val Ala Arg Ile Asn Pro Pro
465                 470                 475                 480

Asn Arg Ser Asn Gln Tyr Ala Asp Ser Val Lys Gly Arg Phe Thr Ile
            485                 490                 495

Ser Ala Asp Thr Ser Lys Asn Thr Ala Tyr Leu Gln Met Asn Ser Leu
            500                 505                 510

Arg Ala Glu Asp Thr Ala Val Tyr Tyr Cys Ala Arg Gly Ser Gly Phe
            515                 520                 525

Arg Trp Val Met Asp Tyr Trp Gly Gln Gly Thr Leu Val Thr Val Ser
            530                 535                 540

Ser Gly Gly Ser Ser Arg Ser Ser Ser Ser Gly Gly Gly Gly Ser Gly
545                 550                 555                 560

Gly Gly Gly Asp Ile Gln Met Thr Gln Ser Pro Ser Ser Leu Ser Ala
                565                 570                 575

Ser Val Gly Asp Arg Val Thr Ile Thr Cys Arg Ala Ser Gln Asp Val
            580                 585                 590

Ser Thr Ala Val Ala Trp Tyr Gln Gln Lys Pro Gly Lys Ala Pro Lys
            595                 600                 605

Leu Leu Ile Tyr Ser Ala Ser Phe Leu Tyr Ser Gly Val Pro Ser Arg
            610                 615                 620

Phe Ser Gly Ser Gly Ser Gly Thr Asp Phe Thr Leu Thr Ile Ser Ser
625                 630                 635                 640

Leu Gln Pro Glu Asp Phe Ala Thr Tyr Tyr Cys Gln Gln Phe Tyr Thr
                645                 650                 655

Thr Pro Ser Thr Phe Gly Gln Gly Thr Lys Val Glu Ile Lys Gly Gly
            660                 665                 670

Gly Ser Glu Gln Lys Leu Ile Ser Glu Glu Asp Leu Gly Gly Gly Ser
            675                 680                 685

Ile Leu Asp Tyr Ser Phe Thr Gly Gly Ala Gly Arg Asp Ile Pro Pro
            690                 695                 700

Pro Gln Ile Glu Glu Ala Cys Glu Leu Pro Glu Cys Gln Val Asp Ala
705                 710                 715                 720

Gly Asn Lys Val Cys Asn Leu Gln Cys Asn Asn His Ala Cys Gly Trp
            725                 730                 735

Asp Gly Gly Asp Cys Ser Leu Asn Phe Asn Asp Pro Trp Lys Asn Cys
            740                 745                 750

Thr Gln Ser Leu Gln Cys Trp Lys Tyr Phe Ser Asp Gly His Cys Asp
            755                 760                 765

Ser Gln Cys Asn Ser Ala Gly Cys Leu Phe Asp Gly Phe Asp Cys Gln
            770                 775                 780

Leu Thr Glu Gly Gln Cys Asn Pro Leu Tyr Asp Gln Tyr Cys Lys Asp
785                 790                 795                 800

His Phe Ser Asp Gly His Cys Asp Gln Gly Cys Asn Ser Ala Glu Cys
                805                 810                 815

Glu Trp Asp Gly Leu Asp Cys Ala Glu His Val Pro Glu Arg Leu Ala

```
                820                 825                 830
Ala Gly Thr Leu Val Leu Val Val Leu Leu Pro Pro Asp Gln Leu Arg
                835                 840                 845
Asn Asn Ser Phe His Phe Leu Arg Glu Leu Ser His Val Leu His Thr
850                 855                 860
Asn Val Val Phe Lys Arg Asp Ala Gln Gly Gln Gln Met Ile Phe Pro
865                 870                 875                 880
Tyr Tyr Gly His Glu Glu Leu Arg Lys His Pro Ile Lys Arg Ser
                885                 890                 895
Thr Val Gly Trp Ala Thr Ser Ser Leu Leu Pro Gly Thr Ser Gly Gly
                900                 905                 910
Arg Gln Arg Arg Glu Leu Asp Pro Met Asp Ile Arg Gly Ser Ile Val
                915                 920                 925
Tyr Leu Glu Ile Asp Asn Arg Gln Cys Val Gln Ser Ser Ser Gln Cys
            930                 935                 940
Phe Gln Ser Ala Thr Asp Val Ala Ala Phe Leu Gly Ala Leu Ala Ser
945                 950                 955                 960
Leu Gly Ser Leu Asn Ile Pro Tyr Lys Ile Glu Ala Val Lys Ser Glu
                965                 970                 975
Pro Val Glu Pro Pro Leu Pro Ser Gln Leu His Leu Met Tyr Val Ala
                980                 985                 990
Ala Ala Ala Phe Val Leu Leu Phe Phe Val Gly Cys Gly Val Leu Leu
                995                 1000                1005
Ser Arg Lys Arg Arg Arg Met Lys Leu Leu Ser Ser Ile Glu Gln
    1010                1015                1020
Ala Cys Asp Ile Cys Arg Leu Lys Lys Leu Lys Cys Ser Lys Glu
    1025                1030                1035
Lys Pro Lys Cys Ala Lys Cys Leu Lys Asn Asn Trp Glu Cys Arg
    1040                1045                1050
Tyr Ser Pro Lys Thr Lys Arg Ser Pro Leu Thr Arg Ala His Leu
    1055                1060                1065
Thr Glu Val Glu Ser Arg Leu Glu Arg Leu Glu Gln Leu Phe Leu
    1070                1075                1080
Leu Ile Phe Pro Arg Glu Asp Leu Asp Met Ile Leu Lys Met Asp
    1085                1090                1095
Ser Leu Gln Asp Ile Lys Ala Leu Leu Thr Gly Leu Phe Val Gln
    1100                1105                1110
Asp Asn Val Asn Lys Asp Ala Val Thr Asp Arg Leu Ala Ser Val
    1115                1120                1125
Glu Thr Asp Met Pro Leu Thr Leu Arg Gln His Arg Ile Ser Ala
    1130                1135                1140
Thr Ser Ser Ser Glu Glu Ser Ser Asn Lys Gly Gln Arg Gln Leu
    1145                1150                1155
Thr Val Ser Ala Ala Ala Gly Gly Ser Gly Gly Ser Gly Gly Ser
    1160                1165                1170
Asp Ala Leu Asp Asp Phe Asp Leu Asp Met Leu Gly Ser Asp Ala
    1175                1180                1185
Leu Asp Asp Phe Asp Leu Asp Met Leu Gly Ser Asp Ala Leu Asp
    1190                1195                1200
Asp Phe Asp Leu Asp Met Leu Gly Ser Asp Ala Leu Asp Asp Phe
    1205                1210                1215
Asp Leu Asp Met Leu Gly Ser
    1220                1225
```

<210> SEQ ID NO 44
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Met Glu Thr Asp Thr Leu Leu Leu Trp Val Leu Leu Leu Trp Val Pro
1               5                   10                  15

Gly Ser Thr Gly Asp Gly Gly Gly Glu Val Gln Leu Val Glu Ser
            20                  25                  30

Gly Gly Gly Leu Val Gln Pro Gly Gly Ser Leu Arg Leu Ser Cys Ala
        35                  40                  45

Ala Ser Gly Phe Thr Phe Ser Ser Tyr Trp Ile His Trp Val Arg Gln
    50                  55                  60

Ala Pro Gly Lys Gly Leu Glu Trp Val Ala Arg Ile Asn Pro Pro Asn
65                  70                  75                  80

Arg Ser Asn Gln Tyr Ala Asp Ser Val Lys Gly Arg Phe Thr Ile Ser
                85                  90                  95

Ala Asp Thr Ser Lys Asn Thr Ala Tyr Leu Gln Met Asn Ser Leu Arg
            100                 105                 110

Ala Glu Asp Thr Ala Val Tyr Tyr Cys Ala Arg Gly Ser Gly Phe Arg
        115                 120                 125

Trp Val Met Asp Tyr Trp Gly Gln Gly Thr Leu Val Thr Val Ser Ser
130                 135                 140

Gly Gly Ser Ser Arg Ser Ser Ser Gly Gly Gly Ser Gly Gly
145                 150                 155                 160

Gly Gly Asp Ile Gln Met Thr Gln Ser Pro Ser Ser Leu Ser Ala Ser
                165                 170                 175

Val Gly Asp Arg Val Thr Ile Thr Cys Arg Ala Ser Gln Asp Val Ser
            180                 185                 190

Thr Ala Val Ala Trp Tyr Gln Gln Lys Pro Gly Lys Ala Pro Lys Leu
        195                 200                 205

Leu Ile Tyr Ser Ala Ser Phe Leu Tyr Ser Gly Val Pro Ser Arg Phe
    210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Phe Tyr Thr Thr
                245                 250                 255

Pro Ser Thr Phe Gly Gln Gly Thr Lys Val Glu Ile Lys Gly Gly Gly
            260                 265                 270

Ser Glu Gln Lys Leu Ile Ser Glu Glu Asp Leu Gly Gly Gly Ser Ala
        275                 280                 285

Val Gly Gln Asp Thr Gln Glu Val Ile Val Val Pro His Ser Leu Pro
    290                 295                 300

Phe Lys Val Val Val Ile Ser Ala Ile Leu Ala Leu Val Val Leu Thr
305                 310                 315                 320

Ile Ile Ser Leu Ile Ile Leu Ile Met Leu Trp Gln Lys Lys Pro Arg
                325                 330                 335

Arg Thr Met Val Ser Lys Gly Glu Glu Asp Asn Met Ala Ile Ile Lys
            340                 345                 350

Glu Phe Met Arg Phe Lys Val His Met Glu Gly Ser Val Asn Gly His
```

```
                355                 360                 365
Glu Phe Glu Ile Glu Gly Glu Gly Gly Arg Pro Tyr Glu Gly Thr
370                 375                 380

Gln Thr Ala Lys Leu Lys Val Thr Lys Gly Gly Pro Leu Pro Phe Ala
385                 390                 395                 400

Trp Asp Ile Leu Ser Pro Gln Phe Met Tyr Gly Ser Lys Ala Tyr Val
                405                 410                 415

Lys His Pro Ala Asp Ile Pro Asp Tyr Leu Lys Leu Ser Phe Pro Glu
                420                 425                 430

Gly Phe Lys Trp Glu Arg Val Met Asn Phe Glu Asp Gly Gly Val Val
                435                 440                 445

Thr Val Thr Gln Asp Ser Ser Leu Gln Asp Gly Glu Phe Ile Tyr Lys
450                 455                 460

Val Lys Leu Arg Gly Thr Asn Phe Pro Ser Asp Gly Pro Val Met Gln
465                 470                 475                 480

Lys Lys Thr Met Gly Trp Glu Ala Ser Ser Glu Arg Met Tyr Pro Glu
                485                 490                 495

Asp Gly Ala Leu Lys Gly Glu Ile Lys Gln Arg Leu Lys Leu Lys Asp
                500                 505                 510

Gly Gly His Tyr Asp Ala Glu Val Lys Thr Thr Tyr Lys Ala Lys Lys
                515                 520                 525

Pro Val Gln Leu Pro Gly Ala Tyr Asn Val Asn Ile Lys Leu Asp Ile
530                 535                 540

Thr Ser His Asn Glu Asp Tyr Thr Ile Val Glu Gln Tyr Glu Arg Ala
545                 550                 555                 560

Glu Gly Arg His Ser Thr Gly Gly Met Asp Glu Leu Tyr Lys
                565                 570

<210> SEQ ID NO 45
<211> LENGTH: 1245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gly Arg Arg Ser Ala Leu Ala Leu Ala Val Val Ser Ala Leu Leu
1               5                   10                  15

Cys Gln Val Trp Ser Ser Gly Val Phe Glu Leu Lys Leu Gln Glu Phe
                20                  25                  30

Val Asn Lys Lys Gly Leu Leu Gly Asn Arg Asn Cys Cys Arg Gly Gly
                35                  40                  45

Ser Gly Pro Pro Cys Ala Cys Arg Thr Phe Phe Arg Val Cys Leu Lys
50                  55                  60

His Tyr Gln Ala Ser Val Ser Pro Glu Pro Pro Cys Thr Tyr Gly Ser
65                  70                  75                  80

Ala Val Thr Ala Val Leu Gly Val Asp Ser Phe Ser Leu Pro Asp Gly
                85                  90                  95

Ala Gly Ile Asp Pro Ala Phe Ser Asn Pro Ile Arg Phe Pro Phe Gly
                100                 105                 110

Phe Thr Trp Pro Gly Thr Phe Ser Leu Ile Ile Glu Ala Leu His Thr
                115                 120                 125

Asp Ser Pro Asp Asp Leu Ala Thr Glu Asn Pro Glu Arg Leu Ile Ser
130                 135                 140
```

-continued

Arg Leu Thr Thr Gln Arg His Leu Thr Val Gly Glu Glu Trp Ser Gln
145                 150                 155                 160

Asp Leu His Ser Ser Gly Arg Thr Asp Leu Arg Tyr Ser Tyr Arg Phe
            165                 170                 175

Val Cys Asp Glu His Tyr Tyr Gly Glu Gly Cys Ser Val Phe Cys Arg
        180                 185                 190

Pro Arg Asp Asp Ala Phe Gly His Phe Thr Cys Gly Glu Arg Gly Glu
    195                 200                 205

Lys Met Cys Asp Pro Gly Trp Lys Gly Gln Tyr Cys Thr Asp Pro Ile
210                 215                 220

Cys Leu Pro Gly Cys Asp Asp Gln His Gly Tyr Cys Asp Lys Pro Gly
225                 230                 235                 240

Glu Cys Lys Cys Arg Val Gly Trp Gln Gly Arg Tyr Cys Asp Glu Cys
                245                 250                 255

Ile Arg Tyr Pro Gly Cys Leu His Gly Thr Cys Gln Gln Pro Trp Gln
            260                 265                 270

Cys Asn Cys Gln Glu Gly Trp Gly Gly Leu Phe Cys Asn Gln Asp Leu
        275                 280                 285

Asn Tyr Cys Thr His His Lys Pro Cys Arg Asn Gly Ala Thr Cys Thr
    290                 295                 300

Asn Thr Gly Gln Gly Ser Tyr Thr Cys Ser Cys Arg Pro Gly Tyr Thr
305                 310                 315                 320

Gly Ala Asn Cys Glu Leu Glu Val Asp Glu Cys Ala Pro Ser Pro Cys
                325                 330                 335

Arg Asn Gly Gly Ser Cys Thr Asp Leu Glu Asp Ser Tyr Ser Cys Thr
            340                 345                 350

Cys Pro Pro Gly Phe Tyr Gly Lys Val Cys Glu Leu Ser Ala Met Thr
        355                 360                 365

Cys Ala Asp Gly Pro Cys Phe Asn Gly Gly Arg Cys Ser Asp Asn Pro
    370                 375                 380

Asp Gly Gly Tyr Thr Cys His Cys Pro Ala Gly Phe Ser Gly Phe Asn
385                 390                 395                 400

Cys Glu Lys Lys Ile Asp Leu Cys Ser Ser Ser Pro Cys Ser Asn Gly
                405                 410                 415

Ala Lys Cys Val Asp Leu Gly Asn Ser Tyr Leu Cys Arg Cys Gln Thr
            420                 425                 430

Gly Phe Ser Gly Arg Tyr Cys Glu Asp Asn Val Asp Asp Cys Ala Ser
        435                 440                 445

Ser Pro Cys Ala Asn Gly Gly Thr Cys Arg Asp Ser Val Asn Asp Phe
    450                 455                 460

Ser Cys Thr Cys Pro Pro Gly Tyr Thr Gly Arg Asn Cys Ser Ala Pro
465                 470                 475                 480

Val Ser Arg Cys Glu His Ala Pro Cys His Asn Gly Ala Thr Cys His
                485                 490                 495

Gln Arg Gly Gln Arg Tyr Met Cys Glu Cys Ala Gln Gly Tyr Gly Gly
            500                 505                 510

Ala Asn Cys Gln Phe Leu Leu Pro Glu Pro Pro Pro Asp Leu Ile Val
        515                 520                 525

Ala Ala Gln Gly Gly Ser Phe Pro Trp Ser Arg Ala Asp Met Ala Ser
    530                 535                 540

Met Thr Gly Gly Gln Gln Met Gly Ser Thr Glu Asp Val Val Cys Cys
545                 550                 555                 560

His Ser Ile Tyr Gly Lys Lys Lys Gly Asp Ile Asp Thr Tyr Arg Tyr

```
                565                 570                 575
Ile Gly Ser Ser Gly Thr Gly Cys Val Val Ile Val Gly Arg Ile Val
            580                 585                 590
Leu Ser Gly Ser Gly Thr Ser Ala Pro Ile Thr Ala Tyr Ala Gln Gln
            595                 600                 605
Thr Arg Gly Leu Leu Gly Cys Ile Ile Thr Ser Leu Thr Gly Arg Asp
            610                 615                 620
Lys Asn Gln Val Glu Gly Glu Val Gln Ile Val Ser Thr Ala Thr Gln
625                 630                 635                 640
Thr Phe Leu Ala Thr Cys Ile Asn Gly Val Cys Trp Ala Val Tyr His
                645                 650                 655
Gly Ala Gly Thr Arg Thr Ile Ala Ser Pro Lys Gly Pro Val Ile Gln
                660                 665                 670
Met Tyr Thr Asn Val Asp Gln Asp Leu Val Gly Trp Pro Ala Pro Gln
                675                 680                 685
Gly Ser Arg Ser Leu Thr Pro Cys Thr Cys Gly Ser Ser Asp Leu Tyr
            690                 695                 700
Leu Val Thr Arg His Ala Asp Val Ile Pro Val Arg Arg Arg Gly Asp
705                 710                 715                 720
Ser Arg Gly Ser Leu Leu Ser Pro Arg Pro Ile Ser Tyr Leu Lys Gly
                725                 730                 735
Ser Ser Gly Gly Pro Leu Leu Cys Pro Ala Gly His Ala Val Gly Leu
            740                 745                 750
Phe Arg Ala Ala Val Cys Thr Arg Gly Val Ala Lys Ala Val Asp Phe
            755                 760                 765
Ile Pro Val Glu Asn Leu Glu Thr Thr Met Arg Ser Pro Val Phe Thr
770                 775                 780
Asp Asn Ser Ser Pro Pro Ala Val Thr Leu Thr His Pro Ile Thr Lys
785                 790                 795                 800
Ile Asp Arg Glu Val Leu Tyr Gln Glu Phe Asp Glu Met Glu Glu Cys
                805                 810                 815
Ser Gln His Tyr Pro Tyr Asp Val Pro Asp Tyr Ala Gly Ala Ser Ala
            820                 825                 830
Val Ala Val Cys Ala Gly Val Val Leu Val Leu Leu Leu Leu Leu Gly
            835                 840                 845
Cys Ala Ala Val Val Cys Val Arg Leu Lys Leu Gln Lys His Gln
            850                 855                 860
Pro Pro Pro Asp Pro Cys Gly Gly Glu Thr Glu Thr Met Asn Asn Leu
865                 870                 875                 880
Ala Asn Cys Gln Arg Glu Lys Asp Val Ser Val Ser Ile Ile Gly Ala
                885                 890                 895
Thr Gln Ile Lys Asn Thr Asn Lys Lys Ala Asp Phe His Gly Asp His
                900                 905                 910
Gly Ala Asp Lys Ser Ser Phe Lys Ala Arg Tyr Pro Thr Val Asp Tyr
            915                 920                 925
Asn Leu Ile Arg Asp Leu Lys Gly Asp Glu Ala Thr Val Arg Asp Ala
930                 935                 940
His Ser Lys Arg Asp Thr Lys Cys Gln Ser Gln Gly Ser Val Gly Glu
945                 950                 955                 960
Glu Lys Ser Thr Ser Thr Leu Arg Gly Gly Glu Val Pro Asp Arg Lys
                965                 970                 975
Arg Pro Glu Ser Val Tyr Ser Thr Ser Lys Asp Thr Lys Tyr Gln Ser
                980                 985                 990
```

Val Tyr Val Leu Ser Ala Glu Lys Asp Glu Cys Val Ile Ala Thr Glu
        995                 1000                1005

Val Val Ser Lys Gly Glu Glu Asp Asn Met Ala Ile Ile Lys Glu
    1010                1015                1020

Phe Met Arg Phe Lys Val His Met Glu Gly Ser Val Asn Gly His
    1025                1030                1035

Glu Phe Glu Ile Glu Gly Glu Gly Glu Gly Arg Pro Tyr Glu Gly
    1040                1045                1050

Thr Gln Thr Ala Lys Leu Lys Val Thr Lys Gly Gly Pro Leu Pro
    1055                1060                1065

Phe Ala Trp Asp Ile Leu Ser Pro Gln Phe Met Tyr Gly Ser Lys
    1070                1075                1080

Ala Tyr Val Lys His Pro Ala Asp Ile Pro Asp Tyr Leu Lys Leu
    1085                1090                1095

Ser Phe Pro Glu Gly Phe Lys Trp Glu Arg Val Met Asn Phe Glu
    1100                1105                1110

Asp Gly Gly Val Val Thr Val Thr Gln Asp Ser Ser Leu Gln Asp
    1115                1120                1125

Gly Glu Phe Ile Tyr Lys Val Lys Leu Arg Gly Thr Asn Phe Pro
    1130                1135                1140

Ser Asp Gly Pro Val Met Gln Lys Lys Thr Met Gly Trp Glu Ala
    1145                1150                1155

Ser Ser Glu Arg Met Tyr Pro Glu Asp Gly Ala Leu Lys Gly Glu
    1160                1165                1170

Ile Lys Gln Arg Leu Lys Leu Lys Asp Gly Gly His Tyr Asp Ala
    1175                1180                1185

Glu Val Lys Thr Thr Tyr Lys Ala Lys Lys Pro Val Gln Leu Pro
    1190                1195                1200

Gly Ala Tyr Asn Val Asn Ile Lys Leu Asp Ile Thr Ser His Asn
    1205                1210                1215

Glu Asp Tyr Thr Ile Val Glu Gln Tyr Glu Arg Ala Glu Gly Arg
    1220                1225                1230

His Ser Thr Gly Gly Met Asp Glu Leu Tyr Lys Ser
    1235                1240                1245

<210> SEQ ID NO 46
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Pro Pro Pro Gln Ile Glu Glu Ala Cys Glu Leu Pro Glu Cys Gln Val
1               5                   10                  15

Asp Ala Gly Asn Lys Val Cys Asn Leu Gln Cys Asn Asn His Ala Cys
            20                  25                  30

Gly Trp Asp Gly Gly Asp Cys Ser Leu Asn Phe Asn Asp Pro Trp Lys
        35                  40                  45

Asn Cys Thr Gln Ser Leu Gln Cys Trp Lys Tyr Phe Ser Asp Gly His
    50                  55                  60

Cys Asp Ser Gln Cys Asn Ser Ala Gly Cys Leu Phe Asp Gly Phe Asp
65                  70                  75                  80

Cys Gln Leu Thr Glu Gly Gln Cys Asn Pro Leu Tyr Asp Gln Tyr Cys

```
                    85                  90                  95
Lys Asp His Phe Ser Asp Gly His Cys Asp Gln Gly Cys Asn Ser Ala
                100                 105                 110
Glu Cys Glu Trp Asp Gly Leu Asp Cys Ala Glu His Val Pro Glu Arg
            115                 120                 125
Leu Ala Gly Thr Leu Val Leu Val Val Leu Pro Pro Asp Gln
        130                 135                 140
Leu Arg Asn Asn Ser Phe His Phe Leu Arg Glu Leu Ser His Val Leu
145                 150                 155                 160
His Thr Asn Val Val Phe Lys Arg Asp Ala Gln Gly Gln Gln Met Ile
                165                 170                 175
Phe Pro Tyr Tyr Gly His Glu Glu Leu Arg Lys His Pro Ile Lys
            180                 185                 190
Arg Ser Thr Val Gly Trp Ala Thr Ser Leu Leu Pro Gly Thr Ser
            195                 200                 205
Gly Gly Arg Gln Arg Arg Glu Leu Asp Pro Met Asp Ile Arg Gly Ser
        210                 215                 220
Ile Val Tyr Leu Glu Ile Asp Asn Arg Gln Cys Val Gln Ser Ser Ser
225                 230                 235                 240
Gln Cys Phe Gln Ser Ala Thr Asp Val Ala Ala Phe Leu Gly Ala Leu
                245                 250                 255
Ala Ser Leu Gly Ser Leu Asn Ile Pro Tyr Lys Ile Glu Ala Val Lys
            260                 265                 270
Ser Glu Pro Val Glu Pro Leu Pro Ser Gln Leu His Leu Met Tyr
            275                 280                 285
Val Ala Ala Ala Phe Val Leu Leu Phe Phe Val Gly Cys Gly Val
        290                 295                 300
Leu Leu Ser Arg Lys Arg Arg
305                 310

<210> SEQ ID NO 47
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Pro Pro Ser Thr Pro Pro Ala Thr Cys Leu Ser Gln Tyr Cys Ala Asp
1               5                   10                  15
Lys Ala Arg Asp Gly Val Cys Asp Glu Ala Cys Asn Ser His Ala Cys
            20                  25                  30
Gln Trp Asp Gly Gly Asp Cys Ser Leu Thr Met Glu Asn Pro Trp Ala
        35                  40                  45
Asn Cys Ser Ser Pro Leu Pro Cys Trp Asp Tyr Ile Asn Asn Gln Cys
    50                  55                  60
Asp Glu Leu Cys Asn Thr Val Glu Cys Leu Phe Asp Asn Phe Glu Cys
65                  70                  75                  80
Gln Gly Asn Ser Lys Thr Cys Lys Tyr Asp Lys Tyr Cys Ala Asp His
                85                  90                  95
Phe Lys Asp Asn His Cys Asp Gln Gly Cys Asn Ser Glu Glu Cys Gly
            100                 105                 110
Trp Asp Gly Leu Asp Cys Ala Ala Asp Gln Pro Glu Asn Leu Ala Glu
        115                 120                 125
```

```
Gly Thr Leu Val Ile Val Val Leu Met Pro Pro Glu Gln Leu Leu Gln
    130                 135                 140

Asp Ala Arg Ser Phe Leu Arg Ala Leu Gly Thr Leu Leu His Thr Asn
145                 150                 155                 160

Leu Arg Ile Lys Arg Asp Ser Gln Gly Glu Leu Met Val Tyr Pro Tyr
                165                 170                 175

Tyr Gly Glu Lys Ser Ala Ala Met Lys Lys Gln Arg Met Thr Arg Arg
                180                 185                 190

Ser Leu Pro Gly Glu Gln Glu Gln Glu Val Ala Gly Ser Lys Val Phe
                195                 200                 205

Leu Glu Ile Asp Asn Arg Gln Cys Val Gln Asp Ser Asp His Cys Phe
210                 215                 220

Lys Asn Thr Asp Ala Ala Ala Leu Leu Ala Ser His Ala Ile Gln
225                 230                 235                 240

Gly Thr Leu Ser Tyr Pro Leu Val Ser Val Ser Glu Ser Leu Thr
                245                 250                 255

Pro Glu Arg Thr Gln Leu Leu Tyr Leu Leu Ala Val Ala Val Val Ile
                260                 265                 270

Ile Leu Phe Ile Ile Leu Leu Gly Val Ile Met Ala Lys Arg Lys Arg
                275                 280                 285

Lys

<210> SEQ ID NO 48
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Ile His Trp Val Arg Gln Ala Pro Gly Lys Gly Leu Glu Trp Val
            35                  40                  45

Ala Arg Ile Asn Pro Pro Asn Arg Ser Asn Gln Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Phe Arg Trp Val Met Asp Tyr Trp Gly Gln Gly
                100                 105                 110

Thr Leu Val Thr Val Ser Ser Gly Ser Ser Arg Ser Ser Ser Ser
            115                 120                 125

Gly Gly Gly Gly Ser Gly Gly Gly Asp Ile Gln Met Thr Gln Ser
            130                 135                 140

Pro Ser Ser Leu Ser Ala Ser Val Gly Asp Arg Val Thr Ile Thr Cys
145                 150                 155                 160

Arg Ala Ser Gln Asp Val Ser Thr Ala Val Ala Trp Tyr Gln Gln Lys
                165                 170                 175

Pro Gly Lys Ala Pro Lys Leu Leu Ile Tyr Ser Ala Ser Phe Leu Tyr
                180                 185                 190
```

Ser Gly Val Pro Ser Arg Phe Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Phe Tyr Thr Thr Pro Ser Thr Phe Gly Gln Gly Thr Lys
225                 230                 235                 240

Val Glu Ile Lys

<210> SEQ ID NO 49
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Gly Met Ser Trp Val Arg Gln Ala Pro Gly Lys Gly Leu Glu Trp Val
        35                  40                  45

Ser Tyr Ile Tyr Pro Tyr Ser Gly Ala Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Ser Gly Tyr Tyr Arg Ile Ser Ser Ala Met Asp Val Trp
            100                 105                 110

Gly Gln Gly Thr Leu Val Thr Val Ser Ala Gly Gly Ser Ser Arg Ser
        115                 120                 125

Ser Ser Ser Gly Gly Gly Gly Ser Gly Gly Gly Gly Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Asn Ile Lys Arg Phe Leu Ala Trp Tyr
                165                 170                 175

Gln Gln Lys Pro Gly Lys Ala Pro Lys Leu Leu Ile Tyr Gly Ala Ser
            180                 185                 190

Thr Arg Glu Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Tyr Tyr Arg Ser Pro His Thr Phe Gly Gln
225                 230                 235                 240

Gly Thr Lys Val Glu Ile Lys
                245

<210> SEQ ID NO 50
<211> LENGTH: 1674
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
atgaagttgc tgagcagcat agagcaagca tgtgatatct gccggttgaa gaagctgaag    60
tgtagcaagg agaagcccaa gtgcgccaag tgtctcaaga ataattggga gtgtaggtat   120
agccccaaga ccaagcgaag cccgcttacg agagcacacc ttaccgaggt cgagagccgc   180
ctggaaagac tcgaacaact ttttcttctg attttcccca gggaggacct ggacatgatc   240
ctgaagatgg acagcctcca ggacatcaaa gcccttctta ccgggctgtt cgtgcaggac   300
aacgtcaaca aggatgcggt gaccgacaga ttggcgagcg tggagacgga catgcccttg   360
accctcagac aacataggat cagcgcgaca agctcatctg aagaatctag caataaggga   420
cagcgacagc tgaccgttag tggggcgtct gcaggcatgg ccagcatgac tggtggacag   480
caaatgggt cgacggagga cgtggtgtgc tgccactcaa tctacggcaa gaagaagggt   540
gatatcgaca cctaccgata cataggctct tccgggacag gctgcgtggt catagtgggc   600
aggatcgtct tgtccggatc cggcactagt gcgcccatca cggcgtacgc ccagcagacg   660
agaggcctcc tagggtgtat aatcaccagc ctgactggcc gggacaaaaa ccaagtggag   720
ggtgaggtcc agatcgtgtc aactgctacc caaaccttcc tggcaacgtg catcaatggg   780
gtatgctggg cagtctacca cggggccgga acgaggacca tcgcatcacc caagggtcct   840
gtcatccaga tgtataccaa tgtggaccaa gaccttgtgg ctggcccgc tcctcaaggt   900
tcccgctcat tgacaccctg tacctgcggc tcctcggacc tttacctggt cacgaggcac   960
gccgatgtca ttcccgtgcg ccggcgaggt gatagcaggg gtagcctgct ttcgccccgg  1020
cccatttcct acttgaaagg ctcctcgggg ggtccgctgt tgtgccccgc gggacacgcc  1080
gtgggcctat tcagggccgc ggtgtgcacc cgtggagtgg ctaaagcggt ggactttatc  1140
cctgtggaga acctagagac aaccatgaga tccccggtgt tcacggacaa ctcctctcca  1200
ccagcagtca ccctgacgca cccaatcacc aaaatcgata gggaggttct ctaccaggag  1260
ttcgatgaga tggaagagtg ctctcagcac tatccctacg atgtgcccga ttacgctggc  1320
gcgtctgcat gcgccaactt taatcaaagt ggaaacatcg cggacagctc actcagcttt  1380
accttcacca atagcagtaa cgggccgaac ctcataacca cccagaccaa cagccaggcc  1440
ttgagccagc cgatcgcctc atctaacgtg catgataact ttatgaacaa cgagatcacc  1500
gcgagtaaga tagacgacgg gaacaacagc aagcccctta gcccaggttg gacgaccag  1560
accgcctaca acgctttcgg cattacgacc ggcatgttca acaccacgac catggacgat  1620
gtgtacaact acctgttcga tgacgaagac acaccgccaa accccaaaaa agaa         1674
```

<210> SEQ ID NO 51
<211> LENGTH: 1518
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

```
atgaagttgc tgagcagcat agagcaagca tgtgatatct gccggttgaa gaagctgaag    60
tgtagcaagg agaagcccaa gtgcgccaag tgtctcaaga ataattggga gtgtaggtat   120
agccccaaga ccaagcgaag cccgcttacg agagcacacc ttaccgaggt cgagagccgc   180
ctggaaagac tcgaacaact ttttcttctg attttcccca gggaggacct ggacatgatc   240
ctgaagatgg acagcctcca ggacatcaaa gcccttctta ccgggctgtt cgtgcaggac   300
```

```
aacgtcaaca aggatgcggt gaccgacaga ttggcgagcg tggagacgga catgcccttg    360
accctcagac aacataggat cagcgcgaca agctcatctg aagaatctag caataaggga    420
cagcgacagc tgaccgttag tggggcgtct gcaggcatgg ccagcatgac tggtggacag    480
caaatgggt cgacggagga cgtggtgtgc tgccactcaa tctacggcaa gaagaagggt     540
gatatcgaca cctaccgata cataggctct tccgggacag gctgcgtggt catagtgggc    600
aggatcgtct tgtccggatc cggcactagt gcgcccatca cggcgtacgc ccagcagacg    660
agaggcctcc tagggtgtat aatcaccagc ctgactggcc gggacaaaaa ccaagtggag    720
ggtgaggtcc agatcgtgtc aactgctacc caaaccttcc tggcaacgtg catcaatggg    780
gtatgctggg cagtctacca cggggccgga acgaggacca tcgcatcacc caagggtcct    840
gtcatccaga tgtataccaa tgtgaccaa gaccttgtgg gctggcccgc tcctcaaggt     900
tcccgctcat tgacaccctg tacctgcggc tcctcggacc tttacctggt cacgaggcac    960
gccgatgtca ttcccgtgcg ccggcgaggt gatagcaggg gtagcctgct ttcgccccgg   1020
cccatttcct acttgaaagg ctcctcgggg ggtccgctgt tgtgccccgc gggacacgcc   1080
gtgggcctat tcagggccgc ggtgtgcacc cgtggagtgg ctaaagcggt ggactttatc   1140
cctgtggaga acctagagac aaccatgaga tccccggtgt tcacggacaa ctcctctcca   1200
ccagcagtca ccctgacgca cccaatcacc aaaatcgata gggaggttct ctaccaggag   1260
ttcgatgaga tggaagagtg ctctcagcac tatccctacg atgtgcccga ttacgctggc   1320
gcgtcgtctg catgccccaa gaagaagagg aaggtgtcgc cagggatccg tcgacttgac   1380
gcgttgatat caacaagttt gtacaaaaaa gcaggctaca aagaggccag cggttccgga   1440
cgggctgacg cattggacga ttttgatctg gatatgctgg gaagtgacgc cctcgatgat   1500
tttgaccttg acatgctt                                                 1518

<210> SEQ ID NO 52
<211> LENGTH: 1596
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
atgaagttgc tgagcagcat agagcaagca tgtgatatct gccggttgaa gaagctgaag     60
tgtagcaagg agaagcccaa gtgcgccaag tgtctcaaga ataattggga gtgtaggtat    120
agccccaaga ccaagcgaag cccgcttacg agagcacacc ttaccgaggt cgagagccgc    180
ctggaaagac tcgaacaact ttttcttctg attttcccca gggaggacct ggacatgatc    240
ctgaagatgg acagcctcca ggacatcaaa gcccttctta ccgggctgtt cgtgcaggac    300
aacgtcaaca aggatgcggt gaccgacaga ttggcgagcg tggagacgga catgcccttg    360
accctcagac aacataggat cagcgcgaca agctcatctg aagaatctag caataaggga    420
cagcgacagc tgaccgttag tggggcgtct gcaggcatgg ccagcatgac tggtggacag    480
caaatgggt cgacggagga cgtggtgtgc tgccactcaa tctacggcaa gaagaagggt     540
gatatcgaca cctaccgata cataggctct tccgggacag gctgcgtggt catagtgggc    600
aggatcgtct tgtccggatc cggcactagt gcgcccatca cggcgtacgc ccagcagacg    660
agaggcctcc tagggtgtat aatcaccagc ctgactggcc gggacaaaaa ccaagtggag    720
ggtgaggtcc agatcgtgtc aactgctacc caaaccttcc tggcaacgtg catcaatggg    780
```

| | |
|---|---|
| gtatgctggg cagtctacca cggggccgga acgaggacca tcgcatcacc caagggtcct | 840 |
| gtcatccaga tgtataccaa tgtggaccaa gaccttgtgg gctggcccgc tcctcaaggt | 900 |
| tcccgctcat tgacaccctg tacctgcggc tcctcggacc tttacctggt cacgaggcac | 960 |
| gccgatgtca ttcccgtgcg ccggcgaggt gatagcaggg gtagcctgct ttcgccccgg | 1020 |
| cccatttcct acttgaaagg ctcctcgggg gtccgctgt tgtgccccgc gggacacgcc | 1080 |
| gtgggcctat tcagggccgc ggtgtgcacc cgtggagtgg ctaaagcggt ggactttatc | 1140 |
| cctgtggaga acctagagac aaccatgaga tccccggtgt tcacggacaa ctcctctcca | 1200 |
| ccagcagtca ccctgacgca cccaatcacc aaaatcgata gggaggttct ctaccaggag | 1260 |
| ttcgatgaga tggaagagtg ctctcagcac tatccctacg atgtgcccga ttacgctggc | 1320 |
| gcgtcgtctg catgccccaa gaagaagagg aaggtgtcgc cagggatccg tcgacttgac | 1380 |
| gcgttgatat caacaagttt gtacaaaaaa gcaggctaca agaggccag cggttccgga | 1440 |
| cgggctgacg cattgacga ttttgatctg gatatgctgg gaagtgacgc cctcgatgat | 1500 |
| tttgaccttg acatgcttgg ttcggatgcc cttgatgact ttgacctcga catgctcggc | 1560 |
| agtgacgccc ttgatgattt cgacctggac atgctg | 1596 |

<210> SEQ ID NO 53
<211> LENGTH: 2427
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

| | |
|---|---|
| atgaagttgc tgagcagcat agagcaagca tgtgatatct gccggttgaa gaagctgaag | 60 |
| tgtagcaagg agaagcccaa gtgcgccaag tgtctcaaga ataattggga gtgtaggtat | 120 |
| agccccaaga ccaagcgaag cccgcttacg agagcacacc ttaccgaggt cgagagccgc | 180 |
| ctggaaagac tcgaacaact ttttcttctg attttcccca gggaggacct ggacatgatc | 240 |
| ctgaagatgg acagcctcca ggacatcaaa gcccttctta ccgggctgtt cgtgcaggac | 300 |
| aacgtcaaca aggatgcggt gaccgacaga ttggcgagcg tggagacgga catgcccttg | 360 |
| accctcagac aacataggat cagcgcgaca agctcatctg aagaatctag caataaggga | 420 |
| cagcgacagc tgaccgttag tgggcgtct gcaggcatgg ccagcatgac tggtggacag | 480 |
| caaatggggt cgacggagga cgtggtgtgc tgccactcaa tctacggcaa gaagaagggt | 540 |
| gatatcgaca cctaccgata cataggctct tccgggacag gctgcgtggt catagtgggc | 600 |
| aggatcgtct tgtccggatc cggcactagt gcgcccatca cggcgtacgc ccagcagacg | 660 |
| agaggcctcc tagggtgtat aatcaccagc ctgactggcc gggacaaaaa ccaagtggag | 720 |
| ggtgaggtcc agatcgtgtc aactgctacc caaaccttcc tggcaacgtg catcaatggg | 780 |
| gtatgctggg cagtctacca cggggccgga acgaggacca tcgcatcacc caagggtcct | 840 |
| gtcatccaga tgtataccaa tgtggaccaa gaccttgtgg gctggcccgc tcctcaaggt | 900 |
| tcccgctcat tgacaccctg tacctgcggc tcctcggacc tttacctggt cacgaggcac | 960 |
| gccgatgtca ttcccgtgcg ccggcgaggt gatagcaggg gtagcctgct ttcgccccgg | 1020 |
| cccatttcct acttgaaagg ctcctcgggg gtccgctgt tgtgccccgc gggacacgcc | 1080 |
| gtgggcctat tcagggccgc ggtgtgcacc cgtggagtgg ctaaagcggt ggactttatc | 1140 |
| cctgtggaga acctagagac aaccatgaga tccccggtgt tcacggacaa ctcctctcca | 1200 |

-continued

| | |
|---|---|
| ccagcagtca ccctgacgca cccaatcacc aaaatcgata gggaggttct ctaccaggag | 1260 |
| ttcgatgaga tggaagagtg ctctcagcac tatccctacg atgtgcccga ttacgctggc | 1320 |
| gcgtcgtctg catgccccaa gaagaagagg aaggtgtcgc cagggatccg tcgacttgac | 1380 |
| gcgttgatat caacaagttt gtacaaaaaa gcaggctaca aagaggccag cggttccgga | 1440 |
| cgggctgacg cattggacga ttttgatctg gatatgctgg aagtgacgc cctcgatgat | 1500 |
| tttgaccttg acatgcttgg ttcggatgcc cttgatgact ttgacctcga catgctcggc | 1560 |
| agtgacgccc ttgatgattt cgacctggac atgctgatta actctagaag ttccggatct | 1620 |
| ccgaaaaaga aacgcaaagt tggtagccag tacctgcccg acaccgacga ccggcaccgg | 1680 |
| atcgaggaaa agcggaagcg gacctacgag acattcaaga gcatcatgaa gaagtccccc | 1740 |
| ttcagcggcc ccaccgaccc tagacctcca cctagaagaa tcgccgtgcc cagcagatcc | 1800 |
| agcgccagcg tgccaaaacc tgccccccag ccttacccct tcaccagcag cctgagcacc | 1860 |
| atcaactacg acgagttccc taccatggtg ttccccagcg gccagatctc tcaggcctct | 1920 |
| gctctggctc cagcccctcc tcaggtgctg cctcaggctc ctgctcctgc accagctcca | 1980 |
| gccatggtgt ctgcactggc tcaggcacca gcaccgtgc ctgtgctggc tcctggacct | 2040 |
| ccacaggctg tggctccacc agcccctaaa cctacacagg ccggcgaggg cacactgtct | 2100 |
| gaagctctgc tgcagctgca gttcgacgac gaggatctgg agccctgct gggaaacagc | 2160 |
| accgatcctg ccgtgttcac cgacctggcc agcgtggaca cagcgagtt ccagcagctg | 2220 |
| ctgaaccagg gcatccctgt ggcccctcac accaccgagc ccatgctgat ggaataccc | 2280 |
| gaggccatca cccggctcgt gacaggcgct cagaggcctc ctgatccagc tcctgccct | 2340 |
| ctgggagcac caggcctgcc taatggactg ctgtctggcg acgaggactt cagctctatc | 2400 |
| gccgatatgg atttctcagc cttgctg | 2427 |

<210> SEQ ID NO 54
<211> LENGTH: 3015
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 54

| | |
|---|---|
| atgaagttgc tgagcagcat agagcaagca tgtgatatct gccggttgaa gaagctgaag | 60 |
| tgtagcaagg agaagcccaa gtgcgccaag tgtctcaaga ataattggga gtgtaggtat | 120 |
| agccccaaga ccaagcgaag cccgcttacg agagcacacc ttaccgaggt cgagagccgc | 180 |
| ctggaaagac tcgaacaact ttttcttctg attttcccca gggaggacct ggacatgatc | 240 |
| ctgaagatgg acagcctcca ggacatcaaa gcccttctta ccgggctgtt cgtgcaggac | 300 |
| aacgtcaaca aggatgcggt gaccgacaga ttggcgagcg tggagacgga catgcccttg | 360 |
| accctcagac aacataggat cagcgcgaca agctcatctg aagaatctag caataaggga | 420 |
| cagcgacagc tgaccgttag tggggcgtct gcaggcatgg ccagcatgac tggtggacag | 480 |
| caaatggggt cgacggagga cgtggtgtgc tgccactcaa tctacggcaa gaagaagggt | 540 |
| gatatcgaca cctaccgata cataggctct tccgggacag gctgcgtggt catagtgggc | 600 |
| aggatcgtct tgtccggatc cggcactagt gcgcccatca cggcgtacgc ccagcagacg | 660 |
| agaggcctcc tagggtgtat aatcaccagc ctgactggcc gggacaaaaa ccaagtggag | 720 |
| ggtgaggtcc agatcgtgtc aactgctacc caaaccttcc tggcaacgtg catcaatggg | 780 |

| | |
|---|---|
| gtatgctggg cagtctacca cggggccgga acgaggacca tcgcatcacc caagggtcct | 840 |
| gtcatccaga tgtataccaa tgtggaccaa gaccttgtgg gctggcccgc tcctcaaggt | 900 |
| tcccgctcat tgacaccctg tacctgcggc tcctcggacc tttacctggt cacgaggcac | 960 |
| gccgatgtca ttcccgtgcg ccggcgaggt gatagcaggg gtagcctgct ttcgccccgg | 1020 |
| cccatttcct acttgaaagg ctcctcgggg ggtccgctgt tgtgcccgc gggacacgcc | 1080 |
| gtgggcctat tcagggccgc ggtgtgcacc cgtggagtgg ctaaagcggt ggactttatc | 1140 |
| cctgtggaga acctagagac aaccatgaga tccccggtgt tcacggacaa ctcctctcca | 1200 |
| ccagcagtca ccctgacgca cccaatcacc aaaatcgata gggaggttct ctaccaggag | 1260 |
| ttcgatgaga tggaagagtg ctctcagcac tatccctacg atgtgcccga ttacgctggc | 1320 |
| gcgtcgtctg catgccccaa gaagaagagg aaggtgtcgc cagggatccg tcgacttgac | 1380 |
| gcgttgatat caacaagttt gtacaaaaaa gcaggctaca aagaggccag cggttccgga | 1440 |
| cgggctgacg cattggacga ttttgatctg gatatgctgg gaagtgacgc cctcgatgat | 1500 |
| tttgaccttg acatgcttgg ttcggatgcc cttgatgact ttgacctcga catgctcggc | 1560 |
| agtgacgccc ttgatgattt cgacctggac atgctgatta actctagaag ttccggatct | 1620 |
| ccgaaaaaga aacgcaaagt tggtagccag tacctgcccg acaccgacga ccggcaccgg | 1680 |
| atcgaggaaa agcggaagcg gacctacgag acattcaaga gcatcatgaa gaagtccccc | 1740 |
| ttcagcggcc ccaccgaccc tagacctcca cctagaagaa tcgccgtgcc cagcagatcc | 1800 |
| agcgccagcg tgccaaaacc tgccccccag ccttacccct tcaccagcag cctgagcacc | 1860 |
| atcaactacg acgagttccc taccatggtg ttccccagcg ccagatctc tcaggcctct | 1920 |
| gctctggctc cagcccctcc tcaggtgctg cctcaggctc ctgctcctgc accagctcca | 1980 |
| gccatggtgt ctgcactggc tcaggcacca gcacccgtgc ctgtgctggc tcctggacct | 2040 |
| ccacaggctg tggctccacc agcccctaaa cctacacagg ccggcgaggg cacactgtct | 2100 |
| gaagctctgc tgcagctgca gttcgacgac gaggatctgg gagccctgct gggaaacagc | 2160 |
| accgatcctg ccgtgttcac cgacctggcc agcgtggaca cagcgagtt ccagcagctg | 2220 |
| ctgaaccagg gcatccctgt ggcccctcac accaccgagc ccatgctgat ggaatacccc | 2280 |
| gaggccatca cccggctcgt gacaggcgct cagaggcctc ctgatccagc tcctgcccct | 2340 |
| ctgggagcac caggcctgcc taatggactg ctgtctggcg acgaggactt cagctctatc | 2400 |
| gccgatatgg atttctcagc cttgctgggc tctggcagcg gcagccggga ttccagggaa | 2460 |
| gggatgtttt tgccgaagcc tgaggccggc tccgctatta gtgacgtgtt tgagggccgc | 2520 |
| gaggtgtgcc agccaaaacg aatccggcca tttcatcctc caggaagtcc atgggccaac | 2580 |
| cgcccactcc ccgccagcct cgcaccaaca ccaaccggtc cagtacatga gccagtcggg | 2640 |
| tcactgaccc cggcaccagt ccctcagcca ctggatccag cgcccgcagt gactcccgag | 2700 |
| gccagtcacc tgttggagga tcccgatgaa gagacgagcc aggctgtcaa agcccttcgg | 2760 |
| gagatggccg atactgtgat tccccagaag gaagaggctg caatctgtgg ccaaatggac | 2820 |
| ctttcccatc cgcccccaag gggccatctg gatgagctga caaccacact tgagtccatg | 2880 |
| accgaggatc tgaacctgga ctcacccctg accccggaat tgaacgagat tctggatacc | 2940 |
| ttcctgaacg acgagtgcct cttgcatgcc atgcatatca gcacaggact gtccatcttc | 3000 |
| gacacatctc tgttt | 3015 |

<210> SEQ ID NO 55
<211> LENGTH: 2601

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atgtctagac tggacaagag caaagtcata acggagctc tggaattact caatggtgtc        60
ggtatcgaag gcctgacgac aaggaaactc gctcaaaagc tgggagttga gcagcctacc      120
ctgtactggc acgtgaagaa caagcgggcc ctgctcgatg ccctgccaat cgagatgctg      180
gacaggcatc atacccactt ctgcccctg gaaggcgagt catggcaaga ctttctgcgg       240
aacaacgcca agtcataccg ctgtgctctc ctctcacatc gcgacggggc taaagtgcat      300
ctcggcaccc gcccaacaga gaaacagtac gaaaccctgg aaaatcagct cgcgttcctg      360
tgtcagcaag gcttctccct ggagaacgca ctgtacgctc tgtccgccgt gggccacttt      420
acactgggct gcgtattgga ggaacaggag catcaagtag caaaagagga aagagagaca      480
cctaccaccg attctatgcc cccacttctg agacaagcaa ttgagctgtt cgaccggcag      540
ggagccgaac ctgccttcct tttcggcctg gaactaatca tatgtggcct ggagaaacag      600
ctaaagtgcg aaagcggggc gtctgcaggc atggccagca tgactggtgg acagcaaatg      660
gggtcgacgg aggacgtggt gtgctgccac tcaatctacg gcaagaagaa gggtgatatc      720
gacacctacc gatacatagg ctcttccggg acaggctgcg tggtcatagt gggcaggatc      780
gtcttgtccg gatccggcac tagtgcgccc atcacggcgt acgcccagca gacgagaggc      840
ctcctagggt gtataatcac cagcctgact ggccgggaca aaaaccaagt ggagggtgag      900
gtccagatcg tgtcaactgc tacccaaacc ttcctggcaa cgtgcatcaa tggggtatgc      960
tgggcagtct accacggggc cggaacgagg accatcgcat cacccaaggg tcctgtcatc     1020
cagatgtata ccaatgtgga ccaagaccttt gtgggctggc ccgctcctca aggttcccgc    1080
tcattgacac cctgtacctg cggctcctcg gacctttacc tggtcacgag gcacgccgat     1140
gtcattcccg tgcgccggcg aggtgatagc aggggtagcc tgctttcgcc ccggcccatt     1200
tcctacttga aaggctcctc ggggggtccg ctgttgtgcc ccgcgggaca cgccgtgggc     1260
ctattcaggg ccgcggtgtg cacccgtgga gtggctaaag cggtggactt tatccctgtg     1320
gagaacctag agacaaccat gagatccccg gtgttcacgg acaactcctc tccaccagca     1380
gtcaccctga cgcacccaat caccaaaatc gatagggagg ttctctacca ggagttcgat     1440
gagatggaag agtgctctca gcactatccc tacgatgtgc ccgattacgc tggcgcgtcg     1500
tctgcatgcc ccaagaagaa gaggaaggtg tcgccaggga tccgtcgact tgacgcgttg     1560
atatcaacaa gtttgtacaa aaaagcaggc tacaaagagg ccagcggttc cggacgggct     1620
gacgcattgg acgattttga tctggatatg ctgggaagtg acgccctcga tgattttgac     1680
cttgacatgc ttggttcgga tgcccttgat gactttgacc tcgacatgct cggcagtgac     1740
gcccttgatg atttcgacct ggacatgctg attaactcta gaagttccgg atctccgaaa     1800
aagaaacgca agttggtag ccagtacctg cccgacaccg acgaccggca ccggatcgag      1860
gaaaagcgga gcggacccta cgagacattc aagagcatca tgaagaagtc ccccttcagc    1920
ggccccaccg accctagacc tccacctaga agaatcgccg tgcccagcag atccagcgcc    1980
agcgtgccaa aacctgcccc ccagcctac cccttcacca gcagcctgag caccatcaac     2040
tacgacgagt ccctaccat ggtgttcccc agcggccaga tctctcaggc ctctgctctg      2100
gctccagccc ctcctcaggt gctgcctcag gctcctgctc ctgcaccagc tccagccatg    2160
```

```
gtgtctgcac tggctcaggc accagcaccc gtgcctgtgc tggctcctgg acctccacag    2220
gctgtggctc caccagcccc taaacctaca caggccggcg agggcacact gtctgaagct    2280
ctgctgcagc tgcagttcga cgacgaggat ctgggagccc tgctgggaaa cagcaccgat    2340
cctgccgtgt tcaccgacct ggccagcgtg acaacagcg agttccagca gctgctgaac     2400
cagggcatcc ctgtggcccc tcacaccacc gagcccatgc tgatggaata ccccgaggcc    2460
atcacccggc tcgtgacagg cgctcagagg cctcctgatc cagctcctgc ccctctggga    2520
gcaccaggcc tgcctaatgg actgctgtct ggcgacgagg acttcagctc tatcgccgat    2580
atggatttct cagccttgct g                                              2601
```

<210> SEQ ID NO 56
<211> LENGTH: 2679
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
atggagaccg acaccctgct cctgtgggtg ttgttgctct gggtcccagg ttctaccggc     60
gacggaggag cggcgaagt acagctggtg gagtccggcg gtggcctcgt gcaacccgga    120
gggtccttga ggctgtcctg tgcagccagc ggtttcacgt tcagcagcta ctggattcac    180
tgggtgaggc aagctccggg caagggcctg gagtgggttg cgaggataaa ccccccccaac   240 aggtccaacc agtacgccga tagcgtgaag gtcggttca ccatcagcgc cgacactagc     300
aagaacacgg cctacctgca gatgaactct ctgagggccg aggacacagc ggtgtactat    360
tgcgccaggg gctcagggtt tcgatgggtc atggattact ggggccaagg caccctggtt    420
accgtttcta gcggcggatc tagcaggagc tcatcatccg ggggtggcgg agcggaggt    480 ggtggggata ttcagatgac gcaatctccg tcctccctca gcgcaagcgt gggcgacagg    540
gtgaccatta cttgtcgcgc ctctcaggat gtgagcactg ctgtggcctg gtatcaacaa   600 aaaccccggca aagcccccaa actgctgatc tactctgcca gctttctgta ctcaggcgtg    660
cccagcaggt tttccggctc cggcagcggc accgacttca cccttaccat tagcagcctg    720
cagcccgagg attttgcaac ctactactgc caacagttct acaccactcc cagcactttc    780
ggccagggca cgaaggttga gatcaagggg ggaggaagtg agcaaaagct gatttccgag    840
gaggaccttg gaggggctc cgccgtgggg caagacaccc aggaggtgat cgtggtgcct    900
catagcctcc ctttcaaagt ggtggtgatt tcagccatcc tggcattggt tgtgctgacc    960
atcataagct tgattatact gatcatgctt tggcagaaga gcccaggcg tacgatggcc   1020 agcatgactg gtgacagca atggggtcg acggaggacg tggtgtgctg ccactcaatc    1080
tacggcaaga agaagggtga tatcgacacc taccgataca taggctcttc cgggacaggc   1140
tgcgtggtca tagtgggcag gatcgtcttg tccggatccg gcactagtgc gcccatcacg   1200
gcgtacgccc agcagacgag aggcctccta gggtgtataa tcaccagcct gactggccgg   1260
gacaaaaacc aagtggaggg tgaggtccag atcgtgtcaa ctgctaccca aaccttcctg   1320
gcaacgtgca tcaatggggt atgctgggca gtctaccacg gggccggaac gaggaccatc   1380
gcatcaccca agggtcctgt catccagatg tataccaatg tggaccaaga ccttgtgggc   1440
tggcccgctc tcaaggttc ccgctcattg acacccgtga cctgcggctc ctcggaccct    1500
tacctggtca cgaggcacgc cgatgtcatt cccgtgcgcc ggcgaggtga tagcaggggt   1560
```

```
agcctgcttt cgccccggcc catttcctac ttgaaaggct cctcgggggg tccgctgttg    1620
tgccccgcgg gacacgccgt gggcctattc agggccgcgg tgtgcacccg tggagtggct    1680
aaagcggtgg actttatccc tgtggagaac ctagagacaa ccatgagatc cccggtgttc    1740
acggacaact cctctccacc agcagtcacc ctgacgcacc caatcaccaa aatcgatagg    1800
gaggttctct accaggagtt cgatgagatg aagagtgct  ctcagcacta tccctacgat    1860
gtgcccgatt acgctggcgc gtctgcatgc ggtaccatga agttgctgag cagcatagag    1920
caagcatgtg atatctgccg gttgaagaag ctgaagtgta gcaaggagaa gcccaagtgc    1980
gccaagtgtc tcaagaataa ttgggagtgt aggtatagcc ccaagaccaa gcgaagcccg    2040
cttacgagag cacaccttac cgaggtcgag agccgcctgg aaagactcga caactttttt    2100
cttctgattt tccccaggga ggacctggac atgatcctga agatggacag cctccaggac    2160
atcaaagccc ttcttaccgg gctgttcgtg caggacaacg tcaacaagga tgcggtgacc    2220
gacagattgg cgagcgtgga gacggacatg cccttgaccc tcagacaaca taggatcagc    2280
gcgacaagct catctgaaga atctagcaat aagggacagc gacagctgac cgttagtgcc    2340
aactttaatc aaagtggaaa catcgcggac agctcactca gctttacctt caccaatagc    2400
agtaacgggc cgaacctcat aaccacccag accaacagcc aggccttgag ccagccgatc    2460
gcctcatcta acgtgcatga taactttatg aacaacgaga tcaccgcgag taagatagac    2520
gacgggaaca acagcaagcc ccttagccca ggttggacgg accagaccgc ctacaacgct    2580
ttcggcatta cgaccggcat gttcaacacc acgaccatgg acgatgtgta caactacctg    2640
ttcgatgacg aagacacacc gccaaacccc aaaaaagaa                           2679

<210> SEQ ID NO 57
<211> LENGTH: 3366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
atggagacag ataccctcct cctttgggtg ctccttctct gggtgcccgg gtccacagga     60 gacggggggcg gaggcatggt ttctaaagga gaggagctca taaaagaaaa catgcatatg    120
aagctctata tggaaggtac cgtagacaac caccatttca aatgcacctc cgagggggag    180
ggtaagcctt atgaaggcac acagacaatg cggattaaag ttgtcgaagg ggaccactc     240 cccctttgcct tcgacatact ggcaacttct ttcctgtacg gcagcaaaac attcatcaat    300
cacactcagg ggataccaga tttcttcaag cagagcttcc ccgaaggctt tacttgggaa    360
cgagtaacta cctacgagga cgggggggtc ctcaccgcca cccaggatac aagtctccag    420
gacgggtgct tgatctacaa tgtaaagata agagggtgtaa actttacatc aaacggcccc    480
gtcatgcaaa agaaaaccct tggttgggag cattcaccg  agacactgta ccctgcagac    540
ggaggactcg aaggccgcaa cgatatggct cttaagctcg taggcggtag ccaccttatc    600
gccaacgcta agaccaccta ccgaagtaaa agccagccaa aaaacctgaa atgcctggt     660 gtttattacg tagactaccg cctcgagcgc atcaaggagg caaacaacga aacctatgtg    720
gagcaacacg aagtcgccgt ggctcgctat tgcgacctgc catctaagtt gggtcacaaa    780
ctcaacggtg gcgggtcaga gcagaaactt atctcagagg aagatctggg tggaggatca    840
gctgtggggc aggataccca agaggtcata gttgtaccac atagtctgcc attcaaggtc    900
```

```
gttgttataa gcgctatctt ggccctcgtc gtcctgacca tcatcagctt gattattctc    960
ataatgcttt ggcagaagaa acccagacgg accatggcct caatgactgg agggcagcag   1020
atggggagca ctgaggatgt tgtatgttgt catagcattt atgggaaaaa aaaaggcgac   1080
atcgacacct atagatatat cggaagtagt gggaccggct gcgtggtgat cgtagggcgg   1140
atagtgctgt ctggctccgg cactagtgcg cccatcacgg cgtacgccca gcagacgaga   1200
ggcctcctag ggtgtataat caccagcctg actggccggg acaaaaacca agtggagggt   1260
gaggtccaga tcgtgtcaac tgctacccaa accttcctgg caacgtgcat caatgggta    1320
tgctgggcag tctaccacgg ggccggaacg aggaccatcg catcacccaa gggtcctgtc   1380
atccagatgt ataccaatgt ggaccaagac cttgtgggct ggcccgctcc tcaaggttcc   1440
cgctcattga caccctgtac ctgcggctcc tcggaccttt acctggtcac gaggcacgcc   1500
gatgtcattc ccgtgcgccg gcgaggtgat agcagggta gcctgctttc gccccggccc    1560
atttcctact tgaaaggctc ctcggggggt ccgctgttgt gccccgcggg acacgccgtg   1620
ggcctattca gggccgcggt gtgcacccgt ggagtggcta aagcggtgga ctttatccct   1680
gtggagaacc tagagacaac catgagatcc ccggtgttca cggacaactc ctctccacca   1740
gcagtcaccc tgacgcaccc aatcaccaaa atcgataggg aggttctcta ccaggagttc   1800
gatgagatgg aagagtgctc tcagcactat ccctacgatg tgcccgatta cgctggcgcg   1860
tctgcatgcg gtaccatgaa gttgctgagc agcatagagc aagcatgtga tatctgccgg   1920
ttgaagaagc tgaagtgtag caaggagaag cccaagtgcg ccaagtgtct caagaataat   1980
tgggagtgta ggtatagccc caagaccaag cgaagcccgc ttacgagagc acaccttacc   2040
gaggtcgaga gccgcctgga aagactcgaa caacttttc ttctgatttt ccccagggag    2100
gacctggaca tgatcctgaa gatggacagc ctccaggaca tcaaagccct tcttaccggg   2160
ctgttcgtgc aggacaacgt caacaaggat gcggtgaccg acagattggc gagcgtggag   2220
acggacatgc ccttgaccct cagacaacat aggatcagcg cgacaagctc atctgaagaa   2280
tctagcaata agggacagcg acagctgacc gttagtatgg tgagcaaggg cgaggaggat   2340
aacatggcca tcatcaagga gttcatgcgc ttcaaggtgc acatggaggg ctccgtgaac   2400
ggccacgagt tcgagatcga gggcgagggc gagggccgcc cctacgaggg cacccagacc   2460
gccaagctga aggtgaccaa gggtggcccc ctgcccttcg cctgggacat cctgtcccct   2520
cagttcatgt acggctccaa ggcctacgtg aagcaccccg ccgacatccc cgactacttg   2580
aagctgtcct tccccgaggg cttcaagtgg gagcgcgtga tgaacttcga ggacggcggc   2640
gtggtgaccg tgacccagga ctcctccctg caggacggcg agttcatcta caaggtgaag   2700
ctgcgcggca ccaacttccc ctccgacggc cccgtaatgc agaagaagac catgggctgg   2760
gaggcctcct ccgagcggat gtaccccgag gacggcgccc tgaagggcga gatcaagcag   2820
aggctgaagc tgaaggacgg cggccactac gacgctgagg tcaagaccac ctacaaggcc   2880
aagaagcccg tgcagctgcc cggcgcctac aacgtcaaca tcaagttgga catcacctcc   2940
cacaacgagg actacaccat cgtggaacag tacgaacgcg ccgagggccg ccactccacc   3000
ggcggcatgg acgagctgta caaggccaac tttaatcaaa gtggaaacat cgcggacagc   3060
tcactcagct ttaccttcac caatagcagt aacgggccga acctcataac cacccagacc   3120
aacagccagg ccttgagcca gccgatcgcc tcatctaacg tgcatgataa ctttatgaac   3180
aacgagatca ccgcgagtaa gatagacgac gggaacaaca gcaagcccct tagcccaggt   3240
```

<210> SEQ ID NO 58
<211> LENGTH: 1731
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
tggacggacc agaccgccta caacgctttc ggcattacga ccggcatgtt caacaccacg    3300
accatggacg atgtgtacaa ctacctgttc gatgacgaag acacaccgcc aaaccccaaa    3360
aaagaa                                                                3366
```

```
atgggctgca tcaagagcaa gcgcaaggac aacctgaacg acgacggcgt ggacatgaag     60
cgtacgatgg ccagcatgac tggtggacag caaatgggcgt cgacggagga cgtggtgtgc   120
tgccactcaa tctacggcaa gaagaagggt gatatcgaca cctaccgata cataggctct    180
tccgggacag gctgcgtggt catagtgggc aggatcgtct tgtccggatc cggcactagt    240
gcgcccatca cggcgtacgc ccagcagacg agaggcctcc tagggtgtat aatcaccagc    300
ctgactggcc gggacaaaaa ccaagtggag ggtgaggtcc agatcgtgtc aactgctacc    360
caaaccttcc tggcaacgtg catcaatggg gtatgctggg cagtctacca cggggccgga    420
acgaggacca tcgcatcacc caagggtcct gtcatccaga tgtataccaa tgtggaccaa    480
gaccttgtgg gctggcccgc tcctcaaggt tcccgctcat tgacaccctg tacctgcggc    540
tcctcggacc tttacctggt cacgaggcac gccgatgtca ttcccgtgcg ccggcgaggt    600
gatagcaggg gtagcctgct ttcgccccgg cccatttcct acttgaaagg ctcctcgggg    660
ggtccgctgt tgtgccccgc gggacacgcc gtgggcctat tcagggccgc ggtgtgcacc    720
cgtggagtgg ctaaagcggt ggactttatc cctgtggaga acctagagac aaccatgaga    780
tccccggtgt tcacggacaa ctcctctcca ccagcagtca ccctgacgca cccaatcacc    840
aaaatcgata gggaggttct ctaccaggag ttcgatgaga tggaagagtg ctctcagcac    900
tatccctacg atgtgcccga ttacgctggc cgtctgcat gcggtaccat gaagttgctg    960
agcagcatag agcaagcatg tgatatctgc cggttgaaga agctgaagtg tagcaaggag   1020
aagcccaagt gcgccaagtg tctcaagaat aattgggagt gtaggtatag ccccaagacc   1080
aagcgaagcc cgcttacgag agcacacctt accgaggtcg agagccgcct ggaaagactc   1140
gaacaacttt ttcttctgat tttccccagg gaggacctgg acatgatcct gaagatggac   1200
agcctccagg acatcaaagc ccttcttacc gggctgttcg tgcaggacaa cgtcaacaag   1260
gatgcggtga ccgacagatt ggcgagcgtg gagacggaca tgcccttgac cctcagacaa   1320
cataggatca gcgcgacaag ctcatctgaa gaatctagca ataagggaca gcgacagctg   1380
accgttagtg ccaactttaa tcaaagtgga acatcgcgg acagctcact cagctttacc   1440
ttcaccaata gcagtaacgg gccgaacctc ataaccaccc agaccaacag ccaggccttg   1500
agccagccga tcgcctcatc taacgtgcat gataacttta tgaacaacga gatcaccgcg   1560
agtaagatag acgacgggaa caacagcaag cccttagcc aggttggac ggaccagacc   1620
gcctacaacg ctttcggcat tacgaccggc atgttcaaca ccacgaccat ggacgatgtg   1680
tacaactacc tgttcgatga cgaagacaca ccgccaaacc caaaaaaga a             1731
```

<210> SEQ ID NO 59
<211> LENGTH: 2487
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 59

```
atggagaccg acaccctgct cctgtgggtg ttgttgctct gggtcccagg ttctaccggc      60
gacggaggag gcggcgaagt acagctggtg gagtccggcg gtggcctcgt gcaacccgga     120
gggtccttga ggctgtcctg tgcagccagc ggtttcacgt tcagcagcta ctggattcac     180
tgggtgaggc aagctccggg caagggcctg gagtgggttg cgaggataaa cccccccaac     240
aggtccaacc agtacgccga tagcgtgaag ggtcggttca ccatcagcgc cgacactagc     300
aagaacacgg cctacctgca gatgaactct ctgagggccg aggacacagc ggtgtactat     360
tgcgccaggg gctcagggtt tcgatgggtc atggattact ggggccaagg cacccggtt     420
accgtttcta gcggcggatc tagcaggagc tcatcatccg ggggtggcgg gagcggaggt     480
ggtggggata ttcagatgac gcaatctccg tcctccctca gcgcaagcgt gggcgacagg     540
gtgaccatta cttgtcgcgc ctctcaggat gtgagcactg ctgtggcctg gtatcaacaa     600
aaacccggca agcccccaa actgctgatc tactctgcca gctttctgta ctcaggcgtg     660
cccagcaggt tttccggctc cggcagcggc accgacttca cccttaccat tagcagcctg     720
cagcccgagg attttgcaac ctactactgc caacagttct acaccactcc cagcactttc     780
ggccagggca cgaaggttga gatcaagggg ggaggaagtg agcaaaagct gatttccgag     840
gaggaccttg aggggggctc cgccgtgggg caagacaccc aggaggtgat cgtggtgcct     900
catagcctcc ctttcaaagt ggtggtgatt tcagccatcc tggcattggt tgtgctgacc     960
atcataagct tgattatact gatcatgctt tggcagaaga agcccaggcg tacgatggcc    1020
agcatgactg gtggacagca atggggtcg acggaggacg tggtgtgctg ccactcaatc    1080
tacggcaaga agaagggtga tatcgacacc taccgataca taggctcttc cgggacaggc    1140
tgcgtggtca tagtgggcag gatcgtcttg tccggatccg gcactagtgc gcccatcacg    1200
gcgtacgccc agcagacgag aggcctccta gggtgtataa tcaccagcct gactggccgg    1260
gacaaaaacc aagtggaggg tgaggtccag atcgtgtcaa ctgctaccca aaccttcctg    1320
gcaacgtgca tcaatggggt atgctgggca gtctaccacg gggccggaac gaggaccatc    1380
gcatcaccca agggtcctgt catccagatg tataccaatg tggaccaaga ccttgtgggc    1440
tggcccgctc ctcaaggttc ccgctcattg acaccctgta cctgcggctc ctcggacctt    1500
tacctggtca cgaggcacgc cgatgtcatt cccgtgcgcc ggcgaggtga tagcagggt    1560
agcctgcttt cgccccggcc catttcctac ttgaaaggct cctcgggggg tccgctgttg    1620
tgccccgcgg gacacgccgt gggcctattc agggccgcgg tgtgcacccg tggagtggct    1680
aaagcggtgg actttatccc tgtggagaac ctagagacaa ccatgagatc cccggtgttc    1740
acggacaact cctctccacc agcagtcacc ctgacgcacc aatcaccaa atcgatagg    1800
gaggttctct accaggagtt cgatgagatg gaagagtgct ctcagcacta tccctacgat    1860
gtgcccgatt acgctggcgc gtctgcatgc ggtaccatga agttgctgag cagcatagag    1920
caagcatgtg atatctgccg gttgaagaag ctgaagtgta gcaaggagaa gcccaagtgc    1980
gccaagtgtc tcaagaataa ttgggagtgt aggtatagcc ccaagaccaa gcgaagcccg    2040
cttacgagag cacaccttac cgaggtcgag agccgcctgg aaagactcga caactttttt    2100
cttctgattt tccccaggga ggacctggac atgatcctga agatggacag cctccaggac    2160
```

| | | |
|---|---|---|
| atcaaagccc ttcttaccgg gctgttcgtg caggacaacg tcaacaagga tgcggtgacc | 2220 | |
| gacagattgg cgagcgtgga gacggacatg cccttgaccc tcagacaaca taggatcagc | 2280 | |
| gcgacaagct catctgaaga atctagcaat aagggacagc gacagctgac cgttagtgac | 2340 | |
| gcattggacg attttgatct ggatatgctg ggaagtgacg ccctcgatga ttttgacctt | 2400 | |
| gacatgcttg gttcggatgc ccttgatgac tttgacctcg acatgctcgg cagtgacgcc | 2460 | |
| cttgatgatt tcgacctgga catgctg | 2487 | |

<210> SEQ ID NO 60
<211> LENGTH: 6675
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

| | | |
|---|---|---|
| atggacaaga agtactccat tgggctcgct atcggcacaa acagcgtcgg ctgggccgtc | 60 | |
| attacggacg agtacaaggt gccgagcaaa aaattcaaag ttctgggcaa taccgatcgc | 120 | |
| cacagcataa agaagaacct cattggcgcc ctcctgttcg actccgggga gacggccgaa | 180 | |
| gccacgcggc tcaaaagaac agcacggcgc agatataccc gcagaaagaa tcggatctgc | 240 | |
| tacctgcagg agatctttag taatgagatg gctaaggtgg atgactcttt cttccatagg | 300 | |
| ctggaggagt cctttttggt ggaggaggat aaaaagcacg agcgccaccc aatctttggc | 360 | |
| aatatcgtgg acgaggtggc gtaccatgaa aagtacccaa ccatatatca tctgaggaag | 420 | |
| aagcttgtag acagtactga taaggctgac ttgcggttga tctatctcgc gctggcgcat | 480 | |
| atgatcaaat ttcggggaca cttcctcatc gaggggacc tgaacccaga caacagcgat | 540 | |
| gtcgacaaac tctttatcca actggttcag acttacaatc agcttttcga agagaacccg | 600 | |
| atcaacgcat ccgagttga cgccaaagca atcctgagcg ctaggctgtc caaatcccgg | 660 | |
| cggctcgaaa acctcatcgc acagctccct ggggagaaga gaacggcct gtttggtaat | 720 | |
| cttatcgccc tgtcactcgg gctgacccc aactttaaat ctaacttcga cctggccgaa | 780 | |
| gatgccaagc ttcaactgag caaagacacc tacgatgatg atctcgacaa tctgctggcc | 840 | |
| cagatcggcg accagtacgc agacctttt ttggcggcaa agaacctgtc agacgccatt | 900 | |
| ctgctgagtg atattctgcg agtgaacacg gagatcacca agctccgct gagcgctagt | 960 | |
| atgatcaagc gctatgatga gcaccaccaa gacttgactt tgctgaaggc ccttgtcaga | 1020 | |
| cagcaactgc ctgagaagta caaggaaatt ttcttcgatc agtctaaaaa tggctacgcc | 1080 | |
| ggatacattg acggcggagc aagccaggag gaattttaca aatttattaa gcccatcttg | 1140 | |
| gaaaaaatgg acggcaccga ggagctgctg gtaaagctta acagagaaga tctgttgcgc | 1200 | |
| aaacagcgca ctttcgacaa tggaagcatc ccccaccaga ttcacctggg cgaactgcac | 1260 | |
| gctatcctca ggcggcaaga ggatttctac ccctttttga agataacag ggaaaagatt | 1320 | |
| gagaaaatcc tcacatttcg gatacctac tatgtaggcc ccctcgcccg ggaaattcc | 1380 | |
| agattcgcgt ggatgactcg caaatcagaa gagaccatca ctccctggaa cttcgaggaa | 1440 | |
| gtcgtggata aggggcctc tgcccagtcc ttcatcgaaa ggatgactaa cttttataaa | 1500 | |
| aatctgccta acgaaaaggt gcttcctaaa cactctctgc tgtacgagta cttcacagtt | 1560 | |
| tataacgagc tcaccaaggt caaatacgtc acagaaggga tgagaaagcc agcattcctg | 1620 | |
| tctggagagc agaagaaagc tatcgtggac ctcctcttca gacgaaccg gaaagttacc | 1680 | |

-continued

```
gtgaaacagc tcaaagaaga ctatttcaaa aagattgaat gtttcgactc tgttgaaatc    1740
agcggagtgg aggatcgctt caacgcatcc ctgggaacgt atcacgatct cctgaaaatc    1800
attaaagaca aggacttcct ggacaatgag gagaacgagg acattcttga ggacattgtc    1860
ctcaccctta cgttgtttga agataggag atgattgaag aacgcttgaa aacttacgct    1920
catctcttcg acgacaaagt catgaaacag ctcaagaggc gccgatatac aggatggggg    1980
cggctgtcaa gaaaactgat caatgggatc cgagacaagc agagtggaaa gacaatcctg    2040
gattttctta gtccgatgg atttgccaac cggaacttca tgcagttgat ccatgatgac    2100
tctctcacct ttaaggagga catccagaaa gcacaagttt ctggccaggg ggacagtctt    2160
cacgagcaca tcgctaatct tgcaggtagc ccagctatca aaaagggaat actgcagacc    2220
gttaaggtcg tggatgaact cgtcaaagta atgggaaggc ataagcccga gaatatcgtt    2280
atcgagatgg cccgagagaa ccaaactacc cagaagggac agaagaacag tagggaaagg    2340
atgaagagga ttgaagaggg tataaaagaa ctggggtccc aaatccttaa ggaacaccca    2400
gttgaaaaca cccagcttca gaatgagaag ctctacctgt actacctgca gaacggcagg    2460
gacatgtacg tggatcagga actggacatc aatcggctct ccgactacga cgtggctgct    2520
atcgtgcccc agtcttttct caaagatgat tctattgata taaagtgtt gacaagatcc    2580 gataaagcta gagggaagag tgataacgtc ccctcagaag aagttgtcaa gaaaatgaaa    2640
aattattggc ggcagctgct gaacgccaaa ctgatcacac aacggaagtt cgataatctg    2700
actaaggctg aacgaggtgg cctgtctgag ttggataaag ccggcttcat caaaaggcag    2760
cttgttgaga cacgccagat caccaagcac gtggcccaaa ttctcgattc acgcatgaac    2820
accaagtacg atgaaaatga caaactgatt cgagaggtga agttattac tctgaagtct    2880 aagctggtct cagatttcag aaaggacttt cagttttata aggtgagaga gatcaacaat    2940
taccaccatg cgcatgatgc ctacctgaat gcagtggtag gcactgcact tatcaaaaaa    3000
tatcccaagc ttgaatctga atttgtttac ggagactata agtgtacga tgttaggaaa    3060 atgatcgcaa agtctgagca ggaaataggc aaggccaccg ctaagtactt cttttacagc    3120
aatattatga atttttcaa gaccgagatt acactggcca atggagagat tcggaagcga    3180
ccacttatcg aaacaaacgg agaaacagga gaaatcgtgt gggacaaggg tagggatttc    3240
gcgacagtcc ggaaggtcct gtccatgccg caggtgaaca tcgttaaaaa gaccgaagta    3300
cagaccggag gcttctccaa ggaaagtatc ctcccgaaaa ggaacagcga caagctgatc    3360
gcacgcaaaa aagattggga ccccaagaaa tacggcggat tcgattctcc tacagtcgct    3420
tacagtgtac tggttgtggc caaagtggag aaagggaagt ctaaaaaact caaaagcgtc    3480
aaggaactgc tgggcatcac aatcatggag cgatcaagct tcgaaaaaaa ccccatcgac    3540
tttctcgagg cgaaaggata taagaggtc aaaaaagacc tcatcattaa gcttcccaag    3600
tactctctct ttgagcttga aaacggccgg aaacgaatgc tcgctagtgc gggcgagctg    3660
cagaaaggta acgagctggc actgcccctc aaatacgtta atttcttgta tctggccagc    3720
cactatgaaa agctcaaagg gtctcccgaa gataatgagc agaagcagct gttcgtggaa    3780
caacacaaac actaccttga tgagatcatc gagcaaataa gcgaattctc caaaagagtg    3840
atcctcgccg acgctaacct cgataaggtg ctttctgctt acaataagca cagggataag    3900
cccatcaggg agcaggcaga aaacattatc cacttgttta ctctgaccaa cttgggcgcg    3960
cctgcagcct tcaagtactt cgacaccacc atagacagaa agcggtacac ctctacaaag    4020
gaggtcctgg acgccacact gattcatcag tcaattacgg ggctctatga aacaagaatc    4080
```

```
gacctctctc agctcggtgg agacagcagg gctgacatgg ccagcatgac tggtggacag    4140
caaatggggt cgacggagga cgtggtgtgc tgccactcaa tctacggcaa gaagaagggt    4200
gatatcgaca cctaccgata cataggctct ccgggacag gctgcgtggt catagtgggc     4260
aggatcgtct tgtccggatc cggcactagt gcgcccatca cggcgtacgc ccagcagacg    4320
agaggcctcc tagggtgtat aatcaccagc ctgactggcc gggacaaaaa ccaagtggag    4380
ggtgaggtcc agatcgtgtc aactgctacc caaaccttcc tggcaacgtg catcaatggg    4440
gtatgctggg cagtctacca cggggccgga acgaggacca tcgcatcacc caagggtcct    4500
gtcatccaga tgtataccaa tgtggaccaa gaccttgtgg gctggcccgc tcctcaaggt    4560
tcccgctcat tgacaccctg tacctgcggc tcctcggacc tttacctggt cacgaggcac    4620
gccgatgtca ttcccgtgcg ccggcgaggt gatagcaggg gtagcctgct ttcgccccgg    4680
cccatttcct acttgaaagg ctcctcgggg gtccgctgt tgtgccccgc gggacacgcc     4740
gtgggcctat tcagggccgc ggtgtgcacc cgtggagtgg ctaaagcggt ggactttatc    4800
cctgtggaga acctagagac aaccatgaga tccccggtgt tcacggacaa ctcctctcca    4860
ccagcagtca ccctgacgca cccaatcacc aaaatcgata gggaggttct ctaccaggag    4920
ttcgatgaga tggaagagtg ctctcagcac tatccctacg atgtgcccga ttacgctggc    4980
gcgtctgcat gccccaagaa gaagaggaag gtgtcgccag ggatccgtcg acttgacgcg    5040
ttgatatcaa caagtttgta caaaaaagca ggctacaaag aggccagcgg ttccggacgg    5100
gctgacgcat tggacgattt tgatctggat atgctgggaa gtgacgccct cgatgatttt    5160
gaccttgaca tgcttggttc ggatgccctt gatgactttg acctcgacat gctcggcagt    5220
gacgcccttg atgatttcga cctggacatg ctgattaact ctagaagttc cggatctccg    5280
aaaaagaaac gcaaagttgg tagccagtac ctgcccgaca ccgacgaccg gcaccggatc    5340
gaggaaaagc ggaagcggac ctacgagaca ttcaagagca tcatgaagaa gtcccccttc    5400
agcggcccca ccgaccctag acctccacct agaagaatcg ccgtgccag cagatccagc    5460 gccagcgtgc caaaacctgc cccccagcct taccccttca ccagcagcct gagcaccatc    5520
aactacgacg agttccctac catggtgttc cccagcggcc agatctctca ggcctctgct    5580
ctggctccag cccctcctca ggtgctgcct caggctcctg ctcctgcacc agctccagcc    5640
atggtgtctg cactggctca ggcaccagca cccgtgcctg tgctggctcc tggacctcca    5700
caggctgtgg ctccaccagc ccctaaacct acacaggccg cgagggcac actgtctgaa    5760 gctctgctgc agctgcagtt cgacgacgag gatctgggag ccctgctggg aaacagcacc    5820
gatcctgccg tgttcaccga cctggccagc gtggacaaca gcgagttcca gcagctgctg    5880
aaccagggca tccctgtggc ccctcacacc accgagccca tgctgatgga ataccccgag    5940
gccatcaccc ggctcgtgac aggcgctcag aggcctcctg atccagctcc tgcccctctg    6000
ggagcaccag gcctgcctaa tggactgctg tctggcgacg aggacttcag ctctatcgcc    6060
gatatggatt tctcagcctt gctgggctct ggcagcggca gccgggattc cagggaaggg    6120 atgttttttgc cgaagcctga ggccggctcc gctattagtg acgtgtttga gggccgcgag    6180
gtgtgccagc caaaacgaat ccggccattt catcctccag gaagtccatg gccaaccgc    6240 ccactccccg ccagcctcgc accaacacca accggtccag tacatgagcc agtcgggtca    6300
ctgaccccgg caccagtccc tcagccactg gatccagcgc ccgcagtgac tcccgaggcc    6360
agtcacctgt tggaggatcc cgatgaagag acgagccagg ctgtcaaagc ccttcgggag    6420
```

| | | |
|---|---|---|
| atggccgata ctgtgattcc ccagaaggaa gaggctgcaa tctgtggcca aatggacctt | 6480 |
| tcccatccgc ccccaagggg ccatctggat gagctgacaa ccacacttga gtccatgacc | 6540 |
| gaggatctga acctggactc accccctgacc ccggaattga acgagattct ggataccttc | 6600 |
| ctgaacgacg agtgcctctt gcatgccatg catatcagca caggactgtc catcttcgac | 6660 |
| acatctctgt tttga | 6675 |

<210> SEQ ID NO 61
<211> LENGTH: 7239
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

| | | |
|---|---|---|
| atggacaaag actgcgaaat gaagcgcacc accctggata gccctctggg caagctggaa | 60 |
| ctgtctgggt gcgaacaggg cctgcaccgt atcatcttcc tgggcaaagg aacatctgcc | 120 |
| gccgacgccg tggaagtgcc tgccccagcc gccgtgctgg gcggaccaga gccactgatg | 180 |
| caggccaccg cctggctcaa cgcctacttt caccagcctg aggccatcga ggagttccct | 240 |
| gtgccagccc tgcaccaccc agtgttccag caggagagct ttacccgcca ggtgctgtgg | 300 |
| aaactgctga agtggtgaa gttcggagag gtcatcagct acagccacct ggccgccctg | 360 |
| gccggcaatc ccgccgccac cgccgccgtg aaaaccgccc tgagcggaaa tcccgtgccc | 420 |
| attctgatcc cctgccaccg ggtggtgcag ggcgacctgg acgtgggggg ctacgagggc | 480 |
| gggctcgccg tgaaagagtg gctgctggcc cacgagggcc acagactggg caagcctggg | 540 |
| ctgggtcctg caggcgacgc caccatggac aagaagtact ccattgggct cgctatcggc | 600 |
| acaaacagcg tcggctgggc cgtcattacg gacgagtaca aggtgccgag caaaaaattc | 660 |
| aaagttctgg gcaataccga tcgccacagc ataaagaaga acctcattgg cgccctcctg | 720 |
| ttcgactccg gggagacggc cgaagccacg cggctcaaaa gaacagcacg cgcagatat | 780 |
| acccgcagaa agaatcggat ctgctacctg caggagatct ttagtaatga gatggctaag | 840 |
| gtggatgact ctttcttcca taggctggag gagtcctttt tggtggagga ggataaaaag | 900 |
| cacgagcgcc acccaatctt tggcaatatc gtggacgagg tggcgtacca tgaaaagtac | 960 |
| ccaaccatat atcatctgag gaagaagctt gtagacagta ctgataaggc tgacttgcgg | 1020 |
| ttgatctatc tcgcgctggc gcatatgatc aaatttcggg gacacttcct catcgagggg | 1080 |
| gacctgaacc cagacaacag cgatgtcgac aaactcttta tccaactggt tcagacttac | 1140 |
| aatcagcttt tcgaagagaa cccgatcaac gcatccggag ttgacgccaa agcaatcctg | 1200 |
| agcgctaggc tgtccaaatc ccggcggctc gaaaacctca tcgcacagct ccctggggag | 1260 |
| aagaagaacg gcctgtttgg taatcttatc gccctgtcac tcgggctgac ccccaacttt | 1320 |
| aaatctaact tcgacctggc cgaagatgcc aagcttcaac tgagcaaaga cacctacgat | 1380 |
| gatgatctcg acaatctgct ggcccagatc ggcgaccagt acgcagacct ttttttggcg | 1440 |
| gcaaagaacc tgtcagacgc cattctgctg agtgatattc tgcgagtgaa cacggagatc | 1500 |
| accaaagctc cgctgagcgc tagtatgatc aagcgctatg atgagcacca ccaagacttg | 1560 |
| actttgctga aggcccttgt cagacagcaa ctgcctgaga agtacaagga aatttttcttc | 1620 |
| gatcagtcta aaaatggcta cgccggatac attgacggcg gagcaagcca ggaggaattt | 1680 |
| tacaaattta ttaagcccat cttggaaaaa atggacggca ccgaggagct gctggtaaag | 1740 |

```
cttaacagag aagatctgtt gcgcaaacag cgcactttcg acaatggaag catccccac    1800
cagattcacc tgggcgaact gcacgctatc ctcaggcggc aagaggattt ctacccttt    1860
ttgaaagata acagggaaaa gattgagaaa atcctcacat ttcggatacc ctactatgta   1920
ggccccctcg cccggggaaa ttccagattc gcgtggatga ctcgcaaatc agaagagacc   1980
atcactccct ggaacttcga ggaagtcgtg gataagggg cctctgccca gtccttcatc    2040
gaaaggatga ctaactttga taaaaatctg cctaacgaaa aggtgcttcc taaacactct   2100
ctgctgtacg agtacttcac agtttataac gagctcacca aggtcaaata cgtcacagaa   2160
gggatgagaa agccagcatt cctgtctgga gagcagaaga aagctatcgt ggacctcctc   2220
ttcaagacga accggaaagt taccgtgaaa cagctcaaag aagactattt caaaaagatt   2280
gaatgtttcg actctgttga aatcagcgga gtggaggatc gcttcaacgc atccctggga   2340
acgtatcacg atctcctgaa aatcattaaa gacaaggact cctggacaa tgaggagaac    2400
gaggacattc ttgaggacat tgtcctcacc cttacgttgt ttgaagatag ggagatgatt   2460
gaagaacgct tgaaaactta cgctcatctc ttcgacgaca aagtcatgaa acagctcaag   2520
aggcgccgat atacaggatg ggggcggctg tcaagaaaac tgatcaatgg gatccgagac   2580
aagcagagtg gaaagacaat cctggatttt cttaagtccg atggatttgc caaccggaac   2640
ttcatgcagt tgatccatga tgactctctc acctttaagg aggacatcca gaaagcacaa   2700
gtttctggcc aggggacag tcttcacgag cacatcgcta atcttgcagg tagcccagct    2760
atcaaaaagg gaatactgca gaccgttaag gtcgtggatg aactcgtcaa agtaatggga   2820
aggcataagc ccgagaatat cgttatcgag atggcccgag agaaccaaac tacccagaag   2880
ggacagaaga acagtaggga aaggatgaag aggattgaag agggtataaa gaactgggg    2940
tcccaaatcc ttaaggaaca cccagttgaa aacacccagc ttcagaatga gaagctctac   3000
ctgtactacc tgcagaacgg cagggacatg tacgtggatc aggaactgga catcaatcgg   3060
ctctccgact acgacgtggc tgctatcgtg ccccagtctt ttctcaaaga tgattctatt   3120
gataataaag tgttgacaag atccgataaa gctagaggga agagtgataa cgtcccctca   3180
gaagaagttg tcaagaaaat gaaaaattat tggcggcagc tgctgaacgc caaactgatc   3240
acacaacgga agttcgataa tctgactaag gctgaacgag gtggcctgtc tgagttggat   3300
aaaagccggc tcatcaaaag gcagcttgtt gagacacgcc agatcaccaa gcacgtggcc   3360
caaattctcg attcacgcat gaacaccaag tacgatgaaa atgacaaact gattcgagag   3420
gtgaaagtta ttactctgaa gtctaagctg gtctcagatt tcagaaagga ctttcagttt   3480
tataaggtga gagagatcaa caattaccac catgcgcatg atgcctacct gaatgcagtg   3540
gtaggcactg cacttatcaa aaaatatccc aagcttgaat ctgaatttgt ttacggagac   3600
tataaagtgt acgatgttag gaaaatgatc gcaaagtctg agcaggaaat aggcaaggcc   3660
accgctaagt acttctttta cagcaatatt atgaattttt tcaagaccga gattacactg   3720
gccaatggag agattcggaa gcgaccactt atcgaaacaa acgagaaac aggagaaatc    3780
gtgtgggaca agggtaggga tttcgcgaca gtccggaagg tcctgtccat gccgcaggtg   3840
aacatcgtta aaagaccga agtacagacc ggaggcttct ccaaggaaag tatcctcccg    3900
aaaaggaaca gcgacaagct gatcgcacgc aaaaagatt gggaccccaa gaaatacggc    3960
ggattcgatt ctcctacagt cgcttacagt gtactggttg tggccaaagt ggagaaaggg   4020
aagtctaaaa aactcaaaag cgtcaaggaa ctgctgggca tcacaatcat ggagcgatca   4080
agcttcgaaa aaaaccccat cgactttctc gaggcgaaag gatataaaga ggtcaaaaaa   4140
```

```
gacctcatca ttaagcttcc caagtactct ctctttgagc ttgaaaacgg ccggaaacga    4200
atgctcgcta gtgcgggcga gctgcagaaa ggtaacgagc tggcactgcc ctctaaatac    4260
gttaatttct tgtatctggc cagccactat gaaaagctca aagggtctcc cgaagataat    4320
gagcagaagc agctgttcgt ggaacaacac aaacactacc ttgatgagat catcgagcaa    4380
ataagcgaat tctccaaaag agtgatcctc gccgacgcta acctcgataa ggtgctttct    4440
gcttacaata gcacaggga taagcccatc agggagcagg cagaaaacat tatccacttg    4500
tttactctga ccaacttggg cgcgcctgca gccttcaagt acttcgacac caccatagac    4560
agaaagcggt acacctctac aaaggaggtc ctggacgcca cactgattca tcagtcaatt    4620
acggggctct atgaaacaag aatcgacctc tctcagctcg gtggagacag cagggctgac    4680
atggccagca tgactggtgg acagcaaatg gggtcgacgg aggacgtggt gtgctgccac    4740
tcaatctacg gcaagaagaa gggtgatatc gacacctacc gatacatagg ctcttccggg    4800
acaggctgcg tggtcatagt gggcaggatc gtcttgtccg gatccggcac tagtgcgccc    4860
atcacggcgt acgccagca gacgagaggc ctcctagggt gtataatcac cagcctgact    4920
ggccgggaca aaaaccaagt ggagggtgag gtccagatcg tgtcaactgc tacccaaacc    4980
ttcctggcaa cgtgcatcaa tggggtatgc tgggcagtct accacggggc cggaacgagg    5040
accatcgcat cacccaaggg tcctgtcatc cagatgtata ccaatgtgga ccaagacctt    5100
gtgggctggc ccgctcctca aggttcccgc tcattgacac cctgtacctg cggctcctcg    5160
gacctttacc tggtcacgag gcacgccgat gtcattcccg tgcgccggcg aggtgatagc    5220
aggggtagcc tgctttcgcc ccggcccatt tcctacttga aaggctcctc ggggggtccg    5280
ctgttgtgcc ccgcgggaca cgccgtgggc ctattcaggg ccgcggtgtg cacccgtgga    5340
gtggctaaag cggtggactt tatccctgtg gagaacctag agacaaccat gagatccccg    5400
gtgttcacgg acaactcctc tccaccagca gtcaccctga cgcacccaat caccaaaatc    5460
gatagggagg ttctctacca ggagttcgat gagatggaag agtgctctca gcactatccc    5520
tacgatgtgc ccgattacgc tggcgcgtct gcatgcccca agaagaagag gaaggtgtcg    5580
ccagggatcc gtcgacttga cgcgttgata tcaacaagtt tgtacaaaaa agcaggctac    5640
aaagaggcca gcggttccgg acgggctgac gcattggacg attttgatct ggatatgctg    5700
ggaagtgacg ccctcgatga ttttgacctt gacatgcttg gttcggatgc ccttgatgac    5760
tttgacctcg acatgctcgg cagtgacgcc cttgatgatt tcgacctgga catgctgatt    5820
aactctagaa gttccggatc tccgaaaaag aaacgcaaag ttggtagcca gtacctgccc    5880
gacaccgacg accggcaccg gatcgaggaa aagcggaagc ggaccctacga gacattcaag    5940
agcatcatga agaagtcccc cttcagcggg cccaccgacc ctagacctcc acctagaaga    6000
atcgccgtgc cagcagatc cagcgccagc gtgccaaaac ctgcccccca gccttacccc    6060
ttcaccagca gcctgagcac catcaactac gacgagttcc ctaccatggt gttcccagc     6120
ggccagatct ctcaggcctc tgctctggct ccagccccctc ctcaggtgct gcctcaggct    6180
cctgctcctg caccagctcc agccatggtg tctgcactgg ctcaggcacc agcaccgtg     6240
cctgtgctgg ctcctggacc tccacaggct gtggctccac cagccctaa acctacacag    6300
gccggcgagg gcacactgtc tgaagctctg ctgcagctgc agttcgacga cgaggatctg    6360
ggagccctgc tggaaacag caccgatcct gccgtgttca ccgacctggc cagcgtggac    6420
aacagcgagt ccagcagct gctgaaccag ggcatccctg tggcccctca caccaccgag    6480
```

```
cccatgctga tggaatacccc cgaggccatc acccggctcg tgacaggcgc tcagaggcct    6540
cctgatccag ctcctgcccc tctgggagca ccaggcctgc ctaatggact gctgtctggc    6600
gacgaggact tcagctctat cgccgatatg gatttctcag ccttgctggg ctctggcagc    6660
ggcagccggg attccaggga agggatgttt ttgccgaagc ctgaggccgg ctccgctatt    6720
agtgacgtgt ttgagggccg cgaggtgtgc cagccaaaac gaatccggcc atttcatcct    6780
ccaggaagtc catgggccaa ccgcccactc cccgccagcc tcgcaccaac accaaccggt    6840
ccagtacatg agccagtcgg gtcactgacc ccggcaccag tccctcagcc actggatcca    6900
gcgcccgcag tgactcccga ggccagtcac ctgttggagg atcccgatga agagacgagc    6960
caggctgtca aagcccttcg ggagatggcc gatactgtga ttccccagaa ggaagaggct    7020
gcaatctgtg gccaaatgga cctttcccat ccgcccccaa ggggccatct ggatgagctg    7080
acaaccacac ttgagtccat gaccgaggat ctgaacctgg actcacccct gaccccggaa    7140
ttgaacgaga ttctggatac cttcctgaac gacgagtgcc tcttgcatgc catgcatatc    7200
agcacaggac tgtccatctt cgacacatct ctgttttga                           7239

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gcagacgcga ggaaggaggg cgc                                              23

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gcctctggga ggtcctgtcc ggctc                                            25

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tgggtcttcg gaggacagta ctc                                              23

<210> SEQ ID NO 65
<211> LENGTH: 3735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
atgggccgtc ggagcgctct agcccttgcc gtggtctcag ccctgctgtg ccaggtctgg    60
agctctggcg tatttgagct gaagctgcag gagttcgtca acaagaaggg gctgctgggg    120
```

```
aaccgcaact gctgccgcgg gggctctggc ccgccgtgcg cctgcaggac cttctttcgc    180
gtatgcctca agcattacca ggccagcgtg tccccggagc caccctgcac ctacggcagt    240
gcggtcaccg cagtgctggg tgtcgactcc ttcagcctgc ctgatggcgc aggcatcgac    300
cccgccttca gcaaccccat ccgattcccc ttcggattca cctggccagg taccttctct    360
ctgatcattg aagccctcca cacagattct cctgacgacc tcgcaacaga aacccagaa     420 agactcatca gccgcctgac cacacagagg cacctcactg tgggagaaga gtggtctcag    480
gaccttcaca gtagcggccg cacagacctc cgctactctt accggtttgt gtgtgatgaa    540
cactactatg gagaaggctg ctccgtgttc tgccgaccgc gggatgatgc ctttggccac    600
ttcacctgcg gggagagagg ggagaagatg tgcgaccctg gctggaaagg ccagtactgc    660
actgacccca tttgtctgcc aggctgtgat gaccaacatg gatattgtga caaaccgggg    720
gaatgcaagt gcagagttgg ctggcagggc cgctactgcg atgaatgcat ccgatacca    780 ggctgtctcc atggtacctg ccagcagccc tggcagtgta actgccagga aggctggggg    840
ggcctcttct gcaaccagga tctgaactac tgcactcacc ataagccatg caggaacgga    900
gccacctgca ccaacacggg ccaggggagc tacacatgct cttgccgacc cgggtataca    960
ggggccaact gtgagctgga ggtagatgag tgtgctccca gccctgcag gaatggaggg    1020 agctgcacgg atcttgagga cagctactct tgcacctgcc ctcctggctt ctatggcaag    1080
gtctgtgagc tgagcgccat gacgtgtgca gatggtcctt gcttcaatgg gggacgatgt    1140
tcggataacc ccgatggagg ctacacctgc cattgccctg cgggcttctc tggcttcaac    1200
tgtgagaaga agattgatct ctgtagctct tccccttgtt ctaacggtgc caagtgtgtg    1260
gacctcggca actcctacct gtgccgatgt cagactggct ctccgggag gtactgcgag    1320 gacaatgtgg atgactgtgc ctcttctccc tgtgcaaacg ggggcacctg ccgggacagt    1380
gtgaacgatt tctcctgtac ctgcccacct ggctacacag gcaggaactg cagcgcccct    1440
gtcagcaggt gtgagcatgc accctgtcat aacggggcca cctgccacca gaggggccaa    1500
cgctacatgt gtgagtgcgc ccagggctat ggcggcgcca actgccagtt cctgctccct    1560
gagccaccac cagacctcat agtggcggcc cagggcgggc ccttcccctg gagcagggct    1620
gacatggcca gcatgactgg tggacagcaa atggggtcga cggaggacgt ggtgtgctgc    1680
cactcaatct acggcaagaa gaagggtgat atcgacacct accgatacat aggctcttcc    1740
gggacaggct gcgtggtcat agtgggcagg atcgtcttgt ccggatccgg cactagtgcg    1800
cccatcacgg cgtacgccca gcagacgaga ggcctcctag ggtgtataat caccagcctg    1860
actggccggg acaaaaacca agtggagggt gaggtccaga tcgtgtcaac tgctacccaa    1920
accttcctgg caacgtgcat caatgggta tgctgggcag tctaccacgg ggccggaacg    1980
aggaccatcg catcacccaa gggtcctgtc atccagatgt ataccaatgt ggaccaagac    2040
cttgtgggct ggcccgctcc tcaaggttcc cgctcattga cccctgtac ctgcggctcc    2100 tcggaccttt acctggtcac gaggcacgcc gatgtcattc ccgtgcgccg gcgaggtgat    2160
agcaggggta gcctgctttc gccccggccc atttcctact tgaaaggctc ctcgggggt    2220 ccgctgttgt gccccgcggg acacgccgtg ggcctattca gggccgcggt gtgcacccgt    2280
ggagtggcta aagcggtgga ctttatccct gtggagaacc tagagacaac catgagatcc    2340
ccggtgttca cggacaactc ctctccacca gcagtcaccc tgacgcaccc aatcaccaaa    2400
atcgataggg aggttctcta ccaggagttc gatgagatgg aagagtgctc tcagcactat    2460
```

| | |
|---|---|
| ccctacgatg tgcccgatta cgctggcgcg tctgcagtgg ctgtgtgtgc cggggtggtg | 2520 |
| cttgtcctcc tgctgctgct gggctgtgct gctgtggtgg tctgcgtccg gctgaagcta | 2580 |
| cagaaacacc agcctccgcc tgatccttgc gggggagaga cagagaccat gaacaaccta | 2640 |
| gccaattgcc agcgtgagaa ggatgttttct gttagcatca ttggggctac acagatcaag | 2700 |
| aacaccaaca agaaggcgga cttttcatggg gaccatggtg ctgacaagag cagctttaag | 2760 |
| gcccgatacc ccactgtgga ctataacctc attcgagacc tcaagggaga tgaagccacg | 2820 |
| gtcagggatg cacacagcaa acgtgacacc aagtgccagt cacagggctc tgtaggagaa | 2880 |
| gagaagagca cctcaacgct cagggtggg gaggttcccg acagaaaaag gcccgagtct | 2940 |
| gtctactcta cttcaaagga caccaagtac cagtcggtgt atgttctatc tgcagaaaag | 3000 |
| gatgagtgtg ttatagcgac tgaggttgtg agcaagggcg aggaggataa catgaccatc | 3060 |
| atcaaggagt tcatgcgctt caaggtgcac atggagggct ccgtgaacgg ccacgagttc | 3120 |
| gagatcgagg gcgagggcga gggccgcccc tacgagggca cccagaccgc caagctgaag | 3180 |
| gtgaccaagg gtggcccct gcccttcgcc tgggacatcc tgtccctca gttcatgtac | 3240 |
| ggctccaagg cctacgtgaa gcaccccgcc gacatccccg actacttgaa gctgtccttc | 3300 |
| cccgagggct tcaagtggga gcgcgtgatg aacttcgagg acggcggcgt ggtgaccgtg | 3360 |
| acccaggact cctccctgca ggacggcgag ttcatctaca aggtgaagct gcgcggcacc | 3420 |
| aacttcccct ccgacggccc cgtaatgcag aagaagacca tgggctggga ggcctcctcc | 3480 |
| gagcggatgt accccgagga cggcgccctg aagggcgaga tcaagcagag gctgaagctg | 3540 |
| aaggacggcg gccactacga cgctgaggtc aagaccacct acaaggccaa gaagcccgtg | 3600 |
| cagctgcccg gcgcctacaa cgtcaacatc aagttggaca tcacctccca caacgaggac | 3660 |
| tacaccatcg tggaacagta cgaacgcgcc gagggccgcc actccaccgg cggcatggac | 3720 |
| gagctgtaca agtct | 3735 |

<210> SEQ ID NO 66
<211> LENGTH: 7677
<212> TYPE: DNA
<213> ORGANISM: Homo sapiens

<400> SEQUENCE: 66

| | |
|---|---|
| atgccgccgc tcctggcgcc cctgctctgc ctggcgctgc tgcccgcgct cgccgcacga | 60 |
| ggcccgcgat gctcccagcc cggtgagacc tgcctgaatg gcgggaagtg tgaagcggcc | 120 |
| aatggcacgg aggcctgcgt ctgtggcggg gccttcgtgg gccgcgatg ccaggacccc | 180 |
| aacccgtgcc tcagcacccc ctgcaagaac gccgggacat gccacgtggt ggaccgcaga | 240 |
| ggcgtggcag actatgcctg cagctgtgcc ctgggcttct ctgggcccct ctgcctgaca | 300 |
| cccctggaca tgcctgcct caccaacccc tgccgcaacg gggcacctg cgacctgctc | 360 |
| acgctgacgg agtacaagtg ccgctgcccg cccggctggt cagggaaatc gtgccagcag | 420 |
| gctgacccgt gcgcctccaa cccctgcgcc aacgtggca gtgcctgcc cttcgaggcc | 480 |
| tcctacatct gccactgccc acccagcttc catggcccca cctgccggca ggatgtcaac | 540 |
| gagtgtggcc agaagcccgg gctttgccgc acggaggca cctgccacaa cgaggtcggc | 600 |
| tcctaccgct gcgtctgccg cgccacccac actggcccca actgcgagcg ccctacgtg | 660 |
| cccctgcagcc cctcgccctg ccagaacggg gcacctgcc gcccacgggc gacgtcacc | 720 |
| cacgagtgtg cctgcctgcc aggcttcacc ggccagaact gtgaggaaaa tatcgacgat | 780 |
| tgtccaggaa acaactgcaa gaacggggt gcctgtgtgg acggcgtgaa cacctacaac | 840 |

```
tgccgctgcc cgccagagtg gacaggtcag tactgtaccg aggatgtgga cgagtgccag      900
ctgatgccaa atgcctgcca gaacggcggg acctgccaca acacccacgg tggctacaac      960
tgcgtgtgtg tcaacggctg gactggtgag gactgcagcg agaacattga tgactgtgcc     1020
agcgccgcct gcttccacgg cgccacctgc catgaccgtg tggcctcctt ctactgcgag     1080
tgtcccatg gccgcacagg tctgctgtgc cacctcaacg acgcatgcat cagcaacccc     1140
tgtaacgagg gctccaactg cgacaccaac cctgtcaatg gcaaggccat ctgcacctgc     1200
ccctcggggt acacgggccc ggcctgcagc caggacgtgg atgagtgctc gctgggtgcc     1260
aaccctgcg agcatgcggg caagtgcatc aacacgctgg gctccttcga gtgccagtgt     1320
ctgcagggct acacgggccc ccgatgcgag atcgacgtca acgagtgcgt ctcgaacccg     1380
tgccagaacg acgccacctg cctggaccag attggggagt ccagtgcat ctgcatgccc     1440
ggctacgagg gtgtgcactg cgaggtcaac acagacgagt gtgccagcag ccctgcctg     1500
cacaatggcc gctgcctgga caagatcaat gagttccagt gcgagtgccc cacgggcttc     1560
actgggcatc tgtgccagta cgatgtggac gagtgtgcca gcacccctg caagaatggt     1620
gccaagtgcc tggacggacc caacacttac acctgtgtgt gcacggaagg gtacacgggg     1680
acgcactgcg aggtggacat cgatgagtgc gaccccgacc cctgccacta cggctcctgc     1740
aaggacggct cgccaccctt cacctgcctc tgccgcccag gctacacggg ccaccactgc     1800
gagaccaaca tcaacgagtg ctccagccag ccctgccgcc acgggggcac ctgccaggac     1860
cgcgacaacg cctacctctg cttctgcctg aagggaccca caggacccaa ctgcgagatc     1920
aacctggatg actgtgccag cagcccctgc gactcgggca cctgtctgga caagatcgat     1980
ggctacgagt gtgcctgtga gccgggctac acagggagca tgtgtaacat caacatcgat     2040
gagtgtgcgg gcaacccctg ccacaacggg ggcacctgcg aggacggcat caatggcttc     2100
acctgccgct gccccgaggg ctaccacgac cccacctgcc tgtctgaggt caatgagtgc     2160
aacagcaacc cctgcgtcca cggggcctgc cgggacagcc tcaacgggta caagtgcgac     2220
tgtgaccctg ggtggagtgg gaccaactgt gacatcaaca acaatgagtg tgaatccaac     2280
ccttgtgtca acgcggcac ctgcaaagac atgaccagtg gctacgtgtg cacctgccgg     2340
gagggcttca gcgttcccaa ctgccagacc aacatcaacg agtgtgcgtc caacccatgt     2400
ctgaaccagg gcacgtgtat tgacgacgtt gccgggtaca agtgcaactg cctgctgccc     2460
tacacaggtg ccacgtgtga ggtggtgctg gccccgtgtg cccccagccc ctgcagaaac     2520
ggcggggagt gcaggcaatc cgaggactat gagagcttct cctgtgtctg ccccacgggc     2580
tggcaagcag ggcagacctg tgaggtcgac atcaacgagt gcgttctgag cccgtgccgg     2640
cacggcgcat cctgccagaa cacccacggc ggctaccgct gccactgcca ggccggctac     2700
agtgggcgca actgcgagac cgacatcgac gactgccggc caacccgtg tcacaacggg     2760
ggctcctgca cagacggcat caacacggcc ttctgcgact gcctgccgg cttccggggc     2820
actttctgtg aggaggacat caacgagtgt gccagtgacc cctgccgcaa cggggccaac     2880
tgcacggact gcgtggacag ctacacgtgc acctgccccg caggcttcag cgggatccac     2940
tgtgagaaca cacgcctga ctgcacagag agctcctgct tcaacggtgg cacctgcgtg     3000
gacggcatca actcgttcac ctgcctgtgt ccacccggct tcacgggcag ctactgccag     3060
cacgatgtca atgagtgcga ctcacagccc tgcctgcatg gcggcacctg tcaggacggc     3120
tgcggctcct acaggtgcac ctgcccccag ggctacactg gccccaactg ccagaacctt     3180
```

```
gtgcactggt gtgactcctc gccctgcaag aacggcggca aatgctggca gacccacacc    3240
cagtaccgct gcgagtgccc cagcggctgg accggccttt actgcgacgt gcccagcgtg    3300
tcctgtgagg tggctgcgca gcgacaaggt gttgacgttg cccgcctgtg ccagcatgga    3360
gggctctgtg tggacgcggg caacacgcac cactgccgct gccaggcggg ctacacaggc    3420
agctactgtg aggacctggt ggacgagtgc tcacccagcc cctgccagaa cggggccacc    3480
tgcacggact acctgggcgg ctactcctgc aagtgcgtgg ccggctacca cggggtgaac    3540
tgctctgagg agatcgacga gtgcctctcc caccccctgcc agaacggggg cacctgcctc    3600 gacctccccca acacctacaa gtgctcctgc ccacggggca ctcagggtgt gcactgtgag    3660
atcaacgtgg acgactgcaa tccccccgtt gaccccgtgt cccggagccc caagtgcttt    3720
aacaacggca cctgcgtgga ccaggtgggc ggctacagct gcacctgccc gccgggcttc    3780
gtgggtgagc gctgtgaggg ggatgtcaac gagtgcctgt ccaatccctg cgacgcccgt    3840
ggcacccaga actgcgtgca gcgcgtcaat gacttccact gcgagtgccg tgctggtcac    3900
accgggcgcc gctgcgagtc cgtcatcaat ggctgcaaag gcaagccctg caagaatggg    3960
ggcacctgcg ccgtggcctc caacaccgcc cgcgggttca tctgcaagtg ccctgcgggc    4020
ttcgagggcg ccacgtgtga gaatgacgct cgtacctgcg gcagcctgcg ctgcctcaac    4080
ggcggcacat gcatctccgg cccgcgcagc cccacctgcc tgtgcctggg cccttcacg    4140 ggcccccgaat gccagttccc ggccagcagc ccctgcctgg gcggcaaccc ctgctacaac    4200
caggggacct gtgagcccac atccgagagc cccttctacc gttgcctgtg ccccgccaaa    4260
ttcaacgggc tcttgtgcca catcctggac tacagcttcg ggggtggggc cgggcgcgac    4320 atcccccccgc cgctgatcga ggaggcgtgc gagctgcccg agtgccagga ggacgcgggc    4380
aacaaggtct gcagcctgca gtgcaacaac acgcgtgcg gctgggacgg cggtgactgc    4440
tccctcaact tcaatgaccc ctggaagaac tgcacgcagt ctctgcagtg ctggaagtac    4500
ttcagtgacg gccactgtga cagccagtgc aactcagccg gctgcctctt cgacggcttt    4560
gactgccagc gtgcggaagg ccagtgcaac cccctgtacg accagtactg caaggaccac    4620
ttcagcgacg gccactgcga ccagggctgc aacagcgcgg agtgcgagtg ggacgggctg    4680
gactgtgcgg agcatgtacc cgagaggctg gcggccggca cgctggtggt ggtggtgctg    4740
atgccgccgg agcagctgcg caacagctcc ttccacttcc tgcgggagct cagccgcgtg    4800
ctgcacacca acgtggtctt caagcgtgac gcacacggcc agcagatgat cttcccctac    4860 tacgccgcg aggaggagct gcgcaagcac cccatcaagc gtgccgccga gggctgggcc    4920
gcacctgacg ccctgctggg ccaggtgaag gcctcgctgc tccctggtgg cagcgagggt    4980
gggcggcggc ggagggagct ggaccccatg gacgtccgcg gctccatcgt ctacctggag    5040
attgacaacc ggcagtgtgt gcaggcctcc tcgcagtgct tccagagtgc caccgacgtg    5100
gccgcattcc tgggagcgct cgcctcgctg ggcagcctca acatcccta caagatcgag    5160 gccgtgcaga gtgagaccgt ggagccgccc ccgccgcgcg agctgcactt catgtacgtg    5220
gcggcggccg cctttgtgct tctgttcttc gtgggctgcg gggtgctgct gtcccgcaag    5280
cgccggcggc agcatggcca gctctggttc cctgagggct tcaaagtgtc tgaggccagc    5340
aagaagaagc ggcgggagcc cctcggcgag gactccgtgg gcctcaagcc cctgaagaac    5400
gcttcagacg gtgccctcat ggacgacaac cagaatgagt gggggggacga ggacctggag    5460 accaagaagt tccggttcga ggagcccgtg gttctgcctg acctggacga ccagacagac    5520
caccggcagt ggactcagca gcacctggat gccgctgacc tgcgcatgtc tgccatggcc    5580
```

```
cccacaccgc cccagggtga ggttgacgcc gactgcatgg acgtcaatgt ccgcgggcct    5640
gatggcttca ccccgctcat gatcgcctcc tgcagcgggg gcggcctgga gacgggcaac    5700
agcgaggaag aggaggacgc gccggccgtc atctccgact tcatctacca gggcgccagc    5760
ctgcacaacc agacagaccg cacggggcgag accgccttgc acctggccgc ccgctactca    5820
cgctctgatg ccgccaagcg cctgctggag gccagcgcag atgccaacat ccaggacaac    5880
atgggccgca ccccgctgca tgcggctgtg tctgccgacg cacaaggtgt cttccagatc    5940
ctgatccgga accgagccac agacctggat gcccgcatgc atgatggcac gacgccactg    6000
atcctggctg cccgcctggc cgtggagggc atgctggagg acctcatcaa ctcacacgcc    6060
gacgtcaacg ccgtagatga cctgggcaag tccgccctgc actgggccgc cgccgtgaac    6120
aatgtggatg ccgcagttgt gctcctgaag aacggggcta caaagatat gcagaacaac    6180 agggaggaga caccctgtt tctggccgcc cgggagggca gctacgagac cgccaaggtg    6240
ctgctggacc actttgccaa ccgggacatc acggatcata tggaccgcct gccgcgcgac    6300
atcgcacagg agcgcatgca tcacgacatc gtgaggctgc tggacgagta caacctggtg    6360
cgcagcccgc agctgcacgg agcccgcgct ggggcacgc ccaccctgtc gccccgctc    6420 tgctcgccca acggctacct gggcagcctc aagcccggcg tgcagggcaa gaaggtccgc    6480
aagcccagca gcaaaggcct ggcctgtgga agcaaggagg ccaaggacct caaggcacgg    6540
aggaagaagt cccaggacgg caagggctgc ctgctggaca gctccggcat gctctcgccc    6600
gtggactccc tggagtcacc ccatggctac ctgtcagacg tggcctcgcc gccactgctg    6660 ccctcccccgt tccagcagtc tccgtccgtg cccctcaacc acctgcctgg gatgcccgac    6720
acccacctgg gcatcgggca cctgaacgtg cgggccaagc ccgagatggc ggcgctgggt    6780
gggggcggcc ggctggcctt tgagactggc ccacctcgtc tctcccacct gcctgtggcc    6840
tctggcacca gcaccgtcct gggctccagc agcggagggg ccctgaattt cactgtgggc    6900
gggtccacca gtttgaatgg tcaatgcgag tggctgtccc ggctgcagag cggcatggtg    6960
ccgaaccaat acaaccctct gcgggggagt gtggcaccag gcccctgag cacacaggcc    7020 ccctccctgc agcatggcat ggtaggcccg ctgcacagta gccttgctgc cagcgccctg    7080
tcccagatga tgagctacca gggcctgccc agcacccggc tggccaccca gcctcacctg    7140
gtgcagaccc agcaggtgca gccacaaaac ttacagatgc agcagcagaa cctgcagcca    7200
gcaaacatcc agcagcagca aagcctgcag ccgccaccac caccaccaca gccgcacctt    7260
ggcgtgagct cagcagccag cggccacctg gccggagct tcctgagtgg agagccgagc    7320
caggcagacg tgcagccact gggcccagc agcctggcgg tgcacactat tctgccccag    7380
gagagccccg ccctgcccac gtcgctgcca tcctcgctgg tcccacccgt gaccgcagcc    7440
cagttcctga cgcccccctc gcagcacagc tactcctcgc ctgtggacaa caccccagc    7500 caccagctac aggtgcctga gcaccccttc ctcacccgt ccctgagtc ccctgaccag    7560 tggtccagct cgtccccgca ttccaacgtc tccgactggt ccgagggcgt ctccagccct    7620
cccaccagca tgcagtccca gatcgcccgc attccggagg ccttcaaggc tagctaa    7677
```

<210> SEQ ID NO 67
<211> LENGTH: 1584
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
gccaccatgg cattgcccgt gaccgccctg ctgctgccac tggccttgtt gctccacgcc      60
gcgcggccag aacagaagct gatcagcgag gaggatctga ccggtgtgag caagggcgag     120
gagctgttca ccggggtggt gcccatcctg gtcgagctgg acggcgacgt aaacggccac     180
aagttctccg tgcggggcga gggcgagggc gatgccacca acggcaagct gaccctgaag     240
ttcatcagca ccaccggcaa gctgcccgtg ccctggccca ccctcgtgac caccctgacc     300
tacggcgtgc agagcttctc ccgctacccc gaccacatga gcgccacga cttcttcaag     360
agcgccatgc ccgaaggcta cgtccaggag cgcaccatct ccttcaagga cgacggcacc     420
tacaagaccc gcgccgaggt gaagttcgag ggcgacaccc tggtgaaccg catcgagctg     480
aagggcatcg acttcaagga ggacggcaac atcctgggc acaagctgga gtacaacttc      540
aactcccaca acgtctatat caccgccgac aagcagaaga cggcatcaa ggccaacttc      600
aagatccgcc acaacgtgga ggacggctcc gtgcagctcg ccgaccacta ccagcagaac     660
accccccatcg cgacggcccc cgtgctgctg cccgacaacc actacctgtc cacccagtcc    720
aagctgtcca agaccccaa cgagaagcgc gatcacatgg tccttctgga attcgtgacc      780
gccgccggga tcactcacgg catggacgag ctgtacaagg atccccggt ggagcctccg      840
ctgccctcgc agctgcacct catgtacgtg cagcggccg ccttcgtgct cctgttcttt      900
gtgggctgtg gggtgctgct gtcccgcaag cgccggcggg gctcgagcat gaagctgctg     960
agcagcatcg agcaggcctg tgacatctgc cggctgaaga aactgaagtg cagcaaagaa    1020
aagcccaagt gcgccaagtg cctgaagaac aactgggagt gccggtacag ccccaagacc    1080
aagagaagcc ccctgaccag agcccacctg accgaggtgg aaagccggct ggaaagactg    1140
gaacagctgt ttctgctgat cttcccacgc gaggacctgg acatgatcct gaagatggac    1200
agcctgcagg acatcaaggc cctgctgacc ggcctgttcg tgcaggacaa cgtgaacaag    1260
gacgccgtga ccgacagact ggccagcgtg gaaaccgaca tgcccctgac cctgcggcag    1320
cacagaatca cgccaccag cagcagcgag gaaagcagca caagggcca gcggcagctg      1380
acagtgtctg ctgctgcagg cggaagcgga ggctctggcg gatctgatgc cctggacgac    1440
ttcgacctgg atatgctggg cagcgacgcc ctggatgatt ttgatctgga catgctggga    1500
tctgacgctc tggacgattt cgatctcgac atgttgggat cagatgcact ggatgacttt    1560
gacctggaca tgctcggatc atga                                           1584
```

<210> SEQ ID NO 68
<211> LENGTH: 525
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Thr
            20                  25                  30

Gly Val Ser Lys Gly Glu Glu Leu Phe Thr Gly Val Val Pro Ile Leu
        35                  40                  45

Val Glu Leu Asp Gly Asp Val Asn Gly His Lys Phe Ser Val Arg Gly
    50                  55                  60

```
Glu Gly Glu Gly Asp Ala Thr Asn Gly Lys Leu Thr Leu Lys Phe Ile
 65                  70                  75                  80

Ser Thr Thr Gly Lys Leu Pro Val Pro Trp Pro Thr Leu Val Thr Thr
                 85                  90                  95

Leu Thr Tyr Gly Val Gln Ser Phe Ser Arg Tyr Pro Asp His Met Lys
                100                 105                 110

Arg His Asp Phe Phe Lys Ser Ala Met Pro Glu Gly Tyr Val Gln Glu
            115                 120                 125

Arg Thr Ile Ser Phe Lys Asp Asp Gly Thr Tyr Lys Thr Arg Ala Glu
130                 135                 140

Val Lys Phe Glu Gly Asp Thr Leu Val Asn Arg Ile Glu Leu Lys Gly
145                 150                 155                 160

Ile Asp Phe Lys Glu Asp Gly Asn Ile Leu Gly His Lys Leu Glu Tyr
                165                 170                 175

Asn Phe Asn Ser His Asn Val Tyr Ile Thr Ala Asp Lys Gln Lys Asn
                180                 185                 190

Gly Ile Lys Ala Asn Phe Lys Ile Arg His Asn Val Glu Asp Gly Ser
            195                 200                 205

Val Gln Leu Ala Asp His Tyr Gln Gln Asn Thr Pro Ile Gly Asp Gly
210                 215                 220

Pro Val Leu Leu Pro Asp Asn His Tyr Leu Ser Thr Gln Ser Lys Leu
225                 230                 235                 240

Ser Lys Asp Pro Asn Glu Lys Arg Asp His Met Val Leu Leu Glu Phe
                245                 250                 255

Val Thr Ala Ala Gly Ile Thr His Gly Met Asp Glu Leu Tyr Lys Gly
                260                 265                 270

Ser Pro Val Glu Pro Pro Leu Pro Ser Gln Leu His Leu Met Tyr Val
            275                 280                 285

Ala Ala Ala Ala Phe Val Leu Leu Phe Phe Val Gly Cys Gly Val Leu
290                 295                 300

Leu Ser Arg Lys Arg Arg Arg Gly Ser Ser Met Lys Leu Leu Ser Ser
305                 310                 315                 320

Ile Glu Gln Ala Cys Asp Ile Cys Arg Leu Lys Lys Leu Lys Cys Ser
                325                 330                 335

Lys Glu Lys Pro Lys Cys Ala Lys Cys Leu Lys Asn Asn Trp Glu Cys
                340                 345                 350

Arg Tyr Ser Pro Lys Thr Lys Arg Ser Pro Leu Thr Arg Ala His Leu
            355                 360                 365

Thr Glu Val Glu Ser Arg Leu Glu Arg Leu Glu Gln Leu Phe Leu Leu
            370                 375                 380

Ile Phe Pro Arg Glu Asp Leu Asp Met Ile Leu Lys Met Asp Ser Leu
385                 390                 395                 400

Gln Asp Ile Lys Ala Leu Leu Thr Gly Leu Phe Val Gln Asp Asn Val
                405                 410                 415

Asn Lys Asp Ala Val Thr Asp Arg Leu Ala Ser Val Glu Thr Asp Met
                420                 425                 430

Pro Leu Thr Leu Arg Gln His Arg Ile Ser Ala Thr Ser Ser Ser Glu
            435                 440                 445

Glu Ser Ser Asn Lys Gly Gln Arg Gln Leu Thr Val Ser Ala Ala Ala
            450                 455                 460

Gly Gly Ser Gly Gly Ser Gly Gly Ser Asp Ala Leu Asp Asp Phe Asp
465                 470                 475                 480
```

-continued

```
Leu Asp Met Leu Gly Ser Asp Ala Leu Asp Asp Phe Asp Leu Asp Met
                485                 490                 495

Leu Gly Ser Asp Ala Leu Asp Asp Phe Asp Leu Asp Met Leu Gly Ser
            500                 505                 510

Asp Ala Leu Asp Asp Phe Asp Leu Asp Met Leu Gly Ser
        515                 520             525

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 69

His His His His His His
1               5

<210> SEQ ID NO 70
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Val Gln Ser Glu Thr Val Glu Pro Pro Pro Ala Gln Leu His Phe
1               5                   10                  15

Met Tyr Val Ala Ala Ala Phe Val Leu Leu Phe Phe Val Gly Cys
            20                  25                  30

Gly Val Leu Leu Ser Arg Lys Arg Arg Arg Gln His Gly Gln Leu Trp
        35                  40                  45

Phe Pro Glu Gly
    50
```

SYNTHETIC PROTEIN FOR MODULATING GENE EXPRESSION

CROSS-REFERENCE TO RELATED APPLICATION

This application is a continuation under 35 U.S.C. § 120 of co-pending U.S. application Ser. No. 15/994,330 filed May 31, 2018, which claims benefit under 35 U.S.C. § 119(e) of the U.S. Provisional Application No. 62/513,031 filed May 31, 2017 and U.S. Provisional Application No. 62/586,451 filed Nov. 15, 2017, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jun. 29, 2018, is named 701586-089500USPT_SL.txt and is 208,433 bytes in size.

TECHNICAL FIELD

The present invention relates generally to compositions and methods for engineering natural and synthetic Notch signaling.

BACKGROUND OF THE INVENTION

Drug-inducible strategies for regulating protein function and gene activity have been indispensable tools in biological research, yet methods for controlling diverse systems remain lacking. The Notch protein is a transmembrane receptor that acts a mechanical "switch," translating mechanical cues into gene expression. This mechanosensing activity is achieved via Notch's force-sensitive Negative Regulatory Region (NRR), which contains three LNR domains. In the resting state, the LNR domains adopt an autoinhibitory conformation that sterically hinders proteolytic cleavage necessary for receptor activation. Upon the application of a pulling force, however, these LNR domains are displaced, and two concomitant proteolytic cleavages occur that release the Notch intracellular domain to transport to the nucleus and regulate gene expression.

SUMMARY OF THE INVENTION

As described herein, compositions, methods, and systems using antibody domains have been developed through which signaling from natural and synthetic Notch receptors can be regulated or modulated. These compositions, methods, and systems can be used to increase the amount of force required to activate Notch receptors, or to regulate their activity on therapeutic cells. The compositions, methods, and systems described herein are useful for a variety of cell engineering applications, including the creation of engineered cells capable of sensing certain mechanical features of solid tumors (or biomaterials), as well as for precisely controlling therapeutic and/or engineered cells expressing synthetic receptor proteins, such as synthetic Notch receptor proteins.

The compositions, methods, and systems described herein involve, in part, the use of antibody fragments directed against the NRR region of the Notch receptor, a force-sensitive mechanical switch that is ruptured during receptor activation. Binding of these antibodies stabilizes the NRR and prevents Notch activation. Use of scFvs from these antibodies permits the generation of inhibitory "modules" which are used to generate synthetic proteins and receptors for precisely controlling signaling from Notch and synthetic Notch systems. For example, synthetic notch receptors have been created that allow for gene expression to be controlled upon binding of the receptor to various ligands of interest (e.g., surface proteins on cancer cells), such as those described in US20160264665, the contents of which are herein incorporated by reference in their entireties.

As described herein, antibody fragments from anti-NRR antibodies are used as modules for engineering synthetic proteins and receptors for cell-engineering applications. These antibody-derived fragments are used as new genetic tools to reprogram natural and synthetic Notch signaling for synthetic biology applications. In some embodiments, these can be used to allow cells expressing these systems to function as genetically encoded "tensometers," permitting, for example, engineered T cells to activate their cell killing activity in response to the mechanical properties of fibrotic tissues or physical features of solid tumors. In contrast, previous work involving anti-NRR antibodies relied on the use of purified immunoglobulin as an exogenously applied drug or agent.

The compositions, methods, and systems described herein are also directed towards compositions, constructs, and methods for controlling the binding/activation of Notch receptors through the use of synthetic protein ligands that incorporate NS3 protease domains as a Ligand-Inducible Connection (LInC) from the hepatitis C virus. In the absence of an NS-inhibitor drug, the ligand domain is cleaved and becomes incapable of activating the notch receptor. When an NS-inhibitor drug is applied, the NS3 domain remains intact and the ligand is capable of activating the notch receptor. As demonstrated herein, using the NS3 cis-protease from hepatitis C virus (HCV) as a LInC or drug-inducible linker allows precise control of protein function and localization using clinically tested antiviral protease inhibitors. The versatility of the approach is demonstrated in the design of drug-sensitive transcription factors (TFs) and transmembrane signaling proteins, as described herein.

Also provided herein, in some aspects, are isolated nucleic acid sequences encoding the synthetic proteins and protein ligands, and engineered cells genetically modified with the nucleic acids encoding the synthetic proteins and protein ligands described herein.

Accordingly, in some aspects, provided herein are synthetic inhibitor proteins comprising a Notch NRR (Negative Regulatory Region)-binding scFV fused to a transmembrane domain.

In some aspects, provided herein are synthetic autoinhibitory proteins comprising a Notch NRR (Negative Regulatory Region)-binding scFV fused to a transmembrane domain.

In some embodiments of these aspects and all such aspects described herein, the Notch NRR comprises a Notch NRR1 of SEQ ID NO: 8.

In some embodiments of these aspects and all such aspects described herein, the Notch NRR is mutated relative to Notch NRR1 of SEQ ID NO: 8 or is a variant of Notch NRR1 of SEQ ID NO: 8.

In other aspects, provided herein are synthetic Notch receptor proteins comprising, in N-terminal to C-terminal order and in covalent linkage, (i) a ligand binding domain (LBD), (ii) a mutated Notch NRR (Negative Regulatory Region), (iii) a transmembrane domain, and (iv) an intracellular domain, wherein the mutated Notch NRR is bound with high-affinity by a synthetic inhibitor protein comprising a mutated Notch NRR-binding scFV fused to a transmembrane domain.

In some embodiments of these aspects and all such aspects described herein, the mutated Notch NRR is mutated relative to Notch NRR1 of SEQ ID NO: 8.

In some aspects, provided herein are synthetic Notch receptor proteins comprising, in N-terminal to C-terminal order, and in covalent linkage, (i) a ligand binding domain (LBD), (ii) a scFV that binds to an at least one Notch NRR (Negative Regulatory Region), (iii) a Notch NRR bound by the scFV, (iv) a transmembrane domain, and (v) an intracellular domain.

In some embodiments of these aspects and all such aspects described herein, the Notch NRR comprises a Notch NRR1 of SEQ ID NO: 8.

In some embodiments of these aspects and all such aspects described herein, the Notch NRR is mutated relative to Notch NRR1 of SEQ ID NO: 8.

In some aspects, provided herein are synthetic, drug-dependent protein comprising a ligand binding domain (LBD), an NS3 protease domain, and a transmembrane domain.

In some embodiments of these aspects and all such aspects described herein, the LBD and transmembrane domain comprise a sequence of human Delta ligand.

In some embodiments of these aspects and all such aspects described herein, the NS3 domain comprises a sequence of SEQ ID NO: 32.

In some embodiments of these aspects and all such aspects described herein, the synthetic, drug-dependent protein further comprises a targeting domain.

In some embodiments of these aspects and all such aspects described herein, the transmembrane domain comprises the human Notch1 transmembrane domain of SEQ ID NO: 13 or a variant thereof.

In some embodiments of these aspects and all such aspects described herein, the scFV comprises, in N-terminal to C-terminal order and in covalent linkage, a VH domain, a linker domain, and a VL domain.

In some embodiments of these aspects and all such aspects described herein, the scFV is selected from any one of SEQ ID NOs: 15-27.

In some embodiments of these aspects and all such aspects described herein, the synthetic protein further comprises a signal sequence N-terminal to the LBD.

Also provided herein, in some aspects, are isolated nucleic acid sequences encoding any of the synthetic proteins described herein.

Also provided herein, in some aspects, are engineered cells comprising isolated nucleic acid sequences encoding any of the synthetic proteins described herein.

In some embodiments of these aspects and all such aspects described herein, the engineered cell is an engineered T cell.

Provided herein, in some aspects, are engineered cells comprising (i) a nucleic acid sequence encoding a synthetic inhibitor protein comprising a Notch NRR (Negative Regulatory Region)-binding scFV fused to a transmembrane domain, and (ii) a nucleic acid sequence encoding a synthetic Notch receptor protein comprising a mutated Notch NRR.

In some embodiments of these aspects and all such aspects described herein, the engineered cell is an engineered T cell.

In some embodiments of these aspects and all such aspects described herein, the nucleic acid sequence encoding the synthetic inhibitor protein, the nucleic acid sequence encoding the synthetic Notch receptor protein, or both are under operable control of a drug-inducible promoter.

In some aspects, provided herein, are synthetic, drug-sensitive transcription factors, comprising: a DNA-binding domain (DB); a transcriptional activation domain (TA); and a HCV NS3 protease domain; wherein the HCV NS3 protease domain is located in between the DB and the TA.

In some embodiments of these aspects and all such aspects described herein, the HCV NS3 protease domain comprises cleavage activity.

In some embodiments of these aspects and all such aspects described herein, the cleavage activity activates the transcription factor.

In some embodiments of these aspects and all such aspects described herein, the DB is Gal4 DB or Cas9 DB.

In some embodiments of these aspects and all such aspects described herein, the DB is reverse tetracycline repressor.

In some embodiments of these aspects and all such aspects described herein, the TA is Gal4 TA, VP64 TA, VP64-p65 TA, or VPR TA.

In some embodiments of these aspects and all such aspects described herein, the synthetic transcription factor further comprises at least one fluorescent or at least one SNAP tag.

In some embodiments of these aspects and all such aspects described herein, the tag is located at a N-terminus or a C-terminus of the transcription factor.

In some embodiments of these aspects and all such aspects described herein, the transcription factor further comprises at least one targeting sequence.

In some embodiments of these aspects and all such aspects described herein, the targeting sequence is a transmembrane domain or a nuclear localization sequence.

In some embodiments of these aspects and all such aspects described herein, the tag is located at a N-terminus or a C-terminus of the transcription factor.

In some embodiments of these aspects and all such aspects described herein, the transcription factor further comprises at least one lipid modification.

In some embodiments of these aspects and all such aspects described herein, the lipid modification is myristoylation or palmitoylation.

In some embodiments of these aspects and all such aspects described herein, the at least one lipid modification is located at an N-terminus or a C-terminus of the transcription factor.

Provided herein in some aspects are isolated nucleic acid sequences encoding any of the synthetic transcription factor described herein.

Provided herein in some aspects are engineered cells comprising the isolated nucleic acid sequences encoding any of the synthetic transcription factor described herein.

Definitions

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Definitions of common terms in immunology, and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADAM Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

The term "antibody" broadly refers to any immunoglobulin (Ig) molecule and immunologically active portions of immunoglobulin molecules (i.e., molecules that contain an antigen binding site that immunospecifically bind an antigen) comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below, and include but are not limited to a variety of forms, including full length antibodies and antigen-binding portions thereof; including, for example, an immunoglobulin molecule, a monoclonal antibody, a chimeric antibody, a CDR-grafted antibody, a human antibody, a humanized antibody, a single chain antibody, a Fab, a F(ab'), a F(ab')2, a Fv antibody, fragments produced by a Fab expression library, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference) and/or antigen-binding fragments of any of the above (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). Antibodies also refer to immunoglobulin molecules and immunologically active portions of immunoglobulin molecules, i.e., molecules that contain antigen or target binding sites or "antigen-binding fragments." The antibody or immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art. Furthermore, in humans, the light chain can be a kappa chain or a lambda chain.

In a full-length antibody, each heavy chain is comprised of a heavy chain variable domain (abbreviated herein as HCVR or VH) and a heavy chain constant region. The heavy chain constant region is comprised of three domains: CH1, CH2, and CH3. Each light chain is comprised of a light chain variable domain (abbreviated herein LCVR as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. This structure is well-known to those skilled in the art. The chains are usually linked to one another via disulfide bonds.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain, and a CH3 domain, and optionally comprises a CH4 domain. Replacements of amino acid residues in the Fc portion to alter antibody effector function are known in the art (U.S. Pat. Nos. 5,648,260 and 5,624,821). The Fc portion of an antibody mediates several important effector functions, for example, cytokine induction, ADCC, phagocytosis, complement dependent cytotoxicity (CDC), and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to Fc.gamma.Rs and complement C1q, respectively. Neonatal Fc receptors (FcRn) are the critical components determining the circulating half-life of antibodies The term "antigen-binding portion" of an antibody refers to one or more fragments of an antibody that retain the ability to specifically bind to an antigen. Antigen-binding functions of an antibody can be performed by fragments of a full-length antibody. Such antibody fragment embodiments may also be incorporated in bispecific, dual specific, or multi-specific formats such as a dual variable domain (DVD-Ig) format; specifically binding to two or more different antigens (e.g., Notch receptor and a different antigen molecule). Examples of binding fragments encompassed within the term "antigen-binding portion" of an antibody include (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature, 341: 544-546; PCT Publication No. WO 90/05144), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, for example, Bird et al. (1988) Science 242: 423-426; and Huston et al. (1988) Proc. Natl. Acad. Sci. USA 85: 5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al. (1993) Proc. Natl. Acad. Sci. USA 90: 6444-6448; Poljak (1994) Structure 2: 1121-1123); Kontermann and Dubel eds., Antibody Engineering, Springer-Verlag, N.Y. (2001), p. 790 (ISBN 3-540-41354-5). In addition, single chain antibodies also include "linear antibodies" comprising a pair of tandem Fv segments (VH-CH1-VH-CH1) which, together with complementary light chain polypeptides, form a pair of antigen binding regions (Zapata et al. (1995) Protein Eng. 8(10): 1057-1062; and U.S. Pat. No. 5,641,870).

An immunoglobulin constant (C) domain refers to a heavy (CH) or light (CL) chain constant domain. Murine and human IgG heavy chain and light chain constant domain amino acid sequences are known in the art.

As used herein, the term "target" refers to a biological molecule (e.g., peptide, polypeptide, protein, lipid, carbohydrate) to which a polypeptide domain which has a binding site can selectively bind. The target can be, for example, an intracellular target (e.g., an intracellular protein target) or a cell surface target (e.g., a membrane protein, a receptor protein). Preferably, a target is a cell surface target, such as a cell surface protein.

As described herein, an "antigen" is a molecule that is bound by a binding site on a polypeptide agent, such as a binding protein, an antibody or antibody fragment, or antigen-binding fragment thereof. Typically, antigens are bound by antibody ligands and are capable of raising an antibody response in vivo. An antigen can be a polypeptide, protein, nucleic acid or other molecule. In the case of conventional antibodies and fragments thereof, the antibody binding site as defined by the variable loops (L1, L2, L3 and H1, H2, H3) is capable of binding to the antigen. The term "antigenic determinant" refers to an epitope on the antigen recognized by an antigen-binding molecule, and more particularly, by the antigen-binding site of said molecule.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by a binding protein. An epitope may be determined by obtaining an X-ray crystal structure of an antibody:antigen complex and determining which residues on the antigen are within a specified distance of residues on the antibody of interest, wherein the specified distance is, 5A or less, e.g., 5 Å, 4 Å, 3 Å, 2 Å, 1 Å or any distance in between. In some embodiments, an "epitope" can be formed on a polypeptide both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In some embodiments, an epitope comprises of 8 or more contiguous or non-contiguous amino acid residues in the sequence in which at least 50%, 70% or 85% of the residues are within the specified distance of the antibody or binding protein in the X-ray crystal structure.

The terms "specificity" or "specific for" refers to the number of different types of antigens or antigenic determinants to which a binding protein, antibody or antibody fragment, or antigen-binding portion thereof thereof as described herein can bind. The specificity of a binding protein, antibody or antibody fragment, or antigen-binding portion thereof thereof can be determined based on affinity and/or avidity. The affinity, represented by the equilibrium constant for the dissociation (KD) of an antigen with an antigen-binding protein, is a measure of the binding strength between an antigenic determinant and an antigen-binding site on the antigen-binding protein, such as a binding protein, antibody or antibody fragment, or antigen-binding portion thereof thereof: the lesser the value of the KD, the stronger the binding strength between an antigenic determinant and the antigen-binding molecule. Alternatively, the affinity can also be expressed as the affinity constant (KA), which is 1/KD). As will be clear to the skilled person, affinity can be determined in a manner known per se, depending on the specific antigen of interest. Accordingly, a binding protein, antibody or antibody fragment, or antigen-binding portion thereof thereof as defined herein is said to be "specific for" a first target or antigen compared to a second target or antigen when it binds to the first antigen with an affinity (as described above, and suitably expressed, for example as a KD value) that is at least 10 times, such as at least 100 times, and preferably at least 1000 times, and up to 10000 times or more better than the affinity with which said amino acid sequence or polypeptide binds to another target or polypeptide.

Accordingly, as used herein, "selectively binds" or "specifically binds" or "specific binding" in reference to the interaction of an antibody, or antibody fragment thereof, or a binding protein described herein, means that the interaction is dependent upon the presence of a particular structure (e.g., an antigenic determinant or epitope or target) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In certain embodiments, a binding protein or antibody or antigen-binding fragment thereof that specifically binds to an antigen binds to that antigen with a $K_D$ greater than $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M. In other embodiments, a binding protein or antibody or antigen binding fragment thereof that specifically binds to an antigen binds to that antigen with a $K_D$ between $10^{-6}$ and $10^{-7}$M, $10^{-6}$ and $10^{-8}$ M, $10^{-6}$ and $10^{-9}$M, $10^{-6}$ and $10^{-10}$M, $10^{-6}$ and $10^{-11}$ M, $10^{-6}$ and $10^{-12}$M, $10^{-6}$ and $10^{-13}$M, $10^{-6}$ and $10^{-14}$ M, $10^{-9}$ and $10^{-10}$ M, $10^{-9}$ and $10^{-11}$ M, $10^{-9}$ and $10^{-12}$ M, $10^{-9}$ and $10^{-13}$ M, $10^{-9}$ and $10^{-14}$ M. In some embodiments, a binding protein or antibody or antigen-binding fragment thereof binds to an epitope, with a $K_D$ $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. In certain embodiments, a binding protein or antibody or antigen-binding fragment thereof is said to "specifically bind" an antigen when it preferentially recognizes its target antigen in a complex mixture of proteins and/or macromolecules. Binding proteins, antibodies or antigen-binding fragments that bind to the same or similar epitopes will likely cross-compete (one prevents the binding or modulating effect of the other). Cross-competition, however, can occur even without epitope overlap, e.g., if epitopes are adjacent in three-dimensional space and/or due to steric hindrance.

The term "antibody fragment," or "antigen-binding fragment" as used herein, refer to a protein fragment that comprises only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 341, 544-546 (1989)) which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. Protein Eng. 8(10): 1057-1062 (1995); and U.S. Pat. No. 5,641,870).

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

The "Fab" fragment contains a variable and constant domain of the light chain and a variable domain and the first constant domain (CH1) of the heavy chain. F(ab') 2 antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the VH and VL domains of antibody, wherein these domains are present in a single polypeptide chain. Generally the Fv polypeptide further comprises a polypeptide linker between the VH and VL domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-315 (1994).

The term "monoclonal antibody" or "mAb" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the invention can be made by the hybridoma method first described by Kohler et al., Nature 256:495 (1975), or can be made by recombinant DNA methods (see, e.g., U.S. Pat. No. 4,816,567). The "monoclonal antibodies" can also be isolated from phage antibody libraries using the techniques described in Clackson et al., Nature 352:624-628 (1991) or Marks et al., J. Mol. Biol. 222:581-597 (1991), for example. A monoclonal antibody can be of any species, including, but not limited to, mouse, rat, goat, rabbit, and human monoclonal antibodies. Various methods for making monoclonal antibodies specific for an antigen, such as Notch, as described herein, are available in the art. For example, the monoclonal antibodies can be made using the hybridoma method first described by Kohler et al., Nature, 256:495 (1975), or by recombinant DNA methods (U.S. Pat. No. 4,816,567). "Monoclonal antibodies" can also be isolated from or produced using phage antibody libraries using the techniques originally described in Clackson et al., Nature 352:624-628 (1991), Marks et al., J. Mol. Biol. 222:581-597 (1991), McCafferty et al., Nature, 348:552-554 (1990), Marks et al., Bio/Technology, 10:779-783 (1992)), Waterhouse et al., Nuc. Acids. Res., 21:2265-2266 (1993), and techniques known to those of ordinary skill in the art.

The term "human antibody" includes antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" does not include antibodies in which CDR sequences derived from the germline of another mammalian species, such as a mouse, have been grafted onto human framework sequences.

The term "recombinant human antibody" includes all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes, or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies that comprise heavy and light chain variable domain sequences from one species and constant region sequences from another species, such as antibodies having murine heavy and light chain variable domains linked to human constant regions.

The term "CDR-grafted antibody" refers to antibodies that comprise heavy and light chain variable domain sequences from one species but in which the sequences of one or more of the CDR regions of VH and/or VL are replaced with CDR sequences of another species, such as antibodies having murine heavy and light chain variable domains in which one or more of the murine CDRs (e.g., CDR3) has been replaced with human CDR sequences.

The term "CDR" refers to the complementarity determining region within antibody variable sequences. There are three CDRs in each of the variable domains of the heavy chain and the light chain, which are designated CDR1, CDR2 and CDR3, for each of the variable domains. The term "CDR set" as used herein refers to a group of three CDRs that occur in a single variable domain capable of binding the antigen. The exact boundaries of these CDRs have been defined differently according to different systems. The system described by Kabat (Kabat et al., Sequences of Proteins of Immunological Interest, National Institutes of Health, Bethesda, Md. (1987) and (1991)) not only provides an unambiguous residue numbering system applicable to any variable domain of an antibody, but also provides precise residue boundaries defining the three CDRs. These CDRs may be referred to as Kabat CDRs. Chothia and coworkers (Chothia et al. (1987) J. Mol. Biol. 196: 901-917; and Chothia et al. (1989) Nature 342: 877-883) found that certain sub-portions within Kabat CDRs adopt nearly identical peptide backbone conformations, despite having great diversity at the level of amino acid sequence. These sub-portions were designated as L1, L2, and L3 or H1, H2, and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan et al. ((1995) FASEB J. 9:133-139) and MacCallum et al. ((1996) J. Mol. Biol. 262(5):732-745). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although exemplary embodiments use Kabat or Chothia defined CDRs.

As used herein, the term "canonical" residue refers to a residue in a CDR or framework that defines a particular canonical CDR structure as defined by Chothia et al. ((1987) J. Mol. Biol. 196: 901-917); and Chothia et al. ((1992) J. Mol. Biol. 227: 799-817), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, "antibody variable domain" refers to the portions of the light and heavy chains of antibody molecules that include amino acid sequences of Complementarity Determining Regions (CDRs; i.e., CDR1, CDR2, and CDR3), and Framework Regions (FRs). Each heavy chain is composed of a variable region of the heavy chain (VH refers to the variable domain of the heavy chain) and a constant region of said heavy chain. The heavy chain constant region consists of three domains CH1, CH2 and CH3. Each light chain is composed of a variable region of said light chain (VL refers to the variable domain of the light chain) and a constant region of the light chain. The light chain constant region consists of a CL domain. The VH and VL regions can be further divided into hypervariable regions referred to as complementarity-determining regions (CDRs) and interspersed with conserved regions referred to as framework regions (FR). Each VH and VL region thus consists of three CDRs and four FRs that are arranged from the N terminus to the C terminus in the following order: FR1, CDR1, FR2, CDR2, FR3, CDR3, FR4. This structure is well known to those skilled in the art. According to the methods used herein, the amino acid positions assigned to CDRs and FRs can be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

The term "multivalent binding protein" denotes a binding protein comprising two or more antigen binding sites. A multivalent binding protein may be engineered to have three or more antigen binding sites, and is generally not a naturally occurring antibody. The term "multispecific binding protein" refers to a binding protein capable of binding two or more related or unrelated targets.

Similarly, unless indicated otherwise, the expression "multivalent antibody" is used throughout this specification to denote an antibody comprising three or more antigen binding sites. For example, the multivalent antibody is engineered to have the three or more antigen binding sites and is generally not a native sequence IgM or IgA antibody.

In some embodiments, the binding protein is a single chain dual variable domain immunoglobulin protein. The terms "single chain dual variable domain immunoglobulin protein" or "scDVD-Ig protein" or scFvDVD-Ig protein" refer to the antigen binding fragment of a DVD molecule that is analogous to an antibody single chain Fv fragment. scDVD-Ig proteins are described in U.S. Ser. Nos. 61/746,659; 14/141,498 (US application 2014/0243228); and Ser. No. 14/141,500 (US application 2014/0221621), which are incorporated herein by reference in their entireties. In an embodiment, the variable domains of a scDVD-Ig protein are antibody variable domains. In an embodiment, the variable domains are non-immunoglobulin variable domains (e.g., receptor).

In some embodiments, the binding protein is a DVD-Fab. The terms "DVD-Fab" or fDVD-Ig protein" refer to the antigen binding fragment of a DVD-Ig molecule that is analogous to an antibody Fab fragment. fDVD-Ig proteins are described in U.S. Ser. Nos. 61/746,663; 14/141,498 (US Application 2014/0243228); and Ser. No. 14/141,501 (US application US 2014/0235476), incorporated herein by reference in their entireties.

In some embodiments, the binding protein is a receptor DVD-Ig protein. The terms "receptor DVD-Ig protein" constructs, or "rDVD-Ig protein" refer to DVD-Ig constructs comprising at least one receptor-like binding domain. rDVD-Ig proteins are described in U.S. Ser. Nos. 61/746,616; and Ser. No. 14/141,499 (US application 2014/0219913), which are incorporated herein by reference in their entireties.

The term "receptor domain" (RD), or receptor binding domain refers to the portion of a cell surface receptor, cytoplasmic receptor, nuclear receptor, or soluble receptor that functions to bind one or more receptor ligands or signaling molecules (e.g., toxins, hormones, neurotransmitters, cytokines, growth factors, or cell recognition molecules).

The terms multi-specific and multivalent IgG-like molecules or "pDVD-Ig" proteins are capable of binding two or more proteins (e.g., antigens). pDVD-Ig proteins are described in U.S. Ser. No. 14/141,502 (US Application 2014/0213771), incorporated herein by reference in its entirety. In certain embodiments, pDVD-Ig proteins are disclosed which are generated by specifically modifying and adapting several concepts. These concepts include but are not limited to: (1) forming Fc heterodimer using CH3 "knobs-into-holes" design, (2) reducing light chain missing pairing by using CH1/CL cross-over, and (3) pairing two separate half IgG molecules at protein production stage using "reduction then oxidation" approach.

In certain embodiments, a binding protein disclosed herein is a "half-DVD-Ig" comprised of one DVD-Ig heavy chain and one DVD-Ig light chain. The half-DVD-Ig protein preferably does not promote cross-linking observed with naturally occurring antibodies which can result in antigen clustering and undesirable activities. See U.S. Patent Publication No. 2012/0201746 which is incorporated by reference herein in its entirety. In some embodiments, the binding protein is a pDVD-Ig protein. In one embodiment, a pDVD-Ig construct may be created by combining two halves of different DVD-Ig molecules, or a half DVD-Ig protein and half IgG molecule.

In some embodiments, the binding protein is an mDVD-Ig protein. As used herein "monobody DVD-Ig protein" or "mDVD-Ig protein" refers to a class of binding molecules wherein one binding arm has been rendered non-functional. mDVD-Ig proteins are described in U.S. Ser. No. 14/141,503 (US Application 2014/0221622) incorporated herein by reference in its entirety.

The Fc regions of the two polypeptide chains that have a formula of VDH-(X1)n-C-(X2)n may each contain a mutation, wherein the mutations on the two Fc regions enhance heterodimerization of the two polypeptide chains. In one aspect, knobs-into-holes mutations may be introduced into these Fc regions to achieve heterodimerization of the Fc regions. See Atwell et al. (1997) J. Mol. Biol. 270:26-35.

In some embodiments, the binding protein is a cross-over DVD-Ig protein. As used herein "cross-over DVD-Ig" protein or "coDVD-Ig" protein refers to a DVD-Ig protein wherein the cross-over of variable domains is used to resolve the issue of affinity loss in the inner antigen-binding domains of some DVD-Ig molecules. coDVD-Ig proteins are described in U.S. Ser. No. 14/141,504, incorporated herein by reference in its entirety.

The term "bispecific antibody", as used herein, refers to full-length antibodies that are generated by quadroma technology (see Milstein et al. (1983) Nature 305: 537-540), by chemical conjugation of two different monoclonal antibodies (see Staerz et al. (1985) Nature 314: 628-631), or by knob-into-hole or similar approaches which introduces mutations in the Fc region (see Holliger et al. (1993) Proc. Natl. Acad. Sci. USA 90(14): 6444-6448), resulting in multiple different immunoglobulin species of which only one is the functional bispecific antibody. By molecular function, a bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen binding arms (in both specificity and CDR sequences), and is monovalent for each antigen it binds.

The term "dual-specific antibody", as used herein, refers to full-length antibodies that can bind two different antigens (or epitopes) in each of its two binding arms (a pair of HC/LC) (see PCT Publication No. WO 02/02773). Accordingly a dual-specific binding protein has two identical antigen binding arms, with identical specificity and identical CDR sequences, and is bivalent for each antigen to which it binds.

A "functional antigen binding site" of a binding protein is one that is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same.

As used herein, the terms "donor" and "donor antibody" refer to an antibody providing one or more CDRs. In an exemplary embodiment, the donor antibody is an antibody from a species different from the antibody from which the framework regions are obtained or derived. In the context of a humanized antibody, the term "donor antibody" refers to a non-human antibody providing one or more CDRs.

As used herein, the terms "acceptor" and "acceptor antibody" refer to the antibody providing or nucleic acid sequence encoding at least 80%, at least 85%, at least 90%, at least 95%, at least 98%, or 100% of the amino acid sequences of one or more of the framework regions. In some embodiments, the term "acceptor" refers to the antibody amino acid providing or nucleic acid sequence encoding the constant region(s). In yet another embodiment, the term "acceptor" refers to the antibody amino acid providing or nucleic acid sequence encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well known in the art, antibodies in development, or antibodies commercially available).

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al. (2002) Crit. Rev. Immunol. 22(3): 183-200; Marchalonis et al. (2001) Adv. Exp. Med. Biol. 484:13-30). One of the advantages provided by various embodiments of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

An "isolated antibody" is intended to refer to an antibody that is substantially free of other antibodies having different antigenic specificities. Moreover, an isolated antibody may be substantially free of other cellular material and/or chemicals.

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

The term "linear antibodies" refers to the antibodies described in Zapata et al., Protein Eng., 8(10): 1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "humanized antibody" refers to antibodies that comprise heavy and light chain variable domain sequences from a non-human species (e.g., a mouse) but in which at least a portion of the VH and/or VL sequence has been altered to be more "human-like", i.e., more similar to human germline variable sequences. Accordingly, "humanized" antibodies are a form of a chimeric antibody, that are engineered or designed to comprise minimal sequence derived from non-human immunoglobulin. For the most part, humanized antibodies are human immunoglobulins (recipient or acceptor antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321: 522-525 (1986); Riechmann et al., Nature 332:323-329 (1988); and Presta, Curr. Op. Struct. Biol. 2:593-596 (1992). As used herein, a "composite human antibody" or "deimmunized antibody" are specific types of engineered or humanized antibodies designed to reduce or eliminate T cell epitopes from the variable domains.

One type of humanized antibody is a CDR-grafted antibody, in which human CDR sequences are introduced into non-human VH and VL sequences to replace the corresponding nonhuman CDR sequences. Also "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab') .sub.2, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain. A humanized antibody may be selected from any class of immunoglobulins, including IgM, IgG, IgD, IgA and IgE, and any isotype including without limitation IgG1, IgG2, IgG3, and IgG4. The humanized antibody may comprise sequences from more than one class or isotype, and particular constant domains may be selected to optimize desired effector functions using techniques well known in the art.

With respect to constructing DVD-Ig or other binding protein molecules, a "linker" is used to denote a single amino acid or a polypeptide ("linker polypeptide") comprising two or more amino acid residues joined by peptide bonds and used to link one or more antigen binding portions. Such linker polypeptides are well known in the art (see, e.g., Holliger et al. (1993) Proc. Natl. Acad. Sci. USA 90: 6444-6448; Poljak (1994) Structure 2: 1121-1123).

A "human antibody," "non-engineered human antibody," or "fully human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. Nature Biotechnology 14:309-314 (1996): Sheets et al. Proc. Natl. Acad. Sci. 95:6157-6162 (1998)); Hoogenboom and Winter, J. Mol. Biol., 227:381 (1991); Marks et al., J. Mol. Biol., 222:581 (1991)). Human antibodies can also be made by introducing human immunoglobulin loci into transgenic animals, e.g., mice in which the endogenous mouse immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody can be prepared via immortalization of human B lymphocytes producing an antibody directed against a target antigen (such B lymphocytes can be recovered from an individual or can have been immunized in vitro). See, e.g., Cole et al., Monoclonal Antibodies and Cancer Therapy, Alan R. Liss, p. 77 (1985); Boerner et al., J. Immunol., 147 (1):86-95 (1991); and U.S. Pat. No. 5,750,373.

An "affinity matured" antibody is one with one or more alterations in one or more CDRs thereof which result an improvement in the affinity of the antibody for antigen, compared to a parent antibody which does not possess those alteration(s). Exemplary affinity matured antibodies will have nanomolar or even picomolar affinities for the target antigen. A variety of procedures for producing affinity matured antibodies are known in the art. For example, Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al., J. Mol. Biol. 226:889-896 (1992). Selective mutation at selective mutagenesis positions and at contact or hypermutation positions with an activity enhancing amino acid residue is described in U.S. Pat. No. 6,914,128.

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same. For multimeric antibodies, the number of functional antigen binding sites can be evaluated using ultracentrifugation analysis as described in Example 2 of U.S. Patent Application Publication No. 20050186208. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

As used herein, a "blocking" or "neutralizing" binding protein, antibody, antibody fragment, antigen-binding fragment or an antibody "antagonist" is one which inhibits or reduces the biological activity of the antigen it specifically binds to the antigen. In certain embodiments, blocking or neutralizing antibodies or antagonist antibodies completely inhibit the biological activity of the antigen. The neutralizing binding protein, antibody, antigen-binding fragment thereof can bind a target, such as Notch, and reduce a biological activity by at least about 20%, 40%, 60%, 80%, 85%, or more. Inhibition of a Notch biological activity by a neutralizing binding protein, antibody or antigen-binding fragment thereof can be assessed by measuring one or more indicators of Notch biological activity well known in the art.

An antibody having a "biological characteristic" or "functional characteristic" of a designated antibody is one which possesses one or more of the biological properties of that antibody which distinguish it from other antibodies that bind to the same antigen, including, for example, binding to a particular epitope, an EC50 value, IC50 value or KD values, as defined elsewhere herein.

In order to screen for antibodies which bind to an epitope on an antigen bound by an antibody of interest, a routine cross-blocking assay such as that described in Antibodies, A Laboratory Manual, Cold Spring Harbor Laboratory, Ed Harlow and David Lane (1988), can be performed.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In one embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e., same residue) or similar (i.e., amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

As used herein, a "targeting sequence" refers to a polypeptide sequence sufficient to direct the localization of, e.g., a polypeptide, to a specific subcellular localization. By way of example, a "targeting sequence" can direct the polypeptide to the, e.g., a transmembrane domain, or to the nucleus, e.g., a nuclear localization sequence. A targeting sequence can be added to a biological molecule (e.g., peptide, polypeptide, protein, lipid, carbohydrate) to direct the polypeptides localization. A targeting sequence can result in the irreversible or reversible localization of a polypeptide.

An "isolated" antibody is one that has been identified and separated and/or recovered from a component of its natural environment. Contaminant components of its natural environment are materials that would interfere with diagnostic or therapeutic uses for the antibody, and can include enzymes, hormones, and other proteinaceous or non-proteinaceous solutes. In certain embodiments, the antibody will be purified (1) to greater than 95% by weight of antibody as determined by, for example, the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, silver stain. Isolated antibody includes the antibody in situ within recombinant cells since at least one component of the antibody's natural environment will not be present. Ordinarily, however, isolated antibody will be prepared by at least one purification step.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). See also Jonsson U. et al., (1993) Ann. Biol. Clin., 51:19-26; Jonsson U. et al., (1991) BioTechniques, 11:620-627 (1991); Johnsson U. et al., (1995) J. Mol. Recognit., 8:125-131; and Johnsson U. et al., (1991) Anal. Biochem., 198:268-277.

The term "binding protein conjugate" or "antibody conjugate" refers to a binding protein or antibody or antigen-binding fragment thereof as described herein chemically linked to a second chemical moiety, such as a therapeutic or cytotoxic agent. The term "agent" is used herein to denote a chemical compound, a mixture of chemical compounds, a biological macromolecule, or an extract made from biological materials. Preferably the therapeutic or cytotoxic agents include, but are not limited to, anti-cancer therapies as discussed herein, as well as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, a binding protein conjugate or antibody conjugate may be a detectably labeled antibody, which is used as the detection antibody.

The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32 and radioactive isotopes of Lu), chemotherapeutic agents, and toxins such as small molecule toxins or enzymatically active toxins of bacterial, fungal, plant or animal origin, including fragments and/or variants thereof.

The terms "crystal" and "crystallized" as used herein, refer to a binding protein, antibody or antigen-binding protein, or antigen binding portion thereof, that exists in the form of a crystal. Crystals are one form of the solid state of matter that is distinct from other forms such as the amorphous solid state or the liquid crystalline state. Crystals are composed of regular, repeating, three-dimensional arrays of atoms, ions, molecules (e.g., proteins such as DVD-Igs), or molecular assemblies (e.g., antigen/binding protein complexes).

By "fragment" is meant a portion of a polypeptide, such as a binding protein, antibody or antibody fragment, or antigen-binding portion thereof thereof, or nucleic acid molecule that contains, preferably, at least 10%, 20%, 30%, 40%, 50%, 60%, 70%, 80%, 90%, 95%, or more of the entire length of the reference nucleic acid molecule or polypeptide. A fragment can contain 10, 20, 30, 40, 50, 60, 70, 80, 90, or 100, 200, 300, 400, 500, 600, or more nucleotides or 10, 20, 30, 40, 50, 60, 70, 80, 90, 100, 120, 140, 160, 180, 190, 200 amino acids or more.

By "reduce" or "inhibit" is meant the ability to cause an overall decrease preferably of 10% or greater, 15% or greater 20% or greater, 25% or greater, 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, 95% or greater, 98% or greater, 99% or greater, or complete or 100% in a parameter, activity, or condition being measured.

The terms "cell lines," "host cells," and "host cells lines" refer to cells that can be genetically engineered to express a nucleic acid sequence encoding any of the synthetic proteins or components thereof described herein. Cell lines are typically derived from a lineage arising from a primary culture that can be maintained in culture for an unlimited time. Genetically engineering the cell line involves transfecting, transforming or transducing the cells with a recombinant polynucleotide molecule, and/or otherwise altering (e.g., by homologous recombination and gene activation or fusion of a recombinant cell with a non-recombinant cell) so as to cause the host cell to express a synthetic protein of interest.

The term "mammalian host cell" is used to refer to a mammalian cell which is capable of being transfected with a nucleic acid sequence and then of expressing a selected recombinant protein of interest. The term includes the progeny of the parent cell, whether or not the progeny is identical in morphology or in genetic make-up to the original parent, so long as the selected gene is present. Suitable mammalian cells for use in the present invention include, but are not limited to Chinese hamster ovary (CHO) cells, baby hamster kidney (BHK) cells, human HeLa cells, monkey COS-1 cell, human embryonic kidney 293 cells, mouse myeloma NSO and human HKB cells (U.S. Pat. No. 6,136,599). The other cell lines are readily available from the ATCC.

The term "recombinant" when used with reference to a cell indicates that the cell replicates a heterologous nucleic acid, or expresses a peptide or protein encoded by a heterologous nucleic acid, such as a nucleic acid sequence encoding a synthetic Notch protein, i.e., a nucleic acid sequence encoding any such recombinant protein of interest. Recombinant cells can contain genes that are not found within the native (non-recombinant) form of the cell. Recombinant cells can also contain genes found in the native form of the cell wherein the genes are modified and reintroduced into the cell by artificial means. The term also encompasses cells that contain a nucleic acid endogenous to the cell that has been modified without removing the nucleic acid from the cell; such modifications include those obtained by gene replacement, site-specific mutation, using techniques such as Crispr, and related techniques. A "recombinant protein" is one which has been produced by a recombinant cell.

As used herein, the terms "recombinant cell," "recombinant cell line," or "modified cell line" refers to a cell line either transiently or stably transformed with one or more nucleic acid constructs, as described herein. Polynucleotides, genetic material, recombinant DNA molecules, expression vectors, and such, used in the compositions and methods described herein can be isolated using standard cloning methods such as those described by Sambrook et al. (Molecular Cloning: A Laboratory Manual, Second Edition, Cold Spring Harbor, N.Y., 1989; which is incorporated herein by reference). Alternatively, the polynucleotides coding for a recombinant protein product used in the compositions and methods described herein can be synthesized using standard techniques that are well known in the art, such as by synthesis on an automated DNA synthesizer.

Peptides, polypeptides and proteins that are produced by recombinant animal cell lines using the cell culture compositions and methods described herein can be referred to as "recombinant protein of interest," "recombinant peptide," "recombinant polypeptide," and "recombinant protein." The expressed protein(s) can be produced intracellularly or secreted into the culture medium from which it can be recovered and/or collected. Accordingly, the term "recombinant protein of interest" refers to a protein or fragment thereof expressed from an exogenous nucleic acid sequence introduced into a host cell.

As used herein, the term "transfection" is used to refer to the uptake of an exogenous nucleic acid by a cell, and a cell has been "transfected" when the exogenous nucleic acid has been introduced inside the cell membrane. A number of transfection techniques are well known in the art and are disclosed herein.

The term "transformation" as used herein refers to a change in a cell's genetic characteristics, and a cell has been transformed when it has been modified to contain a new DNA. For example, a cell is transformed where it is genetically modified from its native state. Following transfection, the transforming nucleic acid can recombine with that of the cell by physically integrating into a chromosome of the cell, can be maintained transiently as an episomal clement without being replicated, or can replicate independently as a plasmid. A cell is considered to have been stably transformed when the transforming nucleic acid is replicated with the division of the cell.

As used herein an "expression vector" refers to a DNA molecule, or a clone of such a molecule, which has been modified through human intervention to contain segments of DNA combined and juxtaposed in a manner that would not otherwise exist in nature. DNA constructs can be engineered to include a first DNA segment encoding an acetylation-resistant engineered PDCL3 polypeptide described herein operably linked to additional DNA segments encoding a desired recombinant protein of interest. In addition, an expression vector can comprise additional DNA segments, such as promoters, transcription terminators, enhancers, and other elements. One or more selectable markers can also be included. DNA constructs useful for expressing cloned DNA segments in a variety of prokaryotic and eukaryotic host cells can be prepared from readily available components or purchased from commercial suppliers.

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells can be cultured in suspension or while attached to a solid substrate. Fluidized bed bioreactors, hollow fiber bioreactors, roller bottles, shake flasks, or stirred tank bioreactors, with or without microcarriers, can be used.

As used herein, "cell culture medium" is a media suitable for growth of animal cells, such as mammalian cells, in in vitro cell culture. Cell culture media formulations are well known in the art. Typically, cell culture media are comprised of buffers, salts, carbohydrates, amino acids, vitamins and trace essential elements. "Serum-free" applies to a cell culture medium that does not contain animal sera, such as fetal bovine serum. Various tissue culture media, including defined culture media, are commercially available.

BRIEF DESCRIPTION OF THE DRAWINGS

[[Intentionally Omitted]]

FIG. 1A shows an illustration of natural cis-inhibition that occurs when Notch and a Notch ligand are expressed on the same cell surface. Interaction of the Notch receptor with its ligand prevents its activation by ligands on adjacent cells. FIG. 1B shows Notch inhibition using a synthetic cis-interacting protein comprising an inhibitory anti-NRR scFv fused to a transmembrane domain. The scFv "clamps" the NRR, preventing its rupture and thus inhibiting Notch activation.

FIG. 2A show a figure depicting the crystal structures of "Ab2" (the scFv used in cis-clamp and as LNR4 domain, left) and the Notch1 NRR (right). Wu et al (2010). Availability of crystal structures allows structure-guided mutations to be made to the scFv that can decrease affinity and tune the stabilizing effects of the scFv. The R99 residue was mutated on the heavy chain of Ab2 to either a lysine (slight reduction in affinity) or an alanine (greater reduction in affinity). FIGS. 2B-2C show co-expression of the Notch receptor with the scFv as a separate transmembrane cis-inhibitor in reporter cells, and cultured them (FIG. 2B) on surface-adsorbed ligand or (FIG. 2C) with ligand-expressing cells. Unaltered Ab2 has inhibitory effects comparable to DAPT (gamma secretase inhibitor), and residue mutations follow expected trends of restoring Notch activity.

FIG. 3A illustrates a schematic of Notch activation. In the resting autoinhibited conformation (i), the three LNR domains sterically block the S2 cleavage site necessary for Notch activation. Upon application of force (ii), the LNR domains are displaced, allowing the activating proteolytic cleavages (iii) that release the intracellular domain (ICD) to regulate gene expression in the nucleus. FIG. 3B shows the protein structure and schematic of the wild type Notch1 NRR (i), which opens in response to about 5 pN of force. Protein structure of the Notch1 NRR in the presence of an NRR-binding scFv, and schematic of the NRR expressed with this scFv as a contiguous part of its structure (ii). This scFv is designed to act as an "LNR4" domain, which should increase the threshold of force activation to >5 pN.

FIG. 4A shows immunohistochemistry of ligand binding domain (LBD) and ICD showing that cells are able to stably express Notch-based receptors that include an LNR4 domain. LBD stained with soluble ligand Dll4/Fc; ICD stained with αGal4 antibody. FIG. 4B shows the LNR4 domain successfully binds the NRR. In the WT Notch core, immunostaining the NRR with an NRR-binding antibody revealed co-localization between the LBD and NRR stains. However, the inclusion of an NRR-binding LNR4 domain sterically inhibits the ability to stain the NRR; co-localization between LBD and NRR signals was not observed. LBD stained with soluble ligand Dll4/Fc; NRR stained with αNRR antibody. FIG. 4C depicts western blot assays in transiently transfected cells that show production of full length receptors at expected masses, with inclusion of an LNR4 domain showing the expected increase in apparent mass (211 vs 239 kDa).

FIGS. 5A-5F show LNR4 increases force threshold of Notch activation in Tension Gauge Tether (TGT) assay. FIG. 5A-5E depict the use of ruptureable double-stranded DNA tethers. Wang et al (2013). One strand of the TGT attaches to a rigid plate through biotin-avidin binding, while the other presents a ligand. The TGT ruptures at a defined force, determined by the orientation of the ligand and the biotin. If the TGT is weaker than the force required to activate the Notch receptor, it ruptures before the LNR domains can be displaced. If it is stronger, the LNR domains are displaced and activation occurs. FIG. 5F shows flow cytometry data of mCherry reporter activity that shows that the WT NRR (which activates at 5 pN) is activated by both 12 pN and 56 pN TGTs. Receptors with an LNR4 domain are activated on 56 pN, but not 12 pN TGTs, indicating decreased mechanical sensitivity.

FIGS. 6A-6C show a schematic depicting drug-dependent Notch activation by the NS-inhibitor BILN-2061 (triangle). FIG. 6A shows that in the absence of drug, the DLL extracellular domain is cleaved from the transmembrane domain (TMD); the resulting soluble DLL ligand is not able to activate Notch receptors. FIG. 6B demonstrates that in the presence of drug, NS3 cleavage is blocked and the DLL extracellular domain remains bound to its TMD in the signaling-competent state. Subsequent binding of the tethered DLL to Notch receptors on an adjacent cell leads to Notch activation and liberation of the Notch intracellular domain (NICD). The liberated NICD is then free to enter the nucleus to mediate gene expression. FIG. 6C shows fluorescence imaging of DLL-NS3-expressing cells and Notch expressing cells (nuclei). Upon activation, Notch-expressing cells exhibit YFP nuclear fluorescence from NICD-mediated activation of a chromosomal histone H2B-YFP gene. In the absence of drug, H2B-YFP is not detected, indicating the absence of Notch signaling. In the presence of drug, however, H2B-YFP expression is observed in Notch-expressing cells adjacent to DLL-NS3-expressing cells, indicating that trans-cellular signaling between these cells is dependent on the inhibition of NS3 activity.

FIG. 7A shows domain topology of the Notch receptor. FIG. 7B shows that Notch is activated upon the binding and endocytosis of ligands presented by neighboring cells. The force applied to the receptor during ligand endocytosis serves to unfold the NRR and initiate successive proteolytic cleavages at S2 and S3. Activation results in the liberation of the NICD, such that it can be transported into the nucleus to effect transcriptional changes.

FIG. 8A shows depictions of an exemplary hN1-scFv with the integrated antibody domain. FIG. 8B shows depictions of hN1-scFv with the reported x-ray structure of the scFv:NRR complex shown in surface rendering. FIG. 8C shows the structure (FIG. 2A). This is valuable for understanding the regions of each scFv that bind portions of each NRR and subsequently designing chimeric scFv's.

FIGS. 15A-15I shows drug inducible "turn-on" and "turn-off" transcription factors (TFs). FIG. 15A Schematic depicting a general exemplary "turn-on" TF design and its stabilization in the presence of an NS3 inhibitor. FIG. 15B Western blot showing the preservation of full-length DBGal4-NS3-TAGal4 (anti-HA; 60.6 kDa) in cells treated with increasing concentrations of BILN-2061. TF stabilization was accompanied by a corresponding increase in the expression of the H2B-Citrine reporter protein (46.5 kDa). DBGal4-NS3-TAGal4 was detected using an HRP-conjugated anti-HA antibody, and signal enhancement was achieved through application of an HRP-conjugated secondary antibody. Enhanced detection showed TF stabilization in cells treated with 0.08 μM of BILN-2061; intact TF remained undetectable in drug-untreated controls. An additional band corresponding to Cho-K1 mediated degradation of the fusion construct was also detected. FIG. 15C Fluorescence images of a Cho-K1 reporter cells (UAS-H2B-Citrine) stably expressing DBGal4-NS3-TAGal4 in the absence and presence of 2.5 μM BILN-2061. FIG. 15D Comparison of drug-induced reporter expression levels (as measured by flow cytometry) of cells expressing "turn-on" TFs containing the indicated TA domains. FIG. 15E Schematic of TMD-NS3-Gal4min cleavage and its drug-activated "turn-off" activity. General design of the "turn-off" TFs containing a generic membrane-localizing element FIG. 15F Fluorescence images of HEK 293A cells expressing the dual-tagged BFP-TMD-NS3-Gal4-mCherry. The mCherry-tagged TF unit localized to the nucleus in the absence of drug and was targeted to ER and PM in cells treated with 3 M BILN-2061. BFP is N-terminal to the TMD; Gal4 is tagged with mCherry. Scale bar is 10 μm. FIG. 15G Schematic of myr-palm-NS3-Gal4min cleavage and stabilization. FIG. 15H Immunostained HeLa cells showing the sequestration and membrane-targeting of $Gal4_{min}$ in drug-treated cells expressing myr-palm-NS3-Gal4min. FIG. 15I Flow cytometry analysis of transiently transfected HEK 293FT cells coexpressing DBrTetR-NS3-TAVP64-p65 and TMD-NS3-$Gal4_{min}$ and containing TRE BFP and UAS H2B-Citrine reporter constructs. Treatment of cells with increasing concentration of BILN-2061 induced concurrent TRE BFP activation and UAS H2B-Citrine repression. Analyses were carried out in media containing 100 ng/mL doxycycline to induce $DBr_{TetR}$ binding to tetO-DNA.

FIGS. 16A-16E show drug-control over endogenous gene expression using dCas9-NS3-NLS/VPR. FIG. 16A Schematic depiction of the drug-inducible stabilization and nuclear localization of dCas9-NS3-NLS/VPR. FIG. 16B Western blot showing the preservation of full-length dCas9-NS3-NLS/VPR copies (250 kDa) in cells treated with 3 μM BILN-2061. An unfused dCas9 domain (160 kDa) is produced in the absence of drug. FIG. 16C Immunostained HeLa cells showing the subcellular localization of the dCas9 domain in the presence or absence of 3 μM BILN-2061. Nuclear localized dCas9 was observed only in drug treated cells. FIG. 16D Schematic of the time-dependent dye labeling strategy used to analyze cells expressing SNAP-dCas9-NS3-NLS/VPR (top), and corresponding fluorescence images of dye-labeled HeLa cells (bottom). Old protein copies produced in the absence of drug were confined to the cytoplasm, whereas those that were made in the presence of drug were able to translocate into the nucleus. FIG. 16E Drug-induced upregulation of CXCR4 expression in HEK 293FT cells coexpressing dCas9-NS3-NLS/VPR and sgRNA targeting the endogenous CXCR4 promoter. Expression of the chemokine receptor was analyzed by staining of cells anti-CXCR4 antibody followed by quantification via flow cytometry.

FIGS. 17A-17F show drug control over ligand presentation and intercellular Notch signaling. FIG. 17A Schematic of representation of an exemplary design of Dll1-NS3-mCherry and FIG. 17B shows its drug-inducible preservation as a cell-surface ligand. FIG. 17C Immunofluorescence staining of fixed (non-permeabilized) cells expressing Dll1-NS3-mCherry. Surface presentation of the Dill extracellular region was induced by treatment of cells with 1.5 μM BILN-2061. FIG. 17D Schematic depiction of trans-cellular signaling between Notch "receiver" cells by Dll1-NS3-mCherry expressing "sender" cells in the absence and presence of drug. FIG. 17E Fluorescence images of cocultured sender and receiver cells. Sender cells expressed the Dll1-NS3-mCherry ligand. Receiver cells constitutively expressed human Notch1 and H2B-Cerulean, and conditionally expressed H2B-Citrine upon up Notch activation. Activated receiver cells were observed only in cocultures treated with drug (1.5 μM BILN-2061). The interface between sender and receiver cells colonies is denoted by the white dotted line. FIG. 17F Magnified region from the inset shown in (17E) shown as an overlay with the corresponding transmitted light image.

FIG. 18 show comparison various commercially available NS3 inhibitors. A clonal Cho-K1 derived cell line containing a stably integrated Gal4-dependent reporter gene (UAS H2B-Citrine) and constitutively expressing DBGal4-NS3-TAGal was tested against various NS3 inhibitors. Cells were treated with drug for ~24 hours and expression of the H2B-Citrine reporter protein was subsequently quantified by flow cytometry.

FIGS. 19A-19B show characterization of the DBrTetR-NS3-TAVP64-p65 "turn-on" TF. FIG. 19A The presence of both doxycycline (to induce rTetR binding to tetO sequences) and an NS3 inhibitor (BILN-2061) was required to activate the expression of an BFP reporter protein under control of the TRE promoter. FIG. 19B Comparison of BFP expression (as quantified by flow cytometry) in HEK 293FT cells co-transfected with an DBrTetR-NS3-TAVP64-p65-encoding plasmid and reporter TRE-BFP DNA and treated with the indicated drugs.

FIGS. 20A-20B show drug-induced gene downregulation using "turn-off" TFs. FIG. 20A Western blot analysis of HEK 293FT cells transiently transfected with DNA encoding TMD-NS3-Gal4min or myr-palm-NS3-Gal4min. Intact proteins were preserved in cells treated with 3 μM BILN-2061. The HEK 293FT cells contained a stably integrated Gal4 dependent reporter gene (UAS H2B-Citrine), the expression of which was detected only in drug untreated cells. The full-length mass of TMD-NS3-$Gal4_{min}$ is 96 kDa, and full-length myr-palm-NS3-Gal4min is 63 kDa. A positive control was carried out in which cells were transfected with a plasmid encoding the Gal4 DB fused to VP64 (Gal4-VP64).

FIG. 20B Drug-induced downregulation of reporter expression in HEK 293FT reporter cells (UAS H2B-Citrine) transiently transfected with constructs encoding TMD-NS3-Gal4min or myr-palm-NS3-$Gal4_{min}$ and treated with the indicated concentrations of the NS3 inhibitor grazoprevir. Values are displayed as mean±s.d., as determined in triplicate.

FIG. 23A Transfected HeLa cells were treated with the indicated concentration of BILN-2061 for 24 h and subsequently fixed and permeabilized before immunostaining with anti-Cas9 antibody and counterstaining with DAPI. FIG. 23B The extent of nuclear localization was analyzed through through analysis of the pixel intensities along the lines indicated in (A) and plotted using the ImageJ-based software package Fiji.

FIG. 24A Schematic of inducible dCas9-mediated transcription via conditional preservation of a sgRNA-binding protein (MCP-NS3-VP64). MCP binds hairpin-modified sgRNA and localizes the VP64 TA domain to the DB scaffold only in drug-treated cells. FIG. 24B Drug-induced activation of a TRE-H2B-Citrine reporter protein via expression of dCas9 combined with MCP-NS3-VP64 and sgRNA targeting the TRE3G promoter. Cells were co-transfected with fluorescent marker (mTurqoise-2) to identify positively transfected cells. H2B-Citrine was induced only in drug-treated cells.

FIG. 25A Sender cells expressing the Dll1-NS3/4A ligand are cultured with receiver cells expressing the Notch transmembrane receptor. Receiver cell population is identified by a constitutively expressed H2B-Cerulean. Notch activation drives reporter activity of H2B-Citrine. Cells are cultured together with or without 1.5 µM BILN-2061 drug for 72 hours before imaging. FIG. 25B FIGS. 26A-26C show data depicting the flow cytometry gating procedures used herein. FIG. 26A Live cells were gated using FSC and SSC as depicted with the black line. FIG. 26B A positive transfection gate was made by gating for the top 1% fluorescing WT cells. FIG. 26C The positive transfection gate was then applied to all transfected cell populations. Geometric mean of reporter fluorescence was then measured from positively transfected cells. Mean intensities from nuclear H2B-Citrine in individual receiver cells was quantified via analysis of images from drug-treated and untreated co-cultures. Expression of the NICD-dependent reporter was compared between receiver cells that were in direct contact with sender cells, as well those that were distant from sender cells. The displayed values are reported as mean intensities, ±s.e.m., with n>100 cells per analyzed group.

FIG. 28A HEK 293FT cells transfected with DNA encoding rTetR-NS3-VP64-p65 were "pulsed" with drug (5 µM BILN-2061, 24 h) and subsequently "chased" with drug-free media for the indicated times. Following each chase, cells were lysed in SDS PAGE loading buffer and the lysates were subsequently analyzed via western. Intact rTetR-NS3-VP64-p65 (93.3 kDa) and the VP64-p65 cleavage product (42.0 kDa) were detected via fused HA tag. NT refers to a non-transfected control. FIG. 28B The reversibility of transcriptional activation by Gal4DB-NS3-VP64 was analyzed using a luciferase-based reporter assay. Applying BILN-2061 and grazoprevir as inducers, a pulse-chase analysis was carried out in which cells were treated drug, then withdrawn from drug for chase periods of the indicated times. At the end of the time course, the luciferase activity of cells was quantified using a luminescence assay. The data were obtained using Cho-K1 reporter cells (UAS-H2B-Citrine) containing a stably-integrated Gal4DB-NS3-VP64 construct. The cells were transfected with a Gal4-dependent luciferase reporter construct (5×GAL4-TATA-luciferase) and treated with 3 µM BILN-2061 or grazoprevir 16 h later. The first chase was initiated at the 12 h time point after drug addiction. "Last 12" refers to control cells that were transfected and maintained in drug-free media, and treated for only the last 12 hours preceding cell lysis. Signal from the "Last 12" samples confirmed that the diminished luciferase activity measured in the chased cells was not due to their decreased drug exposure durations. Luminescence values were normalized to signal from a co-transfected NanoLuciferase control construct (pNL1.1.TK[Nluc/TK]). Values are displayed as mean±s.d., as determined in triplicate.

(FIGS. 31B and 31C) anti-FITC SynNotch receptors containing SN or SN-LWF as the core domain are expressed and tested in HEK 293FT cells. Cells are either plated on fibronectin alone to test background activation (dashed lines) or on fibronectin with BSA-FITC to activate the receptors (solid lines). FIG. 31A discloses SEQ ID NO: 70. In (FIG. 31B), receptors have the Gal4-VP64 ICD, while in (FIG. 31C), receptors have the more potent Gal4-VPR ICD. Values shown are the percentage of cells in the ON state for each case.

(FIG. 32A) Immunostaining of non-permeabilized HeLa cells expressing GFP-binding SynNotch receptors that contain either the WT NRR (top) or the engineered sNRR domain (bottom). Labeling of a myc tag at the N-terminus of the receptors shows that the sNRR domain does not inhibit the cell's ability to express the receptor at its surface. Next, using a soluble antibody to stain the NRR, it was found that ECD and NRR stains co-localize for the NRR-based receptor, as expected since both protein regions are available at the cell surface. The sNRR domain, however, does not stain for the NRR. This indicates that the incorporated scFv successfully interacts with the NRR domain as intended. (FIG. 32B) Western blot analysis of the cells shown in (A). For both receptors, an αMyc blot is able to detect the full-length (FL) and S1-processed (N-term) forms of the receptor. S1-processing by furin protease cleaves the receptor into a noncovalently joined heterodimer, a feature important for surface expression and activity of Notch receptors.

(FIG. 33A) TGTs are double stranded-DNA tethers that rupture at defined forces. One strand of the TGT attaches to a rigid plate, and the other presents a ligand for cells to bind. In this case, the ligand used is fluorescein, which interacts with an αFITC SynNotch. If the tension tolerance of the TGT is weaker than that of the NRR, the TGT will break before the NRR can open. If it is stronger, the NRR domain will unravel, and Notch activation will occur, as visualized by expression of an H2B-mCherry reporter gene. (FIG. 33B) Flow cytometry data and fluorescence imaging of HEK 293FT cells expressing NRR- (left) and sNRR-based (right) SynNotch stimulated with various strengths of TGT ligands. NRR-based receptors activate in response to TGTs 12 pN and stronger, as expected. sNRR-based receptors do not activate until 56 pN of tension tolerance is provided. It is worthwhile to re-emphasize that for the 12, 56, and 100 pN stimuli above, sNRR receptors are binding the same ligand in each instance, but are able to respond different based off the underlying mechanical properties of the ligand.

FIGS. 34A-34E show tunability of sNRR mechanical strength. (FIG. 34A) Crystal structure (PDB 3L95) of the soluble antibody used to design sNRR in complex with its NRR antigen. (FIG. 34B) Flow cytometry data from a collection of mutated sNRR domains stimulated vs TGTs. For each receptor, values are normalized to their reporter fluorescence on the maximum strength stimulus (>100 pN). (FIG. 34C) Selected flow cytometry data from (FIG. 34B) presented in detail. The original sNRR receptor is insensitive to a 12 pN stimulus, and furthermore can discriminate between 43, 54, and >100 pN. Mutating a Tyr residue to a Phe (Y49F) slightly weakens the receptor, inducing a marginal response to 12 pN and decreased discrimination between 43 pN and above. Further mutating to an Ala (Y49A) causes ~50% activation in response to 12 pN and abolishes the ability to discriminate between 43 pN and above. The WT NRR is the weakest, responding identically to all mechanical stimuli. Color legend as in (FIG. 34B). (FIG. 34D) Single-cell traces from timelapse imaging of HeLa cells expressing model sNRR domains. This data further confirms the distinct tensile strengths of engineered sNRR domains and reveals their ability to discriminate forces over time. Values are plotted mean±SD, normalized to each receptor's mean max activation in response to >100 pN. Color legend as in (FIG. 34B). (FIG. 34E) Stochastic modeling of sNRR-TGT interactions. A given sNRR-TGT pair is modeled as having a relative probability of either the TGT rupturing of the receptor activating, as determined by the relative mechanical strengths of the two components. Mechanical strengths are modeled as thermal dissociation rates, and four such strengths are considered for sNRR's and TGT's each, similar to the data presented in (FIG. 34D). Values plotted are the number of receptors that get activated during the stochastic model, normalized as in (FIG. 34D), with 10 runs of the model plotted per pair.

DETAILED DESCRIPTION

Figure 1A:
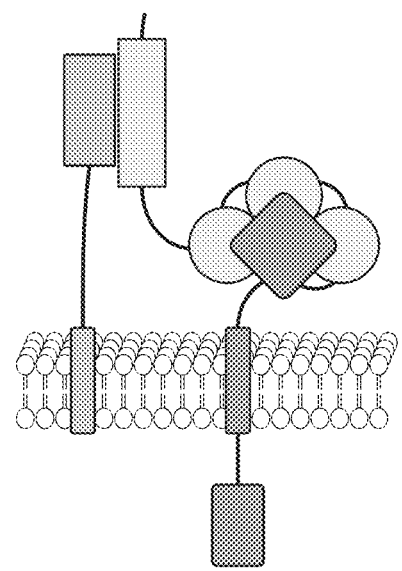
FIGS. 1A-1B depict Notch inhibition by cis-interacting proteins.

As described herein, receptors with increased or decreased force activation thresholds are both novel and have wide-ranging applications, including, but not limited to, generation of cells with ability to detect physical features of solid tumors, mechanical properties of biomaterials, etc. Furthermore, the cis-clamps described herein permit regulation of engineered cells expressing synthetic Notch receptors or "SynNotch receptors," such as, for example, therapeutic T cells, and are useful for reducing the known background activity of these receptors. In addition, drug-inducible Notch activation described herein allows tighter control of therapeutic interventions that utilize Notch receptor transduction mechanisms.

A continuing goal of synthetic biology is to be able to program new functions into cells in ways that can be precisely manipulated for applications in medicine and basic research. Toward this end, researchers have recombined modular domains from natural signaling proteins and genetic control elements to produce new biological "parts" for cellular engineering applications.[1] However, a limitation has been the relatively small number of protein components that are available for designing drug-sensitive systems. In particular, domains that can be used to engineer chemical-control into diverse proteins—in ways that allow them to be tightly and selectively regulated using orthogonal drugs—remain lacking.

Accordingly, provided herein, in some aspects, are synthetic Notch receptors or "SynNotch receptors," having defined and/or programmable force-activation thresholds for applications in cell engineering, T cell immunotherapy, and tissue engineering.

Provided herein, in some aspects, are compositions and methods for regulating SynNotch receptor proteins and reducing their background levels of activity. For example, in some embodiments, genetic regulation of cis-clamps can be used to "turn off" the cell-killing activity of immune cells.

Provided herein, in some aspects, are compositions and methods for drug-inducible control of Notch and/or syn-Notch activation. Such compositions and methods comprise one or more synthetic proteins, such as a synthetic, drug-dependent protein or a synthetic inhibitor protein. As used herein, a "synthetic protein" refers to a non-naturally occurring protein or polypeptide having a desired function for use in the compositions and methods described herein. Such synthetic proteins can comprise one or more domains from or derived from a naturally occurring protein in combination with one or more domains from or derived from another naturally occurring protein to create a synthetic protein having desirable functions that are not found together naturally. Such domains include naturally occurring domains, as well as mutated or engineered domains derived from naturally occurring domains, or portions of a naturally occurring domain having a desired activity. For example, in some embodiments, a synthetic protein comprises one or more NS3 protease domains or one or more Notch Regulatory Region (NRR)-binding domains. Other examples of domains that can be used in the synthetic proteins described herein include transcriptional activation domains, transcriptional repressor domains, DNA-binding domains, such as zinc-finger-binding domains, protease domains, and the like. Other domains contemplated for use in the synthetic proteins described herein include extracellular domains, such as ligand-binding extracellular domains, transmembrane domains, and intracellular domains, such as intracellular signaling domains. In addition, the nucleic acid sequences encoding the synthetic proteins described herein can comprise additional sequence elements such as signal sequences and tag sequences.

Figure 1B:
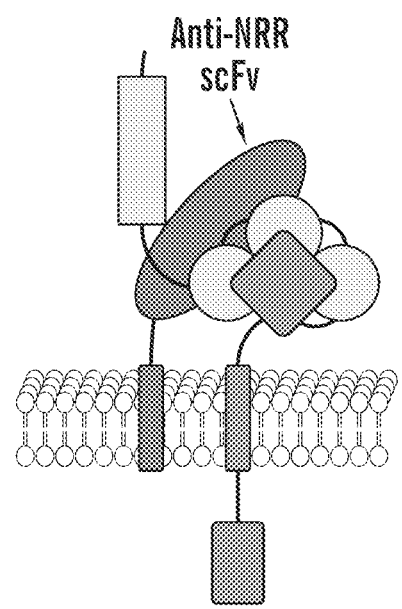

Accordingly, provided herein, in some aspects, are "cis-clamps" or synthetic inhibitor proteins. As used herein, a "synthetic inhibitor protein" comprises a Notch Regulatory Region (NRR)-binding scFv fused to a transmembrane domain and acts to inhibit Notch receptor or synthetic Notch receptor activity. Non-limiting examples of "synthetic inhibitor proteins" described herein include SEQ ID NOs: 42, 42, and 44 and variants thereof having similar or enhanced inhibitory activity. Notch is typically activated by ligands expressed on adjacent cells, but inhibited when ligands are expressed on the same cell through a mechanism known as "cis-inhibition" (FIG. 1A). This cis-interaction serves to prevent cells from receiving signals from their neighbors, and also prevents spontaneous "ligand independent" background activation, reducing Notch background activity. As demonstrated herein, membrane-tethered anti-NRR scFvs can be used as genetically encoded Notch inhibitors, or "cis-clamps" (FIG. 1B). These scFvs are derived from antibodies that bind and stabilize the NRR region of Notch receptors, preventing their activation. As shown herein, these "cis-clamps" or synthetic inhibitor proteins can be used to regulate both endogenous Notch and synthetic Notch ("SynNotch") activity in a manner similar to ligand cis-inhibition.

As known by those of skill in the art, "single-chain Fv" or "scFv" antibody fragments comprise the VH and VL domains of an antibody as a single polypeptide chain. Generally, the Fv polypeptide further comprises a polypeptide linker between the VH and VL domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-315 (1994).

In some embodiments of the aspects described herein, cis-clamps or cis-inhibitors are used for cell engineering applications, such as for use in therapeutic T cells. Notch and/or SynNotch receptors are known to exhibit background "leaky" activation. In engineered cells, these chimeras are used, in some embodiments, as regulatory elements to limit signaling from synthetic Notch receptors and, in some embodiments, to reduce off-target T cell killing in the case of engineered SynNotch T cells.

The cis-clamps described herein are especially useful in situations where ligand co-expression is problematic. For example, typically cis-inhibition of a SynNotch receptor is achieved by co-expressing the receptor and its target ligand on the same cell. However, in the case of cell immunotherapy, ligands used to activate SynNotch receptors on T cells are usually cell surface cancer markers, such that co-expression of these markers would in principle permit cis-inhibition of SynNotch proteins, as well as causing the therapeutic cells to attack one another. Thus, the cis-clamps described herein provide a route through which SynNotch receptors can be regulated without the introduction of cancer marker/antigens to the engineered cells.

Figure 2A:
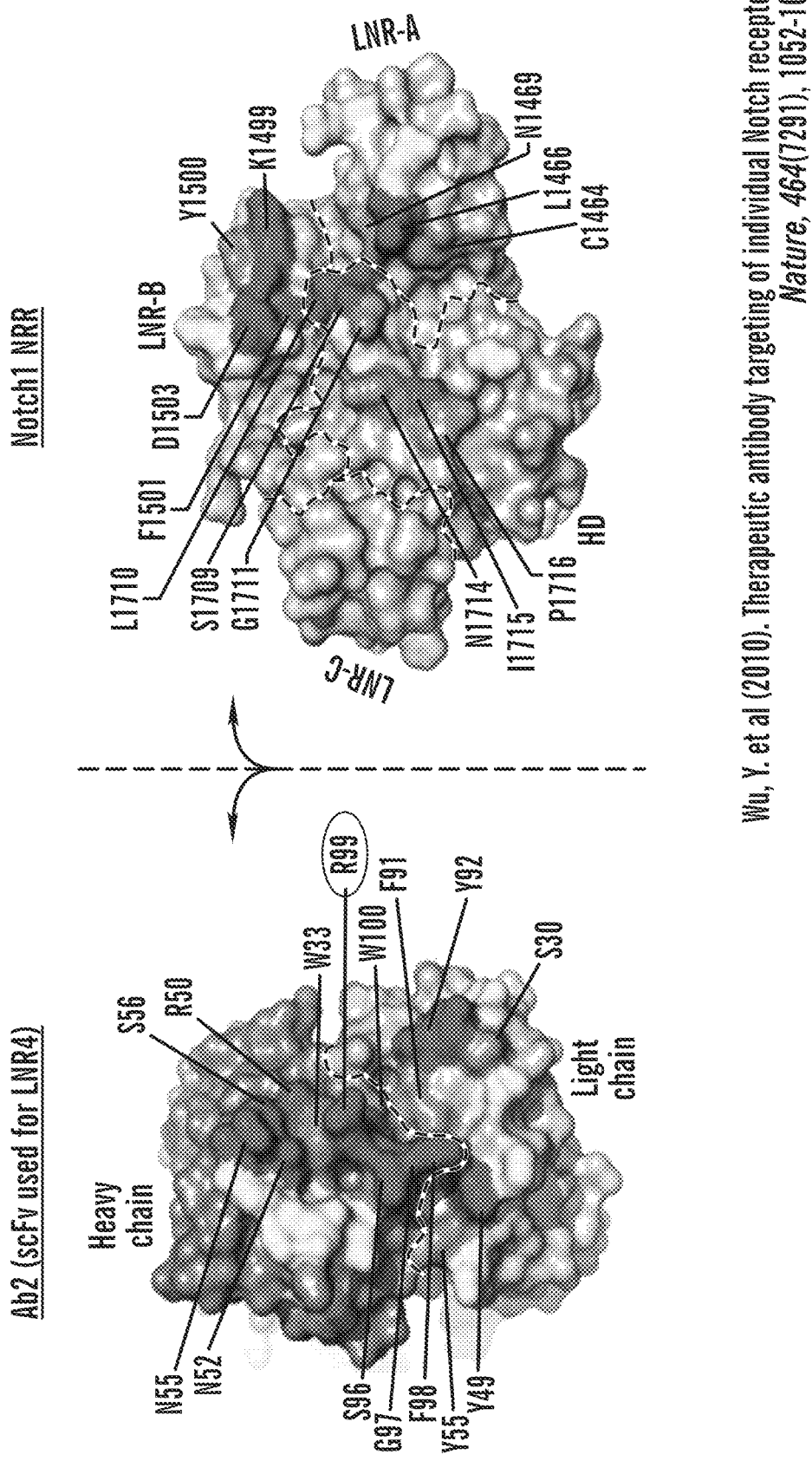
FIGS. 2A-2C show mutating the affinity of the scFv to control force sensitivity.
Figure 2B:
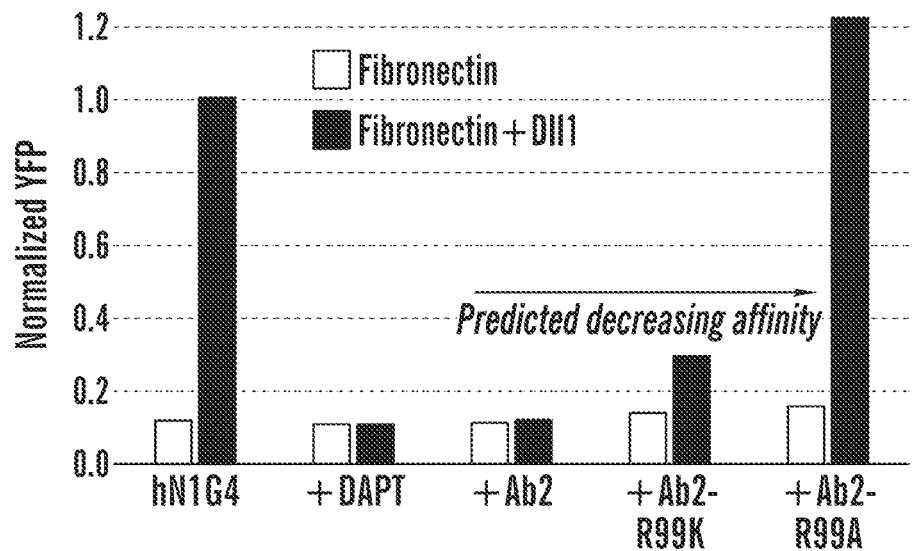
Figure 2C:
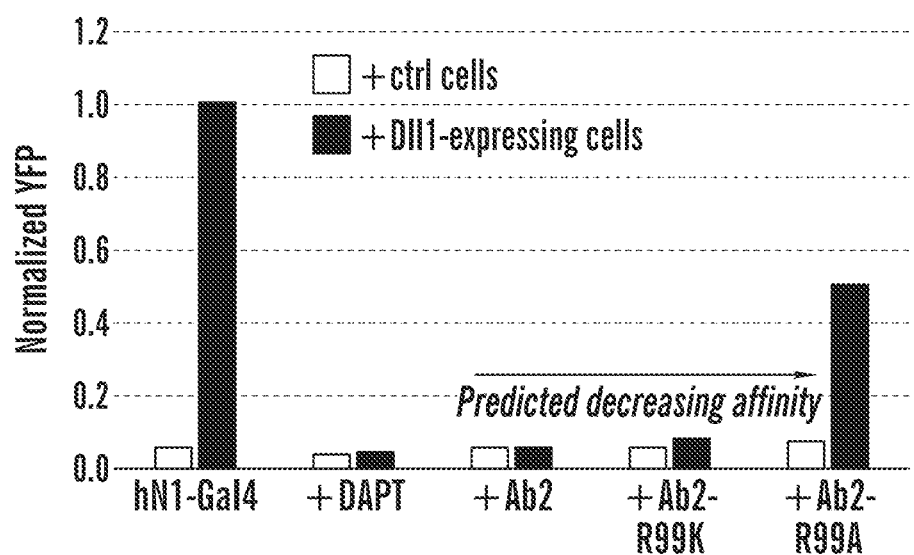

In some embodiments, tuning the affinity of an scFv is performed to engineer mechanical sensitivity, as shown in FIGS. 2A-2C, where an NRR-binding scFv is mutated and expressed as a separate transmembrane cis-clamp. Non-limiting examples of NRR-binding scFv sequences that can be used or be further engineered or modified to be used in some embodiments of the synthetic inhibitor proteins described herein include SEQ ID NOs: 15-27.

In those embodiments where amino acid sequence modification(s) of an scFv, such as an scFv of any one of SEQ ID NO: 15-27, is performed to engineer mechanical sensitivity, amino acid sequence variants of the NRR-binding scFv are prepared by introducing appropriate nucleotide changes into the nucleic acid encoding the scFv, or by peptide synthesis. Such modifications include, for example, deletions from, and/or insertions into and/or substitutions of, residues within the amino acid sequences of the scFv or antibody from which it is derived. Any combination of deletion, insertion, and substitution is made to arrive at the final construct, provided that the final construct possesses the desired characteristics. The amino acid changes also can alter post-translational processes of the scFv, such as changing the number or position of glycosylation sites.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions for antibody-based sequences include an antibody with an N-terminal methionyl residue or the antibody fused to a cytotoxic polypeptide. Other insertional variants of an antibody molecule include the fusion to the N- or C-terminus of the antibody to an enzyme (e.g., for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis typically are the hypervariable regions of the VH and/or VL domains of the scFv.

Substantial modifications in the biological properties of an scFv can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Any cysteine residue not involved in maintaining the proper conformation of antibodies or antibody fragments thereof can be substituted, generally with serine, to improve the oxidative stability of the molecule and prevent aberrant crosslinking. Conversely, cysteine bond(s) can be added to the antibody to improve its stability (particularly where the antibody is an antibody fragment such as an Fv fragment).

A particularly preferred type of substitutional variant involves substituting one or more hypervariable region residues of a parent antibody. Generally, the resulting variant(s) selected for further development will have improved biological properties relative to the parent antibody from which they are generated. A convenient way for generating such substitutional variants involves affinity maturation using phage display.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine can also be used.

Addition of glycosylation sites to the antibodies or antibody fragments thereof described herein is accomplished by altering the amino acid sequence such that it contains one or more of the above-described tripeptide sequences (for N-linked glycosylation sites). The alteration can also be made by the addition of, or substitution by, one or more serine or threonine residues to the sequence of the original antibody (for O-linked glycosylation sites).

Nucleic acid molecules encoding amino acid sequence variants of the scFVs used herein are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

Provided herein, in some aspects, are synthetic Notch receptors with mutated or engineered NRR domains. Mutating the NRR domain and utilizing an scFv that has high affinity to the mutated NRR (but not the native NRR) in either the cis-clamp or auto-inhibitory receptor configurations allow for a more specific system with reduced off-target effects, such as, e.g., the scFv binding the NRR region on notch receptors of adjacent cells).

Figure 3A:
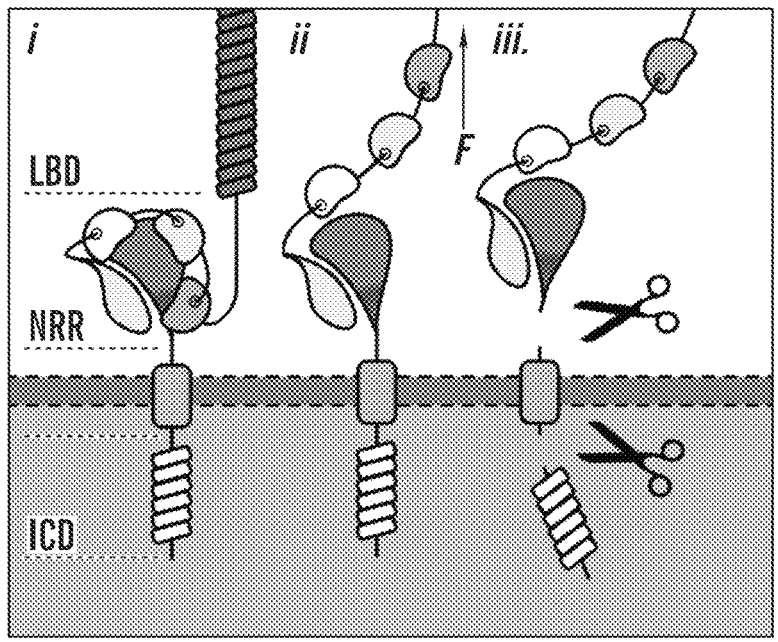
FIGS. 3A-3B illustrate an autoinhibitory approach to controlling mechanical sensitivity of Notch.
Figure 3B:
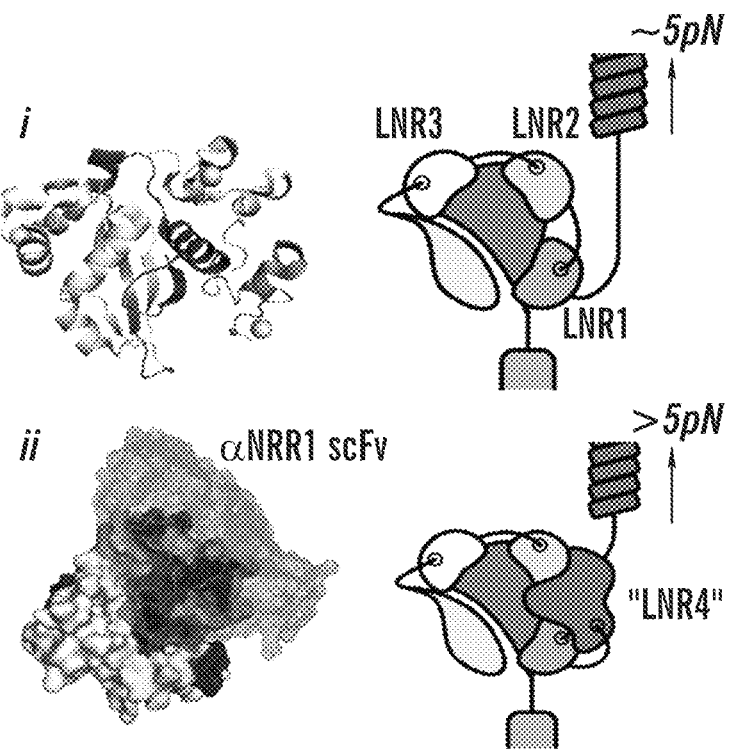
Figure 4C:
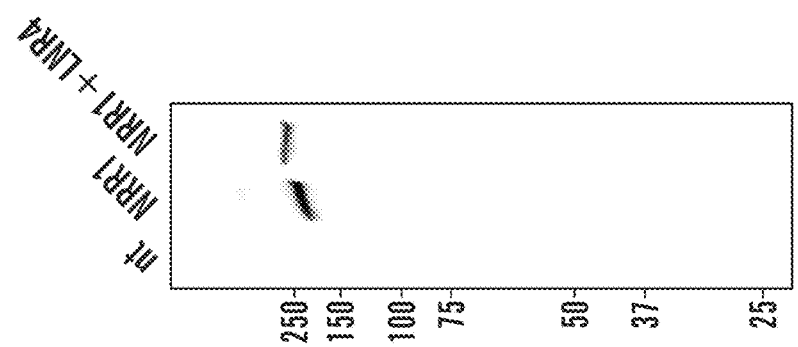
FIGS. 4A-4C show expression of Notch receptors with and without LNR4 domains in HEK 293FT cells. Cells are made to express Notch-based receptors that comprise: a WT Notch LBD, an NRR1 Notch core with or without LNR4, and a Gal4-VP64 ICD.
Figure 4A:
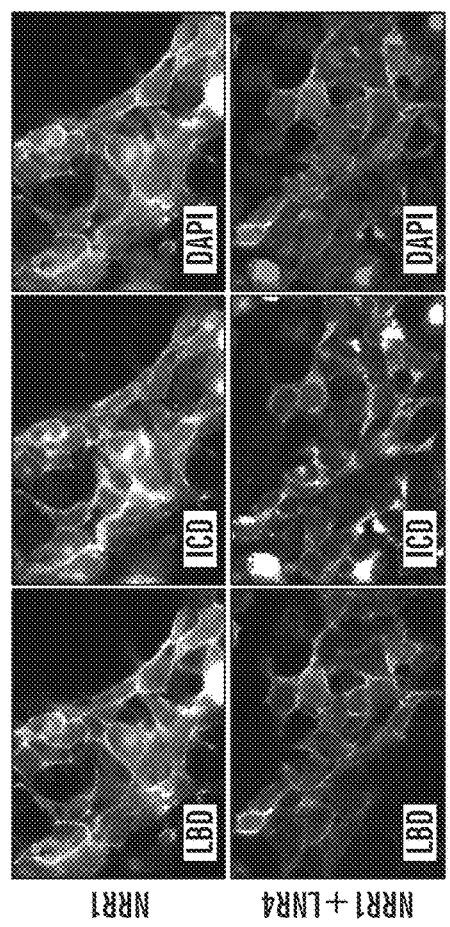
Figure 4B:
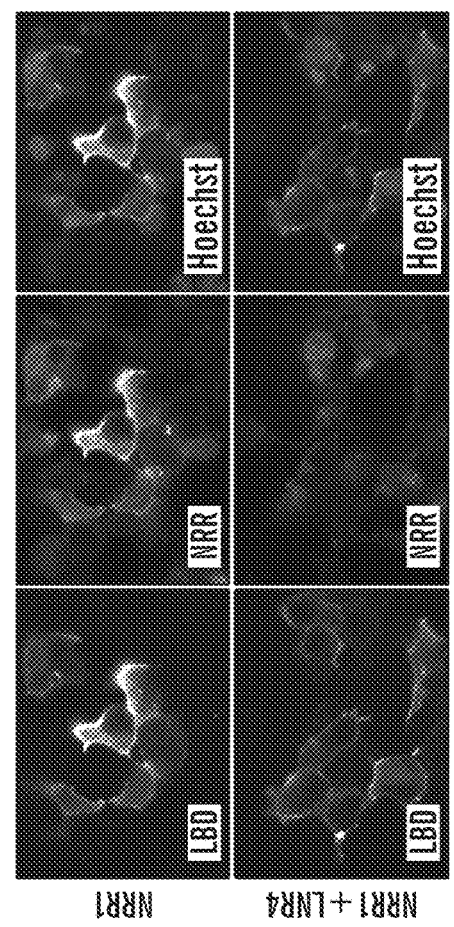
Figure 5F:
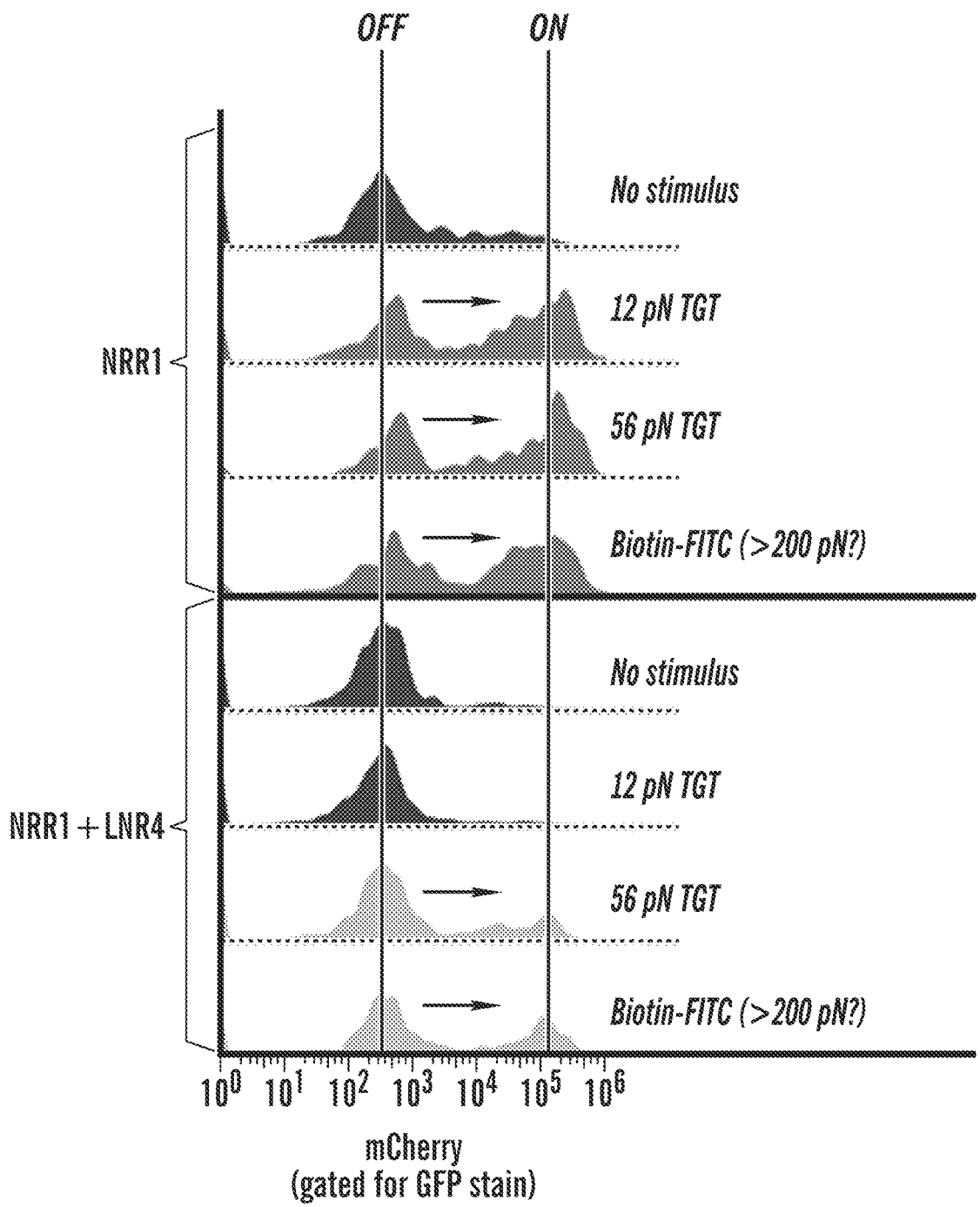

Also provided herein, in some aspects, are synthetic auto-inhibitory Notch receptors that comprise an NRR-binding scFv portion. Similar to the aspects directed to cis-clamps, the scFv portion in the auto-inhibitory Notch receptor stabilizes the NRR region, resulting in more force being required to activate the receptor. In some embodiments, NRR-binding scFv portions are expressed as a contiguous part of Notch-based synthetic receptors to act as a synthetic "fourth LNR domain" (LNR4), offering additional stability to the NRR and increasing the force threshold of Notch activation. This exemplary approach is described in FIGS. 3A-3B.

In some embodiments, the LNR4 domain can be mutated to change the affinity of binding to the NRR in order to tune the mechanical sensitivity of the receptor, as shown in FIGS. 2A-2C for the cis-clamp embodiment.

In some aspects, provided herein are constructs, compositions, and methods for controlling the binding/activation of endogenous and/or synthetic Notch receptors through the use of synthetic proteins acting as ligands and comprising viral protease domains, such as NS3 protease domains from the hepatitis C virus (HCV). The NS3 domain is a serine protease embedded within the HCV polyprotein that excises itself from the precursor polypeptide by cleaving recognition sites flanking it at either end. The enzyme has been a prime drug target of the pharmaceutical industry due to its sequence and structural distinction from human proteases; multiple selective inhibitors against the "NS3" cis-protease are currently in use for treating HCV infections worldwide, and several new compounds are currently under evaluation by the FDA.

Figure 6C:
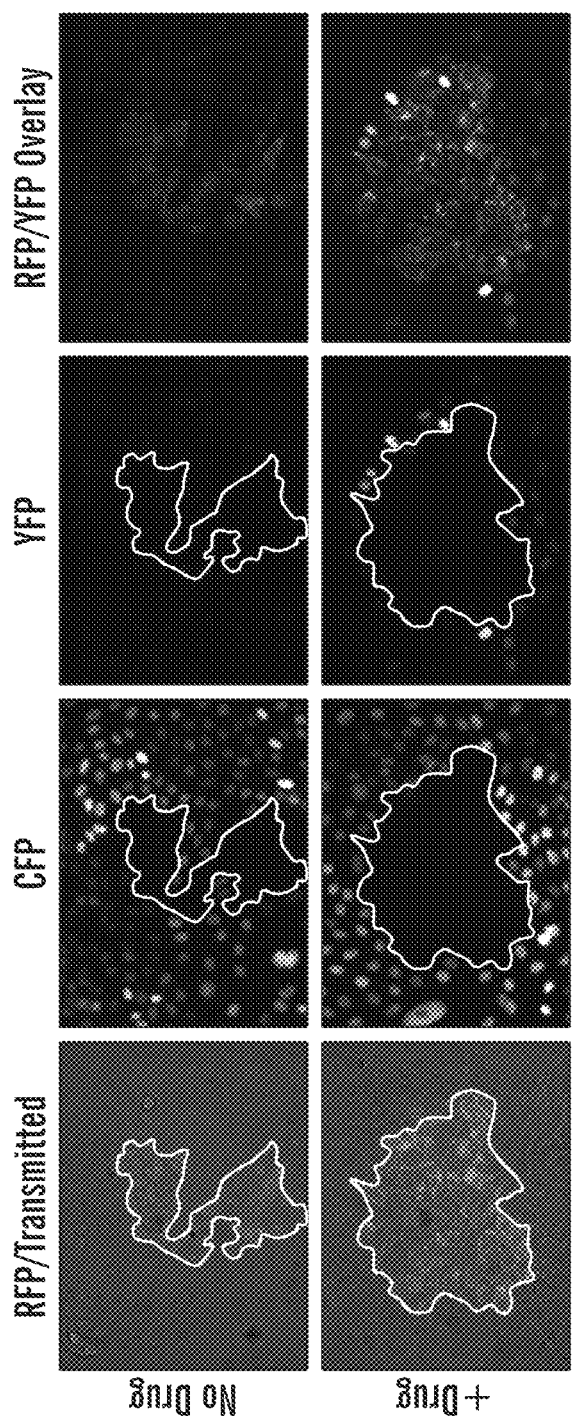

As demonstrated herein, Notch-signaling can be made drug-dependent by insertion of a protease domain, such as the NS3 protease domain of SEQ ID NO: 32 or variants thereof, between the extracellular and transmembrane domains of the Notch ligand Delta or "DLL" (FIGS. 6A-6C). In the absence of drug, the DLL extracellular domain is cleaved from its membrane anchor via NS3, releasing a soluble DLL ligand that is able to bind Notch but cannot activate it. Upon inhibition of NS3, however, DLL extracellular domain remains tethered to the cell surface and thus is able to activate Notch on the surface of opposing cells. This aspect of the technologies described herein has a variety of applications in biology and medicine, and is a powerful tool for developmental signaling, cancer biology, T cell engineering, and tissue engineering. In some embodiments, this system is used to achieve drug-control over "synthetic Notch" receptors in which the native Notch ligand-binding domain is substituted with an alternative protein (such as, e.g., anti-GFP scFv) for activation by cells expressing complementary surface ligands (such as, for example, GFP).

Synthetic proteins (or constructs expressing such synthetic proteins) comprising a receptor ligand (DLL, or any other ligand which binds to the target receptor), NS3 domain, and a targeting domain (e.g., an antibody specific for a cancer cell antigen) can be used, in some embodiments, for therapeutic applications. Once bound to their target (e.g., a cancer cell), these constructs would only activate receptors on adjacent cells when in the presence of an NS-inhibitor drug. Absent the drug, the NS3 domain would be cleaved, releasing the ligand and preventing receptor activation.

In some embodiments, the receptor ligand domain or extracellular domain is the extracellular domain of gamma secretase, nicastrin. Gamma secretase is a membrane protein complex involved in biological functions such as Notch and amyloid precursor protein (APP) processing. Its proteolytic subunit, presenilin, acts by catalyzing the cleavage of intramembrane alpha helices, and in turn allows the release of both the extracellular domain (important in APP pathology) and the intracellular domain (important in Notch developmental biology). The gamma secretase extracellular subunit, nicastrin, has been shown to regulate this process through steric hindrance. Gamma secretase substrates with bulky extracellular domains are resistant to proteolysis, and the regulated shedding of this bulky ectodomain is a key pathway in Notch processing.

The drug-controllable ligands can be used, in some embodiments, with various combinations of other aspects described herein, including the cis-clamp and autoinhibitory Notch receptors.

Also provided herein in some aspects, are modified HCV NS3 protease domains, as versatile protein engineering modules that can be applied to install drug-sensitivity into both intracellular and cell-surface proteins. In its natural context, NS3 is a serine cis-protease that excises itself from the HCV polyprotein by cleaving recognition sites that flank it at either end.[2] Because it is essential for HCV replication, numerous inhibitors targeting the viral protease have been developed. In previous work, NS3 and its inhibitors have been combined to create tools for conditionally linking proteins to imaging tags and degradation sequences.[3-6] Given its successful application in these non-natural contexts, it was determined whether the viral protease could be used to design synthetic and drug-sensitive proteins to gain control over complex cellular processes such as transcription and intercellular signaling.

Figure 15A:
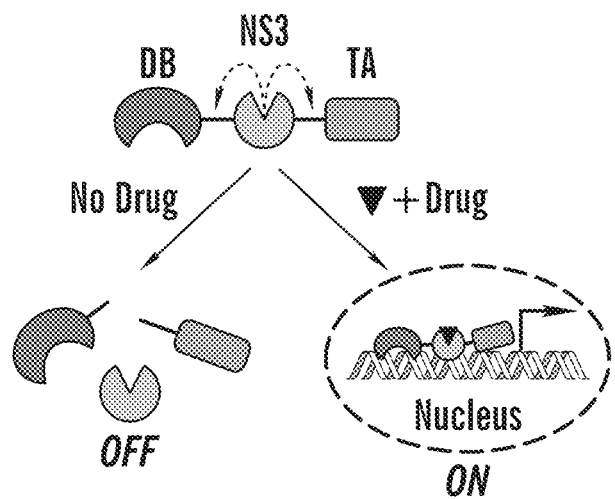

NS3 was tested as a module for engineering drug-sensitive transcription factors (TFs), using the protease as a Ligand-Inducible Connection (LInC) to control the association between modular DNA-binding (DB) and transcriptional activation (TA) domains. In some embodiments, NS3 was inserted in between minimal DB and TA sequences sourced from the yeast TF Gal4, generating Gal4$_{DB}$-NS3-Gal4$_{TA}$ (FIG. 15A). In this configuration, it was expected that the viral protease would serve as a self-immolating linker, excising itself from the fusion construct and, in doing so, separating the DB and TA elements. However, in the presence of an NS3 inhibitor, it was believed that self-excision of the protease would be blocked, resulting in the preservation of full-length TF capable of activating the expression of targeted genes.

Figure 15B:
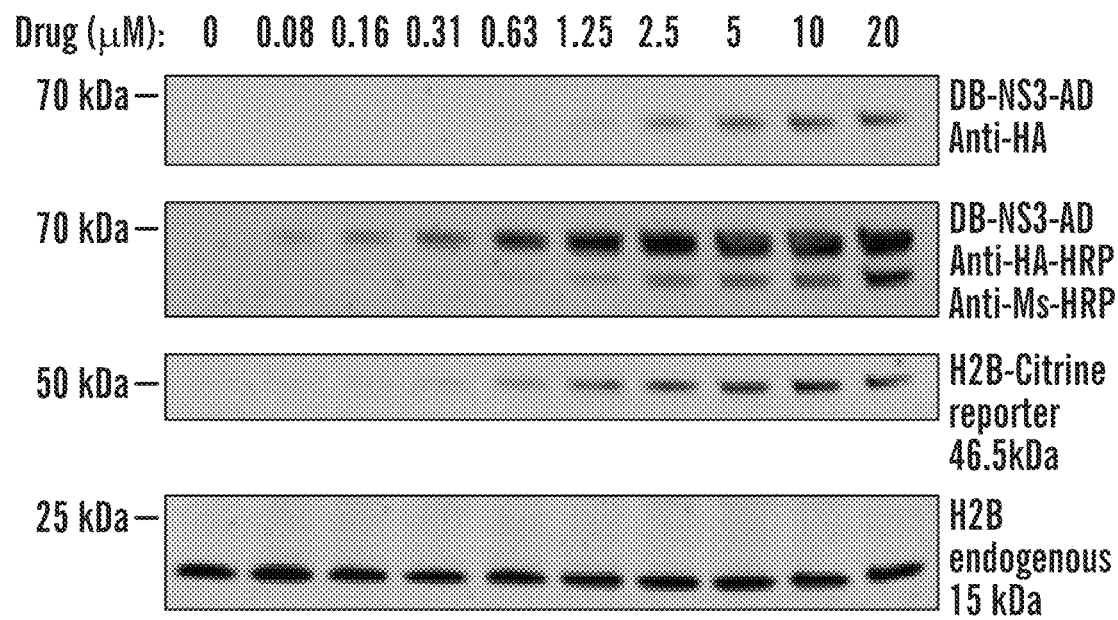
Figure 15C:
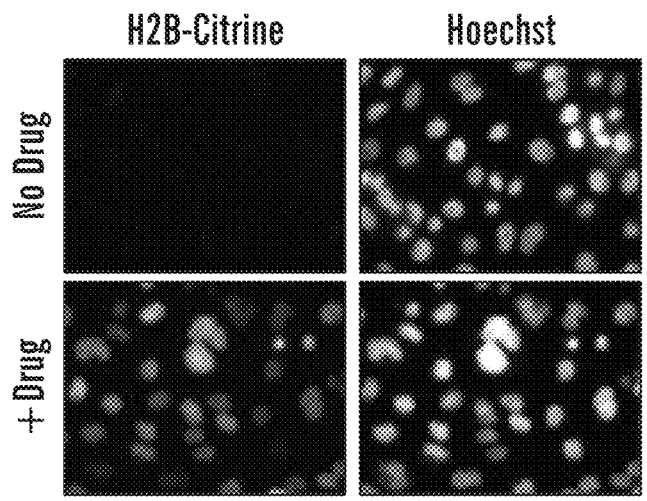
Figure 18:
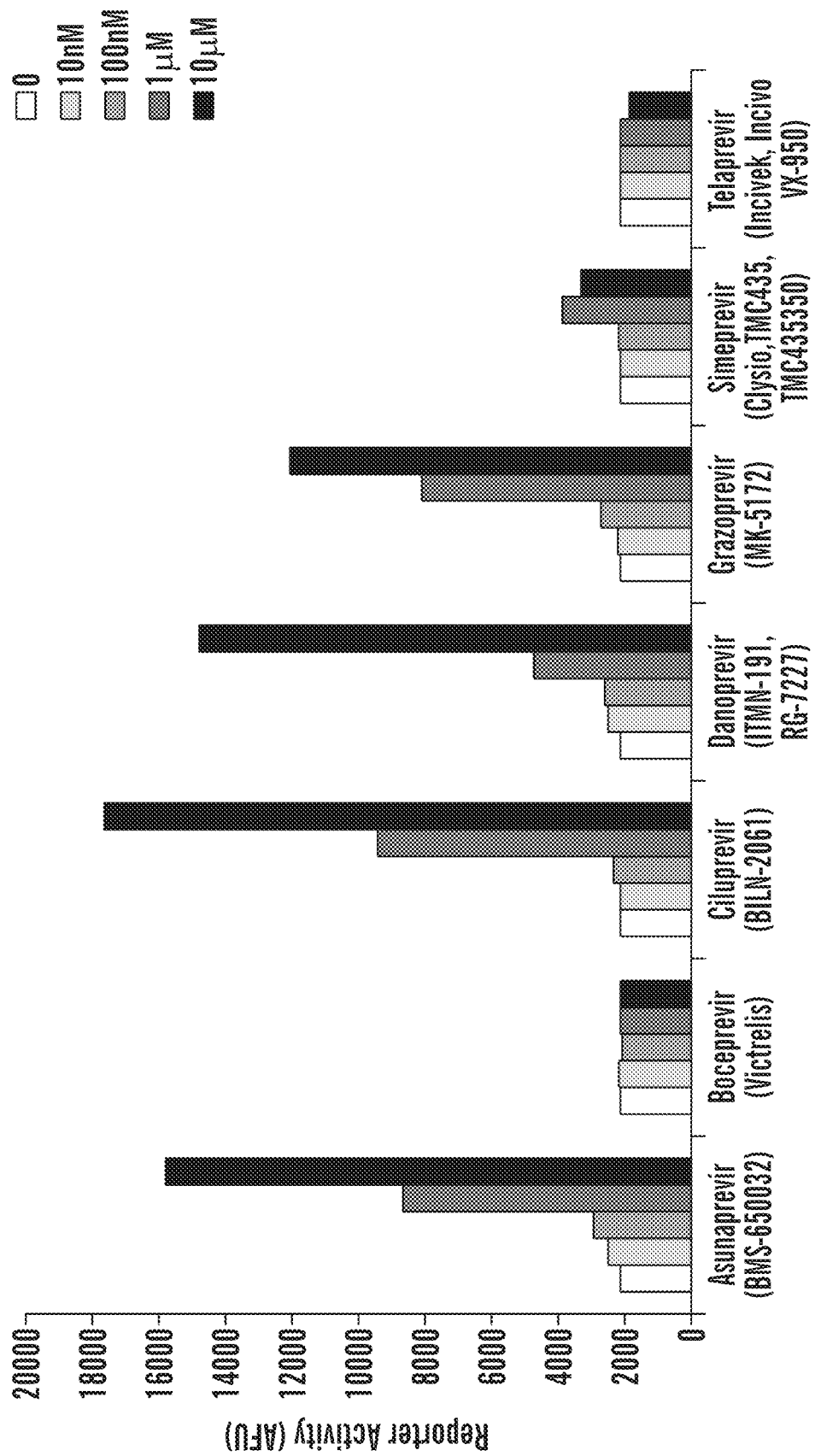

To determine whether DBGal4-NS3-TAGal4 behaved in this manner, the protein was stably expressed in a mammalian cell line containing a Gal4-dependent fluorescent reporter construct (UAS H2B-Citrine). Immunoblotting confirmed that intact DBGal4-NS3-TAGal4 accumulated in cells treated with the selective NS3 inhibitor BILN-2061, while full-length TF was not detected in drug-untreated controls (FIG. 15B). In addition to TF stabilization, analyses by fluorescence imaging, flow cytometry, and antibody detection showed that treatment with NS3 inhibitors also induced expression of H2B-Citrine in a dose-dependent manner (FIGS. 15B-15C). Various commercially available NS3 inhibitors were evaluated and multiple compounds capable of inducing robust transcriptional responses were identified, including BILN-2061, asunaprevir, danoprevir, and grazoprevir (FIG. 18). It was noted that the α-ketoamide-based inhibitors tested (telaprevir and boceprevir) did not induce detectable levels of reporter expression above background. Together, these results indicate that NS3 inhibitors can be used to precisely regulate the association of protease-linked modules in order to achieve inducible control over gene expression.

"NS3 inhibitors," as used herein, refer to inhibitors of NS3 protease domain activity. Typically, NS3 protease inhibitors have been classified into two groups. (1) The first generations inhibitors (boceprevir and telaprevir) are linear α-ketoamide derivatives. These two inhibitors form a covalent bond with the active site of the enzyme in a reversible way. The second generation of inhibitors are mostly linear and macrocyclic noncovalent inhibitors of the NS3-4A enzyme. Accordingly, in some embodiments, non-limiting examples of NS3 inhibitors that can be used with the synthetic protein compositions and methods described herein comprising NS3 protease domains, such as SEQ ID NO: 32, or variants thereof, include paritaprevir, grazoprevir, CH 503034 (Boceprevir), VX-950 (Telaprevir), BI 201335, SCH 900518 (Narlaprevir), SCH6 (SCH446211), BILN 2061 (Ciluprevir), TMC435 (Simeprevir), ITMN-191/RG7227 (Danoprevir), MK-7009 (Vaniprevir), GS-9256, ACH-1625, MK-5172, ABT-450, IDX320, BMS-650032 (Asunaprevir), ACH-806 (GS-9132), and PHX1766.

Figure 15D:
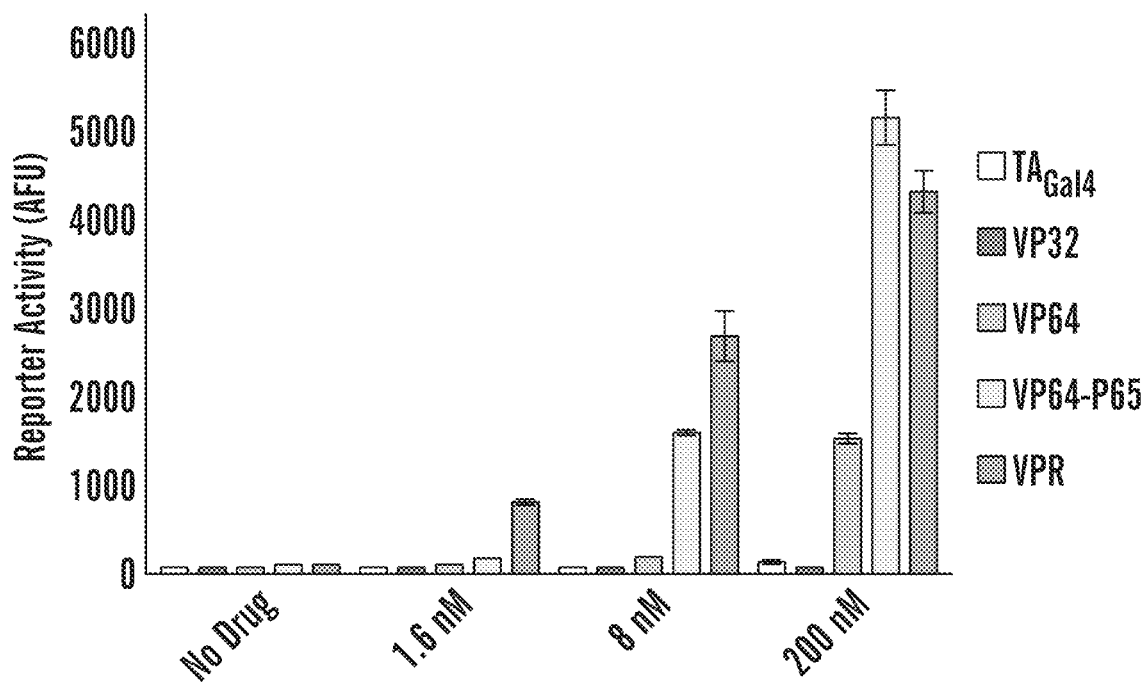
Figure 19A:
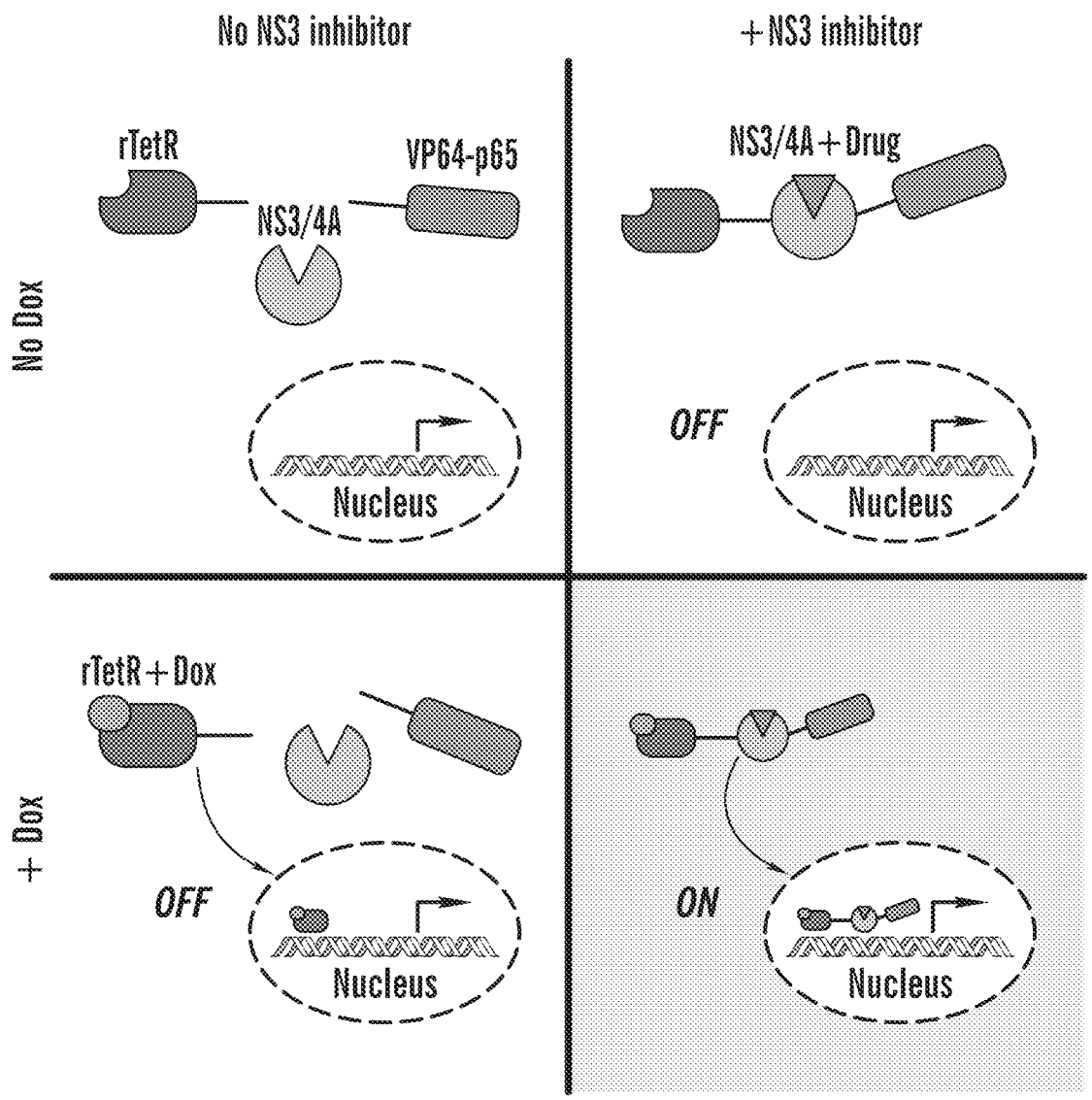
Figure 19B:
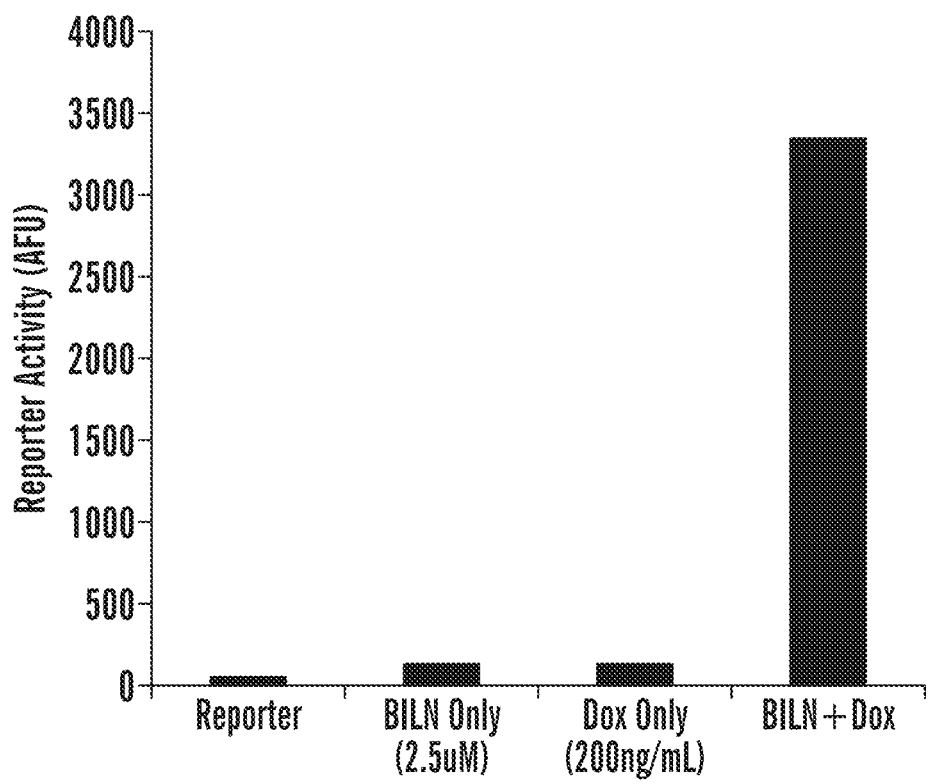
Figures 28A, 28B:
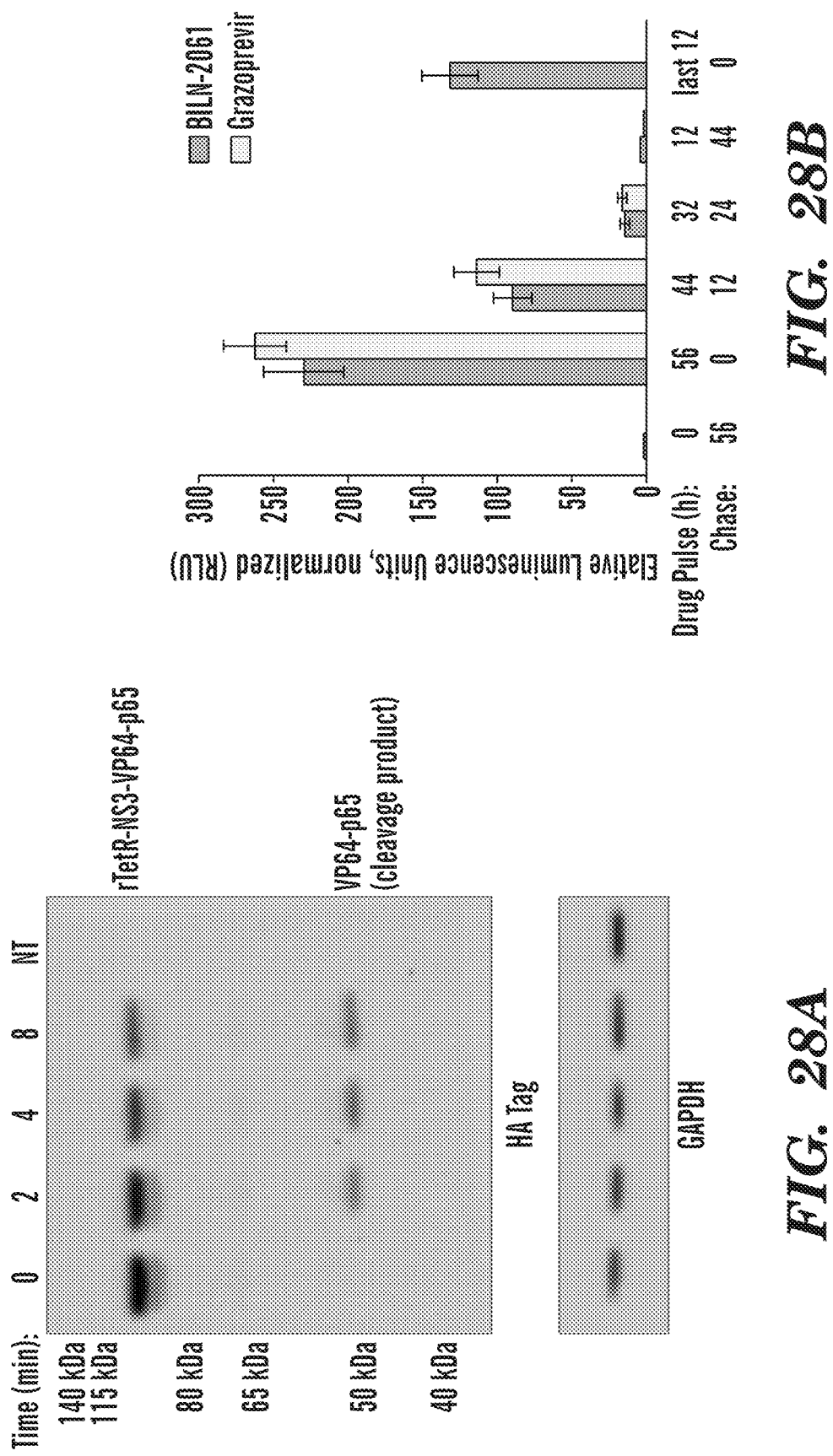
FIGS. 28A and 28B show reversibility of drug-induced "turn-on" TF preservation.

Given the modular framework of the system, it was tested whether different transcription factors possessing tailored properties could be readily engineered. For example, it was tested whether substitution of the Gal4 TA domain with more potent transcriptional effectors (such as VP64, VP64-p65, and VPR)[7] would yield TFs with enhanced drug sensitivity. Indeed, DBGal4-NS3-TAVP64-p65 and DBGal4-NS3-TAVPR resulted in higher reporter expression at decreased drug concentrations (including robust expression at drug concentrations in the low nanomolar range) as compared to the initial DBGal4-NS3-TAGal4 (FIG. 15D). Additionally, TFs with activity against alternative promoters were also designed, including one in which the reverse tetracycline repressor (rTetR)[8] was used as the DB element (DBrTetR-NS3-TAVP64-p65). In transfected cells, DBrTetR-NS3-TAVP64-p65 exhibited "AND" gate activity, requiring both the presence of doxycycline (to induce rTetR binding to tetO sequences) and an NS3 inhibitor in order to activate transcription from the tetO-containing TRE promoter (FIG. 19). Notably, the effects of TF preservation and gene activation were reversed following inhibitor removal (FIG. 28).

To complement the "turn-on" systems described above, a strategy in which NS3 inhibitors could be used to "turn-off" gene expression was also designed for use in other aspects. In this approach, the NS3 protease was used to conditionally link an intact Gal4 (Gal4min) TF to a membrane-targeting domain with the expectation that protease inhibitor could be used to precisely regulate the amount of soluble versus membrane-bound TF. Using a Type-I transmembrane protein as a targeting element, a fusion construct was generated containing NS3 and Gal4min as a C-terminal cytosolic domain (TMD-NS3-Gal4min) (FIG. 15E).

Figure 15H:
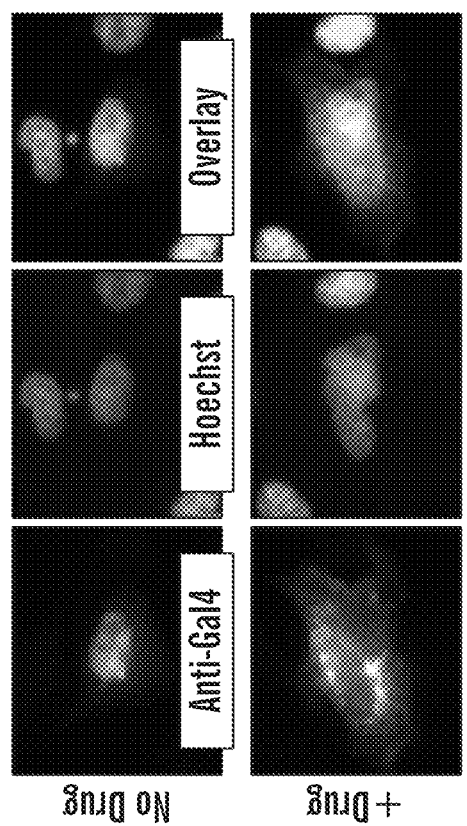
Figure 15G:
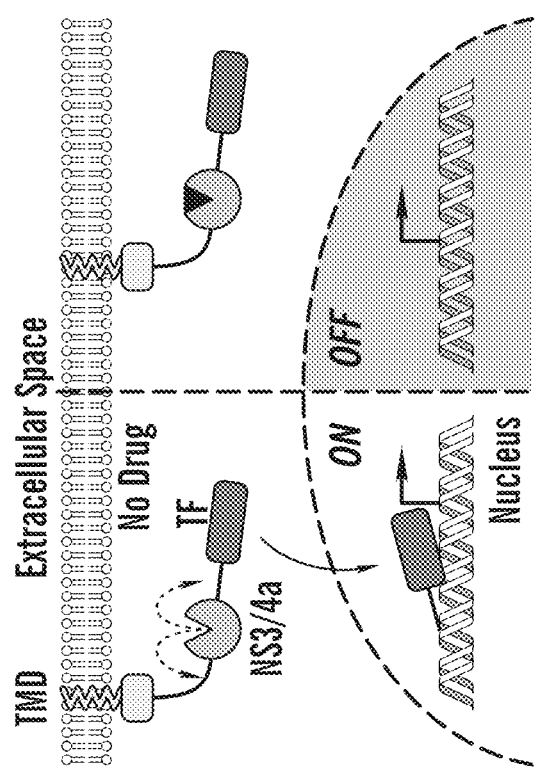

Fluorescence imaging of cells expressing a dual-tagged version of the protein (BFP-TMD-NS3-Gal4$_{min}$-mCherry) showed that Gal4$_{min}$ was released from its BFP-fused transmembrane domain in drug-untreated cells, resulting in a liberated TF unit (tagged with mCherry) that localized predominantly to the nucleus (FIG. 15F). However, in cells in which NS3 activity had been inhibited, the TF remained linked to its targeting element and thus trafficked to endoplasmic reticulum (ER) surface and plasma membrane (PM). A version in which an N-terminal myristoylation and palmitoylation substrate[9] was used as the targeting domain (myr-palm-NS3-Gal4min) exhibited similar behavior, becoming occluded from the nucleus in drug-treated cells (FIGS. 15G-15H).

Figure 20A:
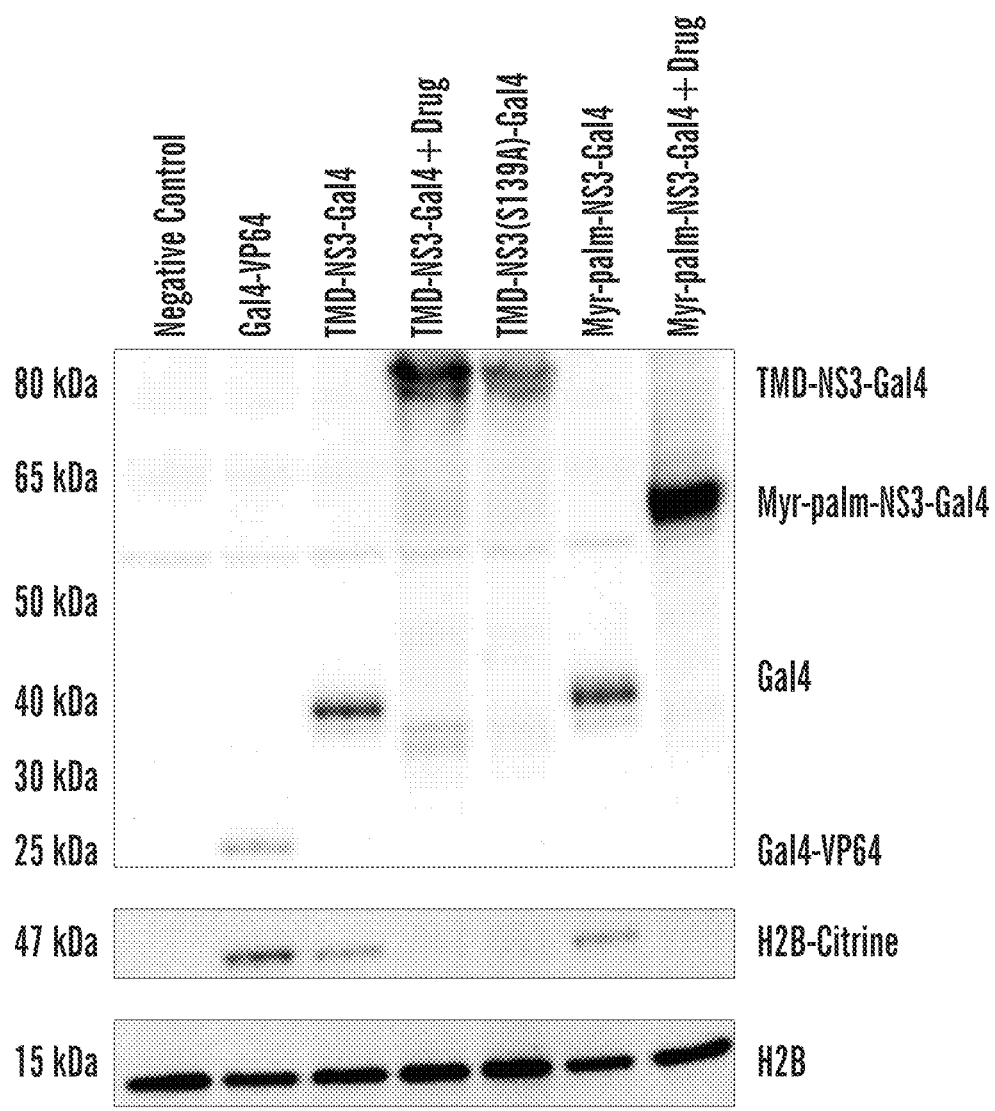
Figure 20B:
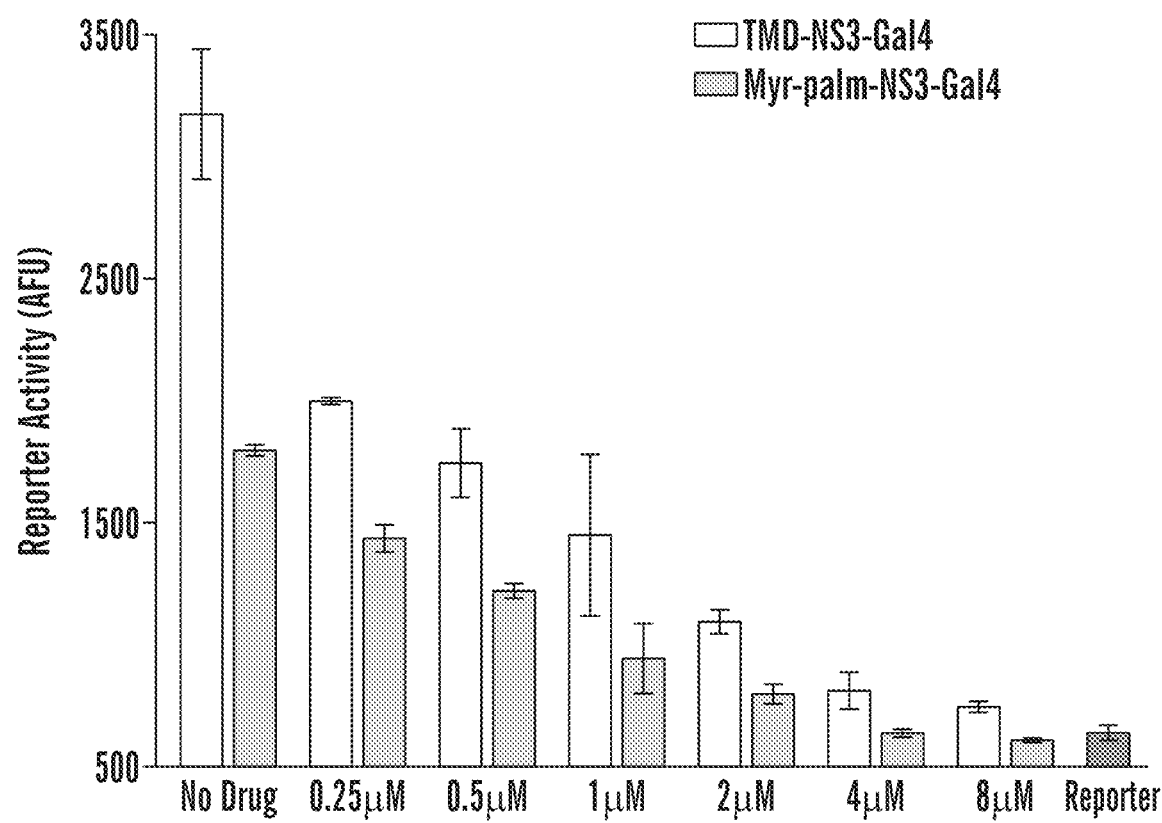
Figures 29A, 29B:
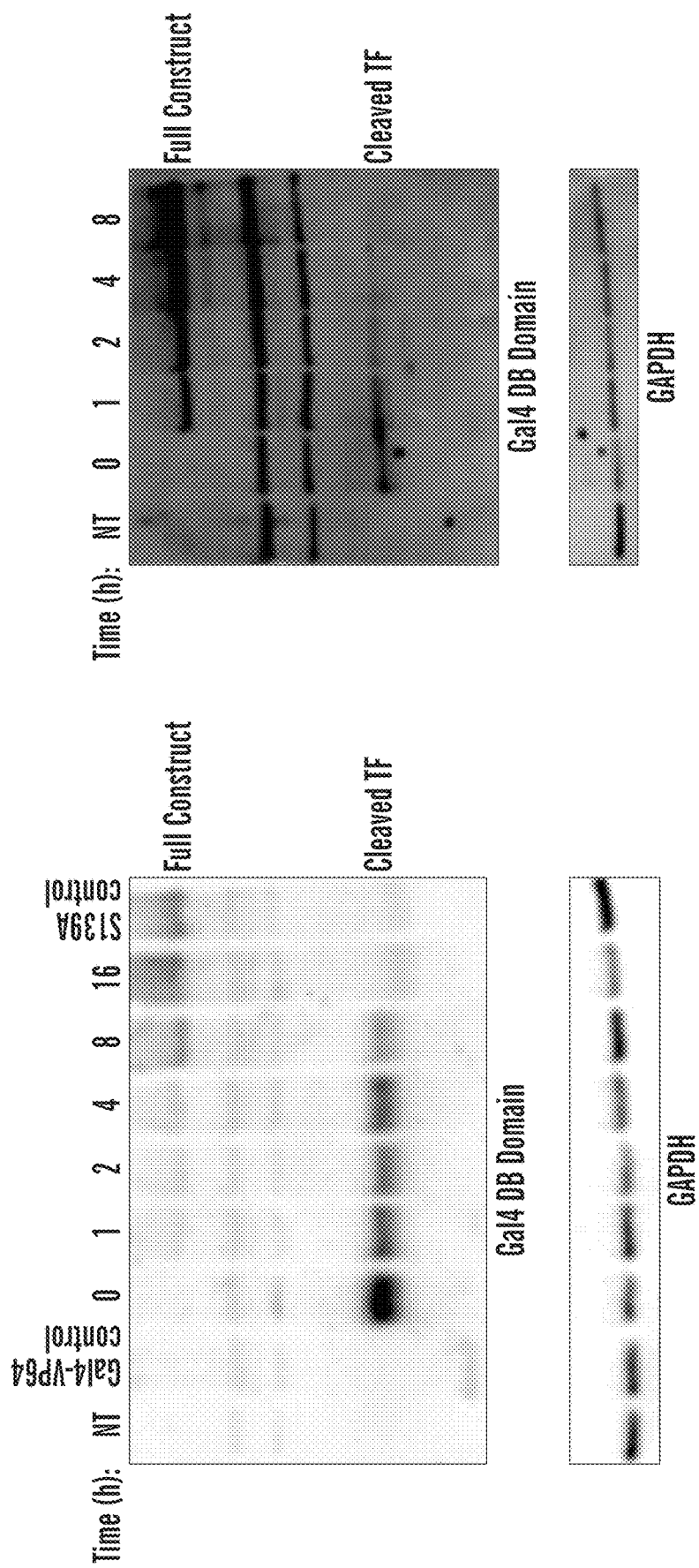
FIGS. 29A and 29B show time-dependent western analysis tracking the degradation of cleaved Gal4$_{min}$ domains. HEK 293FT cells transfected with DNAs encoding either TMD-NS3-Gal4$_{min}$ or TMD-NS3-Gal4$_{min}$-PEST were grown without inhibitor until treatment with 3 µM grazoprevir at the indicated times prior to lysis in SDS PAGE loading buffer and subsequent analysis by western blot. Detection of the intact and cleaved states of each protein was achieved via labeling with an anti-Gal4 DB antibody on western blots loaded with lysates from cells expressing FIG. 29A TMD-NS3-Gal4$_{min}$ or FIG. 29B TMD-NS3-Gal4$_{min}$-PEST. Bands corresponding to the full-length version of each construct ("Full Construct") were detected only in lanes loaded with lysates from drug-treated cells. The intensity of the "Full Construct" bands grew over time, indicating accumulation of the intact proteins following NS3 inhibition. Bands corresponding to cleaved Gal4min and Gal4min-PEST were also observed ("Cleaved TF"), the intensities of which diminished over time. The half-life of the Gal4min-PEST was attenuated relative to that of Gal4$_{min}$. The PEST domain used was derived from the C-terminal region of mouse ornithine decarboxylase, which has previously been used to generate a "destabilized" version of GFP with a reduced half-life of 2 hours.

Given that TFs must localize to the nucleus in order to bind their DNA targets, whether TMD-NS3-Gal4min and myr-palm-NS3-Gal4min would facilitate target gene expression in reporter cells that could be inducibly downregulated through NS3 inhibition was tested. Confirming these were immunoblotting and flow cytometry analyses showing that constructs could be used to achieve drug-inducible suppression of a Gal4-dependent fluorescent reporter gene (FIG. 20). Consistent with these results were analyses showing that exposure to NS3 inhibitors led to the accumulation of membrane-tethered Gal4min (FIGS. 15F-15G, 20A and 20B), as well as the gradual depletion of previously-cleaved TF copies (FIGS. 29A and 29B). Measurements by flow cytometry confirmed that drug treatment suppressed reporter gene expression in a dose-dependent manner (FIGS. 20A and 20B), and live-cell imaging showed that the effect of downregulation could be reversed following inhibitor withdrawal. Together, these results demonstrate that TFs can be conditionally linked to localization signals through NS3, in turn permitting precise control over their spatial distributions and activities.

Figure 15I:
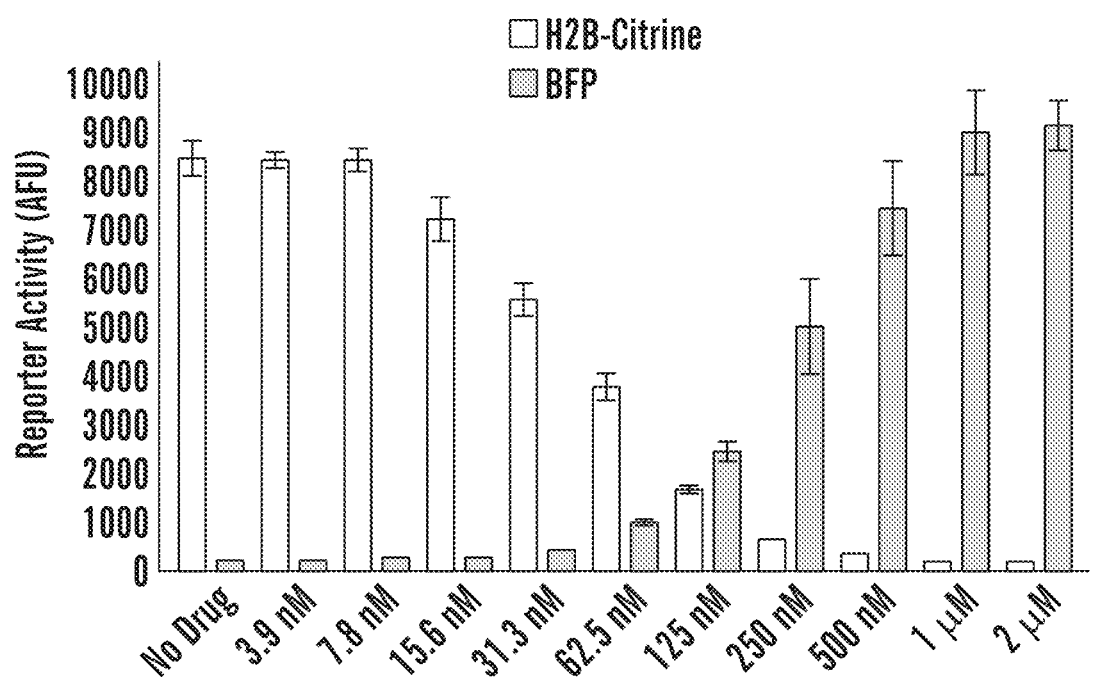

Recognizing that natural gene regulation often involves the synchronized regulation of multiple genes, the "turn-on" and "turn-off" systems were combined to create a platform for simultaneously regulating distinct promoters using drug. In cells that coexpressed both a "turn-on" TF and "turn-off" TF (DBrTetR-NS3-TAVP64-P65 and TMD-NS3-Gal4$_{min}$, respectively), coinciding and inverse regulation of TRE- and UAS-controlled reporter genes were observed (FIG. 15I). These results demonstrate NS3 can be used to control multiple TFs in individual cells to activate concurrent and inverse gene expression changes in response to NS3 inhibition. Such strategies provide powerful approached for generating sophisticated, drug-dependent genetic circuits for programming complex behaviors into therapeutic mammalian cells.

Figure 16A:
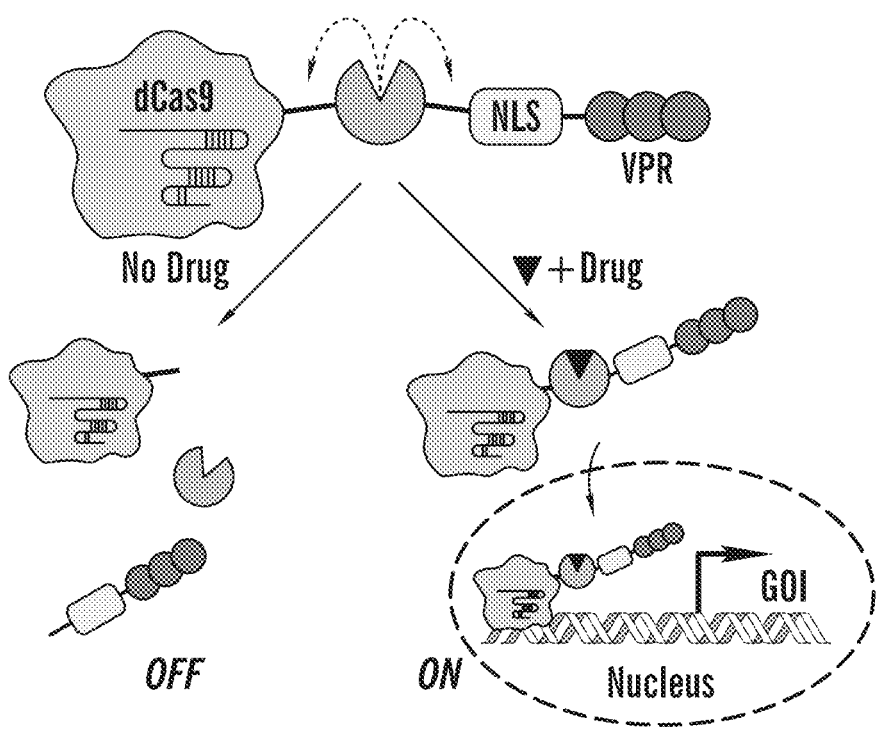

In addition to TFs targeting engineered promoters, in some aspects, provided herein are drug-sensitive proteins or "synthetic drug-dependent proteins" that can be used to upregulate gene expression from endogenous promoter sequences, such as the synthetic drug-dependent protein of SEQ ID NO: 45 or engineered variants thereof. To achieve such control, as described herein, NS3 was integrated into artificial TFs based on dCas9, a catalytically inactive mutant of the Cas9 nuclease that can serve as a programmable DNA-binding domain.[10-11] First, a LInC module (e.g., NS3 protease domain) was integrated into dCas9-VPR[13] in between the DB scaffold and a C-terminal region containing a nuclear localization sequence (NLS) and the VPR TA element (dCas9-NS3-NLS/VPR) (FIG. 16A). In this configuration, it was tested whether NS3 cleavage would not only inactivate the TF, but also prevent cleaved dCas9 from translocating into the nucleus (e.g., would be cytoplasmically contained).

Figure 16B:
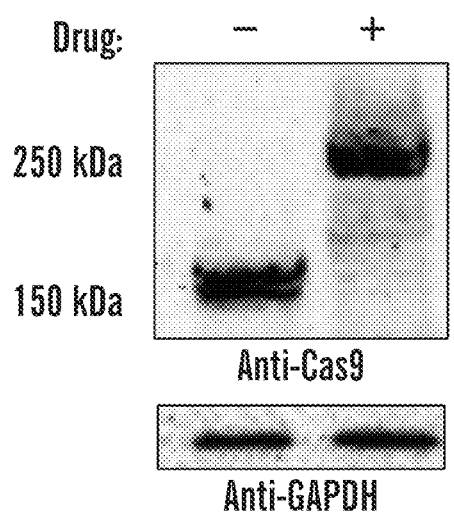
Figure 16C:
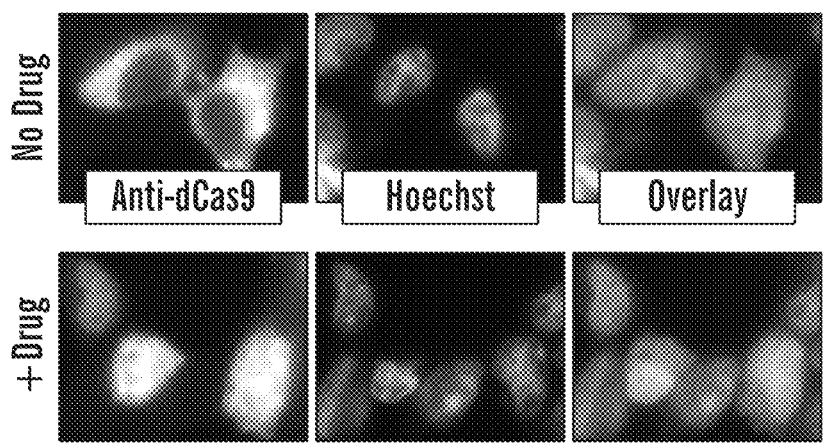
Figure 16D:
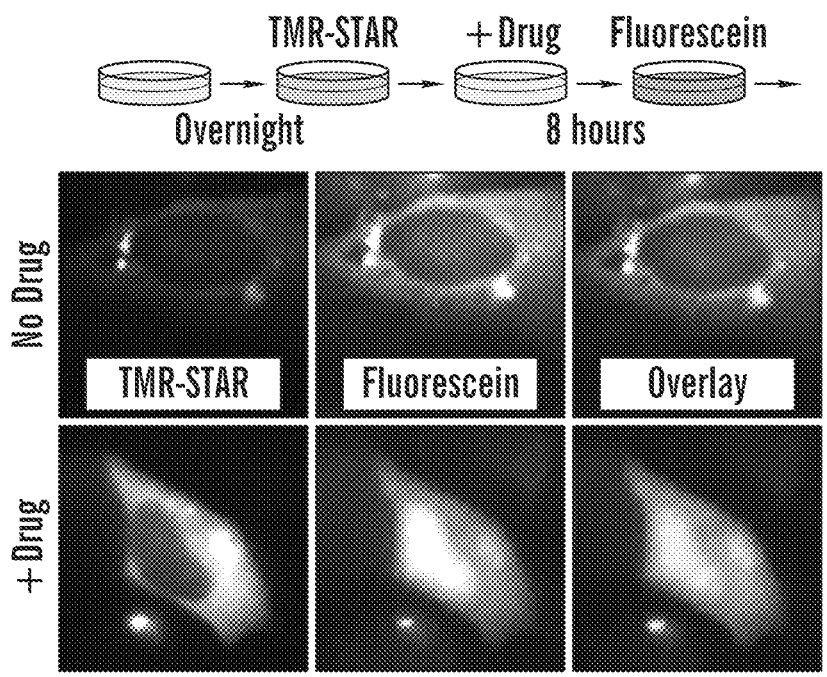
Figure 21A:
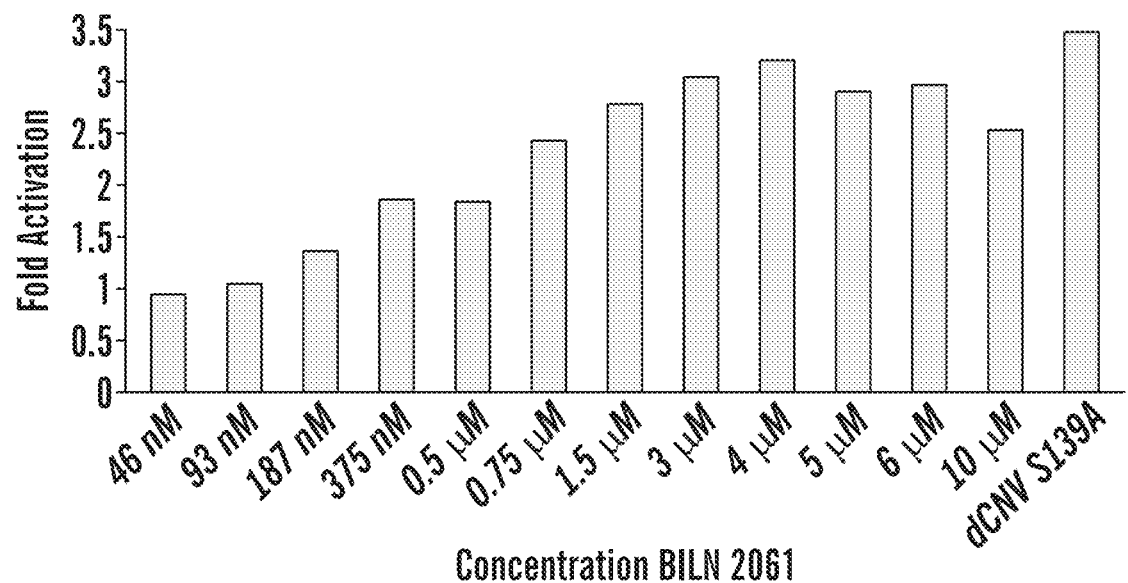
FIGS. 21A-21B show drug-induced activation of a fluorescent reporter gene using dCas9-NS3-NLS/VPR. Flow cytometry FIG. 21A and representative fluorescence images FIG. 21B of H2B-Citrine expression from a reporter construct (UAS H2B-Citrine) as mediated by drug-stabilized dCas9-NS3-NLS/VPR and a corresponding UAS-targeting sgRNA. Flow cytometry analyses of reporter expression levels were compared to activation as mediated by "dCNV S139A," a version of dCas9-NS3-NLS/VPR in which the catalytic serine residue of the NS3 protease was mutated to alanine. The sgRNA construct used (Addgene plasmid #6415) also encoded a constitutively expressed mCherry.
Figure 21B:
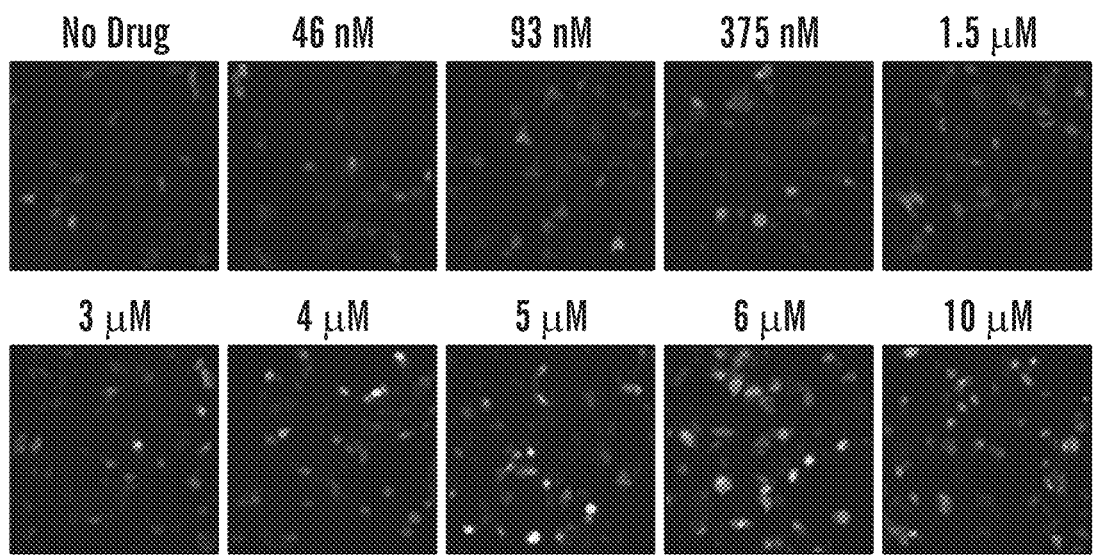

Western blotting of cell lysates demonstrated that full-length copies of dCas9-NS3-NLS/VPR accumulated only in cells cultured in the presence of drug (FIG. 16B), and fluorescence imaging of immunostained cells indicated that the dCas9 domain localized to the nucleus in a drug-dependent manner (FIG. 16C, FIG. 21). In addition, live-cell time-dependent dye labeling experiments carried out using a SNAP-tag fused version of the TF (SNAP-dCas9-NS3-NLS/VPR) showed that only protein copies made in NS3-inhibited cells were transported across the nuclear envelope (FIG. 16D). Given that unfused dCas9 molecules can serve as inhibitors of native expression levels (by binding and occupying targeted DNA sites)[12], the cytoplasmic containment of cleaved dCas9 could serve to prevent undesired gene repression in drug-untreated cells, as the unfused domain has been reported to suppress gene expression in certain cases through binding and occupying targeted DNA sites.

Figure 16E:
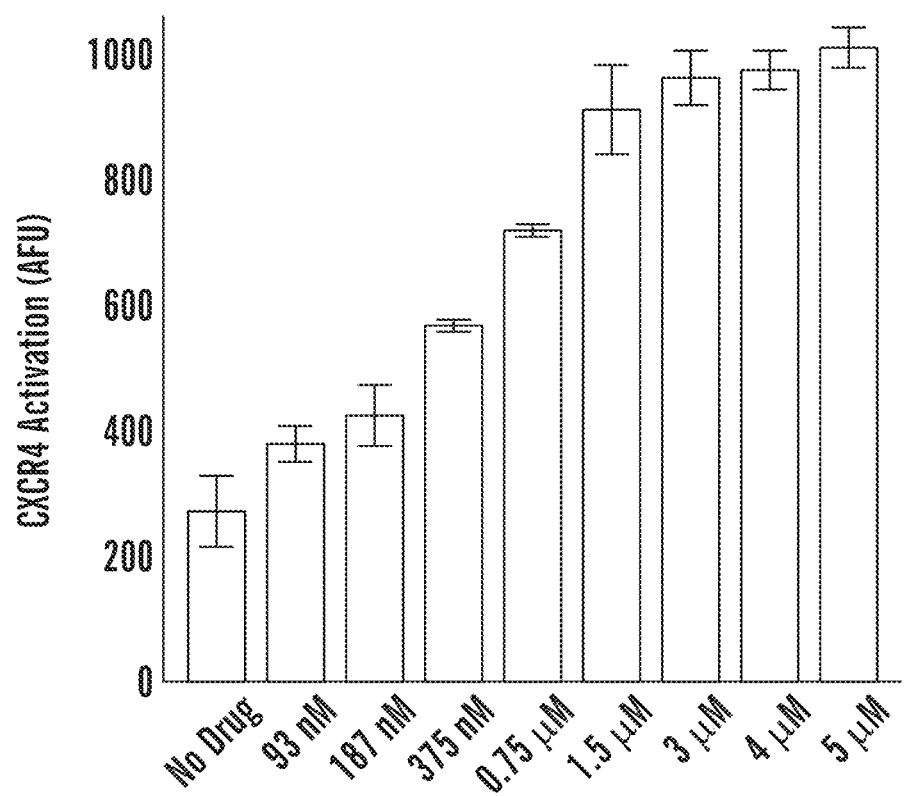
Figure 22:
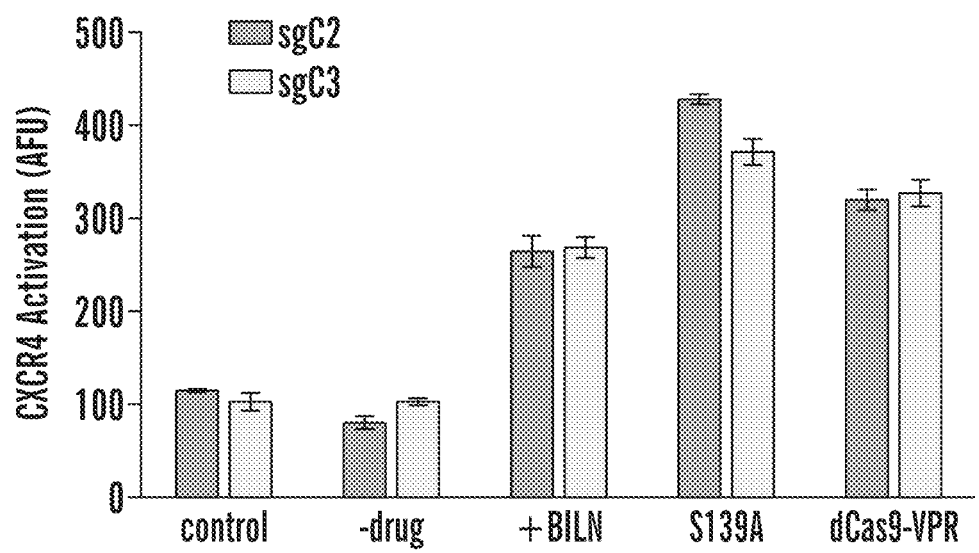
FIG. 22 sgRNAs targeting the CXCR4 promoter were co-transfected into HEK 293FT alongside DNAs encoding either dCas9-VPR, or dCas9-NS3-NLS/VPR. The extent of CXCR4 upregulation was subsequently quantified by flow cytometry using a fluorescently-labeled anti-CXCR4 antibody. Cells containing dCas9-NS3-NLS/VPR were analyzed under drug-treated and untreated conditions (BILN-2061, 3 µM), and compared to catalytically inactive dCas9-NS3-NLS/VPR (NS3 "S139A" mutant), dCas9-VPR containing, and non-transfected HEK 293FT cells (control). Antibody staining of live cells was carried out 24 hours following transfection/drug-treatment. Values are displayed as mean±s.d., as determined in triplicate.
Figure 23A:
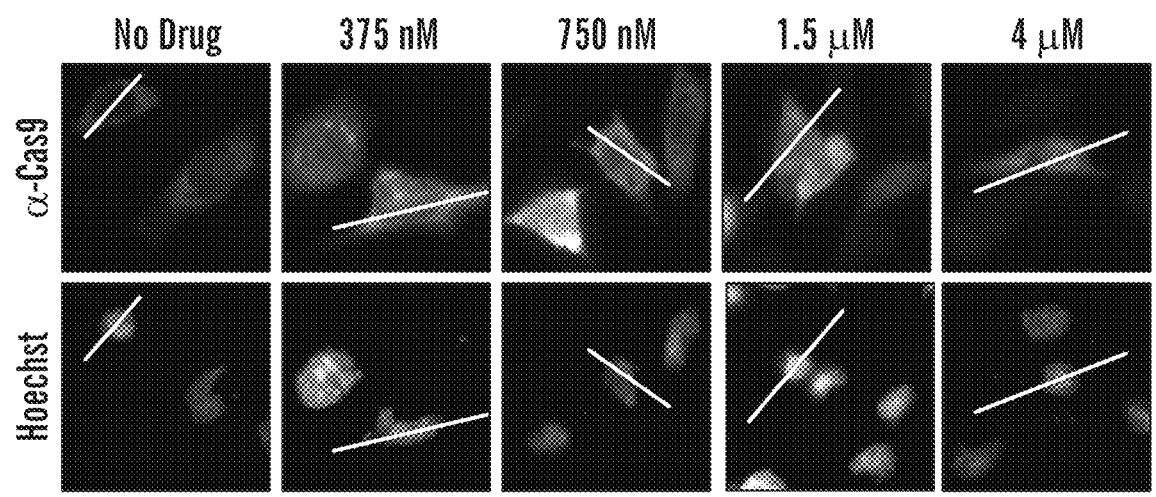
FIGS. 23A-23B show dose-dependent nuclear localization of the dCas9 domain in cells expressing dCas9-NS3-NLS/VPR.
Figure 23B:
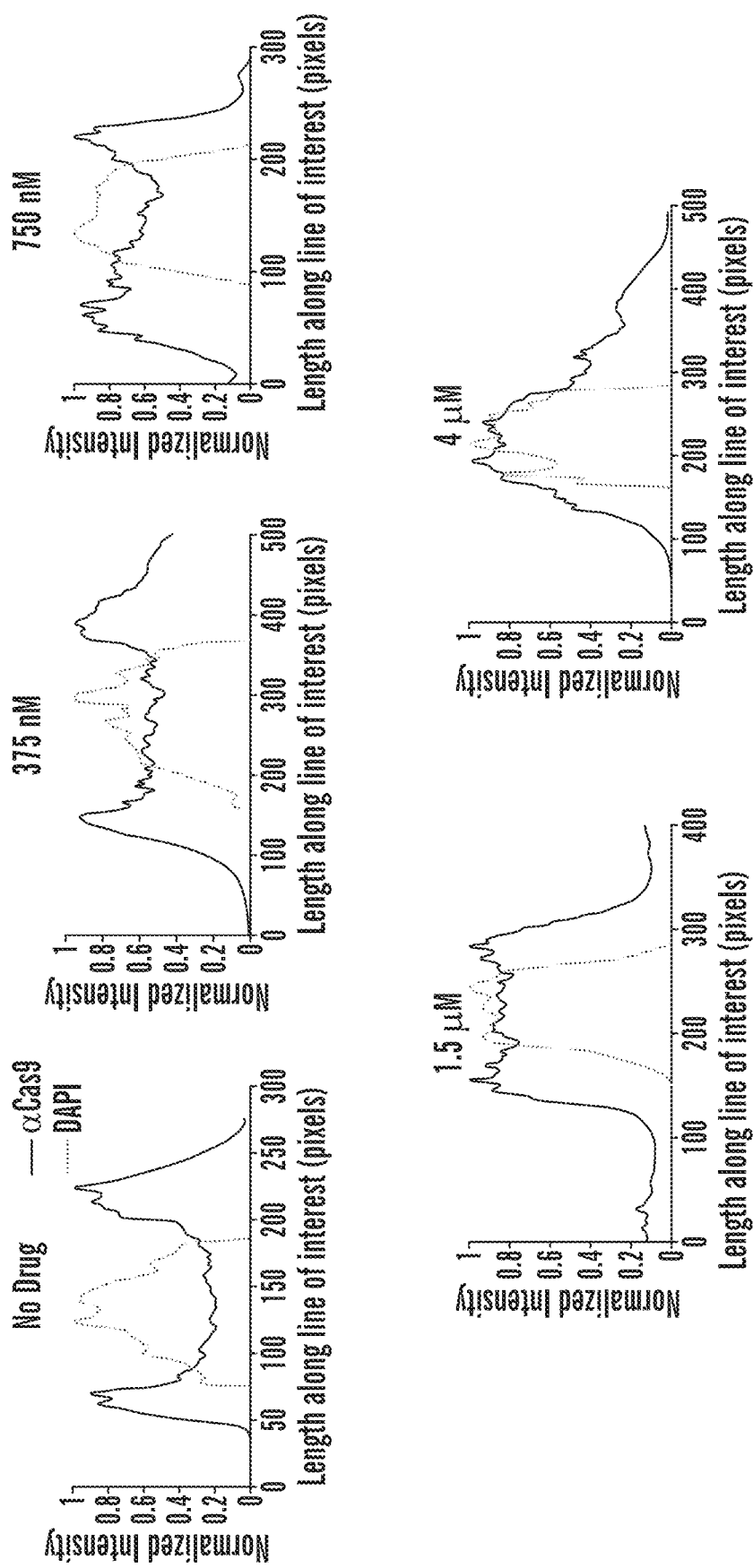
Figure 24A:
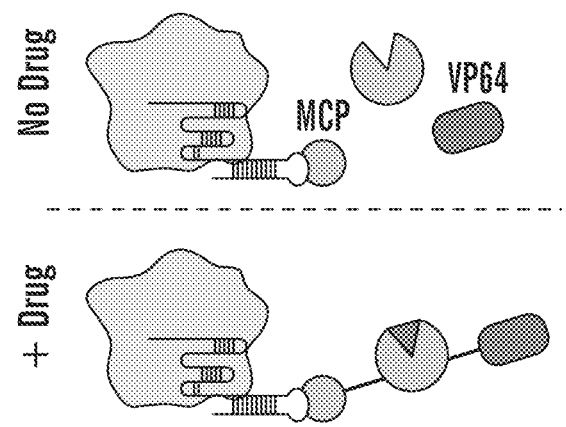
FIGS. 24A-24B show inducible gene activation using MCP-NS3-VP64.
Figure 24B:
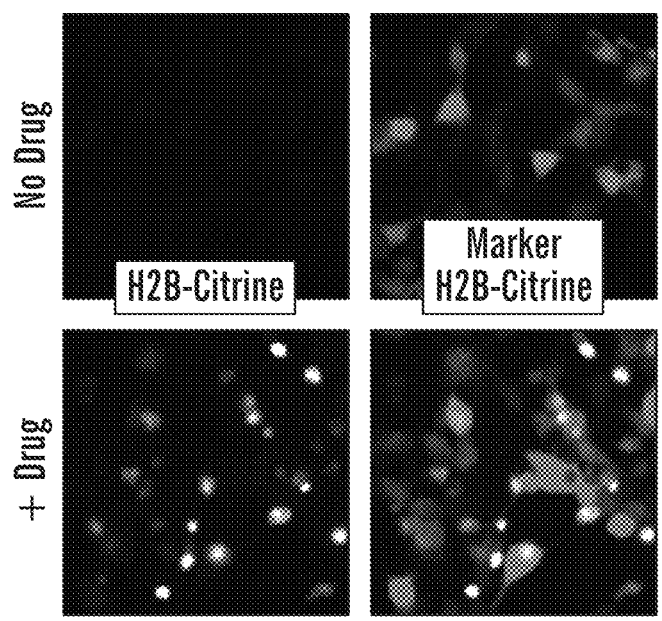

To confirm that dCas9-NS3-NLS/VPR can be used to upregulate gene expression in a drug-inducible manner, the TF was co-expressed with sgRNA sequences targeting either a fluorescent reporter construct (UAS H2B-Citrine), or a chromosomal region upstream of the human gene encoding the chemokine receptor CXCR4.[13] Flow cytometry analyses showed that BILN-2061 can be used to induce upregulation of both gene targets in a dose-dependent manner (FIG. 16E, FIG. 22). In addition, tests using separate sgRNAs targeting distinct regions of the CXCR4 promoter showed that (under saturating drug concentrations) dCas9-NS3-NLS/VPR was able to upregulate receptor expression to a similar extent as dCas9-VPR (FIG. 23). A system in which NS3 was used to regulate TA domain association with a hairpin-modified sgRNA[13] was also developed (FIG. 24). Together, these data indicate that NS3 can also be combined with dCas9 to achieve tunable transcription of endogenous human genes, and also suggest that other sophisticated Cas9-based tools[14] could be designed using a similar approach.

In addition to TFs, certain transmembrane signaling proteins are also known to possess component-based architecture, including the Notch receptor, its ligands, and their synthetic derivatives.[15-17] Thus, it was tested whether NS3 can also be used to regulate intercellular signaling via drug-dependent Notch/SynNotch activation. Toward this end, an NS3-containing version of the Notch ligand Delta-like 1 (Dll1) was designed by integrating the protease into the extracellular portion of the protein (Dll1-NS3), positioning it between the receptor-binding region and transmembrane domain (TMD) (FIG. 17A). In this configuration, it was tested whether NS3 self-excision would yield a soluble ligand that, due to its lack of a membrane tether, would not be presented at cell-surface (FIG. 17B). Indeed, immunostaining of cells stably expressing Dll1-NS3 showed that presentation of Dll1-NS3 at the cell surface was induced upon NS3 inhibition (FIG. 17C).

Figure 17F:
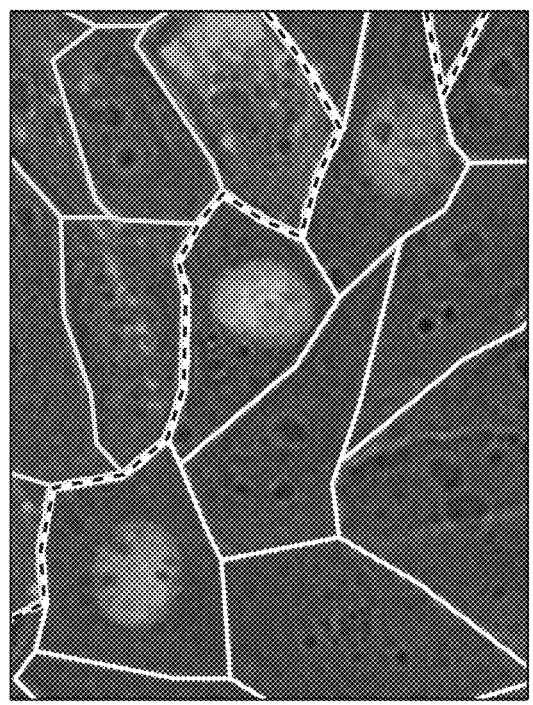
Figure 17E:
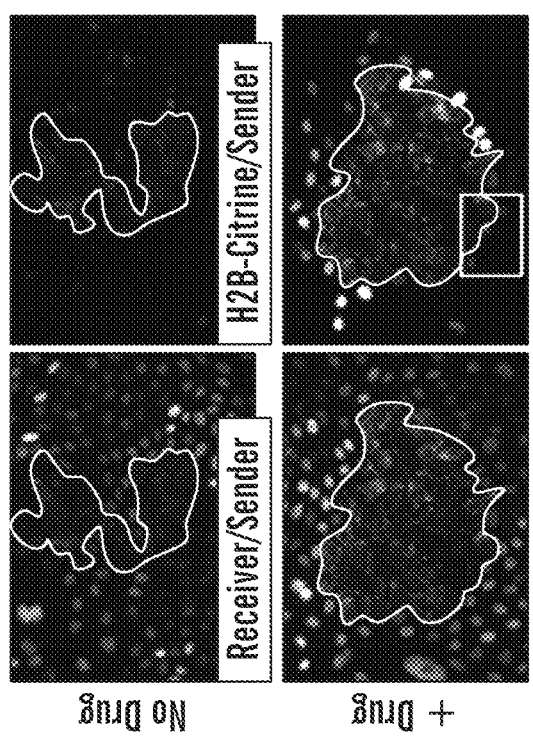
Figure 25A:
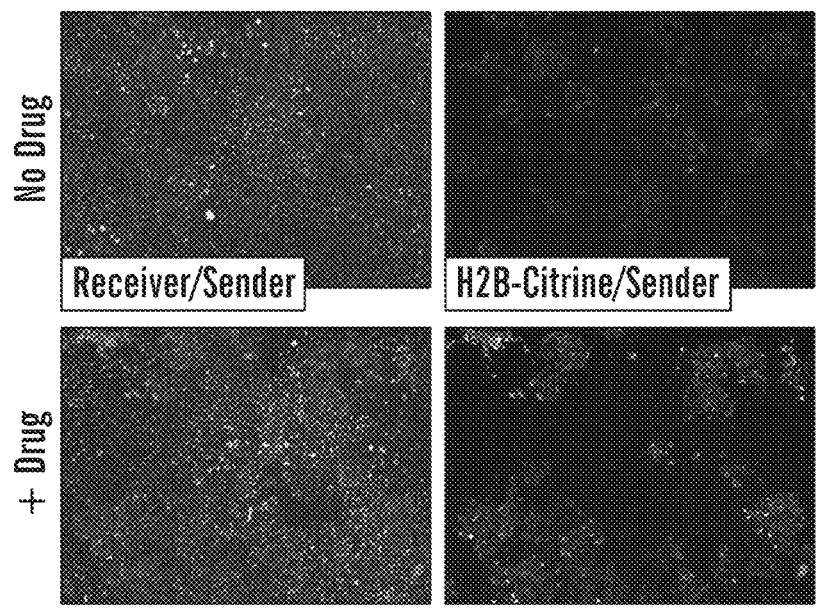
FIGS. 25A and 25B show images of Dll1-NS3/4A-mCherry mediated cell-cell signaling captured by epifluorescence imaging under 10× magnification.
Figure 25B:
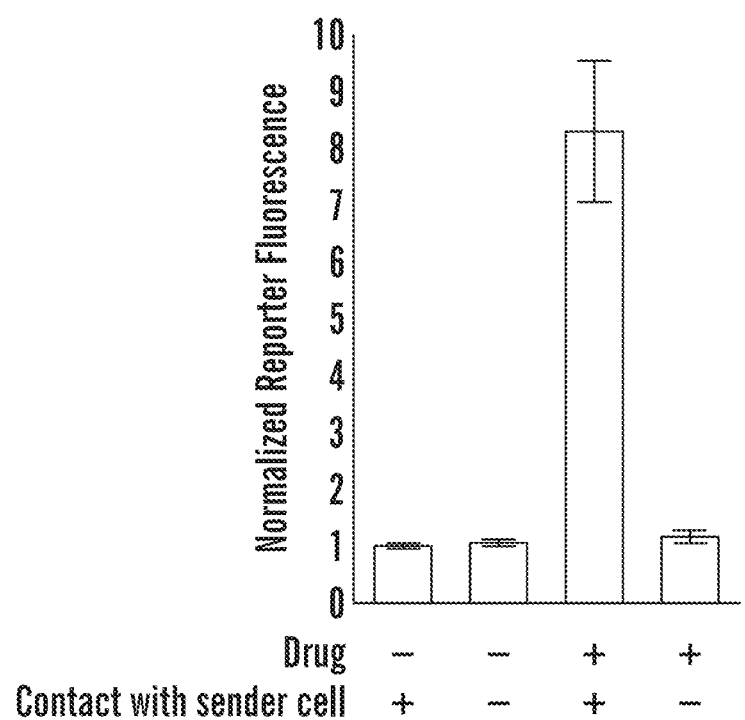
Figures 27A, 27B:
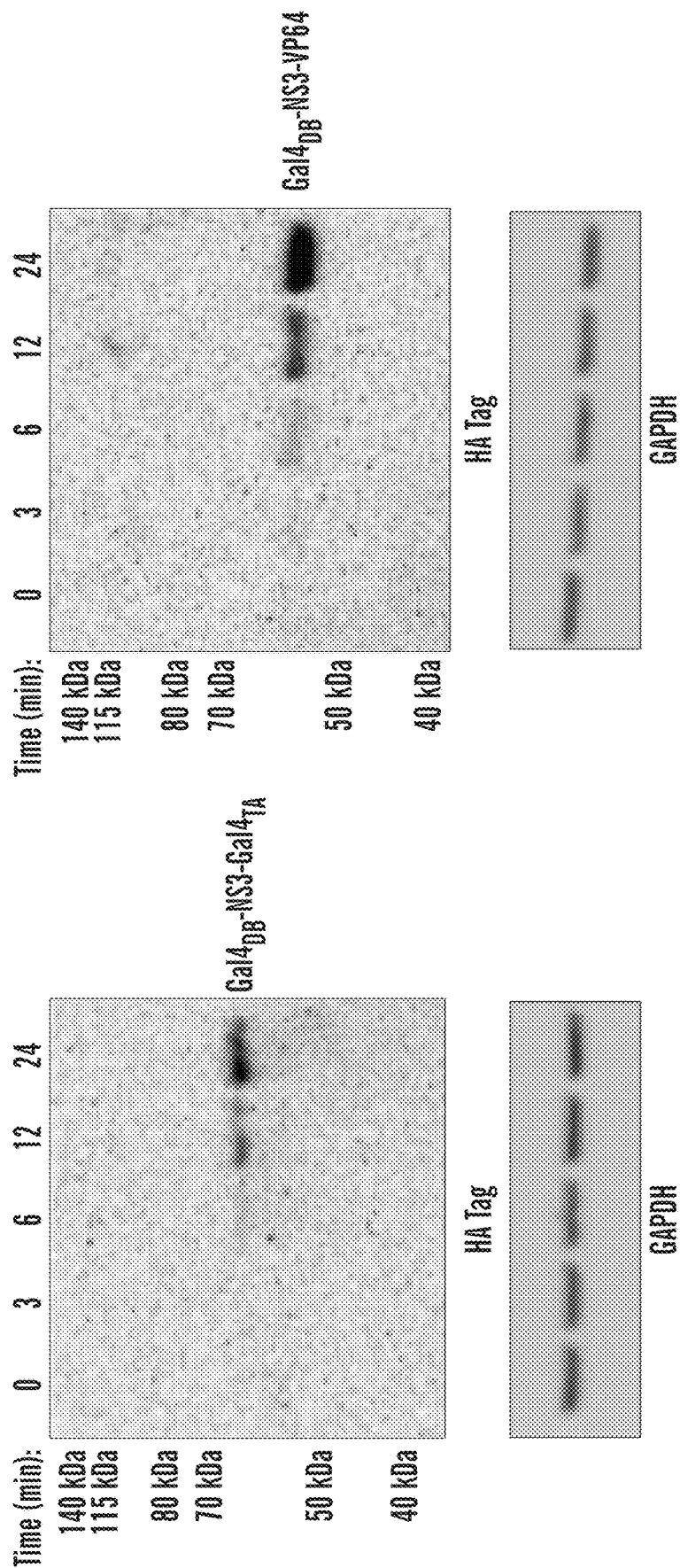
FIGS. 27A and 27B show time-dependent analysis of the drug-induced preservation of Gal4-based TFs containing NS3 upon treatment of cells with grazoprevir. Stable cell lines expressing either Gal4DB-NS3-Gal4TA or Gal4DB-NS3-VP64 were treated with 5 µM grazoprevir for the indicated times prior to cell lysis in SDS-PAGE loading buffer and subsequent analysis by western blot. The drug-induced preservation of intact TF copies was determined via the detection of bands corresponding to the intact masses of each TF. Western blots showing the preservation of full-length copies of FIG. 27A Gal4DB-NS3-Gal4TA (60.6 kDa), and FIG. 27B Gal4DB-NS3-VP64 (57.8 kDa) are displayed. Times refer to the number of minutes in which cells were exposed to drug prior to lysis. Western detection of the TFs was achieved via an HRP-conjugated anti-HA primary antibody, followed by an HRP-conjugated secondary antibody.

In the prevailing model of Notch activation, the endocytosis of membrane-tethered ligand is thought to deliver a mechanical "pulling" energy that is required to trigger the "on" state of the receptor, in turn inducing the release of its intracellular domain (NICD, a transcriptional effector). Because Notch activation requires the endocytosis of membrane-tethered ligands,[18] it was tested whether drug-preserved Dll1-NS3 copies would be able to mediate transcellular signaling. To determine whether protease-containing ligand could activate Notch signaling in a drug-dependent manner, "sender" cells expressing Dll1-NS3 were combined with Notch1-expressing "receiver" cells in a coculture assay (FIG. 17D). Using receiver cells containing a NICD-dependent fluorescent reporter gene (12×CSL H2B-Citrine)[9], Notch activation at sender cell-receiver cell interfaces was observed only in drug-treated cocultures (FIGS. 17E-17F, FIG. 25). Thus, in addition to serving as a versatile module for controlling intracellular proteins, these results demonstrate that NS3 can also be applied in luminal and cell-surface contexts to regulate cell-cell recognition events and in turn control intercellular communication.

The applications described herein demonstrate that the HCV NS3 protease of SEQ ID NO: 32 is a versatile domain that can be used to straightforwardly engineer drug-sensitivity into both intracellular and cell-surface proteins. Through the implementation of simple and intuitive protein designs, tightly-regulated chemical control over complex cellular phenomena was achieved. One significant advantage of the methods described herein is the availability of highly-selective NS3 inhibitors, many of which have been tested for clinical use and can be obtained from commercial sources. Thus, in addition to its potential applications in basic biology investigations, the methods described herein can also serve as a powerful strategy for regulating therapeutic cells in vivo using safe and clinically-approved antiviral drugs.

In some embodiments, the HCV NS3 protease domain and corresponding recognition sites can be substituted with other protease domains and recognition sites from other viruses including, but not limited to, human immunodeficiency virus and human rhinovirus.

In those embodiments of the synthetic or recombinant proteins described herein where one or more of the protein domains is mutated or engineered or modified relative to the endogenous or naturally occurring protein, such as a mutated Notch Negative Regulatory Region (NRR), for such purposes as enhancing binding or efficacy, or stability, techniques known in the art for identifying mutated proteins or domains having one or more desired properties can be used. For example, modified or mutated domains or polypeptides can be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) does not have a major effect on the biological activity of the resulting molecule. Conservative replacements are those that take place within a family of amino acids that are related in their side chains.

Naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Preferred conservative substitutions for use in the synthetic proteins described herein are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Whether a change in the amino acid sequence of a synthetic protein results in a functional variant can be readily determined by assessing the desired activity of the variant synthetic protein or polypeptide relative to the non-mutated version of the synthetic protein.

As known to those of skill in the art, receptors tend to have three regions or domains: an extracellular domain for binding ligands such as proteins, peptides or small molecules, a transmembrane domain that traverses the cellular membrane, and an intracellular or cytoplasmic domain which frequently can participate in some sort of signal transduction event within a cells, such as phosphorylation. Accordingly, in some embodiments of the aspects described herein, the synthetic proteins can comprise various combinations of extracellular, transmembrane, and intracellular domains derived from naturally occurring domains or engineered versions of such domains. Non-limiting examples of transmembrane domains that can be used with the synthetic proteins described herein include SEQ ID NOs: 13, 14, and 31, and engineered or mutant variants thereof. Non-limiting examples of intracellular domains that can be used with the synthetic proteins described herein include the Notch Intracellular Domain (NICD) of SEQ ID NOs: 11, and engineered or mutant variants thereof.

It is also understood that different elements or domains of the synthetic proteins can be arranged in any manner that is consistent with the desired functionality. For example, a synthetic, drug-dependent protein can comprise an extracellular or ligand binding domain (LBD), such as SEQ ID NO: 2 or an engineered variant thereof, an NS3 protease domain of SEQ ID NO: 32 or variant thereof, and a transmembrane domain from N-terminal to C-terminal, in some embodiments. In some embodiments, additional domains or amino acid sequences can be included C- or N-terminal to the various domains comprising the synthetic proteins described herein.

In some embodiments of the aspects described herein, a synthetic protein comprises one or more domains from or derived from a transcriptional regulator. Transcriptional regulators either activate or repress transcription from cognate promoters. Transcriptional activators typically bind nearby to transcriptional promoters and recruit RNA polymerase to directly initiate transcription. Transcriptional repressors bind to transcriptional promoters and sterically hinder transcriptional initiation by RNA polymerase. Other transcriptional regulators serve as either an activator or a repressor depending on where it binds and cellular conditions. Accordingly, as used herein, a "transcriptional activation domain" refers to the domain of a transcription factor that interacts with transcriptional control elements and/or transcriptional regulatory proteins (i.e., transcription factors, RNA polymerases, etc.) to increase and/or activate transcription of one or more genes. Non-limiting examples of transcriptional activation domains include: a herpes simplex virus VP16 activation domain, VP64 (which is a tetrameric derivative of VP16), HIV TAT, a NF B p65 activation domain, p53 activation domains 1 and 2, a CREB (cAMP response element binding protein) activation domain, an E2A activation domain, NFAT (nuclear factor of activated T-cells) activation domain, yeast GAL4, yeast GCN4, yeast HAP 1, MLL, RTG3, GLN3, OAF 1, PIP2, PDR1, PDR3, PHO4, LEU3 glucocorticoid receptor transcription activation domain, B-cell POU homeodomain protein Oct2, plant Ap2, or any others known to one or ordinary skill in the art. A transcriptional activation domain can comprise a wild-type or naturally occurring sequence, or it can be a modified, mutant, or derivative version of the original transcriptional activation domain that has the desired ability to increase and/or activate transcription of one or more genes. In some embodiments, transcription activation domains for use with the synthetic proteins described herein are selected from Gal4, VP64, VP64-p65, and VPR reverse tetracycline repressor.

In some embodiments of the aspects described herein, a synthetic protein comprises one or more "DNA-binding domains" (or "DB domains"). Such "DNA-binding domains" refer to sequence-specific DNA binding domains that bind a particular DNA sequence element. Accordingly, as used herein, a "sequence-specific DNA-binding domain" refers to a protein domain portion that has the ability to selectively bind DNA having a specific, predetermined sequence. A sequence-specific DNA binding domain can comprise a wild-type or naturally occurring sequence, or it can be a modified, mutant, or derivative version of the original domain that has the desired ability to bind to a desired sequence. In some embodiments, the sequence-specific DNA binding domain is engineered to bind a desired sequence. Non-limiting examples of proteins having sequence-specific DNA binding domains that can be used in synthetic proteins described herein include GAL4, GCN4, reverse tetracycline receptor, THY1, SYN1, NSE/RU5', AGRP, CALB2, CAMK2A, CCK, CHAT, DLX6A, EMX1, zinc finger proteins or domains thereof, CRISPR/Cas proteins, such as Cas9, Cas3, Cas4, Cas5, Cas5e (or CasD), Cas6, Cas6e, Cas6f, Cas7, Cas8a1, Cas8a2, Cas8b, Cas8c, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu196, and TALES.

In those embodiments where a CRISPR/Cas-like protein is used, the CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the functions of the systems described herein. In some embodiments of the engineered systems, methods, and compositions thereof disclosed herein, a CRISPR enzyme that is used as a DNA binding protein or domain thereof is mutated with respect to a corresponding wild-type enzyme such that the mutated CRISPR or domain thereof lacks the ability to cleave a nucleic acid sequence containing a DNA binding domain target site. For example, in some embodiments, a D10A mutation is combined with one or more of H840A, N854A, or N863A mutations to produce a Cas9 enzyme substantially lacking all DNA cleavage activity.

In some embodiments of the synthetic proteins described herein, one or more additional "fusion" domains can be added to the synthetic protein to provide additional desired functionality. Well known examples of fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain can be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS6 (SEQ ID NO: 69)) fusion partners. As another example, a fusion domain can be selected so as to facilitate detection of the synthetic proteins. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. Non-limiting tag sequences that can be used in the synthetic proteins described herein include SEQ ID NOs: 5-7 and 33. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. Other types of fusion domains that can be selected include multimerizing (e.g., dimerizing, tetramerizing) domains and functional domain.

In some embodiments, a cell is transfected or transformed with a nucleic acid sequence encoding the synthetic protein of interest.

As used herein, the term "transfection" is used to refer to the uptake of an exogenous nucleic acid by a cell, and a cell has been "transfected" when the exogenous nucleic acid has been introduced inside the cell membrane. A number of transfection techniques are well known in the art and are disclosed herein. See, e.g., Graham et al., 1973, Virology 52:456; Sambrook et al., Molecular Cloning, A Laboratory Manual (Cold Spring Harbor Laboratories, 1989); Davis et al., Basic Methods in Molecular Biology (Elsevier, 1986); and Chu et al., 1981, Gene 13:197. Such techniques can be used to introduce one or more exogenous nucleic acids into suitable host cells.

Suitable techniques of transfection for use with the compositions and methods described herein include, but are not limited to calcium phosphate-mediated transfection, DEAE-dextran mediated transfection, and electroporation. Cationic lipid transfection using commercially available reagents including the Boehringer Mannheim Transfection Reagent (N.fwdarw.1-(2,3-Dioleoyloxy)propyl-N,N,N-trimethyl ammoniummethylsulfate, Boehringer Mannheim, Indianapolis, Ind.) or LIPOFECTIN or LIPOFECTAMIN or DMRIE reagent (GIBCO-BRL, Gaithersburg, Md.) can also be used.

The term "transformation" as used herein refers to a change in a cell's genetic characteristics, and a cell has been transformed when it has been modified to contain a new DNA. For example, a cell is transformed where it is genetically modified from its native state. Following transfection, the transforming nucleic acid can recombine with that of the cell by physically integrating into a chromosome of the cell, can be maintained transiently as an episomal clement without being replicated, or can replicate independently as a plasmid. A cell is considered to have been stably transformed when the transforming nucleic acid is replicated with the division of the cell.

As used herein an "expression vector" refers to a DNA molecule, or a clone of such a molecule, which has been modified through human intervention to contain segments of DNA combined and juxtaposed in a manner that would not otherwise exist in nature. DNA constructs can be engineered to other domains operably linked to nucleic acid segments encoding a desired synthetic or recombinant protein of interest. In addition, an expression vector can comprise additional DNA segments, such as promoters, transcription terminators, enhancers, and other elements. One or more selectable markers can also be included. DNA constructs useful for expressing cloned DNA segments in a variety of prokaryotic and eukaryotic host cells can be prepared from readily available components or purchased from commercial suppliers.

Expression vectors can also comprise DNA segments necessary to direct the secretion of a polypeptide or protein of interest. Such DNA segments can include at least one secretory signal sequence. Secretory signal sequences, also called leader sequences, prepro sequences and/or pre sequences, are amino acid sequences that act to direct the secretion of mature polypeptides or proteins from a cell. Such sequences are characterized by a core of hydrophobic amino acids and are typically (but not exclusively) found at the amino termini of newly synthesized proteins. Very often the secretory peptide is cleaved from the mature protein during secretion. Such secretory peptides contain processing sites that allow cleavage of the secretory peptide from the mature protein as it passes through the secretory pathway. A recombinant protein of interest can contain a secretory signal sequence in its original amino acid sequence, or can be engineered to become a secreted protein by inserting an engineered secretory signal sequence into its original amino acid sequence. The choice of suitable promoters, terminators and secretory signals is well within the level of ordinary skill in the art. Expression of cloned genes in cultured mammalian cells and in *E. coli*, for example, is discussed in detail in Sambrook et al. (Molecular Cloning: A Laboratory Manual, Fourth Edition, Cold Spring Harbor, N.Y., 2012; which is incorporated herein by reference in its entirety). Non-limiting examples of signal sequences for use with the synthetic proteins described herein include SEQ ID NOs: 1 and 41.

After transfection, the host cell can be maintained either transiently transformed or stably transformed with said nucleic acid or expression vector. Introduction of multiple nucleic acids or expression vectors, and selection of cells containing the multiple nucleic acids or expression vectors can be done either simultaneously or, more preferably, sequentially. The technique of establishing a cell line stably transformed with a genetic material or expression vector is well known in the art (Current Protocols in Molecular Biology). In general, after transfection, the growth medium will select for cells containing the nucleic acid construct by, for example, drug selection or deficiency in an essential nutrient, which is complemented by a selectable marker on the nucleic acid construct or co-transfected with the nucleic acid construct. Cultured mammalian cells are generally cultured in commercially available serum-containing or serum-free medium. Selection of a medium appropriate for the particular host cell used is within the level of ordinary skill in the art.

Suitable selectable markers for drug selection used with the compositions and methods described herein include, but are not limited to, neomycin (G418), hygromycin, puromycin, zeocin, colchine, methotrexate, and methionine sulfoximine.

A cell to be engineered with synthetic proteins or combinations thereof described herein can be any cell or host cell. As defined herein, a "cell" or "cellular system" is the basic structural and functional unit of all known independently living organisms. It is the smallest unit of life that is classified as a living thing, and is often called the building block of life. Some organisms, such as most bacteria, are unicellular (consist of a single cell). Other organisms, such as humans, are multicellular. A "natural cell," as defined herein, refers to any prokaryotic or eukaryotic cell found naturally. A "prokaryotic cell" can comprise a cell envelope and a cytoplasmic region that contains the cell genome (DNA) and ribosomes and various sorts of inclusions.

In some embodiments, the cell is a eukaryotic cell. A eukaryotic cell comprises membrane-bound compartments in which specific metabolic activities take place, such as a nucleus. In other embodiments, the cell or cellular system is an artificial or synthetic cell. As defined herein, an "artificial cell" or a "synthetic cell" is a minimal cell formed from artificial parts that can do many things a natural cell can do, such as transcribe and translate proteins and generate ATP.

Once a drug resistant cell population is established, individual clones may be selected and screened for high expressing clones. Methods of establishing cloned cell line are well known in the art, including, but not limited to, using a cloning cylinder, or by limiting dilution. Expression of the recombinant protein of interest from each clone can be measured by methods such as, but not limited to, immunoassay, enzymatic assay, or chromogenic assay. A cell line stably transformed with a first nucleic acid construct may be then used as host cell for transfection with a second or more nucleic acid constructs, and subjected to different drug selections.

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells can be cultured in suspension or while attached to a solid substrate. Fluidized bed bioreactors, hollow fiber bioreactors, roller bottles, shake flasks, or stirred tank bioreactors, with or without microcarriers, can be used.

As used herein, "cell culture medium" is a media suitable for growth of animal cells, such as mammalian cells, in in vitro cell culture. Cell culture media formulations are well known in the art. Typically, cell culture media are comprised of buffers, salts, carbohydrates, amino acids, vitamins and trace essential elements. "Serum-free" applies to a cell culture medium that does not contain animal sera, such as fetal bovine serum. Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kans.), among others. Serum-free versions of such culture media are also available. Cell culture media can be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

As used herein, the term "comprising" means that other elements can also be present in addition to the defined elements presented. The use of "comprising" indicates inclusion rather than limitation. Accordingly, the terms "comprising" means "including principally, but not necessary solely". Furthermore, variation of the word "comprising", such as "comprise" and "comprises", have correspondingly the same meanings. The term "consisting essentially of" means "including principally, but not necessary solely at least one", and as such, is intended to mean a "selection of one or more, and in any combination". Stated another way, the term "consisting essentially of" means that an element can be added, subtracted or substituted without materially affecting the novel characteristics of the invention. This applies equally to steps within a described method as well as compositions and components therein. In other embodiments, the inventions, compositions, methods, and respective components thereof, described herein are intended to be exclusive of any element not deemed an essential element to the component, composition or method ("consisting of"). For example, a composition that comprises elements A and B also encompasses a composition consisting of A, B and C.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, publications, and websites identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Example 1

The Notch protein is a transmembrane receptor that acts a mechanical "switch," translating mechanical cues into gene expression. This mechanosensing activity is achieved via Notch's force-sensitive Negative Regulatory Region, which contains three LNR domains. In the resting state, the LNR domains adopt an autoinhibitory conformation that sterically hinders proteolytic cleavage necessary for receptor activation. Upon the application of a pulling force, however, these LNR domains are displaced, and two concomitant proteolytic cleavages occur that release the Notch intracellular domain to transport to the nucleus and regulate gene expression. Synthetic notch receptors have been created that allow for gene expression to be controlled upon binding of the receptor to various ligands of interest (e.g. surface proteins on cancer cells).

Described herein are strategies through which signaling form natural and synthetic Notch receptors, as disclosed in US patent Application 2016/0264665, which is incorporated herein in its entirety by reference, can be regulated/modulated using antibody domains. These systems are used to increase the amount of force required to activate Notch receptors, or to regulate their activity on therapeutic cells. The described tools are useful for a variety of cell engineering applications, including the creation of engineered cells capable of sensing certain mechanical features of solid tumors (or biomaterials), as well as permit the precise control over therapeutic/engineered cells expressing synthetic Notch receptor proteins.

These systems involve the use of antibody fragments directed against the NRR region of the Notch receptor, a force-sensitive mechanical switch that is ruptured during receptor activation. Binding of these antibodies stabilizes the NRR and prevents Notch activation. Use of scFvs from these antibodies will permit the generation of inhibitory "modules" which we will use to generate synthetic proteins and receptors to precisely control signaling from Notch/SynNotch systems.

Antibody fragments from anti-NRR antibodies are used as new modules for engineering synthetic proteins and receptors for cell-engineering applications. All previous work involving anti-NRR antibodies have relied on the use of purified immunoglobulin as an exogenously applied drug/ agent. In the work described herein, these antibody-derived fragments are used as new "genetic tools" to reprogram natural and synthetic Notch signaling for synthetic biology applications. This allows cells expressing these systems to function as genetically encoded "tensometers," permitting, for example, engineered T cells to activate their cell killing activity in response to the mechanical properties of fibrotic tissues or physical features of solid tumors.

Work described herein is also directed towards constructs and methods for controlling the binding/activation of notch receptors through the use of synthetic ligands that incorporate NS3 protease domains from the hepatitis C virus. In the absence of an NS-inhibitor drug, the ligand domain is cleaved and becomes incapable of activating the notch receptor. When an NS-inhibitor drug is applied, the NS3 domain remains intact and the ligand is capable of activating the notch receptor.

Non-limiting applications for the compositions, systems, and methods thereof described herein include:
  a) SynNotch receptors with defined/programmable force-activation thresholds for applications in cell engineering, T cell immunotherapy, and tissue engineering.
  b) Regulating SynNotch proteins and reducing their background levels of activity. In principle, genetic regulation of cis-clamps could be used to "turn off" the cell-killing activity of immune cells.
  c) Drug-inducible control of notch/synNotch activation Advantages of the compositions, systems, and methods thereof described herein include:
  a) Receptors with increased force activation thresholds are completely novel; potential applications are wide-ranging, including generation of cells with ability to detect physical features of solid tumors, mechanical properties of biomaterials, etc.
  b) cis-clamps will permit regulation on engineered cells expressing SynNotch receptors (including therapeutic T cells) and can be useful for reducing the known background activity of these receptors.
  c) Drug-inducible notch activation that allows tighter control of therapeutic interventions that utilize notch receptor transduction mechanisms Notch Cis-Clamps Some embodiments of the aspects described herein pertain to "cis-clamps" which are synthetic proteins that comprise an NRR-binding scFv fused to a transmembrane domain. Notch is activated by ligands expressed on adjacent cells, but inhibited when ligands are expressed on the same cell through a mechanism known as "cis-inhibition", as shown in FIG. 1A. This cis-interaction serves to prevent cells from receiving signals from their neighbors, and also prevents spontaneous "ligand independent" background activation, reducing Notch background activity.

Figure 12:
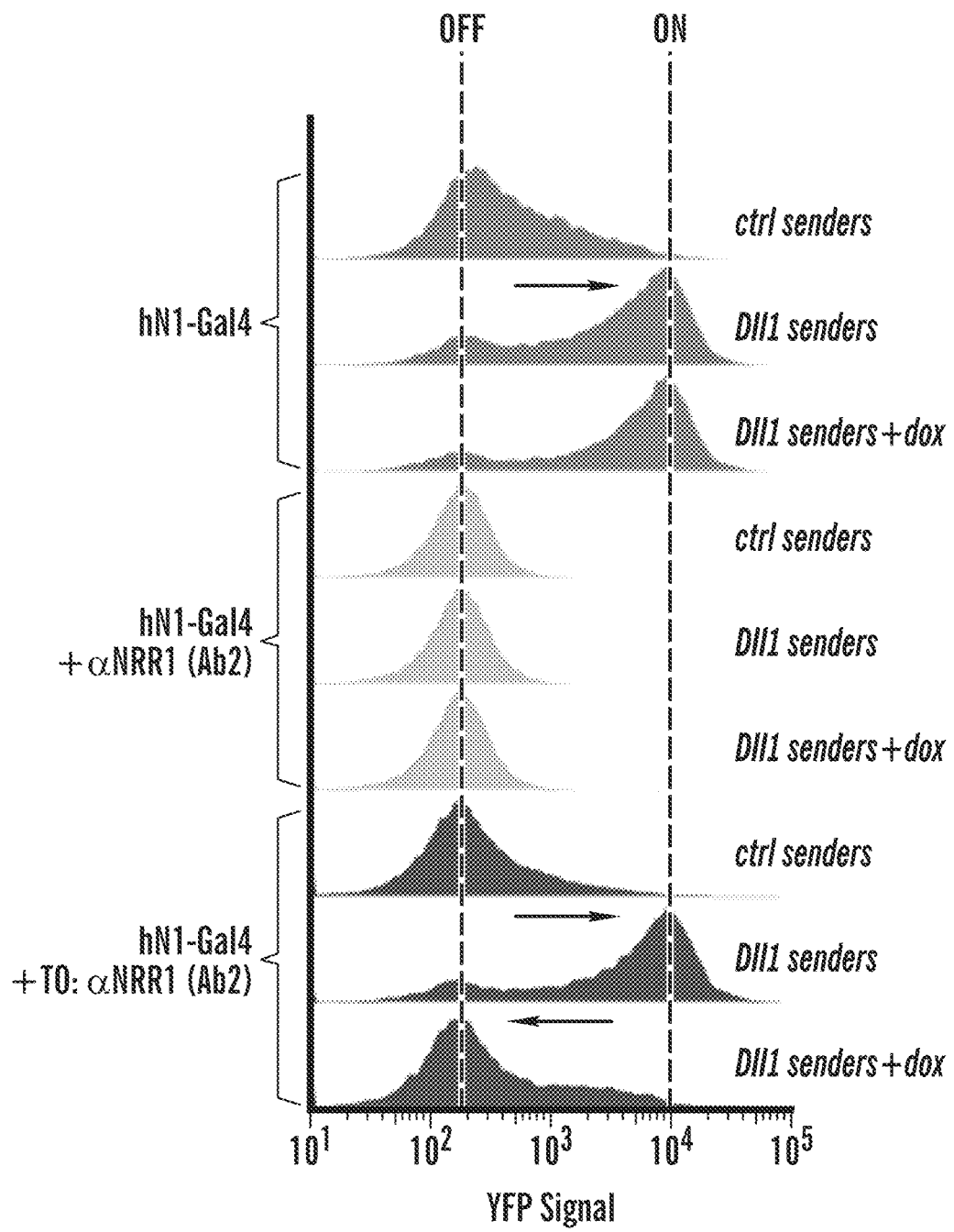
Figure 13A:
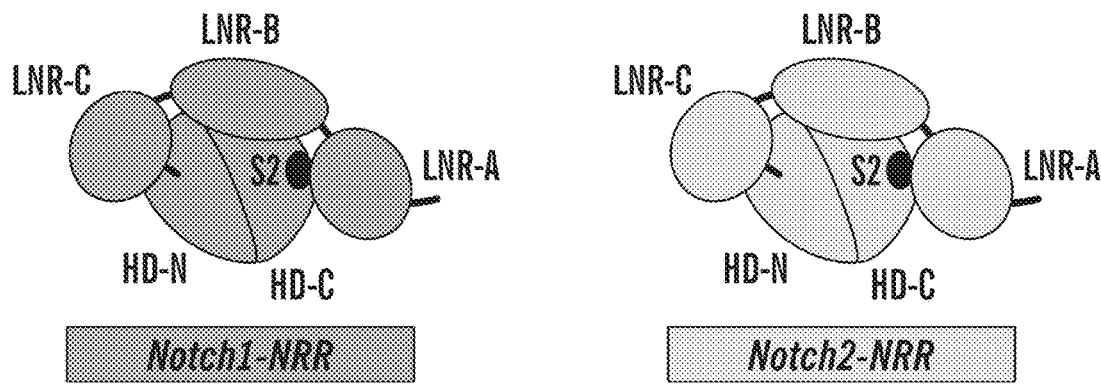
Figure 14:
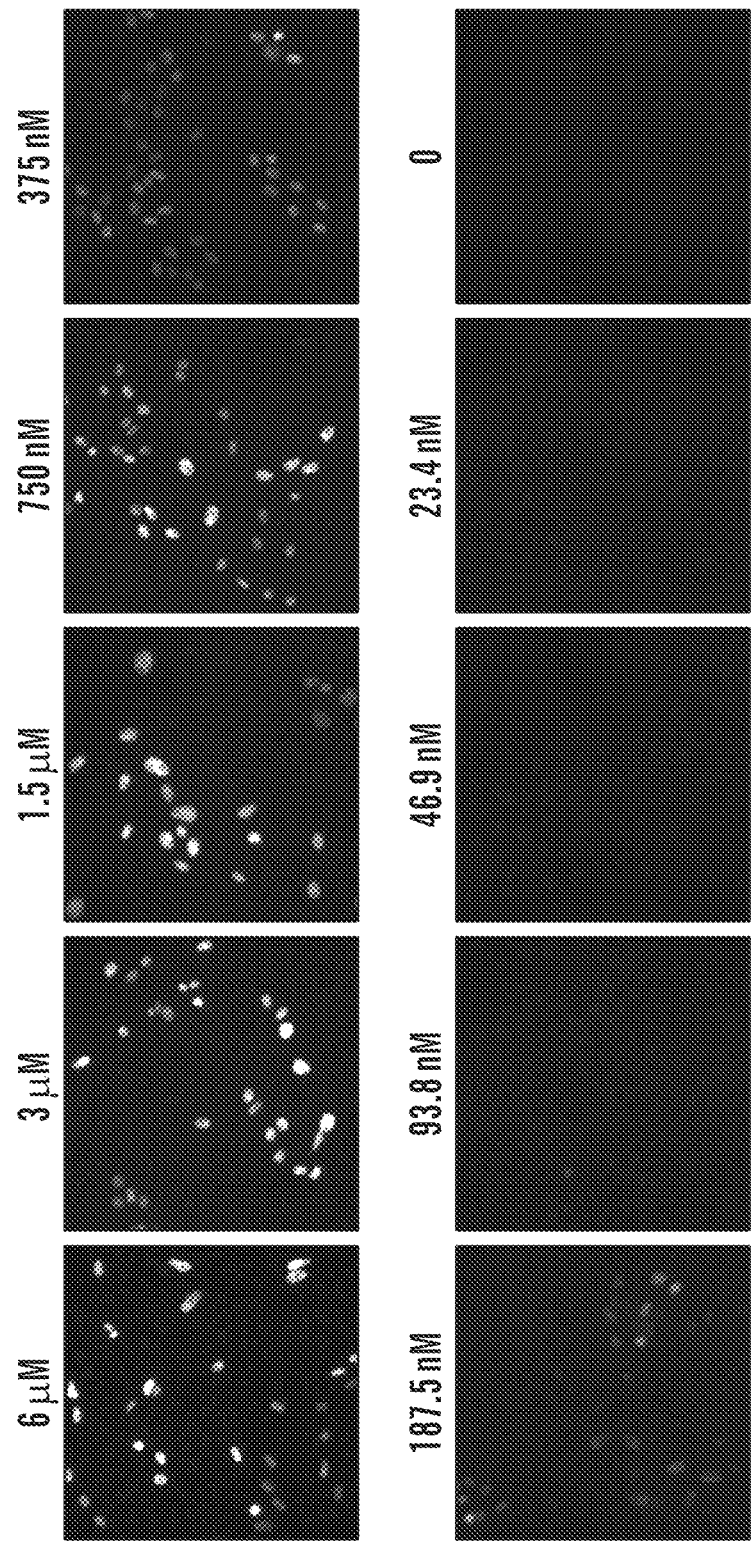
FIG. 14 shows an exemplary drug-dependent NS3-Gal4 transcription factor. NS3 fused between the BD and AD of Gal4 yields a functional transcription factor. This construct is intact and active in the presence of an NS3-inhibiting drug, but cleaved and inactive in the absence of drug.

Cis-inhibitors are useful for cell engineering, including, for example, therapeutic T cells, as Notch/SynNotch receptors are known to exhibit background "leaky" activation. Membrane-tethered anti-NRR scFvs as genetically encoded Notch inhibitors, or "cis-clamps" as utilized here (FIG. 1B). These scFvs are derived from antibodies that are known to bind and stabilize the NRR region of Notch receptors, preventing their activation. These "clamps" can be used to regulate Notch/SynNotch activity in a manner similar to ligand cis-inhibition. In engineered cells, these chimeras can be used as regulatory elements to limit signaling from synthetic Notch receptors and, for instance, reduce off-target T cell killing in the case of engineered SynNotch T cells. As demonstrated in FIG. 12, these genetically encoded inhibitors can be placed under the control of a drug-inducible system, allowing temporal control over SynNotch T cell activity.

cis-clamps are especially useful in situations where ligand co-expression is problematic. The most obvious route toward cis-inhibition of a SynNotch receptor is to co-express the receptor and its target ligand on the same cell. However, in the case of cell immunotherapy, ligands used to activate SynNotch receptors on T cells are usually cell surface cancer markers. While co-expression of these markers would in principle permit cis-inhibition of SynNotch proteins, they could also cause the therapeutic cells to attack one another. Thus, use of cis-clamps provides a novel route through which SynNotch receptors can be regulated without the introduction of cancer marker/antigens to the engineered cells.

Without wishing to be bound or limited by theory, the work described herein indicates that tuning the affinity of the scFv allows for the engineering of mechanical sensitivity. Data presented in FIGS. 2A-2C support this and shows that NRR-binding scFv is mutated and expressed as a separate transmembrane cis-clamp. Strategies for tuning scFv affinity involve, for example, studying available crystal structures of the Notch1 NRR bound to the scFv (Wu et al, 2010) to make structure-guided residue mutations. Amino acid residues on the scFv complementarity-determining regions (CDRs) that tightly interact with the NRR are identifiable targets for engineering, where predictions can be made to substitute residues that will slightly to substantially modify scFv affinity, as shown in FIGS. 2A-2C. Alternatively, instead of targeted mutations, random mutagenesis of these CDRs through techniques such as, for example, error-prone PCR, can also be used to perform the directed evolution of mechanical sensitivity. Other sites within the scFv provide opportunity for tuning include disulfide bridges, alteration of which has been shown to affect overall scFv stability.

Auto-Inhibitory Notch Receptor

Another aspect of the compositions, systems and methods described herein is directed towards synthetic auto-inhibitory notch receptors that contain an NRR-binding scFv. As in the cis-clamp embodiment, the scFv in the auto-inhibitory notch receptor stabilizes the NRR region resulting in more force being required to activate the receptor.

NRR-binding scFv's is expressed as a contiguous part of Notch-based receptors to act as a synthetic "fourth LNR domain" (LNR4), offering additional stability to the NRR and increasing the force threshold of Notch activation. An example of this approach is described in FIGS. 3A and 3B.

The LNR4 domain can also be mutated to change the affinity of binding to the NRR in order to tune the mechanical sensitivity of the receptor, as previously demonstrated in FIG. 2A for the cis-clamp embodiment.

Notch Constructs with Synthetic NRR Domains

Another aspect of the compositions, systems and methods described herein is directed towards synthetic notch receptors with mutated NRR domains. Mutating the NRR domain and utilizing an scFv that has high affinity to the mutated NRR (but not the native NRR) in either the cis-clamp or auto-inhibitory receptor configurations allows for a more specific system with reduced off-target effects (e.g., the scFv binding the NRR region on notch receptors of adjacent cells).

Figure 7B:
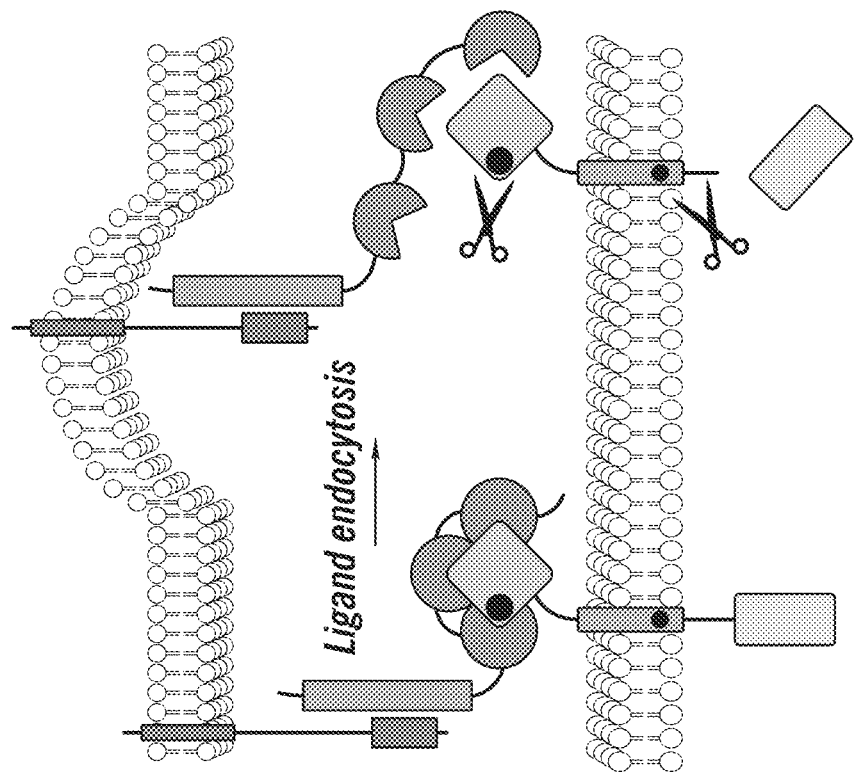
FIGS. 7A-7B depict the structure and activation of Notch receptors.
Figure 7A:
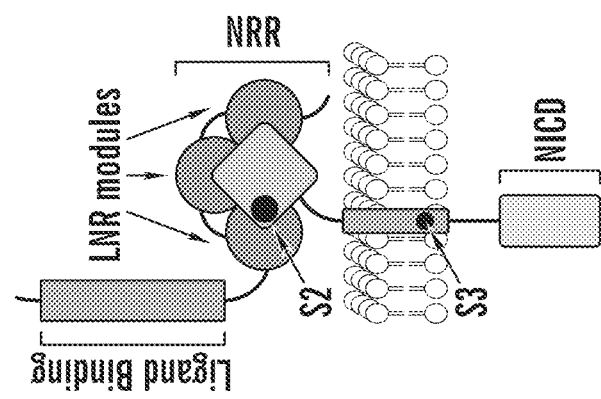

One strategy for creating these synthetic NRR-scFv pairs is to design a chimeric NRR domain that contains components from both the Notch1 and Notch2 NRR domains. Similar to scFv that binds NRR1, scFv's that bind and inhibit NRR2 are generated. It has been demonstrated that these scFv's are specific to their respective NRR domains and that they are unable to bind chimeric NRR1-NRR2 domains with intermixed components. Seeing as these scFv's are specific to each NRR and insensitive to certain NRR chimeras, in some embodiments, design of a reverse chimera, for example, an αNRR1-αNRR2 scFv fusion that is specific to an NRR chimera but insensitive to WT NRR1 and NRR2. Such an scFv can be designed through structure-guided decisions based off the NRR-scFv crystal structure and amino acid alignments between the two NRRs and scFvs, or it can be generated through traditional methods of antibody evolution and purification. A synthetic NRR-scFv pair such as this allows scFv-based regulation of SynNotch activity that is orthogonal to native Notch signaling. FIGS. 13A-13C provides more details on this approach.

Drug-Controllable Notch Signaling

Yet another aspect of the compositions, systems and methods described herein is directed towards constructs and methods for controlling the binding/activation of notch receptors through the use of synthetic ligands that incorporate NS3 protease domains from the hepatitis C virus (HCV). The NS3 domain is a serine protease embedded within the HCV polyprotein that excises itself from the precursor polypeptide by cleaving recognition sites flanking it at either end. The enzyme has been a prime drug target of the pharmaceutical industry due to its sequence and structural distinction from human proteases. Multiple selective inhibitors against the "NS3" cis-protease are currently in use for treating HCV infections worldwide, and several new compounds are currently under evaluation by the FDA.

As described herein, in some embodiments, Notch-signaling can be made drug-dependent by insertion of the NS3 protease domain between the extracellular and transmembrane domains of the Notch ligand Delta (DLL, FIGS. 6A-6C). In the absence of drug, the DLL extracellular domain is cleaved from its membrane anchor via NS3, releasing a soluble DLL ligand that is able to bind Notch but cannot activate it. Upon inhibition of NS3, however, DLL extracellular domain remains tethered to the cell surface and thus is able to activate Notch on the surface of opposing cells. This technology has a variety of applications in biology and medicine, including, but not limited tom developmental signaling, cancer biology, T cell engineering, and tissue engineering. This system is applied, in some embodiments, to achieve drug-control over "synthetic Notch" receptors in which the native Notch ligand-binding domain is substituted with an alternative protein (such as anti-GFP scFv) for activation by cells expressing complementary surface ligands (such as GFP).

In addition, SynNotch activation can alternatively be made drug-dependent by incorporating the NS3 domain into the receptor rather than the ligand. For example, in some embodiments, an NS3 domain could be placed between the DNA binding domain (BD) and the activating domain (AD) of a Notch ICD transcription factor (such as Gal4). In the absence of drug, the ICD would lose its DNA-binding ability and become nonfunctional, whether or not a ligand on a target cell is bound. In the presence of drug, the ICD would remain intact and would regulate gene activity only upon ligand-induced receptor activation. FIG. 14 demonstrates feasibility of placing NS3 between the BD and AD of Gal4 to create a drug-dependent transcription factor with titratable activation. An NS3 domain can also be incorporated into the ECD of Notch, for example between the NRR and LBD, likewise creating a functional receptor only in the presence of an NS3-inhibitor.

Compositions, systems and methods described herein comprising a receptor ligand (DLL, or any other ligand which binds to the target receptor), NS3 domain, and a targeting domain (e.g. an antibody specific for a cancer cell antigen) can be used for a variety of therapeutic applications. Once bound to their target (e.g., a cancer cell), these constructs serve to activate receptors on adjacent cells only when in the presence of an NS-inhibitor drug. Absent the drug, the NS3 domain would be cleaved, releasing the ligand, LBD, or ICD BD and preventing gene regulation through receptor activation. The drug-controllable ligands and receptors can be used with various combinations of the previously described aspects, including the cis-clamp and autoinhibitory Notch receptors.

Example 2

Chemical and Physical Control Over Gene Expression in Mammalian Cells

Provided herein are compositions, systems and methods for measuring and managing biomolecules in living cells. These novel compositions, systems and methods described herein were developed for regulating gene expression in mammalian systems using chemical and physical cues. In addition to serving as valuable tools for studying numerous aspects of biology and disease, these technologies are powerful additions to the "toolkit" for engineering therapeutic cells.

Engineering Cellular Responses to Mechanical Cues.

Cells sense forces via surface receptors that can directly affect changes in gene expression. Described herein is the use of transmembrane signaling protein Notch as a scaffold to engineer new, synthetic mechanoreceptors that are able to activate gene expression in response to defined and programmable amounts of applied force. These engineered receptors are used to design therapeutic mammalian cells capable of detecting various mechanical signals, such as matrix elasticity, or the unique physical features of solid tumors.

Remote Control of Therapeutic Cells Using FDA-Approved Antiviral Drugs.

Tools for regulating the therapeutic properties of engineered cells while they are in the body, and strategies to eliminate them from patients following a successful course of treatment, are necessary to ensure that cell-based therapeutics can be administered safely. The novel compositions, systems and methods described herein were created to control gene expression and signaling in therapeutic cells using FDA-approved antiviral small molecules, permitting in vivo control over these agents using safe, orthogonal, and orally-available drugs.

Engineering Cellular Responses to Mechanical Cues.

Notch proteins regulate a variety of cell fate decisions and are activated through a mechanism involving mechanical force. In mammals, Notch receptors are single-pass transmembrane proteins containing a membrane-proximal domain known as the negative regulatory region (NRR, as shown in FIG. 7A). Biophysical and cellular studies have identified the NRR as a force-activated mechanical switch that serves to regulate the localization of the Notch intracellular domain (NICD), a transcriptional effector that is cleaved from the receptor and transported to the nucleus following activation (FIG. 7B).

In its quiescent state, the NRR adopts an autoinhibited conformation in which three LNR (LIN12-Notch repeat) modules sterically block a protease site (termed S2), which must be cleaved for receptor activation. Notch recognizes ligands of the Delta/Serrate/lag2 (DSL) and is activated upon the binding and endocytosis of ligands expressed by neighboring cells. The force applied to the receptor during ligand endocytosis serves to deliver a mechanical "pulling" energy that is able to displace the LNR modules and reveal the S2 site for cleavage by activating metalloproteases. Cleavage at S2 induces additional proteolysis at an intramembrane site (termed S3), which in turn causes the release of NICD from the plasma membrane, as shown in FIG. 7A.

Increasing the Force Threshold for Notch Activation:

Recent studies have suggested that molecular interactions within the NRR-specifically, the interactions made by and between the LNR modules-define the amount of force needed to activate Notch receptors. Without wishing to be bound or limited by theory, it is hypothesized that synthetic Notch proteins with increased activation thresholds can be created through stabilization of the autoinhibited conformation of the NRR.

Figure 8C:
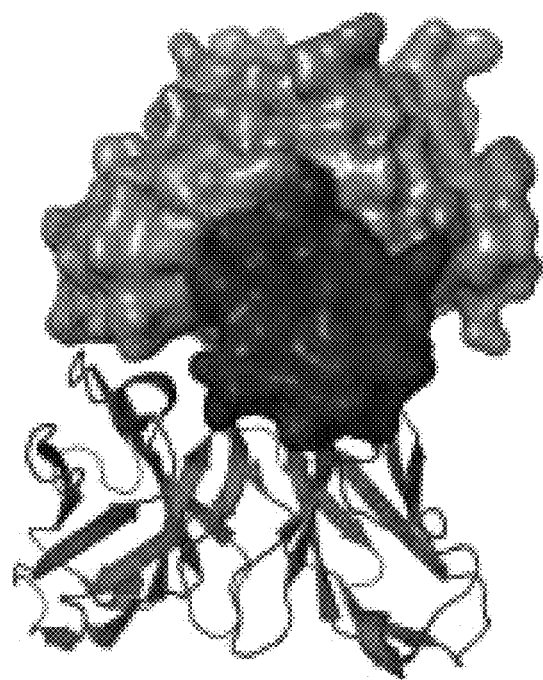
FIGS. 8A-8D illustrate design and expression of an exemplary hN1-scFv.
Figure 8B:
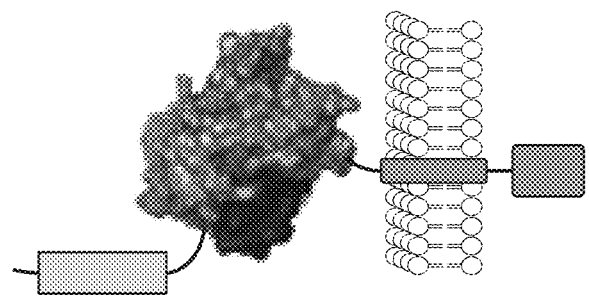
Figure 8A:
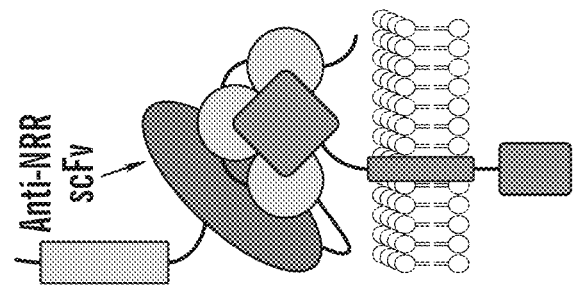

In the work presented herein, human Notch-1 (hN1), a structurally well-characterized receptor that is activated by >5 picoNewtons of pulling energy, is used as a scaffold for engineering new mechanoreceptors. To increase hN1's force requirement, single chain variable fragments (scFvs) derived from anti-hN1 antibodies are introduced that are known to inhibit receptor activation by binding and stabilizing the NRR. These scFvs are integrated into the hN1 ectodomain at positions such that they are able to bind and stabilize their antigen (FIGS. 8A-8B), and previously reported x-ray structures of scFv:NRR complexes (FIG. 8C) are used to guide the selection of these positions.

Figure 8D:
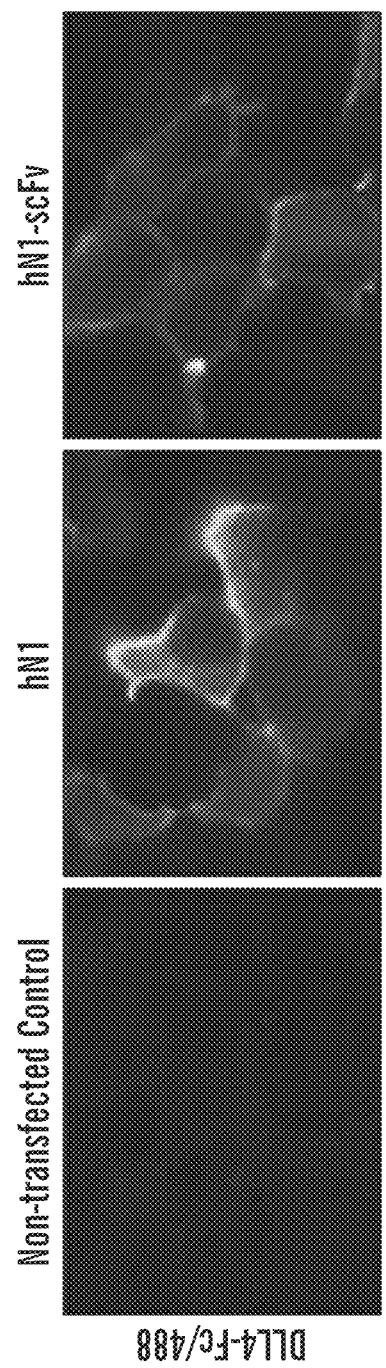

These scFv-containing chimeras exhibit increased force requirements compared to their natural counterparts, as activation of these receptors requires the rupture of the scFv:NRR interaction in addition to that of the LNRs. Work described herein shows that an scFv-fused hN1 (hN1-scFv) is correctly processed in the Golgi apparatus and trafficked to the cell surface to a similar extent as the wild-type hN1 (FIG. 8D). Furthermore, several lines of evidence indicate that the integrated scFv is bound to the NRR within the receptor, and results also indicate that this binding interaction increases the force resistivity of the receptor.

Genetically Encoded "Tensometers" for Sensing the Mechanics of Materials and Solid Tumors:

Previous work has indicated that the forces required to rupture scFv:antigen complexes are correlated with their thermal dissociation rates, and that these forces can be predictably modulated via mutation.[6] Thus, it is anticipated that scFv-containing Notch proteins should be highly susceptible to engineering, and that the activation thresholds of these receptors can be precisely tuned via design, or directed evolution. Single molecule force spectroscopy measurements using various immunoglobulin domains indicate that typical scFv:antigen rupture in response to forces ranging from 20 to 200 pN[7]—thus, it is possible to create Notch receptors with activation thresholds within this regime.

Figure 9A:
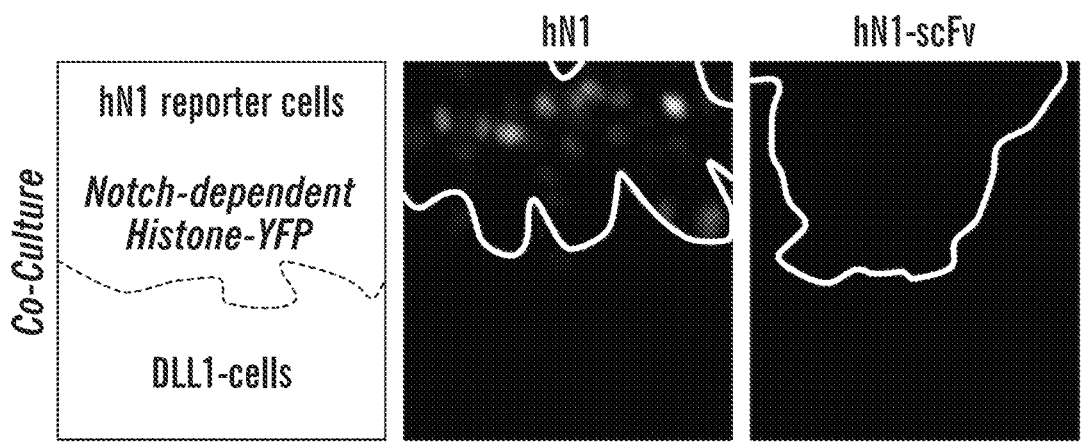
Figure 9B:
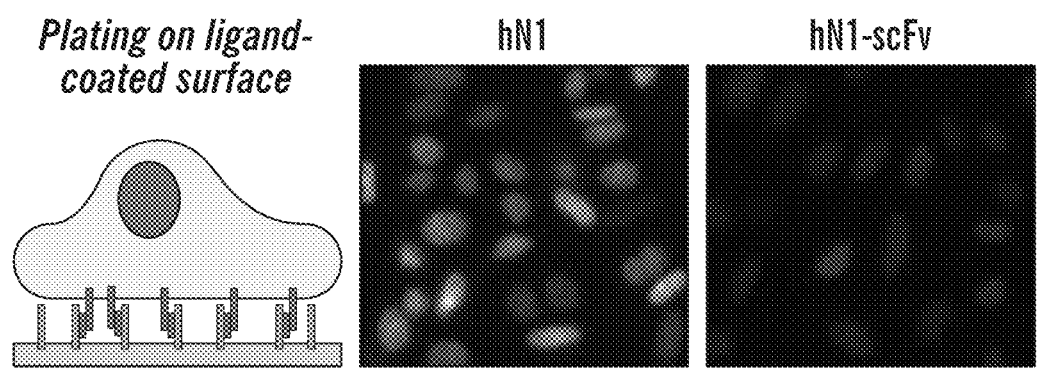

Reinforced Notch receptors have numerous applications in the study of cellular mechanosensation, as well as in the engineering of therapeutic mammalian cells. These receptors can be used to program cells to detect and execute specified gene expression programs in response to certain physical features within in their microenvironments. Indeed, work described herein shows that scFv-bound hN1 receptors are able to discriminate between ligands bound to stiff versus soft substrates, becoming activated only by ligands capable of applying sufficient tension to unbind the scFv from its fused antigen (FIGS. 9A and 9B). These findings show that scFv-containing Notch receptors can act as genetically encoded "tensometers," permitting for example, engineered T cells to activate their cell killing activity in response to the mechanical properties of fibrotic tissues or physical features of solid tumors.

Furthermore, cells expressing a NRR-binding scFv exhibit distinct responses to magnetic fields (compared to hN1-expressing cells) when cultured in the presence of ligand-coated magnetic beads, raising the intriguing possibility that mammalian cells can be engineered to respond to different levels of magnetic force. To define these forces, single molecule measurements (using optical and magnetic tweezers) and biophysical assays (using DNA tension gauge tethers and reporter cells) are used to characterize the mechanics of individual receptors, and molecular dynamics are used to map the energy landscape of these receptors in response to varying degrees of applied energy.

Figure 10:
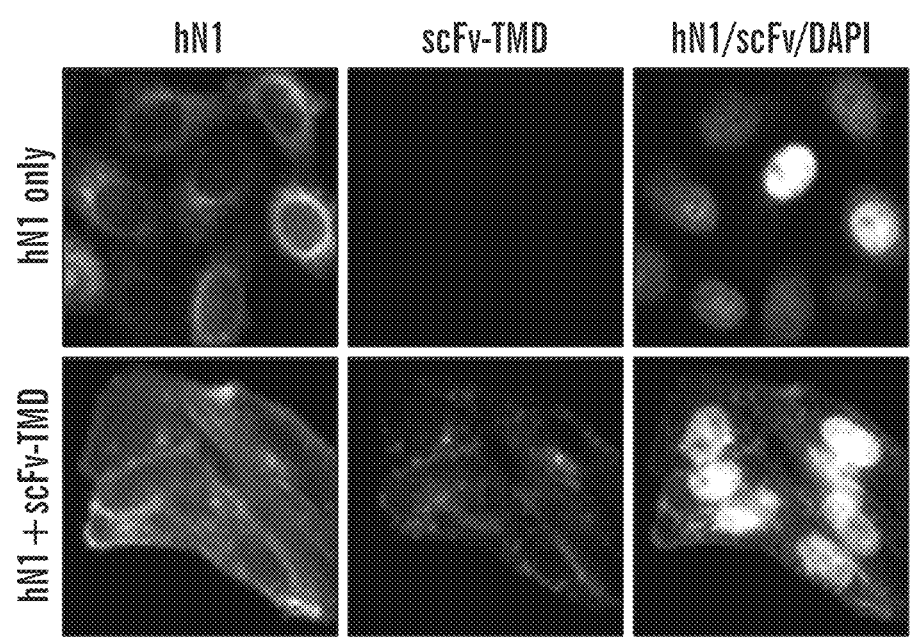

Studies on Notch Receptor Trafficking and Localization:

Recombinant and endogenous hN1 is localized predominantly to the ER in a variety of mammalian cell lines. Expression of a membrane-tethered NRR-binding scFv (scFv-TMD) dramatically increases the surface localization of recombinant hN1 in CHO cells (FIG. 10), as well as the localization of endogenous hN1 in MCF-7 cells.

Furthermore, work described herein shows that low-affinity scFvs are able to increase the surface localization of hN1 without affecting its ability to respond to ligand-expressing cells. "Synthetic Notch" (syn-Notch) receptors (in which the native hN1 ligand-binding region is replaced with domains recognizing alternative targets, such as cancer markers), are used to engineer T cells for immunotherapy applications, thus, the described observations may have important implications for therapeutic cell engineering, as control over receptor localization and concentration are powerful strategies to regulate the activity of such systems.

Remote Control of Therapeutic Cells Using FDA-Approved Antiviral Drugs.

A major challenge associated with the development of cell-based therapies is the risk of unintended toxicities stemming from the residence of engineered cells within patients beyond the course of treatment. Thus, strategies for eliminating such cells—by inducing the expression of a "self-destruct" gene after successful treatment, for example—are necessary to ensure that cell-based therapeutics can be administered safely.

In recent work, researchers have begun to apply existing drug-inducible gene expression tools as regulatory systems for controlling therapeutic cells—however, many of these systems possess features that complicate their translation to clinical applications. For example, rapamycin and tamoxifen are widely used to control the activity of proteins fused to domains recognizing these drugs, but they are also ligands that bind and stimulate endogenous signaling proteins involved in regulating metabolism and immunity. Platforms based on the bacterially derived tetracycline-binding repressor proteins are similarly challenged by the mitotoxic properties of tetracyclines as well as their potent antibiotic activity. While the recently described inducible systems based on abscisic acid- and gibberellin-binding proteins have proven to be highly versatile, use in patients could be complicated by the abundance of these plant-derived hormones in the environment and in plant-based foods.

Inducible Gene-Expression Using Antiviral Drugs:

To circumvent the challenges imposed by the intrinsic bioactivity of these compounds, viral proteases and their corresponding anti-viral inhibitors are used herein to create new inducible systems that are orthogonal to mammalian systems. For example, the activity of diverse proteins can be made drug-sensitive by fusion with the hepatitis C virus (HCV) NS3 protease domain. NS3 is a serine cis-protease that excises itself from the HCV polyprotein by cleaving recognition sites flanking it at either end. Because it is essential for HCV replication, the NS3 protease has been a major target in the drug industry's development of anti-HCV therapeutics—thus, numerous inhibitors targeting this viral domain have previously been identified, including several that are FDA-approved.

NS3 protease domain can be used to render transcription factors (TFs) based on the nuclease-deficient dCas9 subject to drug-control. In an initial design strategy, NS3 is intergrated into the engineered TF dCas9-VPR, (generating dCas9-NS3-VPR, or "dCNV") placing enzyme between the dCas9 scaffold and the "VPR" transactivation domain (TAD). In this configuration, the protease domain serves as a self-immolating linker that leads to the dismemberment of the artificial TF, separating dCas9 from its fused nuclear localization signal (NLS) and VPR motif. However, upon exposure to an NS3 inhibitor, self-excision of the protease is blocked and intact copies of the TF are in turn able to transport into the nucleus to activate the expression of targeted genes. Using an sgRNA sequence complementary to the promoter region of chromosomal DNA encoding the chemokine receptor CXCR4, dCNV was able to activate upregulate expression of the cell surface protein in a drug-dependent manner.

Drug-Inducible Display of Notch and Syn-Notch Ligands:

NS3 is also used to regulate the presentation of Notch and syn-Notch ligands on the surface of engineered mammalian cells. NS3 is integrated into cell-surface ligands such that they are retained on membrane surfaces (and thus able to activate Notch receptors) only in the presence of drug. Work described herein demonstrates that drug-dependent Notch signaling by cells expressing and NS3-fused version of the the Notch ligand DLL1 (DLL1-NS3).

Regulation of Therapeutic Cell Activity:

In addition to the further development of new drug-sensitive TFs and signaling proteins, dCNV and NS3-containing Notch/syn-Notch ligands are applied to regulate the therapeutic properties of engineered T cells, such as such as target-specificity, cell-killing ability, and self-destruction. A key aspect of the proposed approach is that the several FDA approved NS3 inhibitors are already used in the clinic to treat HCV. Thus, these systems are used to modulate therapeutic cells in vivo using molecules that are orally available and already known to be safe.

Materials and Methods

DNA Constructs

Plasmid DNA and detailed sequence information for expression vectors encoding Gal4DB-NS3-Gal4TA, Gal4DB-NS3-VP64, Gal4DB-NS3-VP64-p65, rTetR-NS3-VP64-p65, myr-palm-NS3-Gal4min, dCas9-NS3-NLS/VPR, and SNAP-dCas9-NS3-NLS/VPR can be obtained via AddGene. Standard cloning procedures were used in the generation of all DNA constructs. The pEV-UAS-H2B-citrine reporter plasmid was a gift from Michael Elowitz (Caltech), the TRE-mTagBFP reporter plasmid was a gift from Wilson Wong (Boston University), the 5×GAL4-TATA-luciferase reporter plasmid (Addgene #46756) was a gift from Richard Maurer (Oregon Health Sciences University), the Tet-inducible mCherry reporter (Addgene #64128) and sgRNA1_Tet-inducible Luciferase plasmids (Addgene #64128) were gifts from Moritoshi Sato (University of Tokyo).

NS3 Inhibitors

Asunaprevir, boceprevir, danoprevir, MK-5172 (a.k.a., grazoprevir), and simeprevir were from MedChemExpress. Telaprevir was from Selleck Chemicals. BILN-2061 was a gift from Roger Tsien and Stephen Adams (UC San Diego). Concentrated NS3 inhibitor stocks were dissolved in DMSO at concentrations between 3-10 mM and diluted into cell culture media at the indicated working concentrations.

Mammalian Cell Culture

All mammalian cell lines were cultured in a humidified incubator maintained at 37° C. with 5% C02. HEK 293FT cells (ThermoFisher) were cultured in Dulbecco's modified Eagle medium (DMEM) containing with 10% FBS and supplemented with nonessential amino acids (Life Technologies), Glutamax (Life Technologies), and G418 (500 µg/mL, Invivogen). HeLa cells were obtained from ATCC and were cultured in DMEM containing 10% FBS and supplemented with Glutamax and penicillin/streptomycin. Stable cell lines based on CHO T-REx (ThermoFisher) were were maintained in DMEM containing 10% FBS and supplemented with nonessential amino acids and glutamax.

DNA Transfections

DNA transfections were performed using Lipofectamine 3000 Reagent (ThermoFisher) according to manufacturer's instructions. For imaging experiments, cells were seeded in dishes or well plates containing coverslip bottoms either coated with bovine plasma fibronectin (Product # F, 1141, Sigma-Aldrich) or treated for cell-adherence by the manufacturer (poly-D-lysine by MatTek, or ibiTreat by Ibidi).

Stable Cell Line Generation

Stable cell lines were generated from previously reported CHO-K1 T-REx cells containing stably integrated Gal4- and Notch-dependent reporter constructs (UAS H2B-Citrine and 12×CSL H2B-Citrine, respectively), which were gifts from Michael Elowitz (Caltech). Briefly, cells were transfected with linearized DNAs encoding the engineered protein of interest as well as antibiotic resistance gene for mammalian selection. Transfections were performed in 24-well plates containing 160,000 cells per well seeded the approximately 24 hours prior to transfection. At 48 hours post-transfection, the cells were transferred to 6-well plates and exposed to antibiotic selection using hygromycin (500 µg/mL). Upon elimination of non-transfected control cells (typically after 10 days of culture in the presence of antibiotic), surviving cells were transferred into 96-well plates using a limited dilution procedure in order to isolate single clones.

Antibodies

The following primary antibodies were used: mouse anti-Cas9 (Santa Cruz Biotechnology, sc-517386, 1:500 dilution for western blotting, 1:50 for immunostaining), mouse anti-human CD184 (CXCR-4) APC conjugate (BioLegend, 306510, 1:200 dilution for flow cytometry), polyclonal sheep anti-mouse/rat Dll1 (R&D Systems, AF3970, 1:50 dilution for immunostaining), rabbit anti-Histone H2B (Cell Signalling, 12364, 1:1,000 dilution for western blotting), mouse anti-HA-HRP (Santa-Cruz, sc-7392, 1:1,000 dilution for blotting), rabbit anti-GAPDH (Sigma-Aldrich, G9545, 1:3,000 dilution for western blotting), and polyclonal rabbit anti-Gal4 (Santa Cruz Biotechnology, sc-577, diluted 1:500 for western blotting, 1:200 for immunostaining). The following secondary antibodies were used: goat anti-human AlexaFluor647 conjugate (ThermoFisher, A-21445, 1:1,000 dilution), donkey anti-sheep AlexaFluor647 conjugate (ThermoFisher, A-21448, 1:1,000 dilution), goat anti-rabbit CF647 conjugate (Sigma-Aldrich, SAB4600184, 1:300 dilution), anti-mouse HRP conjugate (Cell Signalling, 7076, 1:3,000 dilution), and anti-rabbit HRP conjugate (Bio-Rad, 170-6515, 1:3,000 dilution).

Preparation of Cell Lysates for Immunoblotting

Cell lysates used in immunoblotting analyses were prepared by direct lysis of drug-treated and untreated cells in 1×LDS-PAGE loading buffer (ThermoFisher) following removal of cell culture media. Such procedure was applied in order to immediately denature proteins upon lysis, thus preventing undesired NS3 cis-cleavage in cell lysates. Viscous solutions were formed upon addition of the lysis reagent, which were clarified through sonication followed by centrifugation. The lysates were subsequently analyzed by standard immunoblotting procedures and probed using the antibodies listed above at the indicated dilutions. Detection of the labeled antigens was carried by chemiluminescence via the SuperSignal West Pico PLUS Chemiluminescent Substrate (Pierce).

Immunofluorescence Staining of Fixed Cells

Cells were rinsed with PBS prior to fixation with formaldehyde (4% v/v, diluted into PBS from fresh vials containing 16% solutions purchased from ThermoFisher). Cells were fixed for 10 minutes at room temperature, followed by rinsing with PBS (three times) to remove residual fixative. When necessary, cells were then permeabilized with Triton-X 100 (0.2%, v/v, in PBS) for 10 minutes, following by rinsing with PBS. Cells were blocked with BSA solution (5%, v/v in PBS) for approximately 30 minutes at room temperature prior to staining with primary antibody solution (typically in PBS, or in the appropriate solution as suggested by the antibody supplier) at the dilutions indicated above for 1 hour at room temperature. Cells were stained with secondary antibody solution (in PBS at the solutions indicated above) for 1 hour at room temperature before imaging.

Time-Dependent Dye Labeling of SNAP-Tagged Proteins

HeLa cells were transfected with DNA encoding SNAP-dCas9-NS3-NLS/VPR as described above herein. Approximately 24 hours later, cells were labeled with the red fluorescent dye SNAP-Cell TMR STAR (New England Biolabs) in complete culture media according to the manufacturer's protocol. The dye was removed by gentle aspiration of the media, followed by rinsing with pre-warmed complete media (three times) to remove residual dye. Cells were subsequently incubated in culture media containing 3 µM BILN-2061. After 8 hours, cells were then labeled with the green fluorescent SNAP-Cell Fluorescein (New England Biolabs). Cells were fixed with 4% formaldehyde prior to imaging.

Luciferase Assay

CHO-K1 cells stably expressing Gal4DB-NS3-VP64 were transfected with DNA encoding a UAS regulated firefly luciferase reporter construct (5×GAL4-TATA-luciferase). A constitutively transcribed NanoLuciferase construct (pNL1.1.TK[Nluc/TK], Promega) was used as a co-transfection control. Approximately 16 hours after transfection, cells were treated with either BILN-2061, or Grazoprevir (both at 3 µM). Following a 12 hour period of drug treatment, a time-series was initiated during which the drug-containing media was removed from individual wells and replaced with drug-free media over the course of a 48 hour period. At the end of the series (approximately 56 hours after the initial drug exposure, and 72 hours after transfection), the amount of luciferase and NanoLuciferase present in cells was quantified using the Nano-Glo Dual Luciferase Reporter Assay System (Promega) according to the manufacturer's protocol. The CHO-K1 cell line used in these analyses also contained a stably integrated UAS H2B-Citrine reporter construct, and fluorescence imaging confirmed the activation of the Gal4-dependent H2B-citrine gene in all drug treated-wells.

Image Acquisition and Analysis

Cells were imaged by epifluorescence microscopy in imaging-compatible vessels containing glass coverslip bottoms (MatTek) or optically clear plastic bottoms (ibidi). During imaging, cells were maintained in PBS, standard culture media, or FluoroBrite DMEM (ThermoFisher). For time-lapse analyses, cells were imaged in culture media supplemented with 30 mM HEPES diluted from a 1 M stock (pH 7.2-7.5, ThermoFisher) and maintained at 37° C. in a heated imaging chamber throughout the duration of the analysis (typically 24 hours). Images were acquired using the ZEN imaging software (Zeiss). Image files were processed using the ImageJ-based image analysis package Fiji. The images were contrasted uniformly across experiments, and where applicable, pixel intensity profiles were plotted using the plot profile tool in Fiji. For the time-lapse analyses, movies were created using the ZEN imaging software.

Flow Cytometry

Cells analyzed by flow cytometry were gated for living cells by scatter detection. The geometric mean measured reporter fluorescence levels were reported in arbitrary fluorescence units (AFU). Reporter activation analyses were performed using stable single-clones, or cells transiently transfected with DNA encoding the analyzed TF (as indicated in the figure captions). For analyses carried out using transiently expressing cells, plasmid DNA encoding a constitutively expressed fluorescent protein marker was co-delivered at the time of transfection and used to identify positively transfected cells populations (see Supplementary FIG. 12). Briefly, transfected cells were were gated to the top 1% of marker fluorescence of non-transfected control cells under the same condition. Transient expression experiments carried out using the "turn-on" TFs (shown in FIG. 1$d$ and 1$i$, and Supplementary FIG. 3) were gated via detection of an mCherry marker that was expressed via an IRES sequence on the TF-encoding plasmid. Transfected cells were incubated for 24-48 h after transfection either in the presence or absence of the indicated NS3 inhibitors before being analysed using an Attune N×T flow cytometer (ThermoFisher). For the analyses in which rTetR-NS3-VP64-p65 and TMD-NS3-Gal4min were combined, 125,000 HEK 293FT cells were transfected with 25 ng of DNA (per ~125,000 cells) with DNA mixtures containing a 3:3:2:2 molar ratio of rTetR-NS3-VP64-p65 to TMD-NS3-Gal4 to TRE mTagBFP to UAS H2B Citrine (as approximated by DNA size).

For expression analyses carried out using dCas9-based TFs, HEK 293FT cells were seeded in 48-well plates and transfected at a density of ~80,000 cells per well. A total 250 ng of DNA was delivered per well in each experiment; sgRNA- and dCas9-encoding constructs were transfected at a 1:1 molar ratio as approximated based on DNA size. The constructs encoding the sgRNAs targeting human CXCR4 promoter were acquired from AddGene and were previously reported ("sgC2" and "sgC3"). Expression of the chemokine receptor was analysed via flow cytometry using a fluorescently-conjugated CXCR-4 antibody; geometric means were recorded.

Statistics and Reproducibility

All flow cytometry and luminescence assay data were collected using 3 biologically independent samples. For fluorescence imaging analyses, >3 images per condition were recorded (encompassing hundreds of cells), and representative images are displayed in the figures. For immu- Bulky Ectodomain Mechanoreceptor Embodiment Gamma secretase is a membrane protein complex involved in biological functions such as Notch and amyloid precursor protein (APP) processing. Its proteolytic subunit, presenilin, acts by catalyzing the cleavage of intramembrane alpha helices, and in turn allows the release of both the extracellular domain (important in APP pathology) and the intracellular domain (important in Notch developmental biology). The gamma secretase extracellular subunit, nicastrin, has been shown to regulate this process through steric hindrance. Gamma secretase substrates with bulky extracellular domains are resistant to proteolysis, and the regulated shedding of this bulky ectodomain is a key pathway in Notch processing.

Figure 30:
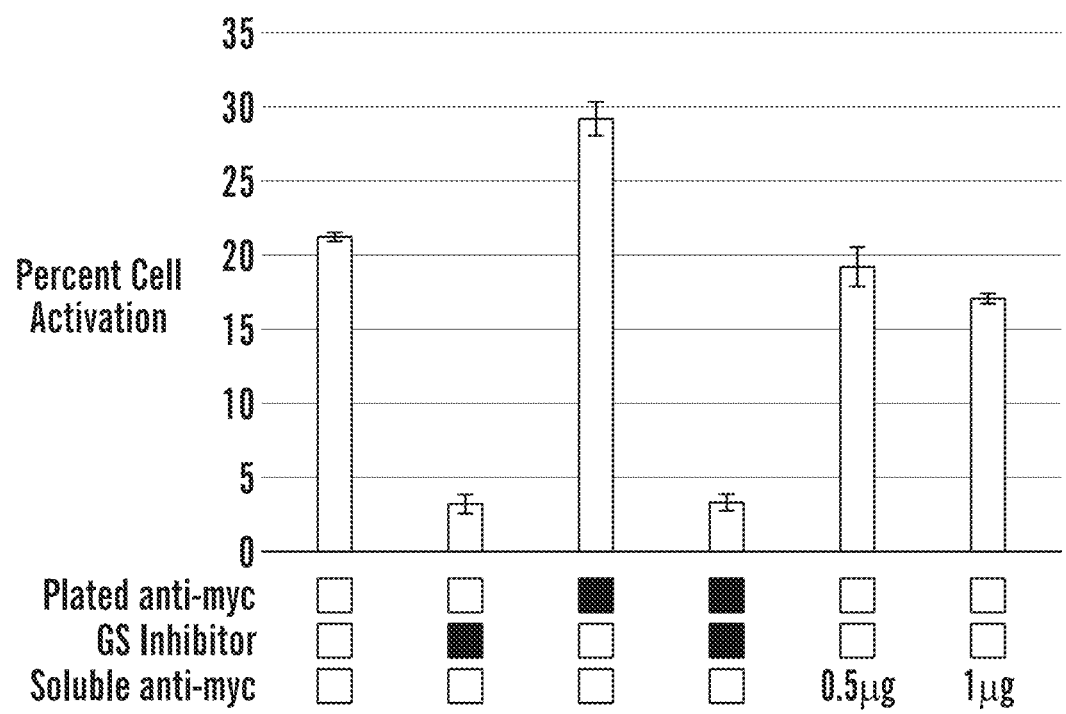
FIG. 30 shows results using a novel mechanoreceptor with a fluorescent protein as its bulky ectodomain. Green fluorescent protein has been shown to unfold at approximately 100 pN (Dietz 2004), and unfolding of this domain would reduce steric hindrance and in turn allow the release of an intracellular transcription factor through gamma secretase processing. Cells transiently transfected with DNA encoding this receptor display increased activation when plated on wells coated with an antibody that binds it. However, this increase in activation only occurred when the antibodies are tethered, and thus are able to apply force to the receptors: soluble antibodies at similar concentrations do not increase activation. Additionally, this process is supported to be gamma secretase dependent, as addition of a gamma secretase inhibitor diminished cell activation. p=0.000269805 (t-test between coated anti-myc and non-coated for percent cell activation); p=0.000763826 (t-test between coated anti-myc and noncoated for fold above receptor).
Figure 30:
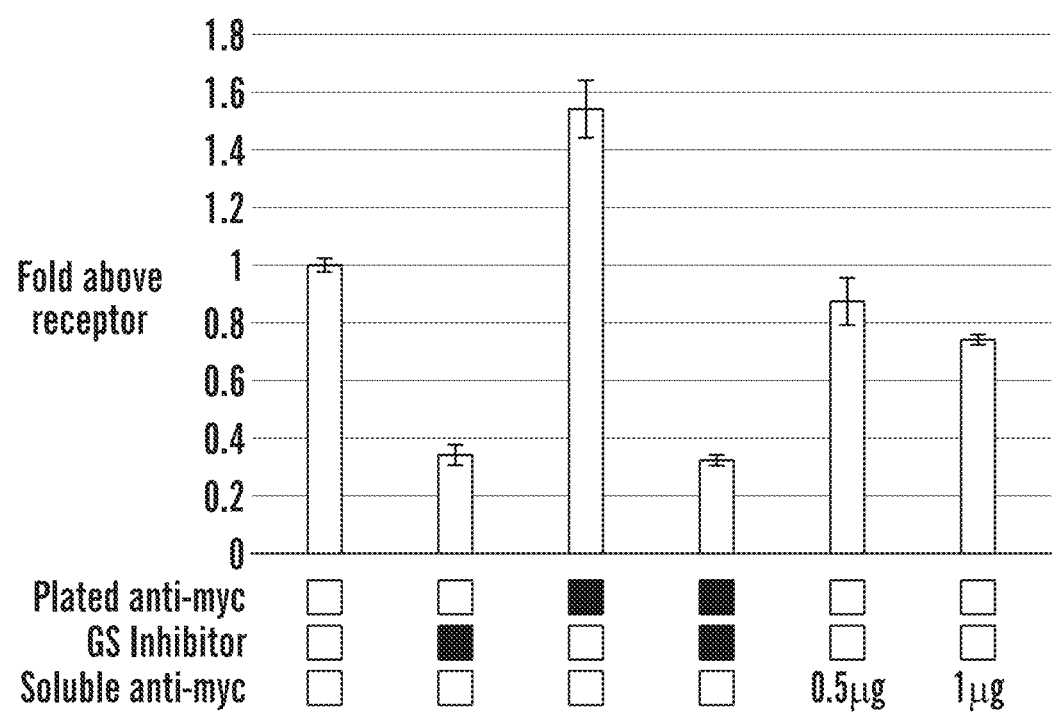

Shown here in FIG. 30 are the results using a novel mechanoreceptor with a fluorescent protein as its bulky ectodomain. Green fluorescent protein has been shown to unfold at approximately 100 pN (Dietz 2004), and unfolding of this domain would reduce steric hindrance and in turn allow the release of an intracellular transcription factor through gamma secretase processing.

Cells transiently transfected with DNA encoding this receptor display increased activation when plated on wells coated with an antibody that binds it. However, this increase in activation only occurred when the antibodies are tethered, and thus are able to apply force to the receptors: soluble antibodies at similar concentrations did not increase activation. Additionally, this process is supported to be gamma secretase dependent, as addition of a gamma secretase inhibitor diminished cell activation.

Wells from an untreated 96 well plate were coated overnight (20 hrs) with 0.005% gelatin and with or without 1 g of an anti-myc antibody. They were then washed 3 times with 200 µL PBS, and reporter cells that had been transfected with a plasmid encoding this protein were plated with media (10% FBS No antibiotics) with or without DAPT, a gamma secretase inhibitor (GS inhibitor). 2 hours later, anti-myc antibody was added to wells, and the cells were cultured overnight (20 hrs) at 37 degrees Celsius. All results are from flow cytometry, gated for live GFP+ cells. 3 samples for each condition.

REFERENCES

1. Lienert, F., Lohmueller, J. J., Garg, A., & Silver, P. A. (2014). Synthetic biology in mammalian cells: next generation research tools and therapeutics. Nature Reviews Molecular Cell Biology, 15, 95107.
2. Failla, C., Tomei, L., & De Francesco, R. (1994). Both NS3 and NS4A are required for proteolytic processing of hepatitis C virus nonstructural proteins. *Journal of Virology,* 68(6), 3753-3760.
3. Lin, M. Z., Glenn, J. S., & Tsien, R. Y. (2008). A drug-controllable tag for visualizing newly synthesized proteins in cells and whole animals. *Proceedings of the National Academy of Sciences,* 105 (22), 7744-7749
4. Butko, M. T., Yang, J., Geng, Y., Kim, H. J., Jeon, N. L., Shu, X., Mackey, M. R., Ellisman, M. H., Tsien, R. Y. & Lin, M. Z. (2012). Fluorescent and photo-oxidizing Time-STAMP tags track protein fates in light and electron microscopy. *Nature Neuroscience,* 15(12), 1742-1751.
5. Palida, S. F., Butko, M. T., Ngo, J. T., Mackey, M. R., Gross, L. A., Ellisman, M. H., & Tsien, R. Y. (2015). PKMζ but not PKCλ, is rapidly synthesized and degraded at the neuronal synapse. *Journal of Neuroscience,* 35(20), 7736-7749.
6. Chung, H. K., Jacobs, C. L., Huo, Y., Yang, J., Krumm, S. A., Plemper, R. K., Tsien, R. Y. & Lin, M. Z. (2015). Tunable and reversible drug control of protein production via a self-excising degron. *Nature Chemical Biology,* 11(9), 713-720.
7. Chavez, A., Scheiman, J., Vora, S., Pruitt, B. W., Tuttle, M, Iyer, E., Lin, S., Kiani, S, Guzman, C., Wiegand, D. J., Ter-Ovanesyan, D., J Braff, J. L., Davidsohn, E., Housden, B. E., Perrimon, N., Weiss, R., Aach, J., Collins, J. J., & Church, G. M. Highly efficient Cas9-mediated transcriptional programming. *Nature Methods,* 12(4), 326-328.
8. Gossen, M., Freundlieb, S., Bender, G., Muller, G., Hillen, W., & Bujard, H. (1995). Transcriptional activation by tetracyclines in mammalian cells. *Science,* 268(5218), 1766-1768.
9. Zacharias, D. A., Violin, J. D., Newton, A. C., & Tsien, R. Y. (2002). Partitioning of lipid-modified monomeric GFPs into membrane microdomains of live cells. *Science,* 296(5569), 913-916.
10. Perez-Pinera, Pablo, et al. RNA-guided gene activation by CRISPR-Cas9-based transcription factors. *Nature Methods* 10.10 (2013): 973-976.
11. Maeder, Morgan L., et al. CRISPR RNA-guided activation of endogenous human genes. *Nature Methods* 10.10 (2013): 977-979.
12. Qi, L. S., Larson, M. H., Gilbert, L. A., Doudna, J. A., Weissman, J. S., Arkin, A. P., & Lim, W. A. Repurposing CRISPR as an RNA-guided platform for sequence-specific control of gene expression. *Cell* 152.5 (2013): 1173-1183.
13. Zalatan, J. G., Lee, M. E., Almeida, R., Gilbert, L. A., Whitehead, E. H., La Russa, M., Tsai, J. C., Weissman, J. S., Dueber, J. E., Qi, L. S. & Lim, W. A. (2015). Engineering complex synthetic transcriptional programs with CRISPR RNA scaffolds. *Cell,* 160(1), 339-350.
14. Komor, Alexis C., Ahmed H. Badran, and David R. Liu. CRISPR-based technologies for the manipulation of eukaryotic genomes. *Cell* 168.1-2 (2017): 20-36.
15. Gordon, W. R., Zimmerman, B., He, L., Miles, L. J., Huang, J., Tiyanont, K., McArthur, D. G., Aster, J. C., Perrimon, N., Loparo, J. J., & Blacklow, S. C (2015). Mechanical allostery: evidence for a force requirement in the proteolytic activation of Notch. *Developmental Cell,* 33(6), 729-736.
16. Morsut, L., Roybal, K. T., Xiong, X., Gordley, R. M., Coyle, S. M., Thomson, M., & Lim, W. A. (2016). Engineering customized cell sensing and response behaviors using synthetic notch receptors. *Cell,* 164(4), 780-791.
17. Roybal, K. T., Rupp, L. J., Morsut, L., Walker, W. J., McNally, K. A., Park, J. S., & Lim, W. A. (2016). Precision tumor recognition by T cells with combinatorial antigen-sensing circuits. *Cell,* 164(4), 770-779.
18. Varnum-Finney, B., Wu, L., Yu, M., Brashem-Stein, C., Staats, S., Flowers, D., Griffin, J. D., & Bernstein, I. D. (2000). Immobilization of Notch ligand, Delta-1, is required for induction of notch signaling. *Journal of Cell Science,* 113(23), 4313-4318.
19. Sprinzak, D., Lakhanpal, A., LeBon, L., Santat, L. A., Fontes, M. E., Anderson, G. A., Garcia-Ojalvo, J. & Elowitz, M. B. (2010). Cis interactions between notch and delta generate mutually exclusive signaling states. *Nature,* 465(7294), 86.

Example 3

Reduction of SynNotch Leakiness by Incorporation of the Juxtamembrane LWF Motif.

SynNotch receptors are designed around a preserved Notch regulatory "core," the minimal protein unit identified as necessary for maintaining the natural Notch signaling mechanism. Specifically, SynNotch cores retain the Negative Regulatory Region (NRR) and Transmembrane Domain (TMD) of natural Notch. Although SynNotch receptors successfully mimic many key Notch signaling characteristics, they fail to recapitulate some regulatory aspects of Notch signaling; natural Notch signaling is tightly regulated, but SynNotch signaling is often observed as noisy or "leaky," with some SynNotch constructs having significant background activation even in the absence of stimulus.

The leakiness of SynNotch receptors may be due the introduction of synthetic protein modules, the absence of natural Notch components, or likely some combination thereof. For example, it has been observed that addition of more powerful transcriptional activators (VPR, as opposed to VP64) leads to an extreme increase in background noise and renders the receptors near inviable.

Figure 31A:
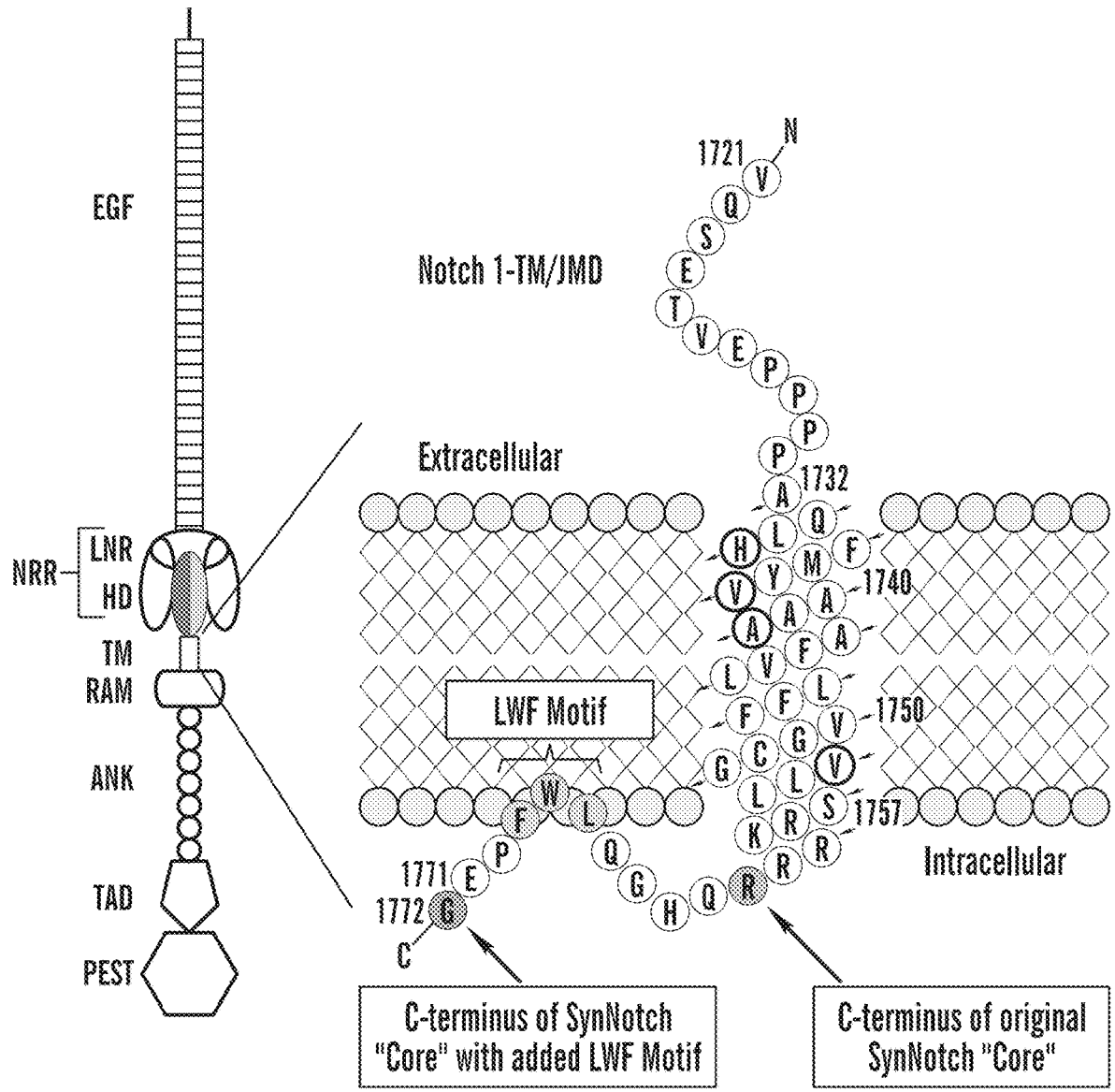
FIGS. 31A-31C show reduction of SynNotch leakiness by incorporation of the juxtamembrane LWF motif (FIG. 31A) Schematic of the Notch TMD and LWF motif, slightly modified from [1] to highlight the difference between the original SynNotch core's C-terminus and the modified SynNotch core's C-terminus, where 10 amino acids are added to include the LWF motif.

Pursuing the hypothesis that the SynNotch regulatory core may be missing an element of the natural receptor important for regulating signaling dynamics, Notch's "LWF motif" was identified as a candidate for reintroduction into SynNotch. The LWF motif, absent in SynNotch, is a hydrophobic stretch of amino acids juxtamembrane to the TMD's C-terminus that was recently modeled to briefly reenter the cytosoloic face of the cell membrane [1] (FIG. 31A). The TMD of Notch contains the S3 site for cleavage by γ-secretase, the final proteolytic event necessary for receptor activation. Dysregulated cleavage by γ-secretase is a likely cause of SynNotch leakiness, as indicated by the ability of DAPT (γ-secretase inhibitor) to suppress leaky receptor activation. Due to the LWF motifs proximity with the TMD and S3, as well as modeled interactions with the cell membrane, without wishing to be bound by a particular theory, it was hypothesized that inclusion of the motif could restore some natural regulation of receptor activity. Because the modeled LWF motif structure was not published until after SynNotch, it was likely not considered in the original SynNotch core design.

Figures 31B, 31C:
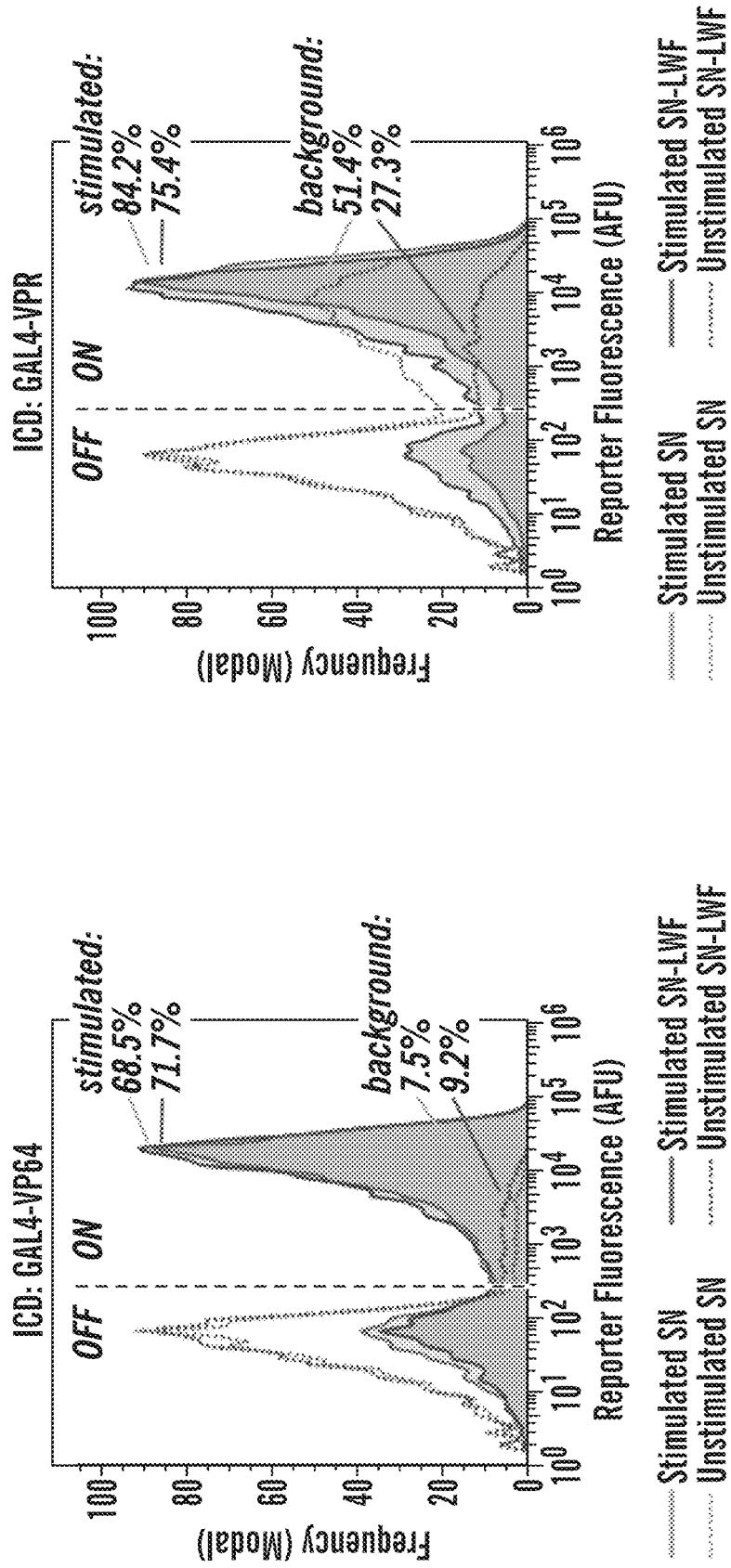

Data herein provides preliminary evidence that inclusion of the LWF motif reduces background activation in SynNotch receptors. In initial experiments, the original SynNotch core design (SN) was compare with a SynNotch core containing the LWF motif (SN-LWF) (FIG. 31A). Each receptor core was test with two different transcription factor intracellular domains (ICD's): Gal4 fused to VP64 ("VP64," a modest transcriptional activator commonly used in SynNotch) and Gal4 fused to VPR ("VPR," a strong transcriptional activator, whose strength is penalized by high background activation in SynNotch constructs). For VP64 ICD's, it was found that both SN-VP64 and SN-LWF-VP64 have low background activation and activate to the same extent when stimulated, as expected for the modest transcriptional activator (FIG. 31B). For the stronger VPR ICD, however, it was found that SN-VPR is significantly leakier than SN-LWF-VPR, while both activate to comparable extents (FIG. 31C). These data indicate that inclusion of the LWF motif in SynNotch may permit the use of valuable transcriptional effectors that are not viable in leaky settings. For example, if tightly regulated like natural Notch signaling, potent domains such as VPR could allow more rapid transcriptional outputs in therapeutic settings, or DNA editors such as Cre and Cas9 could be used without risk of erroneous gene editing.

REFERENCE

[1] Deatherage et al. "Structural and biochemical differences between the Notch and the amyloid precursor protein transmembrane domains." *Science Advances*, 2017.

Example 4

Previously, a design strategy and preliminary data for SynNotch receptors with programmable force-activation thresholds was introduced. Natural and synthetic Notch receptors contain a Negative Regulatory Region (NRR), which is an auto-inhibitory domain that opens in response to tensile forces greater than ~5 pN. This mechanical opening of the NRR is necessary for downstream transcriptional activity of the receptor. In order to create Notch-based receptors with force-activation thresholds above 5 pN, an scFv targeting the NRR was fused to the N-terminus of the NRR itself. Receptors containing this scFv-NRR ("sNRR") domain require greater tensile force for activation due to the additional protein interaction that must be disrupted to open the NRR. Furthermore, the precise amount of force required for receptor activation is determined by scFv binding affinity for the NRR and is thus tunable.

Figure 32A:
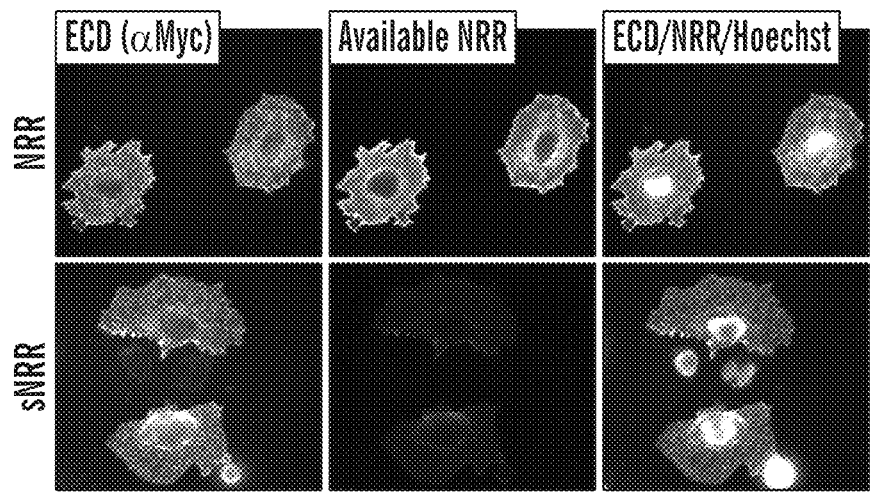
FIGS. 32A and 32B show expression of sNRR-containing receptors.
Figure 32B:
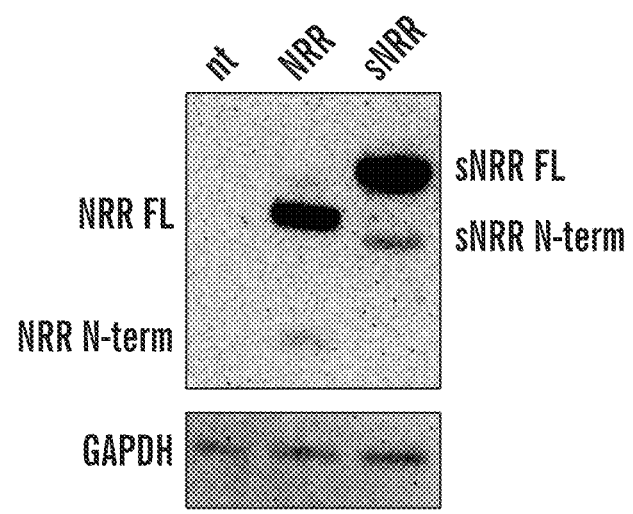

Provided herein are additional embodiments of the synthetic mechanoreceptors, their sNRR domains, and the potential applications of the invention described herein. In certain embodiments, the design criteria for building functional mechanoreceptors include, but are not limited to: they must be expressed at the cell surface (FIGS. 32A and 32B), they must activate in response to physiologically relevant and measurable forces (FIGS. 33A and 33B), and this force-activation threshold must be tunable (FIG. 34A-34E).

Figure 35:
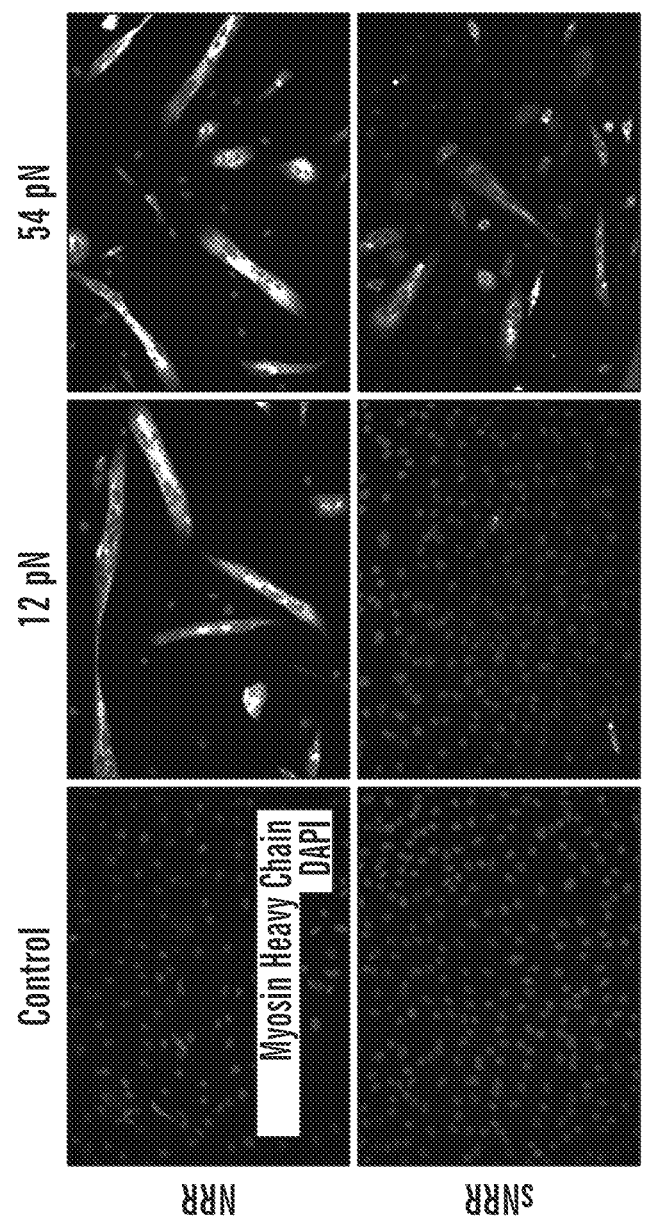
FIG. 35 show force-based gene circuits: myogenic differentiation. αFITC SynNotch receptors with an ICD that drives expression of MyoD are expressed in C3H 10T1/2 fibroblasts and stimulated with 12 and 54 pN TGTs. Fibroblast differentiation down a myogenic lineage is identified by the presence of myosin heavy chain and multinucleation. While cells with NRR-based receptors differentiated in response to both stimuli, cells with sNRR-based receptors only differentiate on 54 pN TGTs.

FIG. 35 shows that SynNotch receptors containing a sNRR domain expressed at the surface of HeLa cells similarly to receptors containing the WT NRR domain. Data presented in FIG. 35 indicate that the receptors can be stably expressed in HEK 293FT cells.

Figure 33A:
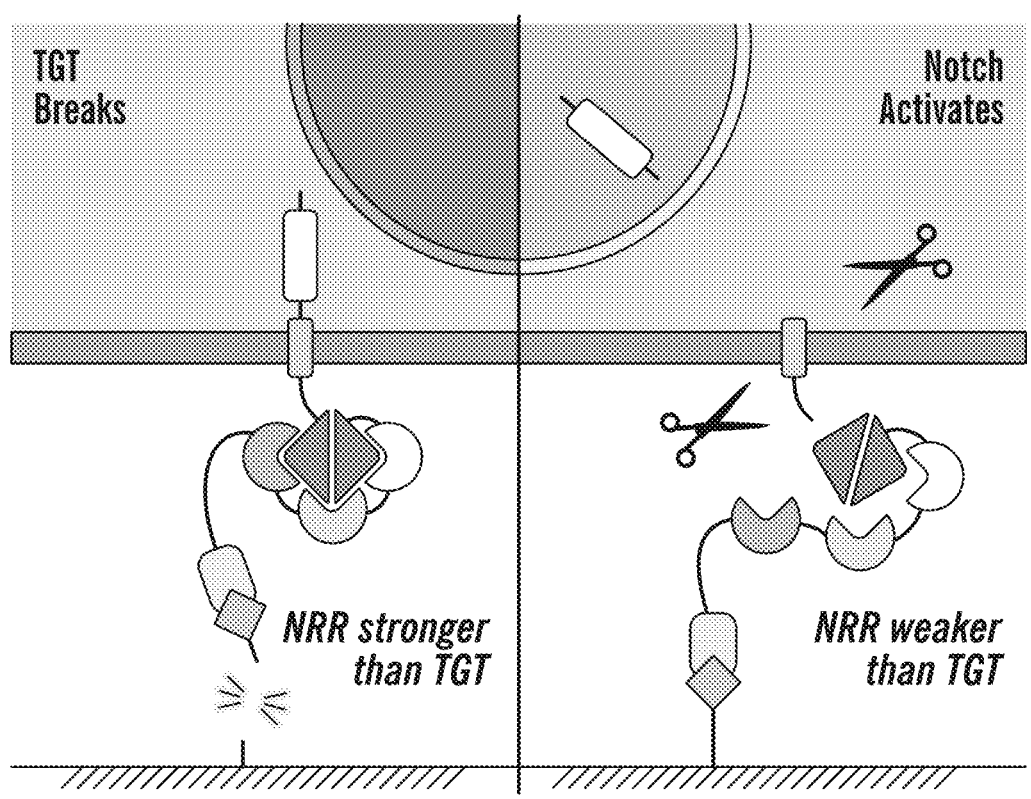
FIGS. 33A and 33B show increased mechanical strength of sNRR domain in TGT assay.
Figure 33B:
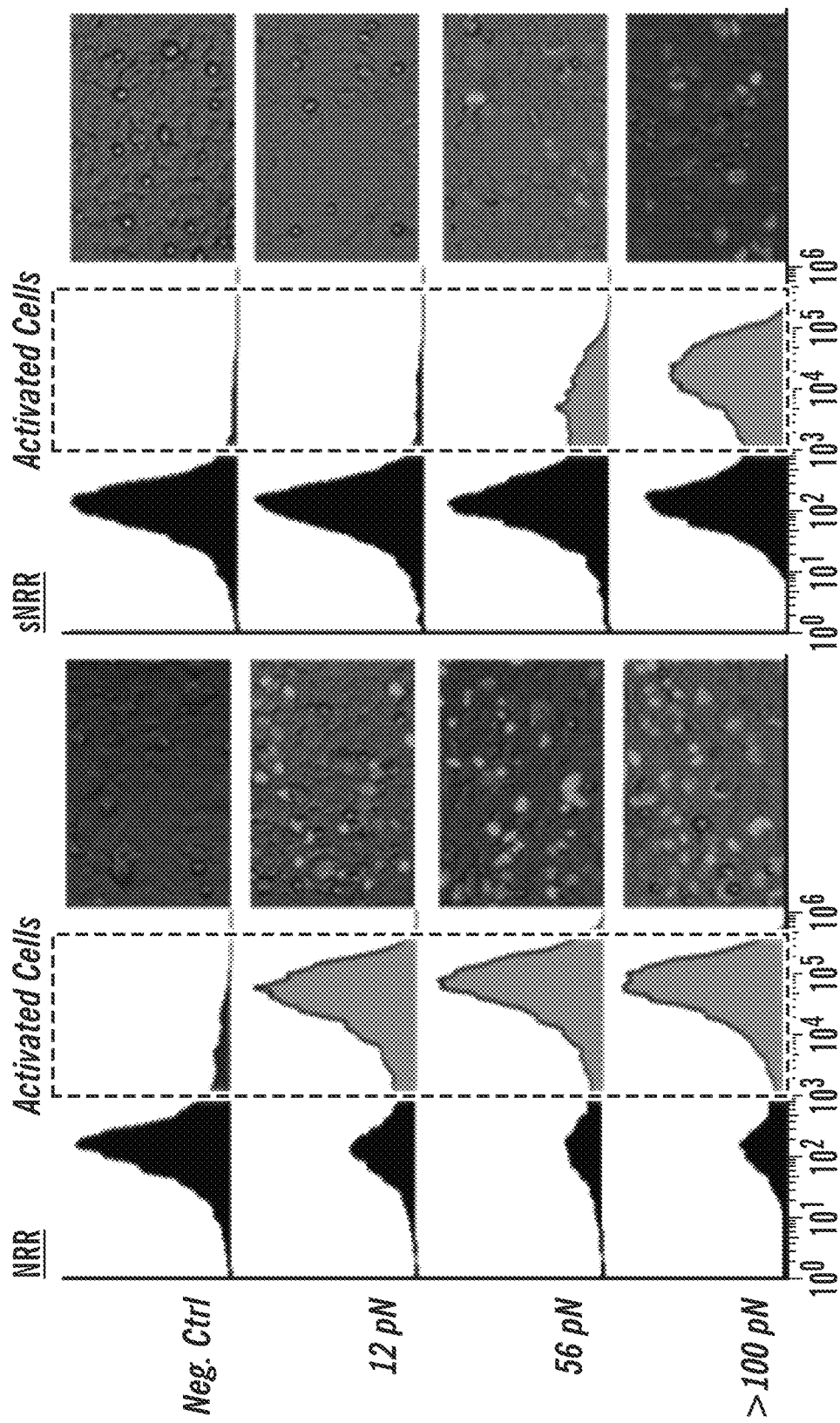
Figure 34C:
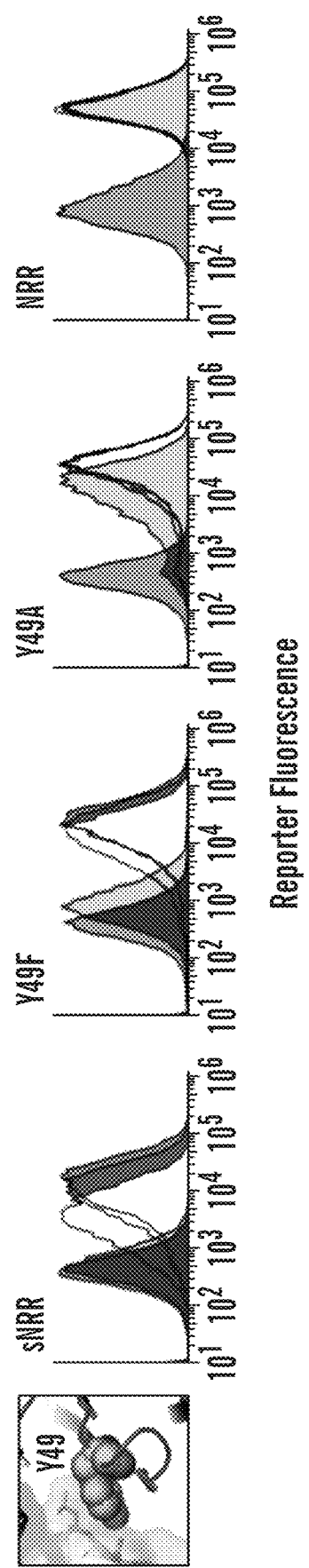

Previously herein, the use of a tension gauge tether (TGT) assay to quantify mechanostability in the engineered receptors described herein was introduced. FIGS. 33A and 33B show evidence for the increased mechanical strength of the sNRR domain described herein. While the WT NRR opens in response to ~5 pN of tensile force, the sNRR domain has a tension tolerance closer to ~50 pN.

Next, it was set out to tune the mechanical strength of sNRR and create a collection of receptors that activate in response definable and physiologically relevant forces. Because the unbinding force of an antibody-antigen pair correlates with its thermal dissociation rate, it was hypothesized that sNRR tension tolerance could be altered by mutating affinity of the scFv for the NRR. Previously presented data shows proof-of-concept evidence for this approach, using two model point mutations on the scFv, which was expressed as a separate transmembrane cis-inhibitor. In FIG. 34A-34E presents further evidence supporting this design strategy. A collection of mutated sNRR domains exhibiting a spectrum of mechanical strengths was generated. Notably, the impact of residue mutation on receptor strength followed predictable trends; more severe point mutations resulted in weaker receptors (Y49A weaker than Y49F, R99A weaker than R99K), and double point mutations were additively weaker than their constituents. Time-course microscopy of cells expressing mutated sNRR receptors further demonstrates the receptors' distinct mechanical characteristics, as well as their ability to discriminate between mechanical stimuli over time. Lastly, provided herein is a mathematical model that captures the observed temporal trends in receptor activation, simply by varying (1) the scFv-NRR dissociation rate vs. (2) the dissociation rate of the TGT double stranded DNA. The ability of such a simple two-parameter model to recapitulate our observed results indicates that mutating scFv-NRR affinity is indeed sufficient to create mechanically distinct receptors.

Importantly, the mechanoreceptors presented herein not only measure an applied force, but respond to and make a decision based off that force. In various embodiments, designer responses to force may be therapeutic in nature, or geared to study/recapitulate natural phenomenon in mechanobiology. For example, stem cells have been shown to differentiate down lineages dictated by their mechanical environment. Presented herein in FIG. 35, this natural process was mimic by using sNRR-based SynNotch to drive myogenic differentiation of fibroblast cells based on mechanical TGT stimulus.

Figure 36:
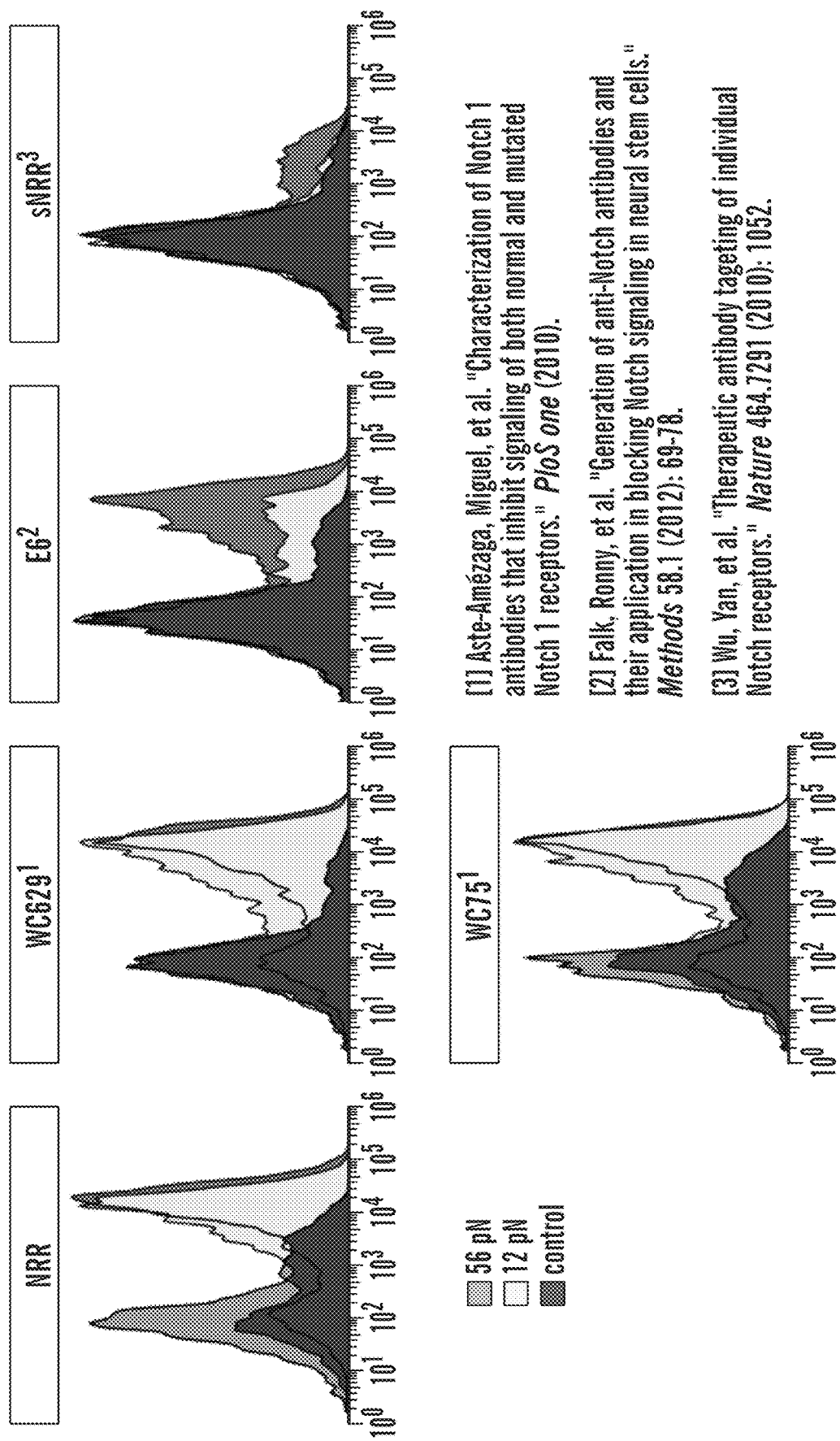
FIG. 36 shows screening of NRR-binding scFv's. Various antibodies known to bind the NRR and inhibit Notch activation are incorporated into SynNotch receptors and stimulated with 12 and 56 pN TGTs. scFv's WC629 and WC75 do not offer detectable mechanical stability, as the receptors are unable to discriminate between the two stimuli, similar to the WT NRR. scFv E6 offers marginal increased mechanostability, while the original sNRR domain offers the greatest mechanical stability, with 56 pN only beginning to stimulate the receptor.

Lastly, data presented herein show that the choice of NRR-binding scFv is nontrivial in the design of sNRR (FIG. 36). Three additional antibodies known to bind the NRR and inhibit Notch activation were incorporated into sNRR domains as scFv's. Although known to be effective as soluble antibodies, these scFv's offer little to no additional mechanical stability to the receptor. The original sNRR was designed to accommodate binding of the particular scFv in use (based off the crystal structure of the antibody-antigen complex), and incorporation of different scFv's would require additional engineering to optimally position them with respect to the NRR.

Sequences

Provided herein are sequences for use, in whole or in part, in the various embodiments of the compositions, methods, and systems described herein.

SEQ ID NO: 1 is an amino acid sequence encoding signal Sequence (SS).

(SEQ ID NO: 1)
AVGQDTQEVIVVPHSLPFKVVVISAILALVVLTIISLIILIMLWQKKPRR
T

SEQ ID NO: 2 is an amino acid sequence encoding human Notch1 LBD.

(SEQ ID NO: 2)
RGPRCSQPGETCLNGGKCEAANGTEACVCGGAFVGPRCQDPNPCLSTPCK

NAGTCHVVDRRGVADYACSCALGFSGPLCLTPLDNACLTNPCRNGGTCDL

LTLTEYKCRCPPGWSGKSCQQADPCASNPCANGGQCLPFEASYICHCPPS

FHGPTCRQDVNECGQKPGLCRHGGTCHNEVGSYRCVCRATHTGPNCERPY

VPCSPSPCQNGGTCRPTGDVTHECACLPGFTGQNCEENIDDCPGNNCKNG

GACVDGVNTYNCRCPPEWTGQYCTEDVDECQLMPNACQNGGTCHNTHGGY

NCVCVNGWTGEDCSENIDDCASAACFHGATCHDRVASFYCECPHGRTGLL

CHLNDACISNPCNEGSNCDTNPVNGKAICTCPSGYTGPACSQDVDECSLG

ANPCEHAGKCINTLGSFECQCLQGYTGPRCEIDVNECVSNPCQNDATCLD

QIGEFQCICMPGYEGVHCEVNTDECASSPCLHNGRCLDKINEFQCECPTG

FTGHLCQYDVDECASTPCKNGAKCLDGPNTYTCVCTEGYTGTHCEVDIDE

CDPDPCHYGSCKDGVATFTCLCRPGYTGHHCETNINECSSQPCRHGGTCQ

DRDNAYLCFCLKGTTGPNCEINLDDCASSPCDSGTCLDKIDGYECACEPG

YTGSMCNINIDECAGNPCHNGGTCEDGINGFTCRCPEGYHDPTCLSEVNE

CNSNPCVHGACRDSLNGYKCDCDPGWSGTNCDINNNECESNPCVNGGTCK

DMTSGYVCTCREGFSGPNCQTNINECASNPCLNQGTCIDDVAGYKCNCLL

PYTGATCEVVLAPCAPSPCRNGGECRQSEDYESFSCVCPTGWQAGQTCEV

DINECVLSPCRHGASCQNTHGGYRCHCQAGYSGRNCETDIDDCRPNPCHN

GGSCTDGINTAFCDCLPGFRGTFCEEDINECASDPCRNGANCTDCVDSYT

CTCPAGFSGIHCENNTPDCTESSCFNGGTCVDGINSFTCLCPPGFTGSYC

QHDVNECDSQPCLHGGTCQDGCGSYRCTCPQGYTGPNCQNLVHWCDSSPC

KNGGKCWQTHTQYRCECPSGWTGLYCDVPSVSCEVAAQRQGVDVARLCQH

GGLCVDAGNTHHCRCQAGYTGSYCEDLVDECSPSPCQNGATCTDYLGGYS

CKCVAGYHGVNCSEEIDECLSHPCQNGGTCLDLPNTYKCSCPRGTQGVHC

EINVDDCNPPVDPVSRSPKCFNNGTCVDQVGGYSCTCPPGFVGERCEGDV

NECLSNPCDARGTQNCVQRVNDFHCECRAGHTGRRCESVINGCKGKPCKN

GGTCAVASNTARGFICKCPAGFEGATCENDARTCGSLRCLNGGTCISGPR

SPTCLCLGPFTGPECQFPASSPCLGGNPCYNQGTCEPTSESPFYRCLCPA

KFNGLLCH

SEQ ID NO: 3 is an amino acid sequence encoding LaG17 anti-GFP nanobody.

(SEQ ID NO: 3)
MADVQLVESGGGLVQAGGSLRLSCAASGRTISMAAMSWFRQAPGKEREFV

AGISRSAGSAVHADSVKGRFTISRDNTKNTLYLQMNSLKAEDTAVYYCAV

RTSGFFGSIPRTGTAFDYWGQGTQVTVS

SEQ ID NO: 4 is an amino acid sequence encoding scFv αFITC.

(SEQ ID NO: 4)
QVQLVESGGNLVQPGGSLRLSCAASGFTFGSFSMSWVRQAPGGGLEWVAG

LSARSSLTHYADSVKGRETISRDNAKNSVYLQMNSLRVEDTAVYYCARRS

YDSSGYAGHEYSYMDVWGQGTLVTVSGGGGSGGGGSGGGGSSVLTQPSSV

SAAPGQKVTISCSGSTSNIGNNYVSWYQQHPGKAPKLMIYDVSKRPSGVP

DRFSGSKSGNSASLDISGLQSEDEADYYCAAWDDSLSEFLFGTGTKLTVL

G

SEQ ID NO: 5 is an amino acid sequence encoding SNAP tag.

(SEQ ID NO: 5)
MDKDCEMKRTTLDSPLGKLELSGCEQGLHRIIFLGKGTSAADAVEVPAPA

AVLGGPEPLMQATAWLNAYFHQPEAIEEFPVPALHHPVFQQESFTRQVLW

KLLKVVKFGEVISYSHLAALAGNPAATAAVKTALSGNPVPILIPCHRVVQ

GDLDVGGYEGGLAVKEWLLAHEGHRLGKPGLG

SEQ ID NO: 6 is an amino acid sequence encoding FLAG tag.

(SEQ ID NO: 6)
DYKDDDDKG

SEQ ID NO: 7 is an amino acid sequence encoding Myc tag.

(SEQ ID NO: 7)
EQKLISEEDL

SEQ ID NO: 8 is an amino acid sequence encoding human NRR1.

(SEQ ID NO: 8)
ILDYSFGGGAGRDIPPPLIEEACELPECQEDAGNKVCSLQCNNHACGWDG
GDCSLNFNDPWKNCTQSLQCWKYFSDGHCDSQCNSAGCLFDGFDCQRAEG
QCNPLYDQYCKDHFSDGHCDQGCNSAECEWDGLDCAEHVPERLAAGTLVV
VVLMPPEQLRNSSFHFLRELSRVLHTNVVFKRDAHGQQMIFPYYGREEEL
RKHPIKRAAEGWAAPDALLGQVKASLLPGGSEGGRRRRELDPMDVRGSIV
YLEIDNRQCVQASSQCFQSATDVAAFLGALASLGSLNIPYKIEAVQSETV
EPPPPAQ

SEQ ID NO: 9 is an amino acid sequence encoding mouse NRR1.

(SEQ ID NO: 9)
ILDYSFTGGAGRDIPPPQIEEACELPECQVDAGNKVCNLQCNNHACGWDG
GDCSLNFNDPWKNCTQSLQCWKYFSDGHCDSQCNSAGCLFDGFDCQLTEG
QCNPLYDQYCKDHFSDGHCDQGCNSAECEWDGLDCAEHVPERLAAGTLVL
VVLLPPDQLRNNSFHFLRELSHVLHTNVVFKRDAQGQQMIFPYYGHEEEL
RKHPIKRSTVGWATSSLLPGTSGGRQRRELDPMDIRGSIVYLEIDNRQCV
QSSSQCFQSATDVAAFLGALASLGSLNIPYKIEAVKSEPVEPPLPSQ

SEQ ID NO: 10 is an amino acid sequence encoding mouse NRR 2.

(SEQ ID NO: 10)
LYTAPPSTPPATCLSQYCADKARDGVCDEACNSHACQWDGGDCSLTMENP
WANCSSPLPCWDYINNQCDELCNTVECLFDNFECQGNSKTCKYDKYCADH
FKDNHCDQGCNSEECGWDGLDCAADQPENLAEGTLVIVVLMPPEQLLQDA
RSFLRALGTLLHTNLRIKRDSQGELMVYPYYGEKSAAMKKQRMTRRSLPG
EQEQEVAGSKVFLEIDNRQCVQDSDHCFKNTDAAAALLASHAIQGTLSYP
LVSVVSESLTPERTQ

SEQ ID NO: 11 is an amino acid sequence encoding NICD.

(SEQ ID NO: 11)
QHGQLWFPEGFKVSEASKKKRREPLGEDSVGLKPLKNASDGALMDDNQE
WGDEDLETKKFRFEEPVVLPDLDDQTDHRQWTQQHLDAADLRMSAMAPTP
PQGEVDADCMDVNVRGPDGFTPLMIASCSGGGLETGNSEEEEDAPAVISD
FIYQGASLHNQTDRTGETALHLAARYSRSDAAKRLLEASADANIQDNMGR
TPLHAAVSADAQGVFQILIRNRATDLDARMHDGTTPLILAARLAVEGMLE
DLINSHADVNAVDDLGKSALHWAAAVNNVDAAVVLLKNGANKDMQNNREE
TPLFLAAREGSYETAKVLLDHFANRDITDHMDRLPRDIAQERMHHDIVRL
LDEYNLVRSPQLHGAPLGGTPTLSPPLCSPNGYLGSLKPGVQGKKVRKPS
SKGLACGSKEAKDLKARRKKSQDGKGCLLDSSGMLSPVDSLESPHGYLSD
VASPPLLPSPFQQSPSVPLNHLPGMPDTHLGIGHLNVAAKPEMAALGGGG
RLAFETGPPRLSHLPVASGTSTVLGSSSGGALNFTVGGSTSLNGQCEWLS
RLQSGMVPNQYNPLRGSVAPGPLSTQAPSLQHGMVGPLHSSLAASALSQM
MSYQGLPSTRLATQPHLVQTQQVQPQNLQMQQQNLQPANIQQQQSLQPPP
PPPQPHLGVSSAASGHLGRSFLSGEPSQADVQPLGPSSLAVHTILPQESP
ALPTSLPSSLVPPVTAAQFLTPPSQHSYSSPVDNTPSHQLQVPEHPFLTP
SPESPDQWSSSSPHSNVSDWSEGVSSPPTSMQSQIARIPEAFK

SEQ ID NO: 12 is an amino acid sequence encoding Gal4DBD-VP64.

(SEQ ID NO: 12)
MKLLSSIEQACDICRLKKLKCSKEKPKCAKCLKNNWECRYSPKTKRSPLT
RAHLTEVESRLERLEQLFLLIFPREDLDMILKMDSLQDIKALLTGLFVQD
NVNKDAVTDRLASVETDMPLTLRQHRISATSSSEESSNKGQRQLTVSAAA
GGSGGSGGSDALDDFDLDMLGSDALDDFDLDMLGSDALDDFDLDMLGSDA
LDDFDLDMLGS

SEQ ID NO: 13 is an amino acid sequence encoding human Notch1 TM.

(SEQ ID NO: 13)
LHFMYVAAAAFVLLFFVGCGVLLSRKRRR

SEQ ID NO: 14 is an amino acid sequence encoding mouse Notch1 TM.

(SEQ ID NO: 14)
LHLMYVAAAAFVLLFFVGCGVLLSRKRRR

SEQ ID NO: 15 is an amino acid sequence encoding Ab2; wherein in SEQ ID NO: 15, bold text depicts the VH domain, underlined text depicts the linker domain, and double underlined text depicts the VL domain).

(SEQ ID NO: 15)
EVQLVESGGGLVQPGGSLRLSCAASGFTFSSYWIHWVRQAPGKGLEWVAR
INPPNRSNQYADSVKGRFTISADTSKNTAYLQMNSLRAEDTAVYYCARGS
GFRWVMDYWGQGTLVTV<u>SSGGSSRSSSSGGGGSGGGG</u><u>DIQMTQSPSSLSA</u>
<u>SVGDRVTITCRASQDVSTAVAWYQQKPGKAPKLLIYSASFLYSGVPSRFS</u>
<u>GSGSGTDFTLTISSLQPEDFATYYCQQFYTTPSTFGQGTKVEIK</u>

The amino acid sequences of SEQ ID NO: 16-24, depict amino acid changes from SEQ ID NO:15

SEQ ID NO: 16 is an amino acid sequence encoding Ab2-VH N55A. The VH N55 mutation is depicted in bold, underlined text.

(SEQ ID NO: 16)
EVQLVESGGGLVQPGGSLRLSCAASGFTFSSYWIHWVRQAPGKGLEWVAR

INPPARSNQYADSVKGRFTISADTSKNTAYLQMNSLRAEDTAVYYCARGS

GFRWVMDYWGQGTLVTVSSGGSSRSSSSGGGGSGGGGDIQMTQSPSSLSA

SVGDRVTITCRASQDVSTAVAWYQQKPGKAPKLLIYSASFLYSGVPSRFS

GSGSGTDFTLTISSLQPEDFATYYCQQFYTTPSTFGQGTKVEIK

SEQ ID NO: 17 is an amino acid sequence encoding Ab2-VH R99K. The VH R55 mutation depicted in bold, underlined text.

(SEQ ID NO: 17)
EVQLVESGGGLVQPGGSLRLSCAASGFTFSSYWIHWVRQAPGKGLEWVAR

INPPNRSNQYADSVKGRFTISADTSKNTAYLQMNSLRAEDTAVYYCARGS

GFKWVMDYWGQGTLVTVSSGGSSRSSSSGGGGSGGGGDIQMTQSPSSLSA

SVGDRVTITCRASQDVSTAVAWYQQKPGKAPKLLIYSASFLYSGVPSRFS

GSGSGTDFTLTISSLQPEDFATYYCQQFYTTPSTFGQGTKVEIK

SEQ ID NO: 18 is an amino acid sequence encoding Ab2-VH R99A. The VH R99 mutation is depicted in bold, underlined text.

(SEQ ID NO: 18)
EVQLVESGGGLVQPGGSLRLSCAASGFTFSSYWIHWVRQAPGKGLEWVAR

INPPNRSNQYADSVKGRFTISADTSKNTAYLQMNSLRAEDTAVYYCARGS

GFAWVMDYWGQGTLVTVSSGGSSRSSSSGGGGSGGGGDIQMTQSPSSLSA

SVGDRVTITCRASQDVSTAVAWYQQKPGKAPKLLIYSASFLYSGVPSRFS

GSGSGTDFTLTISSLQPEDFATYYCQQFYTTPSTFGQGTKVEIK

SEQ ID NO: 19 is an amino acid sequence encoding Ab2-VH C22S/C92A. The VH C22 and C92 mutations are depicted in bold, underlined text.

(SEQ ID NO: 19)
EVQLVESGGGLVQPGGSLRLSSAASGFTFSSYWIHWVRQAPGKGLEWVAR

INPPNRSNQYADSVKGRFTISADTSKNTAYLQMNSLRAEDTAVYYAARGS

GFRWVMDYWGQGTLVTVSSGGSSRSSSSGGGGSGGGGDIQMTQSPSSLSA

SVGDRVTITCRASQDVSTAVAWYQQKPGKAPKLLIYSASFLYSGVPSRFS

GSGSGTDFTLTISSLQPEDFATYYCQQFYTTPSTFGQGTKVEIK

SEQ ID NO: 20 is an amino acid sequence encoding Ab2-VL S30A. The VL S30 mutation is depicted in bold, underlined text.

(SEQ ID NO: 20)
EVQLVESGGGLVQPGGSLRLSCAASGFTFSSYWIHWVRQAPGKGLEWVAR

INPPNRSNQYADSVKGRFTISADTSKNTAYLQMNSLRAEDTAVYYCARGS

GFRWVMDYWGQGTLVTVSSGGSSRSSSSGGGGSGGGGDIQMTQSPSSLSA

SVGDRVTITCRASQDVATAVAWYQQKPGKAPKLLIYSASFLYSGVPSRFS

GSGSGTDFTLTISSLQPEDFATYYCQQFYTTPSTFGQGTKVEIK

SEQ ID NO: 21 is an amino acid sequence encoding Ab2-VL Y49A. The VL Y49 mutation is depicted in bold, underlined text.

(SEQ ID NO: 21)
EVQLVESGGGLVQPGGSLRLSCAASGFTFSSYWIHWVRQAPGKGLEWVAR

INPPNRSNQYADSVKGRFTISADTSKNTAYLQMNSLRAEDTAVYYCARGS

GFRWVMDYWGQGTLVTVSSGGSSRSSSSGGGGSGGGGDIQMTQSPSSLSA

SVGDRVTITCRASQDVSTAVAWYQQKPGKAPKLLIASASFLYSGVPSRFS

GSGSGTDFTLTISSLQPEDFATYYCQQFYTTPSTFGQGTKVEIK

SEQ ID NO: 22 is an amino acid sequence encoding Ab2-VL Y55A. The VL Y55 mutation is depicted in bold, underlined text)

(SEQ ID NO: 22)
EVQLVESGGGLVQPGGSLRLSCAASGFTFSSYWIHWVRQAPGKGLEWVAR

INPPNRSNQYADSVKGRFTISADTSKNTAYLQMNSLRAEDTAVYYCARGS

GFRWVMDYWGQGTLVTVSSGGSSRSSSSGGGGSGGGGDIQMTQSPSSLSA

SVGDRVTITCRASQDVSTAVAWYQQKPGKAPKLLIYSASFLASGVPSRFS

GSGSGTDFTLTISSLQPEDFATYYCQQFYTTPSTFGQGTKVEIK

SEQ ID NO: 23 is an amino acid sequence encoding Ab2-VL F91A. The VL F91 mutation is depicted in bold, underlined text.

(SEQ ID NO: 23)
EVQLVESGGGLVQPGGSLRLSCAASGFTFSSYWIHWVRQAPGKGLEWVAR

INPPNRSNQYADSVKGRFTISADTSKNTAYLQMNSLRAEDTAVYYCARGS

GFRWVMDYWGQGTLVTVSSGGSSRSSSSGGGGSGGGGDIQMTQSPSSLSA

SVGDRVTITCRASQDVSTAVAWYQQKPGKAPKLLIYSASFLYSGVPSRFS

GSGSGTDFTLTISSLQPEDFATYYCQQAYTTPSTFGQGTKVEIK

SEQ ID NO: 24 is an amino acid sequence encoding Ab2-VL Y92A. The VL Y92 mutation shown in bold, underlined text.

(SEQ ID NO: 24)
EVQLVESGGGLVQPGGSLRLSCAASGFTFSSYWIHWVRQAPGKGLEWVAR

INPPNRSNQYADSVKGRFTISADTSKNTAYLQMNSLRAEDTAVYYCARGS

GFRWVMDYWGQGTLVTVSSGGSSRSSSSGGGGSGGGGDIQMTQSPSSLSA

SVGDRVTITCRASQDVSTAVAWYQQKPGKAPKLLIYSASFLYSGVPSRFS

GSGSGTDFTLTISSLQPEDFATYYCQQFATTPSTFGQGTKVEIK

SEQ ID NO: 25 is an amino acid sequence encoding E6.

(SEQ ID NO: 25)
QVQLVESGGNLVQPGGSLRLSCAASGFTFGSFSMSWVRQAPGGGLEWVAG

LSARSSLTHYADSVKGRFTISRDNAKNSVYLQMNSLRVEDTAVYYCARRS

YDSSGYAGHFYSYMDVWGQGTLVTVSGGGGSGGGGSGGGGSSVLTQPSSV

SAAPGQKVTISCSGSTSNIGNNYVSWYQQHPGKAPKLMIYDVSKRPSGVP

DRFSGSKSGNSASLDISGLQSEDEADYYCAAWDDSLSEFLFGTGTKLTVL

G

SEQ ID NO: 26 is an amino acid sequence encoding WC629.

(SEQ ID NO: 26)
EVQLVQSGAEVKKPGSSVKVSCKASGGTLSSYTVSWLRQAPGQGLEWMGR
IIPILDRANYAQKFQGRVTITADKSTSTAYMELNSLRSDDTAVYYCARSI
GAAGDGVWFDPWGQGTMVTVSSGGSSRSSSSGGGGSGGGGQAVLTQPSSV
SGAPGQRVTISCTGSSSNIGAGYDVHWYQQLPGTAPKLLIFDNKNRPSGV
PDRFSGSNSGTSASLAITGLQAEDEAEYYCQSYDNNLSGRVFGGGTKLTV

SEQ ID NO: 27 is an amino acid sequence encoding WC75.

(SEQ ID NO: 27)
LVQPGGSLRLSCAASGFTFDDYAMHWVRQAPGKGLEWVSSISWHSRTIAY
ADSVKGRFSISRDNAKNSLYLQMNSLRPEDTAVYYCAKASYLSTSSSLDY
WGRGTLVTVSSGGSSRSSSSGGGGSGGGGQSVLTQPGSVSGSPGQSITIS
CTGTSSDVGGYNYVSWYQQHPGKAPKLMIYEGSKRPSGVSNRFSGSKSGN
TASLTISGLQAEDEADYYCSSYTTRSTRVFGGGTKLTVL

SEQ ID NO: 28 is an amino acid sequence encoding D3.

(SEQ ID NO: 28)
EVQLVESGGGLVQPGGSLRLSCAASGYTFSSYGMSWVRQAPGKGLEWVS
YIYPYSGATYYADSVKGRFTISADTSKNTAYLQMNSLRAEDTAVYYCAR
HSGYYRISSAMDVWGQGTLVTVSAGGSSRSSSSGGGGSGGGGDIQMTQS
PSSLSASVGDRVTITCRASQNIKRFLAWYQQKPGKAPKLLIYGASTRES
GVPSRFSGSGSGTDFTLTISSLQPEDFATYYCQQYYRSPHTFGQGTKVE
IKRGG

SEQ ID NO: 29 is an amino acid sequence encoding B6.

(SEQ ID NO: 29)
AQVQLVQSGAEVKKPGASVKVSCKASGYTFTSYAMHWVRQAPGQRLEWMG
WMNAGNGNTKYSQKFQGRVTITRDTSASTAYMELSSLRSEDTAVYYCARD
RVPTIPAYRIDYWGQGTLVTVSSLEGGGGSGGGGSGGGASDIQMTQSPSS
VSASVGDRVTITCRASQGISSWLAWYQQKPGKAPRLLIYAASSLQSGVPS
RFSGSGSGTDFTLTISSLQPEDFATYYCQQANSFPLTFGGGTKLEIKR

SEQ ID NO: 30 is an amino acid sequence encoding B9.

(SEQ ID NO: 30)
AQVQLVQSGAEVKKPGASVKVSCKASGYTFTSYAMHWVRQAPGQRLEWMG
WINAGNGNTKYSQKFQGRVTITRDTSASTAYMELSSLRSEDTAVYYCARG
PRSYGAGGMDVWGQGTLVTVSSLEGGGGSGGGGSGGGASDIQMTQSPSSV
SASVGDRVTITCRASQGISSWLAWYQQKPGKAPKFLIYAASSLQSGVPSR
FSGSGSGTDFTLTISSLQPEDFATYYCQQANSFPLTFGGGTKVEIKR

SEQ ID NO: 31 is an amino acid sequence encoding Platelet Derived Growth Factor Receptor (PDGFR) TM domain.

(SEQ ID NO: 31)
AVGQDTQEVIVVPHSLPFKVVVISAILALVVLTIISLIILIMLWQKKPRR
T

SEQ ID NO: 32 is an amino acid sequence encoding NS3. In SEQ IC NO:32, the bold, underlined text depicts the N- and C-terminal cis-cleavage sites and AU1 tag.

(SEQ ID NO: 32)
EDVVCCHSIYGKKKGDIDTYRYIGSSGTGCVVIVGRIVLSGSGTSAPITA
YAQQTRGLLGCIITSLTGRDKNQVEGEVQIVSTATQTFLATCINGVCWAV
YHGAGTRTIASPKGPVIQMYTNVDQDLVGWPAPQGSRSLTPCTCGSSDLY
LVTRHADVIPVRRRGDSRGSLLSPRPISYLKGSSGGPLLCPAGHAVGLFR
AAVCTRGVAKAVDFIPVENLETTMRSPVFTDNSSPPAVTLHPITKIDRE
VLYQEFDEMEECSQH

SEQ ID NO: 33 is an amino acid sequence encoding AU1 tag.

(SEQ ID NO: 33)
DTYRYI

SEQ ID NO: 34 is an amino acid sequence encoding rat Dll1 SS-ECD.

(SEQ ID NO: 34)
MGRRSALALAVVSALLCQVWSSGVFELKLQEFVNKKGLLGNRNCCRGGSG
PPCACRTFFRVCLKHYQASVSPEPPCTYGSAVTAVLGVDSFSLPDGAGID
PAFSNPIRFPFGFTWPGTFSLIIEALHTDSPDDLATENPERLISRLTTQR
HLTVGEEWSQDLHSSGRTDLRYSYRFVCDEHYYGEGCSVFCRPRDDAFGH
FTCGERGEKMCDPGWKGQYCTDPICLPGCDDQHGYCDKPGECKCRVGWQG
RYCDECIRYPGCLHGTCQQPWQCNCQEGWGGLFCNQDLNYCTHHKPCRNG
ATCTNTGQGSYTCSCRPGYTGANCELEVDECAPSPCRNGGSCTDLEDSYS
CTCPPGFYGKVCELSAMTCADGPCFNGGRCSDNPDGGYTCHCPAGFSGFN
CEKKIDLCSSSPCSNGAKCVDLGNSYLCRCQTGFSGRYCEDNVDDCASSP
CANGGTCRDSVNDFSCTCPPGYTGRNCSAPVSRCEHAPCHNGATCHQRGQ
RYMCECAQGYGGANCQFLLPEPPPDLIVAAQGGSFPW

SEQ ID NO: 35 is an amino acid sequence encoding rat Dll1 TM domain and ICD.

(SEQ ID NO: 35)
VAVCAGVVLVLLLLLGCAAVVVCVRLKLQKHQPPPDPCGGETETMNNLAN
CQREKDVSVSIIGATQIKNTNKKADFHGDHGADKSSFKARYPTVDYNLIR
DLKGDEATVRDAHSKRDTKCQSQGSVGEEKSTSTLRGGEVPDRKRPESVY
STSKDTKYQSVYVLSAEKDECVIATEV

SEQ ID NO: 36 is an amino acid sequence encoding human Dll4 SS-ECD.

(SEQ ID NO: 36)
MAAASRSASGWALLLLVALWQQRAAGSGVFQLQLQEFINERGVLASGRPC
EPGCRTFFRVCLKHFQAVVSPGPCTFGTVSTPVLGTNSFAVRDDSSGGGR
NPLQLPFNFTWPGTFSLIIEAWHAPGDDLRPEALPPDALISKIAIQGSLA
VGQNWLLDEQTSTLTRLRYSYRVICSDNYYGDNCSRLCKKRNDHFGHYVC

-continued
QPDGNLSCLPGWTGEYCQQPICLSGCHEQNGYCSKPAECLCRPGWQGRLC

NECIPHNGCRHGTCSTPWQCTCDEGWGGLFCDQDLNYCTHHSPCKNGATC

SNSGQRSYTCTCRPGYTGVDCELELSECDSNPCRNGGSCKDQEDGYHCLC

PPGYYGLHCEHSTLSCADSPCFNGGSCRERNQGANYACECPPNFTGSNCE

KKVDRCTSNPCANGGQCLNRGPSRMCRCRPGFTGTYCELHVSDCARNPCA

HGGTCHDLENGLMCTCPAGFSGRRCEVRTSIDACASSPCFNRATCYTDLS

TDTFVCNCPYGFVGSRCEFPVGLPPSFPW

SEQ ID NO: 37 is an amino acid sequence encoding human Dll4 TM domain and ICD.

(SEQ ID NO: 37)
VAVSLGVGLAVLLVLLGMVAVAVRQLRLRRPDDGSREAMNNLSDFQKDNL

IPAAQLKNTNQKKELEVDCGLDKSNCGKQQNHTLDYNLAPGPLGRGTMPG

KFPHSDKSLGEKAPLRLHSEKPECRISAICSPRDSMYQSVCLISEERNEC

VIATEV

SEQ ID NO: 38 is an amino acid sequence encoding mouse Dll4 SS-ECD.

(SEQ ID NO: 38)
MTPASRSACRWALLLLAVLWPQQRAAGSGIFQLRLQEFVNQRGMLANGQS

CEPGCRTFFRICLKHFQATFSEGPCTFGNVSTPVLGTNSFVVRDKNSGSG

RNPLQLPFNFTWPGTFSLNIQAWHTPGDDLRPETSPGNSLISQIIIQGSL

AVGKIWRTDEQNDTLTRLSYSYRVICSDNYYGESCSRLCKKRDDHFGHYE

CQPDGSLSCLPGWTGKYCDQPICLSGCHEQNGYCSKPDECICRPGWQGRL

CNECIPHNGCRHGTCSIPWQCACDEGWGGLFCDQDLNYCTHHSPCKNGST

CSNSGPKGYTCTCLPGYTGEHCELGLSKCASNPCRNGGSCKDQENSYHCL

CPPGYYGQHCEHSTLTCADSPCFNGGSCRERNQGSSYACECPPNFTGSNC

EKKVDRCTSNPCANGGQCQNRGPSRTCRCRPGFTGTHCELHISDCARSPC

AHGGTCHDLENGPVCTCPAGFSGRRCEVRITHDACASGPCFNGATCYTGL

SPNNFVCNCPYGFVGSRCEFPVGLPPSFPWVA

SEQ ID NO: 39 is an amino acid sequence encoding mouse Dll4 TM domain and ICD.

(SEQ ID NO: 39)
VSLGVGLVVLLVLLVMVVVAVRQLRLRRPDDESREAMNNLSDFQKDNLIP

AAQLKNTNQKKELEVDCGLDKSNCGKLQNHTLDYNLAPGLLGRGGMPGKY

PHSDKSLGEKVPLRLHSEKPECRISAICSPRDSMYQSVCLISEERNECVI

ATEV

SEQ ID NO: 40 is an amino acid sequence encoding mCherry.

(SEQ ID NO: 40)
MVSKGEEDNMAIIKEFMRFKVHMEGSVNGHEFEIEGEGEGRPYEGTQTAK

LKVTKGGPLPFAWDILSPQFMYGSKAYVKHPADIPDYLKLSFPEGFKWER

VMNFEDGGVVTVTQDSSLQDGEFIYKVKLRGTNFPSDGPVMQKKTMGWEA

-continued
SSERMYPEDGALKGEIKQRLKLKDGGHYDAEVKTTYKAKKPVQLPGAYNV

NIKLDITSHNEDYTIVEQYERAEGRHSTGGMDELYK

SEQ ID NO: 41 is an amino acid sequence encoding SS for cis-inhibitors.

(SEQ ID NO: 41)
METDTLLLWVLLLWVPGSTGDGGGG

SEQ ID NO: 42 is an amino acid sequence encoding an exemplary scFv (depicted in bold text) is expressed within a SynNotch as an "LNR4" domain. The underlined text depicts the linker, the double underlined, italic text depicts the linker with myc tag.

(SEQ ID NO: 42)
GGGGSTGDGGGGEVQLVESGGGLVQPGGSLRLSCAASGFTFSSYWIHWVR

QAPGKGLEWVARINPPNRSNQYADSVKGRFTISADTSKNTAYLQMNSLRA

EDTAVYYCARGSGFRWVMDYWGQGTLVTVSSGGSSRSSSSGGGGSGGGGD

IQMTQSPSSLSASVGDRVTITCRASQDVSTAVAWYQQKPGKAPKLLIYSA

SFLYSGVPSRFSGSGSGTDFTLTISSLQPEDFATYYCQQFYTTPSTFGQG

TKVEIK*GGGSEQKLISEEDLGGGS*

SEQ ID NO: 43 is an amino acid sequence encoding an exemplary full construct for a mouse-based SynNotch with myc-tagged LBD that can bind FITC or GFP, an Ab2 LNR4, and a Gal4-VP64 ICD. SEQ ID NO: 43 comprises, from N to C, a Signal Sequence; LBD (which can comprise multiple domains to bind different ligands; depicted in bold text); Notch Core (which comprises a Notch1 NRR, and an optional LNR4 domain expressed N-terminal to the NRR, depicted in underlined text); TM domain (depicted in italicized text); and an ICD (depicted in bold, underlined text).

(SEQ ID NO: 43)
MALPVTALLLPLALLLHAARPEQKLISEEDLQVQLVESGGNLVQPGGSLR

LSCAASGFTFGSFSMSWVRQAPGGGLEWVAGLSARSSLTHYADSVKGRFT

ISRDNAKNSVYLQMNSLRVEDTAVYYCARRSYDSSGYAGHFYSYMDVVVG

QGTLVTVSGGGGSGGGGSGGGGSSVLTQPSSVSAAPGQKVTISCSGSTSN

IGNNYVSWYQQHPGKAPKLMIYDVSKRPSGVPDRFSGSKSGNSASLDISG

LQSEDEADYYCAAWDDSLSEFLFGTGTKLTVLGGGGSMADVQLVESGGGL

VQAGGSLRLSCAASGRTISMAAMSWFRQAPGKEREFVAGISRSAGSAVHA

DSVKGRFTISRDNTKNTLYLQMNSLKAEDTAVYYCAVRTSGFFGSIPRTG

TAFDYWGQGTQVTVSGGGGSTGDGGGGEVQLVESGGGLVQPGGSLRLSCA

ASGFTFSSYWIHWVRQAPGKGLEWVARINPPNRSNQYADSVKGRFTISAD

TSKNTAYLQMNSLRAEDTAVYYCARGSGFRWVMDYWGQGTLVTVSSGGSS

RSSSSGGGGSGGGGDIQMTQSPSSLSASVGDRVTITCRASQDVSTAVAWY

QQKPGKAPKLLIYSASFLYSGVPSRFSGSGSGTDFTLTISSLQPEDFATY

YCQQFYTTPSTFGQGTKVEIKGGGSEQKLISEEDLGGGSILDYSFTGGAG

RDIPPPQIEEACELPECQVDAGNKVCNLQCNNHACGWDGGDCSLNFNDPW

KNCTQSLQCWKYFSDGHCDSQCNSAGCLFDGFDCQLTEGQCNPLYDQYCK

-continued

DHFSDGHCDQGCNSAECEWDGLDCAEHVPERLAAGTLVLVVLLPPDQLRN

NSFHFLRELSHVLHTNVVFKRDAQGQQMIFPYYGHEEELRKHPIKRSTVG

WATSSLLPGTSGGRQRRELDPMDIRGSIVYLEIDNRQCVQSSSQCFQSAT

DVAAFLGALASLGSLNIPYKIEAVKSEPVEPPLPSQL*HLMYVAAAAFVLL*

*FFVGCGVLLSRKRRR*MKLLSSIEQACDICRLKKLKCSKEKPKCAKCLKNN

WECRYSPKTKRSPLTRAHLTEVESRLERLEQLFLLIFPREDLDMILKMDS

LQDIKALLTGLFVQDNVNKDAVTDRLASVETDMPLTLRQHRISATSSSEE

SSNKGQRQLTVSAAAGGSGGSGGSDALDDFDLDMLGSDALDDFDLDMLGS

DALDDFDLDMLGSDALDDFDLDMLGS

SEQ ID NO: 44 is an amino acid sequence encoding an exemplary scFv expressed as a separate transmembrane cis-inhibitor of Notch. SEQ ID NO: 44 comprises, from N to C, Signal Sequence; scFV (depicted in bold text); Myc Tag and TM domain (depicted in italicized text); and mCherry (depicted in underlined text).

(SEQ ID NO: 44)
METDTLLLWVLLLWVPGSTGDGGGGEVQLVESGGGLVQPGGSLRLSCAAS

GFTFSSYWIHWVRQAPGKGLEWVARINPPNRSNQYADSVKGRFTISADTS

KNTAYLQMNSLRAEDTAVYYCARGSGFRWVMDYWGQGTLVTVSSGGSSRS

SSSGGGGSGGGGDIQMTQSPSSLSASVGDRVTITCRASQDVSTAVAWYQQ

KPGKAPKLLIYSASFLYSGVPSRFSGSGSGTDFTLTISSLQPEDFATYYC

QQFYTTPSTFGQGTKVEIK*GGGSEQKLISEEDLGGGSAVGQDTQEVIVVP*

*HSLPFKVVVISAILALVVLTIISLIILIMLWQKKPRRT*MVSKGEEDNMAI

IKEFMRFKVHMEGSVNGHEFEIEGEGEGRPYEGTQTAKLKVTKGGPLPFA

WDILSPQFMYGSKAYVKHPADIPDYLKLSFPEGFKWERVMNFEDGGVVTV

TQDSSLQDGEFIYKVKLRGTNFPSDGPVMQKKTMGWEASSERMYPEDGAL

KGEIKQRLKLKDGGHYDAEVKTTYKAKKPVQLPGAYNVNIKLDITSHNED

YTIVEQYERAEGRHSTGGMDELYK

SEQ ID NO: 45 is an amino acid sequence encoding an exemplary full DLL1-NS3 construct (rat Dll1) with C-terminal mCherry. SEQ ID NO: 45 comprises, from N to C, Signal sequence, Dll1 ECD; T7 tag (depicted in bold text); NS3; HA Tag (depicted in italicized text); TM domain; Dll1 ICD; and mCherry (depicted in underlined text.)

(SEQ ID NO: 45)
MGRRSALALAVVSALLCQVWSSGVFELKLQEFVNKKGLLGNRNCCRGGSG

PPCACRTFFRVCLKHYQASVSPEPPCTYGSAVTAVLGVDSFSLPDGAGID

PAFSNPIRFPFGFTWPGTFSLIIEALHTDSPDDLATENPERLISRLTTQR

HLTVGEEWSQDLHSSGRTDLRYSYRFVCDEHYYGEGCSVFCRPRDDAFGH

FTCGERGEKMCDPGWKGQYCTDPICLPGCDDQHGYCDKPGECKCRVGWQG

RYCDECIRYPGCLHGTCQQPWQCNCQEGWGGLFCNQDLNYCTHHKPCRNG

ATCTNTGQGSYTCSCRPGYTGANCELEVDECAPSPCRNGGSCTDLEDSYS

CTCPPGFYGKVCELSAMTCADGPCFNGGRCSDNPDGGYTCHCPAGFSGFN

CEKKIDLCSSSPCSNGAKCVDLGNSYLCRCQTGFSGRYCEDNVDDCASSP

CANGGTCRDSVNDFSCTCPPGYTGRNCSAPVSRCEHAPCHNGATCHQRGQ

RYMCECAQGYGGANCQFLLPEPPPDLIVAAQGGSFPWSRADMASMTGGQQ

MGSTEDVVCCHSIYGKKKGDIDTYRYIGSSGTGCVVIVGRIVLSGSGTSA

PITAYAQQTRGLLGCIITSLTGRDKNQVEGEVQIVSTATQTFLATCINGV

CWAVYHGAGTRTIASPKGPVIQMYTNVDQDLVGWPAPQGSRSLTPCTCGS

SDLYLVTRHADVIPVRRRGDSRGSLLSPRPISYLKGSSGGPLLCPAGHAV

GLFRAAVCTRGVAKAVDFIPVENLETTMRSPVFTDNSSPPAVTLTHPITK

IDREVLYQEFDEMEECSQH*YPYDVPDYAGASA*VAVCAGVVLVLLLLGCA

AVVVCVRLKLQKHQPPPDPCGGETETMNNLANCQREKDVSVSIIGATQIK

NTNKKADFHGDHGADKSSFKARYPTVDYNLIRDLKGDEATVRDAHSKRDT

KCQSQGSVGEEKSTSTLRGGEVPDRKRPESVYSTSKDTKYQSVYVLSAEK

DECVIATEV<u>VSKGEEDNMAIIKEFMRFKVHMEGSVNGHEFEIEGEGEGRP</u>

<u>YEGTQTAKLKVTKGGPLPFAWDILSPQFMYGSKAYVKHPADIPDYLKLSF</u>

<u>PEGFKWERVMNFEDGGVVTVTQDSSLQDGEFIYKVKLRGTNFPSDGPVMQ</u>

<u>KKTMGWEASSERMYPEDGALKGEIKQRLKLKDGGHYDAEVKTTYKAKKPV</u>

<u>QLPGAYNVNIKLDITSHNEDYTIVEQYERAEGRHSTGGMDELYKS</u>

SEQ ID NO: 50 is a nucleotide sequence encoding $DB_{Gal4}$-NS3-$TA_{Gal4}$. $DB_G$a4 is in bolded text, $TA_{Gal4}$ is in underlined text, NS4A is in italicized text, NS3 is in bolded, underlined text, and NS3 Cut Site is in bolded, italicized text.

(SEQ ID NO: 50)
ATGAAGTTGCTGAGCAGCATAGAGCAAGCATGTGATATCTGCCGGTTGAA

GAAGCTGAAGTGTAGCAAGGAGAAGCCCAAGTGCGCCAAGTGTCTCAAGA

ATAATTGGGAGTGTAGGTATAGCCCCAAGACCAAGCGAAGCCCGCTTACG

AGAGCACACCTTACCGAGGTCGAGAGCCGCCTGGAAAGACTCGAACAACT

TTTTCTTCTGATTTTCCCCAGGGAGGACCTGGACATGATCCTGAAGATGG

ACAGCCTCCAGGACATCAAAGCCCTTCTTACCGGGCTGTTCGTGCAGGAC

AACGTCAACAAGGATGCGGTGACCGACAGATTGGCGAGCGTGGAGACGGA

CATGCCCTTGACCCTCAGACAACATAGGATCAGCGCGACAAGCTCATCTG

AAGAATCTAGCAATAAGGGACAGCGACAGCTGACCGTTAGTgggGCGTCT

GCAggcATGGCCAGCATGACTGGTGGACAGCAAATGGGGTCGACG

*GAGGACGTGGTGTGCTGCCACTCAATCTA*CGGCAAGAAGAAGGGTGATA

TCGACACCTACCGATACATAGGCTCTTCCGGGACA<u>GGCTGCGTGGTCATA</u>

<u>GTGGGCAGGATCGTCTTGTCCGGATCCGGCACTAGT</u>GCGCCCATCACGGC

GTACGCCCAGCAGACGAGAGGCCTCCTAGGGTGTATAATCACCAGCCTGA

CTGGCCGGGACAAAAACCAAGTGGAGGGTGAGGTCCAGATCGTGTCAACT

GCTACCCAAACCTTCCTGGCAACGTGCATCAATGGGGTATGCTGGGCAGT

CTACCACGGGGCCGGAACGAGGACCATCGCATCACCCAAGGGTCCTGTCA

TCCAGATGTATACCAATGTGGACCAAGACCTTGTGGGCTGGCCCGCTCCT

CAAGGTTCCCGCTCATTGACACCCTGTACCTGCGGCTCCTCGGACCTTTA

-continued

```
CCTGGTCACGAGGCACGCCGATGTCATTCCCGTGCGCCGGCGAGGTGATA

GCAGGGGTAGCCTGCTTTCGCCCCGGCCCATTTCCTACTTGAAAGGCTCC

TCGGGGGGTCCGCTGTTGTGCCCCGCGGGACACGCCGTGGGCCTATTCAG

GGCCGCGGTGTGCACCCGTGGAGTGGCTAAAGCGGTGGACTTTATCCCTG

TGGAGAACCTAGAGACAACCATGAGATCCCCGGTGTTCACGGACAACTCC

TCTCCACCAGCAGTCACCCTGACGCACCCAATCACCAAAATCGATAGGGA

GGTT CTCTACCAGGAGTTCGATGAGATGGAAGAGTGCTCTCAGCACT

ATCCCTACGATGTGCCCGATTACGCTGGCGCGTCTGCATGCGCCAACTTT

AATCAAAGTGGAAACATCGCGGACAGCTCACTCAGCTTTACCTTCACCAA

TAGCAGTAACGGGCCGAACCTCATAACCACCCAGACCAACAGCCAGGCCT

TGAGCCAGCCGATCGCCTCATCTAACGTGCATGATAACTTTATGAACAAC

GAGATCACCGCGAGTAAGATAGACGACGGGAACAACAGCAAGCCCCTTAG

CCCAGGTTGGACGGACCAGACCGCCTACAACGCTTTCGGCATTACGACCG

GCATGTTCAACACCACGACCATGGACGATGTGTACAACTACCTGTTCGAT

GACGAAGACACACCGCCAAACCCCAAAAAAGAA
```

SEQ ID NO: 51 is a nucleotide sequence encoding DBGal4-NS3-TAVP32. DBGal4 is in bold, NS4A is in italics, NS3 is in bold/underlined, NS3 Cut Site is in bold/italics, NLS underlined, VP32 is in bold/italics/underlined (SEQ ID NO: 51)
```
ATGAAGTTGCTGAGCAGCATAGAGCAAGCATGTGATATCTGCCGGTTGAA

GAAGCTGAAGTGTAGCAAGGAGAAGCCCAAGTGCGCCAAGTGTCTCAAGA

ATAATTGGGAGTGTAGGTATAGCCCCAAGACCAAGCGAAGCCCGCTTACG

AGAGCACACCTTACCGAGGTCGAGAGCCGCCTGGAAAGACTCGAACAACT

TTTTCTTCTGATTTTCCCCAGGGAGGACCTGGACATGATCCTGAAGATGG

ACAGCCTCCAGGACATCAAAGCCCTTCTTACCGGGCTGTTCGTGCAGGAC

AACGTCAACAAGGATGCGGTGACCGACAGATTGGCGAGCGTGGAGACGGA
```

-continued

```
CATGCCCTTGACCCTCAGACAACATAGGATCAGCGCGACAAGCTCATCTG

AAGAATCTAGCAATAAGGGACAGCGACAGCTGACCGTTAGTgggGCGTCT

GCAggcATGGCCAGCATGACTGGTGGACAGCAAATGGGGTCGACG

GAGGACGTGGTGTGCTGCCACTCAATCTACGGCAAGAAGAAGGGTGATAT

CGACACCTACCGATACATAGGCTCTTCCGGGACAGGCTGCGTGGTCATAG

TGGGCAGGATCGTCTTGTCCGGATCCGGCACTAGTGCGCCCATCACGGCG

TACGCCCAGCAGACGAGAGGCCTCCTAGGGTGTATAATCACCAGCCTGAC

TGGCCGGGACAAAAACCAAGTGGAGGGTGAGGTCCAGATCGTGTCAACTG

CTACCCAAACCTTCCTGGCAACGTGCATCAATGGGGTATGCTGGGCAGTC

TACCACGGGGCCGAACGAGGACCATCGCATCACCCAAGGGTCCTGTCAT

CCAGATGTATACCAATGTGGACCAAGACCTTGTGGGCTGGCCCGCTCCTC

AAGGTTCCCGCTCATTGACACCCTGTACCTGCGGCTCCTCGGACCTTTAC

CTGGTCACGAGGCACGCCGATGTCATTCCCGTGCGCCGGCGAGGTGATAG

CAGGGGTAGCCTGCTTTCGCCCCGGCCCATTTCCTACTTGAAAGGCTCCT

CGGGGGGTCCGCTGTTGTGCCCCGCGGGACACGCCGTGGGCCTATTCAGG

GCCGCGGTGTGCACCCGTGGAGTGGCTAAAGCGGTGGACTTTATCCCTGT

GGAGAACCTAGAGACAACCATGAGATCCCCGGTGTTCACGGACAACTCCT

CTCCACCAGCAGTCACCCTGACGCACCCAATCACCAAAATCGATAGGGAG

GTTCTCTACCAGGAGTTCGATGAGATGGAAGAGTGCTCTCAGCACTATCC

CTACGATGTGCCCGATTACGCTGGCGCGTCGTCTGCATGCCCCAAGAAGA

AGAGGAAGGTGTCGCCAGGGATCCGTCGACTTGACGCGTTGATATCAACA

AGTTTGTACAAAAAAGCAGGCTACAAAGAGGCCAGCGGTTCCGGACGGGC

TGACGCATTGGACGATTTTGATC

TGGATATGCTGGGAAGTGACGCCCTCGATGATTTTGACCTTGACATGCTT
```

SEQ ID NO: 52 is a nucleotide sequence encoding DB$_{Gal4}$-NS3-TA$_{VP64}$. DB$_{Gal4}$ is in bold, NS4A is in italics, NS3 is in bold/underlined, NS3 Cut Site is in bold/italics, NLS is underlined, and VP64 is in bold/italics/underlined.

(SEQ ID NO: 52)
```
ATGAAGTTGCTGAGCAGCATAGAGCAAGCATGTGATATCTGCCGGTTGAA

GAAGCTGAAGTGTAGCAAGGAGAAGCCCAAGTGCGCCAAGTGTCTCAAGA

ATAATTGGGAGTGTAGGTATAGCCCCAAGACCAAGCGAAGCCCGCTTACG

AGAGCACACCTTACCGAGGTCGAGAGCCGCCTGGAAAGACTCGAACAACT

TTTTCTTCTGATTTTCCCCAGGGAGGACCTGGACATGATCCTGAAGATGG

ACAGCCTCCAGGACATCAAAGCCCTTCTTACCGGGCTGTTCGTGCAGGAC

AACGTCAACAAGGATGCGGTGACCGACAGATTGGCGAGCGTGGAGACGGA

CATGCCCTTGACCCTCAGACAACATAGGATCAGCGCGACAAGCTCATCTG

AAGAATCTAGCAATAAGGGACAGCGACAGCTGACCGTTAGTgggGCGTCT

GCAggcATGGCCAGCATGACTGGTGGACAGCAAATGGGGTCGACG

GAGGACGTGGTGTGCTGCCACTCAATCTACGGCAAGAAGAAGGGTGATAT

CGACACCTACCGATACATAGGCTCTTCCGGGACAGGCTGCGTGGTCATAG
```

*TGGGCAGGATCGTCTTGTCCGGATCCGGCACTAGT*GCGCCCATCACGGCG
TACGCCCAGCAGACGAGAGGCCTCCTAGGGTGTATAATCACCAGCCTGAC
TGGCCGGGACAAAAACCAAGTGGAGGGTGAGGTCCAGATCGTGTCAACTG
CTACCCAAACCTTCCTGGCAACGTGCATCAATGGGGTATGCTGGGCAGTC
TACCACGGGGCCGGAACGAGGACCATCGCATCACCCAAGGGTCCTGTCAT
CCAGATGTATACCAATGTGGACCAAGACCTTGTGGGCTGGCCCGCTCCTC
AAGGTTCCCGCTCATTGACACCCTGTACCTGCGGCTCCTCGGACCTTTAC
CTGGTCACGAGGCACGCCGATGTCATTCCCGTGCGCCGGCGAGGTGATAG
CAGGGGTAGCCTGCTTTCGCCCCGGCCCATTTCCTACTTGAAAGGCTCCT
CGGGGGGTCCGCTGTTGTGCCCCGCGGGACACGCCGTGGGCCTATTCAGG
GCCGCGGTGTGCACCCGTGGAGTGGCTAAAGCGGTGGACTTTATCCCTGT
GGAGAACCTAGAGACAACCATGAGATCCCCGGTGTTCACGGACAACTCCT
CTCCACCAGCAGTCACCCTGACGCACCCAATCACCAAAATCGATAGGGAG
GTT*CTCTACCAGGAGTTCGATGAGATGGAAGAGTGCTCTCAGCAC*T
ATCCCTACGATGTGCCCGATTACGCTGGCGCGTCGTCTGCATGCCCCAAG
AAGAAGAGGAAGGTGTCGCCAGGGATCCGTCGACTTGACGCGTTGATATC
AACAAGTTTGTACAAAAAAGCAGGCTACAAAGAGGCCAGCGGTTCCGGAC
GGGCT*GACGCATTGGACGATTTTGATC*
*TGGATATGCTGGGAAGTGACGCCCTCGATGATTTTGACCTTGACATGCTTGGTTCGGA*
*TGCCCTTGATGACTTTGACCTCGACATGCTCGGCAGTGACGCCCTTGATGATTTCGAC*
*CTGGACATGCTG*

SEQ ID NO: 53 is a nucleotide sequence encoding DB$_{Gal4}$-NS3-TA$_{VP64-p65}$. DB$_{Gal4}$ is in bold, NS4A is in italics, NS3 is in bold/underlined, NS3 Cut Site is in bold/italics, NLS is underlined, VP64 is in bold/italics/underlined, P65 is double underlined.

(SEQ ID NO: 53)
ATGAAGTTGCTGAGCAGCATAGAGCAAGCATGTGATATCTGCCGGTTGAA
GAAGCTGAAGTGTAGCAAGGAGAAGCCCAAGTGCGCCAAGTGTCTCAAGA
ATAATTGGGAGTGTAGGTATAGCCCCAAGACCAAGCGAAGCCCGCTTACG
AGAGCACACCTTACCGAGGTCGAGAGCCGCCTGGAAAGACTCGAACAACT
TTTTCTTCTGATTTTCCCCAGGGAGGACCTGGACATGATCCTGAAGATGG
ACAGCCTCCAGGACATCAAAGCCCTTCTTACCGGGCTGTTCGTGCAGGAC
AACGTCAACAAGGATGCGGTGACCGACAGATTGGCGAGCGTGGAGACGGA
CATGCCCTTGACCCTCAGACAACATAGGATCAGCGCGACAAGCTCATCTG
AAGAATCTAGCAATAAGGGACAGCGACAGCTGACCGTTAGTgggGCGTCT
GCAggc*ATGGCCAGCATGACTGGTGGACAGCAAATGGGGTCGACG*
*GAGGACGTGGTGTGCTGCCACTCAATCTA*
CGGCAAGAAGAAGGGTGATATCGACA
CCTACCGATACATAGGCTCTTCCGGGACAGGCTGCGTGGTCATAGTGGGC
AGGATCGTCTTGTCCGGATCCGGCACTAGTGCGCCCATCACGGCGTACGC

-continued
CCAGCAGACGAGAGGCCTCCTAGGGTGTATAATCACCAGCCTGACTGGCC
GGGACAAAAACCAAGTGGAGGGTGAGGTCCAGATCGTGTCAACTGCTACC
CAAACCTTCCTGGCAACGTGCATCAATGGGGTATGCTGGGCAGTCTACCA
CGGGGCCGGAACGAGGACCATCGCATCACCCAAGGGTCCTGTCATCCAGA
TGTATACCAATGTGGACCAAGACCTTGTGGGCTGGCCCGCTCCTCAAGGT
TCCCGCTCATTGACACCCTGTACCTGCGGCTCCTCGGACCTTTACCTGGT
CACGAGGCACGCCGATGTCATTCCCGTGCGCCGGCGAGGTGATAGCAGGG
GTAGCCTGCTTTCGCCCCGGCCCATTTCCTACTTGAAAGGCTCCTCGGGG
GGTCCGCTGTTGTGCCCCGCGGGACACGCCGTGGGCCTATTCAGGGCCGC
GGTGTGCACCCGTGGAGTGGCTAAAGCGGTGGACTTTATCCCTGTGGAGA
ACCTAGAGACAACCATGAGATCCCCGGTGTTCACGGACAACTCCTCTCCA
CCAGCAGTCACCCTGACGCACCCAATCACCAAAATCGATAGGGAGGTT
*CTCTACCAGGAGTTCGATGAGATGGAAGAGTGCTCTCAGCAC*
TATCCCTACGATGTGCCCGATTACGCTGGCGCGTCGTC
TGCATGC<u>CCCAAGAAGAAGAGGAAGGTGTCGCCAGGGATCCGTCGACTTG</u>
ACGCGTTGATATCAACAAGTTTGTACAAAAAAGCAGGCTACAAAGAGGCC
AGCGGTTCCGGACGGGCT *GACGCATTGGACGATTTTGATC*
*TGGATATGCTGGGAAGTGACGCCCTCGATGA*

-continued

_TTTTGACCTTGACATGCTTGGTTCGGA_

_TGCCCTTGATGACTTTGACCTCGACATGCTCG_

_GCAGTGACGCCCTTGATGATTTCGAC_

_CTGGACATGCTG_ATTAACTCTAGAAGTTCCGGATCT

CCGAAAAAGAAACGCAAAGTTGGTAGC
CAGTACCTGCCCGACACCGACGACC

<u>GGCACCGGATCGAGGAAAAGCGGAAGCGGACCTACGAGACATTCAAGAGC</u>

<u>ATCATGAAGAAGTCCCCCTTCAGCGGCCCCACCGACCCTAGACCTCCACC</u>

<u>TAGAAGAATCGCCGTGCCCAGCAGATCCAGCGCCAGCGTGCCAAAACCTG</u>

<u>CCCCCCAGCCTTACCCCTTCACCAGCAGCCTGAGCACCATCAACTACGAC</u>

<u>GAGTTCCCTACCATGGTGTTCCCCAGCGGCCAGATCTCTCAGGCCTCTGC</u>

<u>TCTGGCTCCAGCCCCTCCTCAGGTGCTGCCTCAGGCTCCTGCTCCTGCAC</u>

<u>CAGCTCCAGCCATGGTGTCTGCACTGGCTCAGGCACCAGCACCCGTGCCT</u>

-continued

<u>GTGCTGGCTCCTGGACCTCCACAGGCTGTGGCTCCACCAGCCCCTAAACC</u>

<u>TACACAGGCCGGCGAGGGCACACTGTCTGAAGCTCTGCTGCAGCTGCAGT</u>

<u>TCGACGACGAGGATCTGGGAGCCCTGCTGGGAAACAGCACCGATCCTGCC</u>

<u>GTGTTCACCGACCTGGCCAGCGTGGACAACAGCGAGTTCCAGCAGCTGCT</u>

<u>GAACCAGGGCATCCCTGTGGCCCCTCACACCACCGAGCCCATGCTGATGG</u>

<u>AATACCCCGAGGCCATCACCCGGCTCGTGACAGGCGCTCAGAGGCCTCCT</u>

<u>GATCCAGCTCCTGCCCCTCTGGGAGCACCAGGCCTGCCTAATGGACTGCT</u>

<u>GTCTGGCGACGAGGACTTCAGCTCTATCGCCGATATGGATTTCTCAGCCT</u>

<u>TGCTG</u>

SEQ ID NO: 54 is a nucleotide sequence encoding DB$_{Gal4}$-NS3-TA$_{VPR}$•DB$_{Gal4}$ is in bold, NS4A is in italics, NS3 is in bold/underlined, NS3 Cut Site is in bold/italics, NLS is underlined, VP64 is in bold/italics/underlined, P65 in double underlined, Rta in bold, double underlined.

(SEQ ID NO: 54)

ATGAAGTTGCTGAGCAGCATAGAGCAAGCATGTGATATCTGCCGGTTGAA

GAAGCTGAAGTGTAGCAAGGAGAAGCCCAAGTGCGCCAAGTGTCTCAAGA

ATAATTGGGAGTGTAGGTATAGCCCCAAGACCAAGCGAAGCCCGCTTACG

AGAGCACACCTTACCGAGGTCGAGAGCCGCCTGGAAAGACTCGAACAACT

TTTTCTTCTGATTTTCCCCAGGGAGGACCTGGACATGATCCTGAAGATGG

ACAGCCTCCAGGACATCAAAGCCCTTCTTACCGGGCTGTTCGTGCAGGAC

AACGTCAACAAGGATGCGGTGACCGACAGATTGGCGAGCGTGGAGACGGA

CATGCCCTTGACCCTCAGACAACATAGGATCAGCGCGACAAGCTCATCTG

AAGAATCTAGCAATAAGGGACAGCGACAGCTGACCGTTAGTgggGCGTCT

GCAggcATGGCCAGCATGACTGGTGGACAGCAAATGGGGTCGACG

_GAGGACGTGGTGTGCTGCCACTCAATCTA_

CGGCAAGAAGAAGGGTGATATCGACACCTACCGATACATAG

GCTCTTCCGGGACAGGCTGCGTGGTCATAGTGGGCAGGATCGTCTTGTCC

GGATCCGGCACTAGT<u>GCGCCCATCACGGCGTACGCCCAGCAGACGAGAGG</u>

<u>CCTCCTAGGGTGTATAATCACCAGCCTGACTGGCCGGGACAAAAACCAAG</u>

<u>TGGAGGGTGAGGTCCAGATCGTGTCAACTGCTACCCAAACCTTCCTGGCA</u>

<u>ACGTGCATCAATGGGGTATGCTGGGCAGTCTACCACGGGGCCGGAACGAG</u>

<u>GACCATCGCATCACCCAAGGGTCCTGTCATCCAGATGTATACCAATGTGG</u>

<u>ACCAAGACCTTGTGGGCTGGCCCGCTCCTCAAGGTTCCCGCTCATTGACA</u>

<u>CCCTGTACCTGCGGCTCCTCGGACCTTTACCTGGTCACGAGGCACGCCGA</u>

<u>TGTCATTCCCGTGCGCCGGCGAGGTGATAGCAGGGGTAGCCTGCTTTCGC</u>

<u>CCCGGCCCATTTCCTACTTGAAAGGCTCCTCGGGGGGTCCGCTGTTGTGC</u>

<u>CCCGCGGGACACGCCGTGGGCCTATTCAGGGCCGCGGTGTGCACCCGTGG</u>

<u>AGTGGCTAAAGCGGTGGACTTTATCCCTGTGGAGAACCTAGAGACAACCA</u>

<u>TGAGATCCCCGGTGTTCACGGACAACTCCTCT</u>CCACCAGCAGTCACCCTG

ACGCACCCAATCACCAAAATCGATAGGGAGGTT

_CTCTACCAGGAGTTCGATGAGATGGAAGAGTGCTCTCAGCAC_

-continued

```
TATCCCTACGATGTGCCCGATTACGCTGGCGCGTCGTCTGCATGC

CCCAAGAAGAAGAGGAAGGTGTCGCCAGGGATCCGTCGACTTGACGCGTT

GATATCAACAAGTTTGTACAAAAAAGCAGGCTACAAAGAGGCCAGCGGTT

CCGGACGGGCTGACGCATTGGACGATTTTGATC

TGGATATGCTGGGAAGTGACGCCCTCGATGATTTTGACCTTGACATGCTTGGTTCGGA

TGCCCTTGATGACTTTGACCTCGACATGCTCGGCAGTGACGCCCTTGATGATTTCGAC

CTGGACATGCTGATTAACTCTAGAAGTTCCGGATCTCCGAAAAAG

AAACGCAAAGTTGGTAGCCAGTACCTGCCCGACACCGACGACCGGCACCG

GATCGAGGAAAAGCGGAAGCGGACCTACGAGACATTCAAGAGCATCATGA

AGAAGTCCCCCTTCAGCGGCCCCACCGACCCTAGACCTCCACCTAGAAGA

ATCGCCGTGCCAGCAGATCCAGCGCCAGCGTGCCAAAACCTGCCCCCCA

GCCTTACCCCTTCACCAGCAGCCTGAGCACCATCAACTACGACGAGTTCC

CTACCATGGTGTTCCCCAGCGGCCAGATCTCTCAGGCCTCTGCTCTGGCT

CCAGCCCCTCCTCAGGTGCTGCCTCAGGCTCCTGCTCCTGCACCAGCTCC

AGCCATGGTGTCTGCACTGGCTCAGGCACCAGCACCCGTGCCTGTGCTGG

CTCCTGGACCTCCACAGGCTGTGGCTCCACCAGCCCCTAAACCTACACAG

GCCGGCGAGGGCACACTGTCTGAAGCTCTGCTGCAGCTGCAGTTCGACGA

CGAGGATCTGGGAGCCCTGCTGGGAAACAGCACCGATCCTGCCGTGTTCA

CCGACCTGGCCAGCGTGGACAACAGCGAGTTCCAGCAGCTGCTGAACCAG

GGCATCCCTGTGGCCCCTCACACCACCGAGCCCATGCTGATGGAATACCC

CGAGGCCATCACCCGGCTCGTGACAGGCGCTCAGAGGCCTCCTGATCCAG

CTCCTGCCCCTCTGGGAGCACCAGGCCTGCCTAATGGACTGCTGTCTGGC

GACGAGGACTTCAGCTCTATCGCCGATATGGATTTCTCAGCCTTGCTGGG

CTCTGGCAGCGGCAGCCGGGATTCCAGGGAAGGGATGTTTTTGCCGAAGC

CTGAGGCCGGCTCCGCTATTAGTGACGTGTTTGAGGGCCGCGAGGTGTGC

CAGCCAAAACGAATCCGGCCATTTCATCCTCCAGGAAGTCCATGGGCCAA

CCGCCCACTCCCCGCCAGCCTCGCACCAACACCAACCGGTCCAGTACATG

AGCCAGTCGGGTCACTGACCCCGGCACCAGTCCCTCAGCCACTGGATCCA

GCGCCCGCAGTGACTCCCGAGGCCAGTCACCTGTTGGAGGATCCCGATGA

AGAGACGAGCCAGGCTGTCAAAGCCCTTCGGGAGATGGCCGATACTGTGA

TTCCCCAGAAGGAAGAGGCTGCAATCTGTGGCCAAATGGACCTTTCCCAT

CCGCCCCCAAGGGGCCATCTGGATGAGCTGACAACCACACTTGAGTCCAT

GACCGAGGATCTGAACCTGGACTCACCCCTGACCCCGGAATTGAACGAGA

TTCTGGATACCTTCCTGAACGACGAGTGCCTCTTGCATGCCATGCATATC

AGCACAGGACTGTCCATCTTCGACACATCTCTGTTT
```

SEQ ID NO: 55 is a nucleotide sequence encoding DB$_{rTetR}$-NS3-TA$_{VP64-p65}$. rTet in bold, NS4A in italics, NS3 in bold/underlined, NS3 Cut Site in bold/italics, NLS underlined, VP64 in bold/italics/underlined, and P65 is double underlined.

(SEQ ID NO: 55)
```
ATGTCTAGACTGGACAAGAGCAAAGTCATAAACGGAGCTCTGGAATTACT

CAATGGTGTCGGTATCGAAGGCCTGACGACAAGGAAACTCGCTCAAAAGC
```

-continued

TGGGAGTTGAGCAGCCTACCCTGTACTGGCACGTGAAGAACAAGCGGGCC
CTGCTCGATGCCCTGCCAATCGAGATGCTGGACAGGCATCATACCCACTT
CTGCCCCCTGGAAGGCGAGTCATGGCAAGACTTTCTGCGGAACAACGCCA
AGTCATACCGCTGTGCTCTCCTCTCACATCGCGACGGGGCTAAAGTGCAT
CTCGGCACCCGCCCAACAGAGAAACAGTACGAAACCCTGGAAAATCAGCT
CGCGTTCCTGTGTCAGCAAGGCTTCTCCCTGGAGAACGCACTGTACGCTC
TGTCCGCCGTGGGCCACTTTACACTGGGCTGCGTATTGGAGGAACAGGAG
CATCAAGTAGCAAAAGAGGAAAGAGAGACACCTACCACCGATTCTATGCC
CCCACTTCTGAGACAAGCAATTGAGCTGTTCGACCGGCAGGGAGCCGAAC
CTGCCTTCCTTTTCGGCCTGGAACTAATCATATGTGGCCTGGAGAAACAG
CTAAAGTGCGAAAGCgggGCGTCTGCAggcATGGCCAGCATGACTGGTGG
ACAGCAAATGGGGTCGACG*GAGGACGTGGTGTGCTGCCACTCAATCTA*
CGGCAAGAAGAAGGGTGA
TATCGACACCTACCGATACATAGGCTCTTCCGGGACAGGCTGCGTGGTCA
TAGTGGGCAGGATCGTCTTGTCCGGATCCGGCACTAGTGCGCCCATCACG
GCGTACGCCCAGCAGACGAGAGGCCTCCTAGGGTGTATAATCACCAGCCT
GACTGGCCGGGACAAAAACCAAGTGGAGGGTGAGGTCCAGATCGTGTCAA
CTGCTACCCAAACCTTCCTGGCAACGTGCATCAATGGGGTATGCTGGGCA
GTCTACCACGGGGCCGGAACGAGGACCATCGCATCACCCAAGGGTCCTGT
CATCCAGATGTATACCAATGTGGACCAAGACCTTGTGGGCTGGCCCGCTC
CTCAAGGTTCCCGCTCATTGACACCCTGTACCTGCGGCTCCTCGGACCTT
TACCTGGTCACGAGGCACGCCGATGTCATTCCCGTGCGCCGGCGAGGTGA
TAGCAGGGGTAGCCTGCTTTCGCCCCGGCCCATTTCCTACTTGAAAGGCT
CCTCGGGGGTCCGCTGTTGTGCCCCGCGGGACACGCCGTGGGCCTATTC
AGGGCCGCGGTGTGCACCCGTGGAGTGGCTAAAGCGGTGGACTTTATCCC
TGTGGAGAACCTAGAGACAACCATGAGATCCCCGGTGTTCACGGACAACT
CCTCTCCACCAGCAGTCACCCTGACGCACCCAATCACCAAAATCGATAGG
GAGGTT*CTCTACCAGGAGTTCGATGAGATGGAAGAGTGCTC*

-continued

*TCAGCAC*TATCCCTACGATGTGCCCGATTA
CGCTGGCGCGTCGTCTGCATGC<u>CCCAAGAAGAAGAGGAAGGTGTCGCCAG</u>
<u>GGATCCGTCGACTTGACGCGTTGATATCAACAAGTTTGTACAAAAAAGCA</u>
<u>GGCTACAAAGAGGCCAGCGGTTCCGGACGGGCT</u>*GACGCA*
*TTGGACGATTTTGATCTGGATATGCTGG*
*GAAGTGACGCCCTCGATGATTTTG* *ACCTTG*
*ACATGCTTGGTTCGGATGCCCTTGATGA*
*CTTTGACCTCGACATGCTCGGCAG* *TGACGC*
*CCTTGATGATTTCGACCTGGACATGCTG*ATTA
ACTCTAGAAGTTCCGGATCT<u>CCGAAAAAGAAACGCAAAGTTGGTAGC</u><u>CAG</u>
<u>TACCTGCCCGACACCGACGACCGGCACCGGATCGAGGAAAAGCGGAAGCG</u>
<u>GACCTACGAGACATTCAAGAGCATCATGAAGAAGTCCCCCTTCAGCGGCC</u>
<u>CCACCGACCCTAGACCTCCACCTAGAAGAATCGCCGTGCCCAGCAGATCC</u>
<u>AGCGCCAGCGTGCCAAAACCTGCCCCCCAGCCTTACCCCTTCACCAGCAG</u>
<u>CCTGAGCACCATCAACTACGACGAGTTCCCTACCATGGTGTTCCCCAGCG</u>
<u>GCCAGATCTCTCAGGCCTCTGCTCTGGCTCCAGCCCCTCCTCAGGTGCTG</u>
<u>CCTCAGGCTCCTGCTCCTGCACCAGCTCCAGCCATGGTGTCTGCACTGGC</u>
<u>TCAGGCACCAGCACCCGTGCCTGTGCTGGCTCCTGGACCTCCACAGGCTG</u>
<u>TGGCTCCACCAGCCCCTAAACCTACACAGGCCGGCGAGGGCACACTGTCT</u>
<u>GAAGCTCTGCTGCAGCTGCAGTTCGACGACGAGGATCTGGGAGCCCTGCT</u>
<u>GGGAAACAGCACCGATCCTGCCGTGTTCACCGACCTGGCCAGCGTGGACA</u>
<u>ACAGCGAGTTCCAGCAGCTGCTGAACCAGGGCATCCCTGTGGCCCCTCAC</u>
<u>ACCACCGAGCCCATGCTGATGGAATACCCCGAGGCCATCACCCGGCTCGT</u>
<u>GACAGGCGCTCAGAGGCCTCCTGATCCAGCTCCTGCCCCTCTGGGAGCAC</u>
<u>CAGGCCTGCCTAATGGACTGCTGTCTGGCGACGAGGACTTCAGCTCTATC</u>
<u>GCCGATATGGATTTCTCAGCCTTGCTG</u>

SEQ ID NO: 58 is a nucleotide sequence encoding myr-palm-NS3-Gal4$_{min}$. Myr-palm in bold/italics/underlined, NS4A in italics, NS3 in bold/underlined, NS3 Cut Site in bold/italics, DB$_{Gal4}$ in bold, TA$_{Gal4}$ is double underlined.

(SEQ ID NO: 58)
<u>ATGGGCTGCATCAAGAGCAAGCGCAAGGACAACCTGAACGACGACGGCGTGGACATG</u>
<u>AAG</u>CGTACGATGGCCAGCATGACTGGTGGACAGCAAATGGGGTCGACG
*GAGGACGTGGTGTGCTGCCACTCAATCTAC*GGCAAGAAGAAGG
GTGATATCGACACCTACCGATACATAGGCTCTTCCGGGACA*GGCTGCGTG*
*GTCATAGTGGGCAGGATCGTCTTGTCCGGATCCGGCACTAGT*<u>GCGCCCAT</u>
<u>CACGGCGTACGCCCAGCAGACGAGAGGCCTCCTAGGGTGTATAATCACCA</u>
<u>GCCTGACTGGCCGGGACAAAAACCAAGTGGAGGGTGAGGTCCAGATCGTG</u>
<u>TCAACTGCTACCCAAACCTTCCTGGCAACGTGCATCAATGGGGTATGCTG</u>
<u>GGCAGTCTACCACGGGGCCGGAACGAGGACCATCGCATCACCCAAGGGTC</u>
<u>CTGTCATCCAGATGTATACCAATGTGGACCAAGACCTTGTGGGCTGGCCC</u>

-continued

<u>GCTCCTCAAGGTTCCCGCTCATTGACACCCTGTACCTGCGGCTCCTCGGA</u>

<u>CCTTTACCTGGTCACGAGGCACGCCGATGTCATTCCCGTGCGCCGGCGAG</u>

<u>GTGATAGCAGGGGTAGCCTGCTTTCGCCCCGGCCCATTTCCTACTTGAAA</u>

<u>GGCTCCTCGGGGGGTCCGCTGTTGTGCCCCGCGGGACACGCCGTGGGCCT</u>

<u>ATTCAGGGCCGCGGTGTGCACCCGTGGAGTGGCTAAAGCGGTGGACTTTA</u>

<u>TCCCTGTGGAGAACCTAGAGACAACCATGAGATCCCCGGTGTTCACGGAC</u>

<u>AACTCCTCTCCA</u>CCAGCAGTCACCCTGACGCACCCAATCACCAAAATCGA

TAGGGAGGTT*CTCTACCAGGAGTTCG*

*ATGAGATGGAAGAGTGCTCTCAGCAC*TATCCCTACGATGTGCCCG

ATTACGCTGGCGCGTCTGCATGCGGTACCATGAAGTTGCTGAGCAGCATA

GAGCAAGCATGTGATATCTGCCGGTTGAAGAAGCTGAAGTGTAGCAAGGA

GAAGCCCAAGTGCGCCAAGTGTCTCAAGAATAATTGGGAGTGTAGGTATA

GCCCCAAGACCAAGCGAAGCCCGCTTACGAGAGCACACCTTACCGAGGTC

GAGAGCCGCCTGGAAAGACTCGAACAACTTTTTCTTCTGATTTTCCCCAG

GGAGGACCTGGACATGATCCTGAAGATGGACAGCCTCCAGGACATCAAAG

CCCTTCTTACCGGGCTGTTCGTGCAGGACAACGTCAACAAGGATGCGGTG

ACCGACAGATTGGCGAGCGTGGAGACGGACATGCCCTTGACCCTCAGACA

ACATAGGATCAGCGCGACAAGCTCATCTGAAGAATCTAGCAATAAGGGAC

AGCGACAGCTGACCGTTAGTGCCAACTTTAATCAAAGTGGAAACATCGCG

GACAGCTCACTCAGCTTTACCTTCACCAATAGCAGTAACGGGCCGAACCT

CATAACCACCCAGACCAACAGCCAGGCCTTGAGCCAGCCGATCGCCTCAT

CTAACGTGCATGATAACTTTATGAACAACGAGATCACCGCGAGTAAGATA

<u>GACGACGGGAACAACAGCAAGCCCCTTAGCCCAGGTTGGACGGACCAGAC</u>

<u>CGCCTACAACGCTTTCGGCATTACGACCGGCATGTTCAACACCACGACCA</u>

<u>TGGACGATGTGTACAACTACCTGTTCGATGACGAAGACACACCGCCAAAC</u>

<u>CCCAAAAAAGAA</u>

SEQ ID NOs 62-64 are nucleotide sequences encoding sgRNAs, e.g., used herein. These sequences are further described in Zalatan et al. *Cell.* 2015., Nihongaki et al., Nature Chem Bio. 2015, which are incorporated herein by reference in their entireties.

sgC2[1]

SEQ ID NO: 62

GCAGACGCGAGGAAGGAGGGCGC

-continued sgC3[1]

SEQ ID NO: 63

GCCTCTGGGAGGTCCTGTCCGGCTC

GAL4 sgRNA1[2]

SEQ ID NO: 64

TGGGTCTTCGGAGGACAGTACTC

SEQ ID NO: 65 is a nucleotide sequence encoding NS3-Dll1-mCherry. Signal sequence in bold, Rat Dll1 ECD in italics, NS3 cut site underlined, NS4A in bold/italics, NS3 in bold/underlined, Rat Dll1 TMD/ICD in bold/italics/underlined, mCherry in double underlined.

(SEQ ID NO: 65)

ATGGGCCGTCGGAGCGCTCTAGCCCTTGCCGTGGTCTCAGCCCTGCTGTGCCCA

*GGTCTGGAGCTCTGGCGTATTTGAGCTGAAGCTGCAGGAGTTCGTCAACAAGAAGGGGCT*

*GCTGGGGAACCGCAACTGCTGCCGCGGGGGCTCTGGCCCGCCGTGCGCCTGCAGGACC*

*TTCTTTCGCGTATGCCTCAAGCATTACCAGGCCAGCGTGTCCCCGGAGCCACCCTGCACC*

*TACGGCAGTGCGGTCACCGCAGTGCTGGGTGTCGACTCCTTCAGCCTGCCTGATGGCGC*

-continued

```
AGGCATCGACCCCGCCTTCAGCAACCCCATCCGATTCCCCTTCGGATTCACCTGGCCAGG

TACCTTCTCTCTGATCATTGAAGCCCTCCACACAGATTCTCCTGACGACCTCGCAACAGAA

AACCCAGAAAGACTCATCAGCCGCCTGACCACACAGAGGCACCTCACTGTGGGAGAAGAG

TGGTCTCAGGACCTTCACAGTAGCGGCCGCACAGACCTCCGCTACTCTTACCGGTTTGTG

TGTGATGAACACTACTATGGAGAAGGCTGCTCCGTGTTCTGCCGACCGCGGGATGATGCC

TTTGGCCACTTCACCTGCGGGGAGAGAGGGGAGAAGATGTGCGACCCTGGCTGGAAAGG

CCAGTACTGCACTGACCCCATTTGTCTGCCAGGCTGTGATGACCAACATGGATATTGTGAC

AAACCGGGGGAATGCAAGTGCAGAGTTGGCTGGCAGGGCCGCTACTGCGATGAATGCAT

CCGATACCCAGGCTGTCTCCATGGTACCTGCCAGCAGCCCTGGCAGTGTAACTGCCAGGA

AGGCTGGGGGGCCTCTTCTGCAACCAGGATCTGAACTACTGCACTCACCATAAGCCATG

CAGGAACGGAGCCACCTGCACCAACACGGGCCAGGGGAGCTACACATGCTCTTGCCGAC

CCGGGTATACAGGGGCCAACTGTGAGCTGGAGGTAGATGAGTGTGCTCCCAGCCCCTGC

AGGAATGGAGGGAGCTGCACGGATCTTGAGGACAGCTACTCTTGCACCTGCCCTCCTGG

CTTCTATGGCAAGGTCTGTGAGCTGAGCGCCATGACGTGTGCAGATGGTCCTTGCTTCAA

TGGGGGACGATGTTCGGATAACCCCGATGGAGGCTACACCTGCCATTGCCCTGCGGGCT

TCTCTGGCTTCAACTGTGAGAAGAAGATTGATCTCTGTAGCTCTTCCCCTTGTTCTAACGGT

GCCAAGTGTGTGGACCTCGGCAACTCCTACCTGTGCCGATGTCAGACTGGCTTCTCCGGG

AGGTACTGCGAGGACAATGTGGATGACTGTGCCTCTTCTCCCTGTGCAAACGGGGGCACC

TGCCGGGACAGTGTGAACGATTTCTCCTGTACCTGCCCACCTGGCTACACAGGCAGGAAC

TGCAGCGCCCCTGTCAGCAGGTGTGAGCATGCACCCTGTCATAACGGGGCCACCTGCCA

CCAGAGGGGCCAACGCTACATGTGTGAGTGCGCCCAGGGCTATGGCGGCGCCAACTGCC

AGTTCCTGCTCCCTGAGCCACCACCAGACCTCATAGTGGCGGCCCAGGGCGGGTCCTTC

CCCTGGAGCAGGGCTGACATGGCCAGCATGACTGGTGGACAGCAAATGGGGTCGAC

GGAGGACGTGGTGTGCTGCCACTCAATCTACGGCAAGAAGAAGGGTGATATCGACA

CCTACCGATACATAGGCTCTTCCGGGACA***GGCTGCGTGGTCATAGTGGGCAGGATCG***

*TCTTGTCCGGA*TCCGGCACTAGTGCGCCCATCACGGCGTACGCCCAGCAGACGAG

AGGCCTCCTAGGGTGTATAATCACCAGCCTGACTGGCCGGGACAAAAACCAAG

TGGAGGGTGAGGTCCAGATCGTGTCAACTGCTACCCAAACCTTCCTGGCAACG

TGCATCAATGGGGTATGCTGGGCAGTCTACCACGGGGCCGGAACGAGGACCAT

CGCATCACCCAAGGGTCCTGTCATCCAGATGTATACCAATGTGGACCAAGACCT

TGTGGGCTGGCCCGCTCCTCAAGGTTCCCGCTCATTGACACCCTGTACCTGCG

GCTCCTCGGACCTTTACCTGGTCACGAGGCACGCCGATGTCATTCCCGTGCGC

CGGCGAGGTGATAGCAGGGGTAGCCTGCTTTCGCCCCGGCCCATTTCCTACTT

GAAAGGCTCCTCGGGGGGTCCGCTGTTGTGCCCCGCGGGACACGCCGTGGGCC

TATTCAGGGCCGCGGTGTGCACCCGTGGAGTGGCTAAAGCGGTGGACTTTATC

CCTGTGGAGAACCTAGAGACAACCATGAGATCCCCGGTGTTCACGGACAACTC

CTCT**CCACCAGCAGTCACCCTGACGCACCCAATCACCAAAATCGATAGGGAGGTTC

TCTACCAGGAGTTCGATGAGATGGAAGAGTGCTCTCAGCAC**TATCCCTACGATGTGC

CCGATTACGCTGGCGCGTCTGCA***GTGGCTGTGTGTGCCGGGGTGGTGCTTGTCCTCC***

*TGCTGCTGCTGGGCTGTGCTGCTGTGGTGGTCTGCGTCCGGCTGAAGCTACAGAAACA*
```

*CCAGCCTCCGCCTGATCCTTGCGGGGAGAGACAGAGACCATGAACAACCTAGCCAA*
*TTGCCAGCGTCAGAAGGATGTTTCTGTTAGCATCATTGGGGCTACACAGATCAAGAAC*
*ACCAACAAGAAGGCGGACTTTCATGGGACCATGGTGCTGACAAGAGCAGCTTTAAG*
*GCCCGATACCCCACTGTGGACTATAACCTCATTCGAGACCTCAAGGGAGATGAAGCCA*
*CGGTCAGGGATGCACACAGCAAACGTGACACCAAGTGCCAGTCACAGGGCTCTGTAG*
*GAGAAGAGAAGAGCACCTCAACGCTCAGGGGTGGGGAGGTTCCCGACAGAAAAAGGC*
*CCGAGTCTGTCTACTCTACTTCAAAGGACACCAAGTACCAGTCGGTGTATGTTCTATCT*
*GCAGAAAAGGATGAGTGTGTTATAGCGACTGAGGTT*GTGAGCAAGGGCGAGGAGGAT
AACATGGCCATCATCAAGGAGTTCATGCGCTTCAAGGTGCACATGGAGGGCTCCGTG
AACGGCCACGAGTTCGAGATCGAGGGCGAGGGCGAGGGCCGCCCCTACGAGGGCAC
CCAGACCGCCAAGCTGAAGGTGACCAAGGGTGGCCCCCTGCCCTTCGCCTGGGACA
TCCTGTCCCCTCAGTTCATGTACGGCTCCAAGGCCTACGTGAAGCACCCCGCCGACA
TCCCCGACTACTTGAAGCTGTCCTTCCCCGAGGGCTTCAAGTGGGAGCGCGTGATGA
ACTTCGAGGACGGCGGCGTGGTGACCGTGACCCAGGACTCCTCCCTGCAGGACGGC
GAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGA
CGGCGCCCTGAAGGGCGAGATCAAGCAGAGGCTGAAGCTGAAGGACGGCGGCCACT
ACGACGCTGAGGTCAAGACCACCTACAAGGCCAAGAAGCCCGTGCAGCTGCCCGGC
GCCTACAACGTCAACATCAAGTTGGACATCACCTCCCACAACGAGGACTACACCATC
GTGGAACAGTACGAACGCGCCGAGGGCCGCCACTCCACCGGCGGCATGGACGAGCT
GTACAAGTCT

SEQ ID NO: 66 is a nucleotide sequence encoding hN1.

(SEQ ID NO: 66)
ATGCCGCCGCTCCTGGCGCCCCTGCTCTGCCTGGCGCTGCTGCCCGCGCT
CGCCGCACGAGGCCCGCGATGCTCCCAGCCCGGTGAGACCTGCCTGAATG
GCGGGAAGTGTGAAGCGGCCAATGGCACGGAGGCCTGCGTCTGTGGCGG
GCCTTCGTGGGCCCGCGATGCCAGGACCCCAACCCGTGCCTCAGCACCCC
CTGCAAGAACGCCGGGACATGCCACGTGGTGGACCGCAGAGGCGTGGCAG
ACTATGCCTGCAGCTGTGCCCTGGGCTTCTCTGGGCCCCTCTGCCTGACA
CCCCTGGACAATGCCTGCCTCACCAACCCCTGCCGCAACGGGGGCACCTG
CGACCTGCTCACGCTGACGGAGTACAAGTGCCGCTGCCCGCCCGGCTGGT
CAGGGAAATCGTGCCAGCAGGCTGACCCGTGCGCCTCCAACCCCTGCGCC
AACGGTGGCCAGTGCCTGCCCTTCGAGGCCTCCTACATCTGCCACTGCCC
ACCCAGCTTCCATGGCCCCACCTGCCGGCAGGATGTCAACGAGTGTGGCC
AGAAGCCCGGGCTTTGCCGCCACGGAGGCACCTGCCACAACGAGGTCGGC
TCCTACCGCTGCGTCTGCCGCGCCACCCACACTGGCCCCAACTGCGAGCG
GCCCTACGTGCCCTGCAGCCCCTCGCCCTGCCAGAACGGGGGCACCTGCC
GCCCACGGGCGACGTCACCCACGAGTGTGCCTGCCTGCCAGGCTTCACC
GGCCAGAACTGTGAGGAAAATATCGACGATTGTCCAGGAAACAACTGCAA
GAACGGGGGTGCCTGTGTGGACGGCGTGAACACCTACAACTGCCGCTGCC

CGCCAGAGTGGACAGGTCAGTACTGTACCGAGGATGTGGACGAGTGCCAG
CTGATGCCAAATGCCTGCCAGAACGGCGGGACCTGCCACAACACCCACGG
TGGCTACAACTGCGTGTGTGTCAACGGCTGGACTGGTGAGGACTGCAGCG
AGAACATTGATGACTGTGCCAGCGCCGCCTGCTTCCACGGCGCCACCTGC
CATGACCGTGTGGCCTCCTTCTACTGCGAGTGTCCCCATGGCCGCACAGG
TCTGCTGTGCCACCTCAACGACGCATGCATCAGCAACCCCTGTAACGAGG
GCTCCAACTGCGACACCAACCCTGTCAATGGCAAGGCCATCTGCACCTGC
CCCTCGGGGTACACGGGCCCGGCCTGCAGCCAGGACGTGGATGAGTGCTC
GCTGGGTGCCAACCCCTGCGAGCATGCGGGCAAGTGCATCAACACGCTGG
GCTCCTTCGAGTGCCAGTGTCTGCAGGGCTACACGGGCCCCCGATGCGAG
ATCGACGTCAACGAGTGCGTCTCGAACCCGTGCCAGAACGACGCCACCTG
CCTGGACCAGATTGGGGAGTTCCAGTGCATCTGCATGCCCGGCTACGAGG
GTGTGCACTGCGAGGTCAACACAGACGAGTGTGCCAGCAGCCCCTGCCTG
CACAATGGCCGCTGCCTGGACAAGATCAATGAGTTCCAGTGCGAGTGCCC
CACGGGCTTCACTGGGCATCTGTGCCAGTACGATGTGGACGAGTGTGCCA
GCACCCCCTGCAAGAATGGTGCCAAGTGCCTGGACGGACCCAACACTTAC
ACCTGTGTGTGCACGGAAGGGTACACGGGGACGCACTGCGAGGTGGACAT
CGATGAGTGCGACCCCGACCCCTGCCACTACGGCTCCTGCAAGGACGGCG

-continued

TCGCCACCTTCACCTGCCTCTGCCGCCCAGGCTACACGGGCCACCACTGC
GAGACCAACATCAACGAGTGCTCCAGCCAGCCCTGCCGCCACGGGGGCAC
CTGCCAGGACCGCGACAACGCCTACCTCTGCTTCTGCCTGAAGGGGACCA
CAGGACCCAACTGCGAGATCAACCTGGATGACTGTGCCAGCAGCCCTGC
GACTCGGGCACCTGTCTGGACAAGATCGATGGCTACGAGTGTGCCTGTGA
GCCGGGCTACACAGGGAGCATGTGTAACATCAACATCGATGAGTGTGCGG
GCAACCCCTGCCACAACGGGGGCACCTGCGAGGACGGCATCAATGGCTTC
ACCTGCCGCTGCCCCGAGGGCTACCACGACCCCACCTGCCTGTCTGAGGT
CAATGAGTGCAACAGCAACCCCTGCGTCCACGGGGCCTGCCGGGACAGCC
TCAACGGGTACAAGTGCGACTGTGACCCTGGGTGGAGTGGGACCAACTGT
GACATCAACAACAATGAGTGTGAATCCAACCCTTGTGTCAACGGCGGCAC
CTGCAAAGACATGACCAGTGGCTACGTGTGCACCTGCCGGGAGGGCTTCA
GCGGTCCCAACTGCCAGACCAACATCAACGAGTGTGCGTCCAACCCATGT
CTGAACCAGGGCACGTGTATTGACGACGTTGCCGGGTACAAGTGCAACTG
CCTGCTGCCCTACACAGGTGCCACGTGTGAGGTGGTGCTGGCCCCGTGTG
CCCCCAGCCCCTGCAGAAACGGCGGGGAGTGCAGGCAATCCGAGGACTAT
GAGAGCTTCTCCTGTGTCTGCCCCACGGGCTGGCAAGCAGGGCAGACCTG
TGAGGTCGACATCAACGAGTGCGTTCTGAGCCCGTGCCGGCACGGCCAT
CCTGCCAGAACACCCACGGCGGCTACCGCTGCCACTGCCAGGCCGGCTAC
AGTGGGCGCAACTGCGAGACCGACATCGACGACTGCCGGCCCAACCCGTG
TCACAACGGGGGCTCCTGCACAGACGGCATCAACACGGCCTTCTGCGACT
GCCTGCCCGGCTTCCGGGGCACTTTCTGTGAGGAGGACATCAACGAGTGT
GCCAGTGACCCCTGCCGCAACGGGGCCAACTGCACGGACTGCGTGGACAG
CTACACGTGCACCTGCCCCGCAGGCTTCAGCGGGATCCACTGTGAGAACA
ACACGCCTGACTGCACAGAGAGCTCCTGCTTCAACGGTGGCACCTGCGTG
GACGGCATCAACTCGTTCACCTGCCTGTGTCCACCCGGCTTCACGGGCAG
CTACTGCCAGCACGATGTCAATGAGTGCGACTCACAGCCCTGCCTGCATG
GCGGCACCTGTCAGGACGGCTGCGGCTCCTACAGGTGCACCTGCCCCCAG
GGCTACACTGGCCCAACTGCCAGAACCTTGTGCACTGGTGTGACTCCTC
GCCCTGCAAGAACGGCGGCAAATGCTGGCAGACCCACACCCAGTACCGCT
GCGAGTGCCCCAGCGGCTGGACCGGCCTTTACTGCGACGTGCCCAGCGTG
TCCTGTGAGGTGGCTGCGCAGCGACAAGGTGTTGACGTTGCCCGCCTGTG
CCAGCATGGAGGGCTCTGTGTGGACGCGGGCAACACGCACCACTGCCGCT
GCCAGGCGGGCTACACAGGCAGCTACTGTGAGGACCTGGTGGACGAGTGC
TCACCCAGCCCCTGCCAGAACGGGGCCACCTGCACGGACTACCTGGGCGG
CTACTCCTGCAAGTGCGTGGCCGGCTACCACGGGGTGAACTGCTCTGAGG
AGATCGACGAGTGCCTCTCCCACCCCTGCCAGAACGGGGCACCTGCCTC
GACCTCCCCAACACCTACAAGTGCTCCTGCCCACGGGGCACTCAGGGTGT
GCACTGTGAGATCAACGTGGACGACTGCAATCCCCCCGTTGACCCCGTGT
CCCGGAGCCCCAAGTGCTTTAACAACGGCACCTGCGTGGACCAGGTGGGC

GGCTACAGCTGCACCTGCCCGCCGGGCTTCGTGGGTGAGCGCTGTGAGGG
GGATGTCAACGAGTGCCTGTCCAATCCCTGCGACGCCCGTGGCACCCAGA
ACTGCGTGCAGCGCGTCAATGACTTCCACTGCGAGTGCCGTGCTGGTCAC
ACCGGGCGCCGCTGCGAGTCCGTCATCAATGGCTGCAAAGGCAAGCCCTG
CAAGAATGGGGGCACCTGCGCCGTGGCCTCCAACACCGCCCGCGGGTTCA
TCTGCAAGTGCCCCTGCGGGCTTCGAGGGCGCCACGTGTGAGAATGACGCT
CGTACCTGCGGCAGCCTGCGCTGCCTCAACGGCGGCACATGCATCTCCGG
CCCGCGCAGCCCCACCTGCCTGTGCCTGGGCCCCTTCACGGGCCCCGAAT
GCCAGTTCCCGGCCAGCAGCCCCTGCCTGGGCGGCAACCCCTGCTACAAC
CAGGGGACCTGTGAGCCCACATCCGAGAGCCCCTTCTACCGTTGCCTGTG
CCCCGCCAAATTCAACGGGCTCTTGTGCCACATCCTGGACTACAGCTTCG
GGGGTGGGGCCGGGCGCGACATCCCCCCGCCGCTGATCGAGGAGGCGTGC
GAGCTGCCCGAGTGCCAGGAGGACGCGGGCAACAAGGTCTGCAGCCTGCA
GTGCAACAACCACGCGTGCGGCTGGGACGGCGGTGACTGCTCCCTCAACT
TCAATGACCCCTGGAAGAACTGCACGCAGTCTCTGCAGTGCTGGAAGTAC
TTCAGTGACGGCCACTGTGACAGCCAGTGCAACTCAGCCGGCTGCCTCTT
CGACGGCTTTGACTGCCAGCGTGCGGAAGGCCAGTGCAACCCCCTGTACG
ACCAGTACTGCAAGGACCACTTCAGCGACGGGCACTGCGACCAGGGCTGC
AACAGCGCGGAGTGCGAGTGGGACGGCTGGACTGTGCGGAGCATGTACC
CGAGAGGCTGGCGGCCGGCACGCTGGTGGTGGTGCTGATGCCGCCGG
AGCAGCTGCGCAACAGCTCCTTCCACTTCCTGCGGGAGCTCAGCCGCGTG
CTGCACACCAACGTGGTCTTCAAGCGTGACGCACACGGCCAGCAGATGAT
CTTCCCCTACTACGGCCGCGAGGAGGAGCTGCGCAAGCACCCCATCAAGC
GTGCCGCCGAGGGCTGGGCCGCACCTGACGCCCTGCTGGGCCAGGTGAAG
GCCTCGCTGCTCCCTGGTGGCAGCGAGGGTGGGCGGCGGCGGAGGGAGCT
GGACCCCATGGACGTCCGCGGCTCCATCGTCTACCTGGAGATTGACAACC
GGCAGTGTGTGCAGGCCTCCTCGCAGTGCTTCCAGAGTGCCACCGACGTG
GCCGCATTCCTGGGAGCGCTCGCCTCGCTGGGCAGCCTCAACATCCCCTA
CAAGATCGAGGCCGTGCAGAGTGAGACCGTGGAGCCGCCCCCGCCGGCGC
AGCTGCACTTCATGTACGTGGCGGCGGCCGCCTTTGTGCTTCTGTTCTTC
GTGGGCTGCGGGGTGCTGCTGTCCCGCAAGCGCCGGCGGCAGCATGGCCA
GCTCTGGTTCCCTGAGGGCTTCAAAGTGTCTGAGGCCAGCAAGAAGAAGC
GGCGGGAGCCCCTCGGCGAGGACTCCGTGGGCCTCAAGCCCCTGAAGAAC
GCTTCAGACGGTGCCCTCATGGACGACAACCAGAATGAGTGGGGGGACGA
GGACCTGGAGACCAAGAAGTTCCGGTTCGAGGAGCCCGTGGTTCTGCCTG
ACCTGGACGACCAGACAGACCACCGGCAGTGGACTCAGCAGCACCTGGAT
GCCGCTGACCTGCGCATGTCTGCCATGGCCCCACACCGCCCCAGGGTGA
GGTTGACGCCGACTGCATGGACGTCAATGTCCGCGGGCCTGATGGCTTCA
CCCCGCTCATGATCGCCTCCTGCAGCGGGGGCGGCCTGGAGACGGGCAAC
AGCGAGGAAGAGGAGGACGCGCCGGCCGTCATCTCCGACTTCATCTACCA
GGGCGCCAGCCTGCACAACCAGACAGACCGCACGGGCGAGACCGCCTTGC

-continued

```
ACCTGGCCGCCCGCTACTCACGCTCTGATGCCGCCAAGCGCCTGCTGGAG
GCCAGCGCAGATGCCAACATCCAGGACAACATGGGCCGCACCCCGCTGCA
TGCGGCTGTGTCTGCCGACGCACAAGGTGTCTTCCAGATCCTGATCCGGA
ACCGAGCCACAGACCTGGATGCCCGCATGCATGATGGCACGACGCCACTG
ATCCTGGCTGCCCGCCTGGCCGTGGAGGGCATGCTGGAGGACCTCATCAA
CTCACACGCCGACGTCAACGCCGTAGATGACCTGGGCAAGTCCGCCCTGC
ACTGGGCCGCCGCCGTGAACAATGTGGATGCCGCAGTTGTGCTCCTGAAG
AACGGGGCTAACAAAGATATGCAGAACAACAGGGAGGAGACACCCCTGTT
TCTGGCCGCCCGGGAGGGCAGCTACGAGACCGCCAAGGTGCTGCTGGACC
ACTTTGCCAACCGGGACATCACGGATCATATGGACCGCCTGCCGCGCGAC
ATCGCACAGGAGCGCATGCATCACGACATCGTGAGGCTGCTGGACGAGTA
CAACCTGGTGCGCAGCCCGCAGCTGCACGGAGCCCCGCTGGGGGCACGC
CCACCCTGTCGCCCCCGCTCTGCTCGCCCAACGGCTACCTGGGCAGCCTC
AAGCCCGGCGTGCAGGGCAAGAAGGTCCGCAAGCCCAGCAGCAAAGGCCT
GGCCTGTGGAAGCAAGGAGGCCAAGGACCTCAAGGCACGGAGGAAGAAGT
CCCAGGACGGCAAGGGCTGCCTGCTGGACAGCTCCGGCATGCTCTCGCCC
GTGGACTCCCTGGAGTCACCCCATGGCTACCTGTCAGACGTGGCCTCGCC
GCCACTGCTGCCCTCCCCGTTCCAGCAGTCTCCGTCCGTGCCCCTCAACC
ACCTGCCTGGGATGCCCGACACCCACCTGGGCATCGGGCACCTGAACGTG
GCGGCCAAGCCCGAGATGGCGGCGCTGGGTGGGGCGGCCGGCTGGCCTT
TGAGACTGGCCCACCTCGTCTCTCCCACCTGCCTGTGGCCTCTGGCACCA
GCACCGTCCTGGGCTCCAGCAGCGGAGGGGCCCTGAATTTCACTGTGGGC
GGGTCCACCAGTTTGAATGGTCAATGCGAGTGGCTGTCCCGGCTGCAGAG
CGGCATGGTGCCGAACCAATACAACCCTCTGCGGGGAGTGTGGCACCAG
GCCCCCTGAGCACACAGGCCCCCTCCCTGCAGCATGGCATGGTAGGCCCG
CTGCACAGTAGCCTTGCTGCCAGCGCCCTGTCCCAGATGATGAGCTACCA
GGGCCTGCCCAGCACCCGGCTGGCCACCCAGCCTCACCTGGTGCAGACCC
AGCAGGTGCAGCCACAAAACTTACAGATGCAGCAGCAGAACCTGCAGCCA
GCAAACATCCAGCAGCAGCAAAGCCTGCAGCCGCCACCACCACCACCACA
GCCGCACCTTGGCGTGAGCTCAGCAGCCAGCGGCCACCTGGGCCGGAGCT
TCCTGAGTGGAGAGCCGAGCCAGGCAGACGTGCAGCCACTGGGCCCCAGC
AGCCTGGCGGTGCACACTATTCTGCCCCAGGAGAGCCCCGCCCTGCCCAC
GTCGCTGCCATCCTCGCTGGTCCCACCCGTGACCGCAGCCCAGTTCCTGA
CGCCCCCCTCGCAGCACAGCTACTCCTCGCCTGTGGACAACACCCCCAGC
CACCAGCTACAGGTGCCTGAGCACCCCTTCCTCACCCCGTCCCCTGAGTC
CCCTGACCAGTGGTCCAGCTCGTCCCCGCATTCCAACGTCTCCGACTGGT
CCGAGGGCGTCTCCAGCCCTCCCACCAGCATGCAGTCCCAGATCGCCCGC
ATTCCGGAGGCCTTCAAGGCTAGCTAA.
```

SEQ ID NO: 67 is a nucleotide sequence encoding myc-moxGFP-mN1TMD-GAL4-VP64.

(SEQ ID NO: 67)
```
GCCACCATGGCATTGCCCGTGACCGCCCTGCTGCTGCCACTGGCCTTGTT
GCTCCACGCCGCGCGGCCAGAACAGAAGCTGATCAGCGAGGAGGATCTGA
CCGGTGTGAGCAAGGGCGAGGAGCTGTTCACCGGGGTGGTGCCCATCCTG
GTCGAGCTGGACGGCGACGTAAACGGCCACAAGTTCTCCGTGCGGGGCGA
GGGCGAGGGCGATGCCACCAACGGCAAGCTGACCCTGAAGTTCATCAGCA
CCACCGGCAAGCTGCCCGTGCCCTGGCCCACCCTCGTGACCACCCTGACC
TACGGCGTGCAGAGCTTCTCCCGCTACCCCGACCACATGAAGCGCCACGA
CTTCTTCAAGAGCGCCATGCCCGAAGGCTACGTCCAGGAGCGCACCATCT
CCTTCAAGGACGACGGCACCTACAAGACCCGCGCCGAGGTGAAGTTCGAG
GGCGACACCCTGGTGAACCGCATCGAGCTGAAGGGCATCGACTTCAAGGA
GGACGGCAACATCCTGGGGCACAAGCTGGAGTACAACTTCAACTCCCACA
ACGTCTATATCACCGCCGACAAGCAGAAGAACGGCATCAAGGCCAACTTC
AAGATCCGCCACAACGTGGAGGACGGCTCCGTGCAGCTCGCCGACCACTA
CCAGCAGAACACCCCCATCGGCGACGGCCCCGTGCTGCTGCCCGACAACC
ACTACCTGTCCACCCAGTCCAAGCTGTCCAAAGACCCCAACGAGAAGCGC
GATCACATGGTCCTTCTGGAATTCGTGACCGCCGCCGGGATCACTCACGG
CATGGACGAGCTGTACAAGGGATCCCCGGTGGAGCCTCCGCTGCCCTCGC
AGCTGCACCTCATGTACGTGGCAGCGGCCGCCTTCGTGCTCCTGTTCTTT
GTGGGCTGTGGGGTGCTGCTGTCCCGCAAGCGCCGGCGGGGCTCGAGCAT
GAAGCTGCTGAGCAGCATCGAGCAGGCCTGTGACATCTGCCGGCTGAAGA
AACTGAAGTGCAGCAAAGAAAAGCCCAAGTGCGCCAAGTGCCTGAAGAAC
AACTGGGAGTGCCGGTACAGCCCCAAGACCAAGAGAAGCCCCCTGACCAG
AGCCCACCTGACCGAGGTGGAAAGCCGGCTGGAAAGACTGGAACAGCTGT
TTCTGCTGATCTTCCCACGCGAGGACCTGGACATGATCCTGAAGATGGAC
AGCCTGCAGGACATCAAGGCCCTGCTGACCGGCCTGTTCGTGCAGGACAA
CGTGAACAAGGACGCCGTGACCGACAGACTGGCCAGCGTGGAAACCGACA
TGCCCCTGACCCTGCGGCAGCACAGAATCAGCGCCACCAGCAGCAGCGAG
GAAAGCAGCAACAAGGGCCAGCGGCAGCTGACAGTGTCTGCTGCTGCAGG
CGGAAGCGGAGGCTCTGGCGGATCTGATGCCCTGGACGACTTCGACCTGG
ATATGCTGGGCAGCGACGCCCTGGATGATTTTGATCTGGACATGCTGGGA
TCTGACGCTCTGGACGATTTCGATCTCGACATGTTGGGATCAGATGCACT
GGATGACTTTGACCTGGACATGCTCGGATCATGA
```

The invention claimed is:

1. A synthetic inhibitor or auto-inhibitory protein comprising a Notch NRR (Negative Regulatory Region)-binding scFV fused to a transmembrane domain.

2. The synthetic protein of claim 1, wherein the Notch NRR comprises a Notch NRR1 of SEQ ID NO: 8.

3. The synthetic protein of claim 1, wherein the Notch NRR is mutated relative to Notch NRR1 of SEQ ID NO: 8.

4. The synthetic protein of claim 1, further comprising a synthetic Notch receptor protein comprising a mutated Notch NRR.

5. The synthetic protein of claim 1, wherein the transmembrane domain comprises the human Notch1 transmembrane domain of SEQ ID NO: 13.

6. The synthetic protein of claim 1, wherein the scFV comprises, from N-terminal to C-terminal and in covalent linkage, a $V_H$ domain, a linker domain, and a $V_L$ domain.

7. The synthetic protein of claim 1, wherein the scFV is selected from any one of SEQ ID NOs: 15-27.

8. The synthetic protein of claim 1, further comprising a signal sequence N-terminal to the scFV.

* * * * *

UNITED STATES PATENT AND TRADEMARK OFFICE
CERTIFICATE OF CORRECTION

PATENT NO. : 10,717,782 B2
APPLICATION NO. : 16/141491
DATED : July 21, 2020
INVENTOR(S) : John T. Ngo It is certified that error appears in the above-identified patent and that said Letters Patent is hereby corrected as shown below:

In the Claims

At Column 229, Claim 1, Lines 43-45:
"A synthetic inhibitor or auto-inhibitory protein comprising a Notch NRR (Negative Regulatory Region)-binding scFV fused to a transmembrane domain."

Should be replaced with:
-- A synthetic inhibitor or auto-inhibitory protein comprising a Notch NRR (Negative Regulatory Region)-binding scFV fused to a transmembrane domain, wherein the synthetic protein inhibits Notch receptor or synthetic Notch receptor activity. --

Signed and Sealed this
Fifteenth Day of September, 2020

Andrei Iancu
*Director of the United States Patent and Trademark Office*